US009637453B2

(12) United States Patent
Ng et al.

(10) Patent No.: US 9,637,453 B2
(45) Date of Patent: May 2, 2017

(54) 3-SPIROCYCLIC-6-HYDROXAMIC ACID TETRALINS AS HDAC INHIBITORS

(71) Applicant: Forma Therapeutics, Inc., Watertown, MA (US)

(72) Inventors: Pui Yee Ng, Waltham, MA (US); Heather Davis, Haverhill, MA (US); Kenneth W. Bair, Wellesley, MA (US); Aleksandra Rudnitskaya, Roslindale, MA (US); Xiaozhang Zheng, Lexington, MA (US); Bingsong Han, North Haven, CT (US); Nicholas Barczak, Waterford, CT (US); David R. Lancia, Jr., Boston, MA (US)

(73) Assignee: Forma Therapeutics, Inc., Watertown, MA (US)

( * ) Notice: Subject to any disclaimer, the term of this patent is extended or adjusted under 35 U.S.C. 154(b) by 0 days.

(21) Appl. No.: 15/130,603

(22) Filed: Apr. 15, 2016

(65) Prior Publication Data
US 2016/0304456 A1 Oct. 20, 2016

Related U.S. Application Data

(60) Provisional application No. 62/149,360, filed on Apr. 17, 2015.

(51) Int. Cl.
| | | |
|---|---|---|
| *C07D 209/96* | (2006.01) |
| *C07D 401/04* | (2006.01) |
| *C07D 403/04* | (2006.01) |
| *C07D 417/06* | (2006.01) |
| *C07D 491/107* | (2006.01) |
| *C07D 413/06* | (2006.01) |
| *C07D 405/06* | (2006.01) |
| *C07D 471/04* | (2006.01) |
| *C07D 401/06* | (2006.01) |
| *C07D 403/06* | (2006.01) |
| *C07D 405/04* | (2006.01) |
| *C07D 405/10* | (2006.01) |
| *C07D 221/20* | (2006.01) |
| *C07D 497/10* | (2006.01) |
| *C07D 519/00* | (2006.01) |

(52) U.S. Cl.
CPC ......... *C07D 209/96* (2013.01); *C07D 221/20* (2013.01); *C07D 401/04* (2013.01); *C07D 401/06* (2013.01); *C07D 403/04* (2013.01); *C07D 403/06* (2013.01); *C07D 405/04* (2013.01); *C07D 405/06* (2013.01); *C07D 405/10* (2013.01); *C07D 413/06* (2013.01); *C07D 417/06* (2013.01); *C07D 471/04* (2013.01); *C07D 491/107* (2013.01); *C07D 497/10* (2013.01); *C07D 519/00* (2013.01)

(58) Field of Classification Search
None
See application file for complete search history.

(56) References Cited

U.S. PATENT DOCUMENTS

| 6,992,077 B2 | 1/2006 | Radeke et al. |
| 7,951,795 B2 | 5/2011 | Bell et al. |
| 8,658,641 B2 | 2/2014 | Barvian et al. |

FOREIGN PATENT DOCUMENTS

| WO | WO 2009/127609 | 10/2009 |
| WO | WO 2010/042475 | 4/2010 |
| WO | WO 2011/045265 | 4/2011 |
| WO | WO 2012/088015 | 6/2012 |
| WO | WO 2012/117421 | 9/2012 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Benedetti R, Conte M, Altucci L. "Targeting Histone Deacetylases in Diseases: Where Are We?" *Antioxidants & Redox Signaling*, 23(1), pp. 99-126, 2015.
Dallavalle S, Pisano C, Zunino F. "Development and therapeutic impact of HDAC6-selective inhibitors", *Biochemical Pharmacology*, Sep. 15, 2012; 84(6):756-65.
Kahn JH, Bergman JA. "Development and therapeutic implications of selective histone deacetylase 6 inhibitors", *J Med Chem.* Aug. 22, 2013; 56(16):6297-313.
Tang J, Yan H, Zhuang S. "Histone deacetylases as targets for treatment of multiple diseases", *Clinical Science* (Lond), Jun. 2013; 124(11):651-62.
Varasi, Mario et al. "Discovery, Synthesis, and Pharmacological Evaluation of Spiropiperidine Hydroxamic Acid Based Derivatives as Structurally Novel Histone Deacetylase (HDAC) Inhibitors", *Journal of Medicinal Chemistry*, vol. 54, No. 8, 2011, p. 3051-3064.
West AC, Johnstone RW, "New and emerging HDAC inhibitors for cancer treatment", *Journal of Clinical Investigation*, Jan. 2, 2014; 124(1):30-9.

* cited by examiner

*Primary Examiner* — Kristin Vajda
(74) *Attorney, Agent, or Firm* — Cooley LLP; J. Dean Farmer; Serge Banini

(57) ABSTRACT

The present invention is directed to inhibitors of histone deacetylases (HDACs) such as HDAC6 and HDAC11, and their use in the treatment of diseases such as cell proliferative diseases (e.g., cancer), neurological (e.g., neurodegenerative disease or neurodevelopmental disease), inflammatory or autoimmune disease, infection, metabolic disease, hematologic disease, or cardiovascular disease.

31 Claims, 1 Drawing Sheet

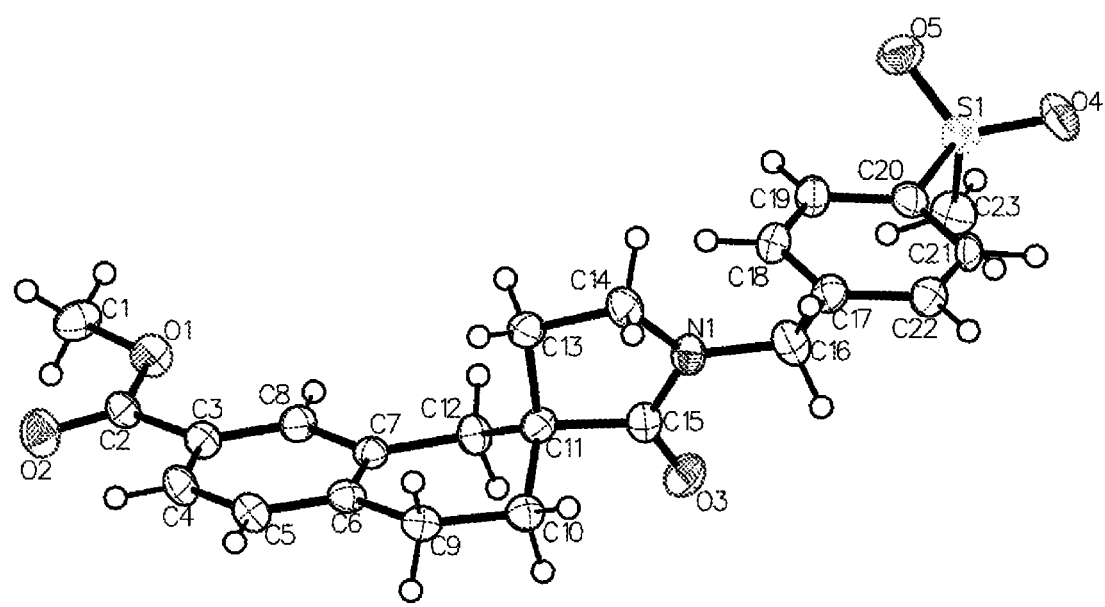

3-SPIROCYCLIC-6-HYDROXAMIC ACID TETRALINS AS HDAC INHIBITORS

CROSS-REFERENCE TO RELATED APPLICATIONS

This application claims the benefit of priority of U.S. Provisional Application No. 62/149,360, filed Apr. 17, 2015, the contents of which are hereby incorporated by reference.

FIELD OF THE INVENTION

The present invention relates to inhibitors of zinc-dependent histone deacetylases (HDACs) useful in the treatment of diseases or disorders associated with HDACs including cell proliferation diseases (e.g., cancer), neurological and inflammatory diseases. Specifically, this invention is concerned with compounds and compositions inhibiting HDACs, methods of treating diseases associated with HDACs, and methods of synthesizing these compounds.

BACKGROUND OF THE INVENTION

Many members of the HDAC family require zinc (Zn) to function properly. For instance, the isozymes histone deacetylase 6 (HDAC6) and histone deacetylase 11 (HDAC11) are zinc-dependent histone deacetylases that possesses histone deacetylase activity. Other family members include HDACs 1-5 and 7-10. (De Ruijter et al, *Biochem. J.* 2003. 370; 737-749).

HDAC6 is a class II HDAC known to deacetylate and associate with α-tubulin, cortactin, heat shock protein 90, α-catenin, glucose-regulated protein 78 kDa, myosin heavy chain 9, heat shock cognate protein 70, and dnaJ homolog subfamily A member 1 (reviewed in Li et al, *FEBS J.* 2013, 280: 775-93; Zhang et al, *Protein Cell.* 2015, 6(1): 42-54). Diseases in which HDAC6 inhibition could have a potential benefit include cancer (reviewed in Aldana-Masangkay et al, *J Biomed. Biotechnol.* 2011, 875824), specifically: multiple myeloma (Hideshima et al, *Proc. Natl. Acad. Sci. USA* 2005, 102(24):8567-8572); lung cancer (Kamemura et al, *Biochem. Biophys. Res. Commun.* 2008, 374(1):84-89); ovarian cancer (Bazzaro et al, *Clin. Cancer Res.* 2008, 14(22):7340-7347); breast cancer (Lee et al, *Cancer Res.* 2008, 68(18): 7561-7569; Park et al, *Oncol. Rep.* 2011, 25: 1677-81; Rey et al, *Eur. J Cell Biol.* 2011, 90: 128-35); prostate cancer (Seidel et al, *Biochem. Pharmacol.* 2015 (15)00714-5); pancreatic cancer (Nawrocki et al, *Cancer Res.* 2006, 66(7): 3773-3781); renal cancer (Cha et al, *Clin. Cancer Res.* 2009, 15(3): 840-850); hepatocellular cancer (Ding et al, *FEBS Lett.* 2013, 587:880-6; Kanno et al, *Oncol. Rep.* 2012, 28: 867-73); lymphomas (Ding et al, *Cancer Cell Int.* 2014, 14:139; Amengual et al, *Clin Cancer Res.* 2015, 21(20): 4663-75); and leukemias such as acute myeloid leukemia (AML) (Fiskus et al, *Blood* 2008, 112(7):2896-2905) and acute lymphoblastic leukemia (ALL) (Rodriguez-Gonzalez et al, *Blood* 2008, 1 12(1 1): Abstract 1923)).

HDAC11 is a class IV HDAC (Gao et al, J Biol Chem. 2002, Jul. 12; 277(28):25748-55) reported to deacetylate or associate with cell cycle-related proteins including Cdt1 (Glozak et al, J Biol Chem. 2009, Apr. 24; 284(17):11446-53), geminin (Wong et al, Cell Cycle. 2010, Nov. 1; 9(21): 4351-63), BubR1 (Watanabe et al, Cell Rep. 2014, Apr. 24; 7(2):552-64), and Cdc25(Lozada et al, Oncotarget. 2016, Mar. 7). HDAC11 was also reported to function in RNA splicing as part of the survival of motor neuron complex (Joshi et al, Mol Syst Biol. 2013, 9:672). Diseases in which HDAC11 inhibition could have potential benefit include cancer (Deubzer et al, Int J Cancer. 2013, May 1; 132(9): 2200-8) and specifically, Hodgkin lymphoma (Buglio et al, Blood. 2011, Mar. 10; 117(10):2910-7).

Inhibition of HDAC6 may also have a role in cardiovascular disease, including pressure overload, chronic ischemia, and infarction-reperfusion injury (Tannous et al, *Circulation* 2008, 117(24):3070-3078); bacterial infection, including those caused by uropathogenic *Escherichia coli* (Dhakal and Mulve, *J. Biol. Chem.* 2008, 284(1):446-454); neurological diseases caused by accumulation of intracellular protein aggregates such as Alzheimer's, Parkinson's and Huntington's disease (reviewed in Simoes-Pires et al, *Mol. Neurodegener.* 2013, 8: 7) or central nervous system trauma caused by tissue injury, oxidative-stress induced neuronal or axonal degeneration (Rivieccio et al, *Proc. Natl. Acad. Sci. USA* 2009, 106(46):19599-195604); and inflammation and autoimmune diseases through enhanced T cell-mediated immune tolerance at least in part through effects on regulatory T cells, including rheumatoid arthritis, psoriasis, spondylitis arthritis, psoriatic arthritis, multiple sclerosis, lupus, colitis and graft versus host disease (reviewed in Wang et al, *Nat. Rev. Drug Disc.* 2009 8(12):969-981; Vishwakarma et al, *Int. Immunopharmacol.* 2013, 16:72-8; Kalin et al, *J. Med. Chem.* 2012, 55:639-51); and fibrotic disease, including kidney fibrosis (Choi et al, *Vascul. Pharmacol.* 2015 72:130-140). Inhibition of HDAC11 may also have a role in inflammatory or autoimmune diseases through effects on IL-10 on immune cells including antigen presenting cells and myeloid-derived suppressor cells (Villagra et al, Nat Immunol. 2009, January; 10(1):92-100; Cheng et al, Mol Immunol. 2014, July; 60(1):44-53; Sahakian et al, Mol Immunol. 2015, February; 63(2):579-85).

Four HDAC inhibitors are currently approved for the treatment of some cancers. These are suberanilohydroxamic acid (Vorinostat; Zolinza®) for the treatment of cutaneous T cell lymphoma and multiple myeloma; Romidepsin (FK228; FR901228; Istodax®) for the treatment of peripheral T cell lymphoma; Panobinostat (LBH-589; Farydak®) for the treatment of multiple myeloma; and belinostat (PXD101; Beleodaq®) for the treatment of peripheral T cell lymphoma. However, these drugs are of limited effectiveness and can give rise to unwanted side effects. Thus, there is a need for HDAC inhibitors with an improved safety-efficacy profile.

SUMMARY OF THE INVENTION

One aspect of the invention relates to compounds of Formula I:

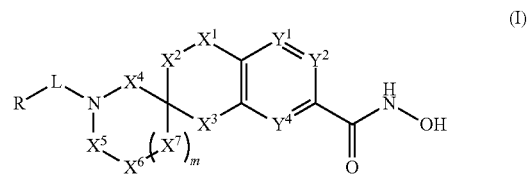

and pharmaceutically acceptable salts, prodrugs, solvates, hydrates, tautomers, or isomers or thereof, wherein:

$X^1$, $X^2$, $X^3$, $X^6$, and $X^7$ are each independently —$CR^1R^2$—, —$NR^3$—, —O—, —C(O)—, —$SO_2$—, —S(O)—, or —S—;

$X^4$ and $X^5$ are each independently —$CR^1R^2$—, —C(O)—, —$SO_2$—, —S(O)—, or —S—;

$Y^1$, $Y^2$ and $Y^4$ are each independently N or $CR^1$;

L is a bond, $-(CR^1R^2)_n-$, $-C(O)NR^3-$, $-S(O)_2-$, $-S(O)_2NR^3-$, $-S(O)-$, $-S(O)NR^3-$, $-C(O)(CR^1R^2)_nO-$, or $-C(O)(CR^1R^2)_n-$;

R is independently $-H$, $-C_1-C_6$alkyl, $-C_2-C_6$alkenyl, $-C_4-C_8$cycloalkenyl, $-C_2-C_6$alkynyl, $-C_3-C_8$cycloalkyl, $-C_5-C_{12}$spirocycle, heterocyclyl, spiroheterocyclyl, aryl, or heteroaryl containing 1-5 heteroatoms selected from the group consisting of N, S, P, or O, wherein each alkyl, alkenyl, cycloalkenyl, alkynyl, cycloalkyl, spirocycle, heterocyclyl, spiroheterocyclyl, aryl, or heteroaryl is optionally substituted with one or more $-OH$, halogen, oxo, $-NO_2$, $-CN$, $-R^1$, $-R^2$, $-SR^3$, $-OR^3$, $-NHR^3$, $-NR^3R^4$, $-S(O)_2NR^3R^4$, $-S(O)_2R^1$, $-C(O)R^1$, $-CO_2R^1$, $-NR^3S(O)_2R^1$, $-S(O)R^1$, $-S(O)NR^3R^4$, $-NR^3S(O)R^1$, heterocycle, aryl, or heteroaryl;

$R^1$ and $R^2$ are independently, at each occurrence, $-H$, $-R^3$, $-R^4$, $-C_1-C_6$alkyl, $-C_2-C_6$alkenyl, $-C_4-C_8$cycloalkenyl, $-C_2-C_6$alkynyl, $-C_3-C_8$cycloalkyl, heterocyclyl, aryl, heteroaryl containing 1-5 heteroatoms selected from the group consisting of N, S, P and O, $-OH$, halogen, $-NO_2$, $-CN$, $-NHC_1-C_6$alkyl, $-N(C_1-C_6$alkyl$)_2$, $-S(O)_2N(C_1-C_6$alkyl$)_2$, $-N(C_1-C_6$alkyl$)S(O)_2R^5$, $-S(O)_2(C_1-C_6$alkyl$)$, $-(C_1-C_6$alkyl$)S(O)_2R^5$, $-C(O)C_1-C_6$alkyl, $-CO_2C_1-C_6$alkyl, $-N(C_1-C_6$alkyl$)S(O)_2C_1-C_6$alkyl, or $-(CHR^5)_nNR^3R^4$, wherein each alkyl, alkenyl, cycloalkenyl, alkynyl, cycloalkyl, heterocyclyl, aryl, or heteroaryl is optionally substituted with one or more $-OH$, halogen, $-NO_2$, oxo, $-CN$, $-R^5$, $-OR^3$, $-NHR^3$, $NR^3R^4$, $-S(O)_2N(R^3)_2-$, $-S(O)_2R^5$, $-C(O)R^5$, $-CO_2R^5$, $-NR^3S(O)_2R^5$, $-S(O)R^5$, $-S(O)NR^3R^4$, $-NR^3S(O)R^5$, heterocycle, aryl, or heteroaryl;

or $R^1$ and $R^2$ can combine with the carbon atom to which they are both attached to form a cycloalkyl, heterocycle, spirocycle, spiroheterocycle, or spirocycloalkenyl;

or $R^1$ and $R^2$, when on adjacent or non-adjacent atoms, can combine to form a heterocycle, cycloalkyl, aryl, heteroaryl containing 1-5 heteroatoms selected from the group consisting of N, S, P and O, or cycloalkenyl;

$R^3$ and $R^4$ are independently, at each occurrence, $-H$, $-C_1-C_6$alkyl, $-C_2-C_6$alkenyl, $-C_4-C_8$cycloalkenyl, $-C_2-C_6$alkynyl, $-C_3-C_8$cycloalkyl, heterocyclyl, aryl, heteroaryl containing 1-5 heteroatoms selected from N, S, P, and O, $-S(O)_2N(C_1-C_6$alkyl$)_2$, $-S(O)_2(C_1-C_6$alkyl$)$, $-(C_1-C_6$alkyl$)S(O)_2R^5$, $-C(O)C_1-C_6$alkyl, $-CO_2C_1-C_6$alkyl, or $-(CHR^5)_nN(C_1-C_6$alkyl$)_2$, wherein each alkyl, alkenyl, cycloalkenyl, alkynyl, cycloalkyl, heterocyclyl, aryl, and heteroaryl is optionally substituted with one or more substituents selected from $-OH$, halogen, $-NO_2$, oxo, $-CN$, $-R^5$, $-O(C_1-C_6)$alkyl, $-NH(C_1-C_6)$alkyl, $-N(C_1-C_6$alkly$)_2$, $-S(O)_2N(C_1-C_6$alkyl$)_2$, $-S(O)_2NHC_1-C_6$alkyl, $-C(O)C_1-C_6$alkyl, $-CO_2C_1-C_6$alkyl, $-N(C_1-C_6$alkyl$)S(O)_2C_1-C_6$alkyl, $-S(O)R^5$, $-S(O)N(C_1-C_6$alkyl$)_2$, $-N(C_1-C_6$alkyl$)S(O)R^5$, heterocycle, aryl, or heteroaryl;

$R^5$ is independently, at each occurrence, $-H$, $-C_1-C_6$alkyl, $-C_2-C_6$alkenyl, $-C_4-C_8$cycloalkenyl, $-C_2-C_6$alkynyl, $-C_3-C_8$cycloalkyl, heterocyclyl, aryl, heteroaryl containing 1-5heteroatoms selected from N, S, P and O, $-OH$, halogen, $-NO_2$, $-CN$, $-NHC_1-C_6$alkyl, $-N(C_1-C_6$alkyl$)_2$, $-S(O)_2NH(C_1-C_6$alkyl$)$, $-S(O)_2N(C_1-C_6$alkyl$)_2$, $-S(O)_2C_1-C_6$alkyl, $-C(O)C_1-C_6$alkyl, $-CO_2C_1-C_6$alkyl, $-N(C_1-C_6$alkyl$)SO_2C_1-C_6$alkyl, $-S(O)(C_1-C_6$alkyl$)$, $-S(O)N(C_1-C_6$alkyl$)_2$, $-N(C_1-C_6$alkyl$)S(O)(C_1-C_6$alkyl$)$ or $-(CH_2)_nN(C_1-C_6$alkyl$)_2$;

n is an integer from 0 to 6; and m is 0, 1, 2 or 3.

In another aspect, the invention relates to compounds of Formula II:

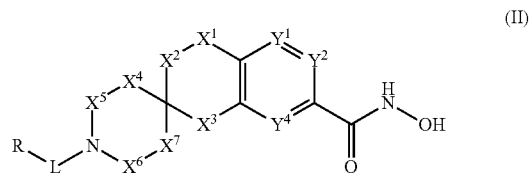

(II)

and pharmaceutically acceptable salts, prodrugs, solvates, hydrates, tautomers or isomers thereof, wherein:

$X^1$ is independently $-CR^1R^2-$, $-NR^3-$, $-O-$, $-SO_2-$, $-S(O)-$, or $-S-$;

$X^2$, $X^3$, $X^4$, and $X^7$ are each independently $-CR^1R^2-$, $-NR^3-$, $-O-$, $-C(O)-$, $-SO_2-$, $-S(O)-$, or $-S-$;

$X^5$ and $X^6$ are each independently $-CR^1R^2-$, $-C(O)-$, $-SO_2-$, $-S(O)-$, or $-S-$;

$Y^1$, $Y^2$ and $Y^4$ are each independently N or $CR^1$;

L is a bond, $-(CR^1R^2)_n-$, $-C(O)NR^3-$, $-S(O)_2-$, $-S(O)_2NR^3-$, $-S(O)-$, $-S(O)NR^3-$, $-C(O)(CR^1R^2)_nO-$, or $-C(O)(CR^1R^2)_n-$;

R is independently $-H$, $-C_1-C_6$alkyl, $-C_2-C_6$alkenyl, $-C_4-C_8$cycloalkenyl, $-C_2-C_6$alkynyl, $-C_3-C_8$cycloalkyl, $-C_5-C_{12}$spirocycle, heterocyclyl, spiroheterocyclyl, aryl, or heteroaryl containing 1-5 heteroatoms selected from the group consisting of N, S, P, or O, wherein each -alkyl, alkenyl, cycloalkenyl, alkynyl, cycloalkyl, spirocycle, heterocyclyl, spiroheterocyclyl, aryl, or heteroaryl is optionally substituted with one or more $-OH$, halogen, oxo, $-NO_2$, $-CN$, $-R^1$, $-R^2$, $-SR^3$, $-OR^3$, $-NHR^3$, $-NR^3R^4$, $-S(O)_2NR^3R^4$, $-S(O)_2R^1$, $-C(O)R^1$, $-CO_2R^1$, $-NR^3S(O)_2R^1$, $-S(O)R^1$, $-S(O)NR^3R^4$, $-NR^3S(O)R^1$, heterocycle, aryl, or heteroaryl;

$R^1$ and $R^2$ are independently, and at each occurrence, $-H$, $-R^3$, $-R^4$, $-C_1-C_6$alkyl, $-C_2-C_6$alkenyl, $-C_4-C_8$cycloalkenyl, $-C_2-C_6$alkynyl, $-C_3-C_8$cycloalkyl, heterocyclyl, aryl, heteroaryl containing 1-5 heteroatoms selected from the group consisting of N, S, P, or O, $-OH$, halogen, $-NO_2$, $-CN$, $-NHC_1-C_6$alkyl, $-N(C_1-C_6$alkyl$)_2$, $-S(O)_2N(C_1-C_6$alkyl$)_2$, $-N(C_1-C_6$alkyl$)S(O)_2R^5$, $-S(O)_2(C_1-C_6$alkyl$)$, $-(C_1-C_6$alkyl$)S(O)_2R^5$, $-C(O)C_1-C_6$alkyl, $-CO_2C_1-C_6$alkyl, $-N(C_1-C_6$alkyl$)S(O)_2C_1-C_6$alkyl, or $-(CHR^5)_nNR^3R^4$, wherein each alkyl, alkenyl, cycloalkenyl, alkynyl, cycloalkyl, heterocyclyl, aryl, or heteroaryl is optionally substituted with one or more substituents selected from $-OH$, halogen, $-NO_2$, oxo, $-CN$, $-R^5$, $-OR^3$, $-NHR^3$, $NR^3R^4$, $-S(O)_2N(R^3)_2-$, $-S(O)_2R^5$, $-C(O)R^5$, $-CO_2R^5$, $-NR^3S(O)_2R^5$, $-S(O)R^5$, $-S(O)NR^3R^4$, $-NR^3S(O)R^5$, heterocycle, aryl, or heteroaryl;

or $R^1$ and $R^2$ can combine with the carbon atom to which they are both attached to form a cycloalkyl, heterocycle, spirocycle, spiroheterocycle, or spirocycloalkenyl;

or $R^1$ and $R^2$, when on adjacent or non-adjacent atoms, can combine to form a heterocycle, cycloalkyl, aryl, heteroaryl containing 1-5 heteroatoms selected from the group consisting of N, S, P and O, or cycloalkenyl;

$R^3$ and $R^4$ are independently, at each occurrence, $-H$, $-C_1-C_6$alkyl, $-C_2-C_6$alkenyl, $-C_4-C_8$cycloalkenyl, $-C_2-C_6$alkynyl, $-C_3-C_8$cycloalkyl, heterocyclyl, aryl, heteroaryl containing 1-5heteroatoms selected from N, S, P and O, $-S(O)_2N(C_1-C_6$alkyl$)_2$, $-S(O)_2(C_1-C_6$alkyl$)$, $-(C_1-C_6$alkyl$)S(O)_2R^5$, $-C(O)C_1-C_6$alkyl, $-CO_2C_1-C_6$alkyl, or —(CHR$^5$)$_n$N(C$_1$-C$_6$alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O(C$_1$-C$_6$)alkyl, —NH(C$_1$-C$_6$)alkyl, —N(C$_1$-C$_6$alkly)$_2$, —S(O)$_2$N(C$_1$-C$_6$alkyl)$_2$, —S(O)$_2$NHC$_1$-C$_6$alkyl, —C(O)C$_1$-C$_6$alkyl, —CO$_2$C$_1$-C$_6$alkyl, —N(C$_1$-C$_6$alkyl)S(O)$_2$C$_1$-C$_6$alkyl, —S(O)R$^5$, —S(O)N(C$_1$-C$_6$alkyl)$_2$, —N(C$_1$-C$_6$alkyl)S(O)R$^5$, heterocycle, aryl, or heteroaryl;

each R$^5$ is independently —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, heterocyclyl, aryl, heteroaryl containing 1-5 heteroatoms selected from N, S, O and P, —OH, halogen, —NO$_2$, —CN, —NHC$_1$-C$_6$alkyl, —N(C$_1$-C$_6$alkyl)$_2$, —S(O)$_2$NH(C$_1$-C$_6$alkyl), —S(O)$_2$N(C$_1$-C$_6$alkyl)$_2$, —S(O)$_2$C$_1$-C$_6$alkyl, —C(O)C$_1$-C$_6$alkyl, —CO$_2$C$_1$-C$_6$alkyl, —N(C$_1$-C$_6$alkyl)SO$_2$C$_1$-C$_6$alkyl, —S(O)(C$_1$-C$_6$alkyl), —S(O)N(C$_1$-C$_6$alkyl)$_2$, —N(C$_1$-C$_6$alkyl)S(O)(C$_1$-C$_6$alkyl) or —(CH$_2$)$_n$N(C$_1$-C$_6$alkyl)$_2$; and n is an integer from 0 to 6.

Another aspect of the invention relates to a method of treating a disease or disorder associated with HDAC6 or HDAC11 modulation in a subject in need thereof, comprising administering to the subject an effective amount of a compound of Formula I or Formula II.

Another aspect of the invention is directed to a method of inhibiting HDAC6 or HDAC11. The method involves administering to a patient in need thereof an effective amount of a compound of Formula I or Formula II.

Another aspect of the invention is directed to pharmaceutical compositions comprising a compound of Formula I or Formula II and a pharmaceutically acceptable carrier. The pharmaceutically acceptable carrier can further include an excipient, diluent, or surfactant. The pharmaceutical composition can be effective for treating a disease or disorder associated with HDAC6 or HDAC11 modulation in a subject in need thereof. The pharmaceutical compositions can comprise the compounds of the present invention for use in treating diseases described herein. The compositions can contain at least one compound of the invention and a pharmaceutically acceptable carrier. The invention also provides the use of the compounds described herein in the manufacture of a medicament for the treatment of a disease associated with HDACs.

The present invention also provides methods for the treatment of human diseases or disorders including, without limitation, oncological, neurological, inflammatory, autoimmune, infectious, metabolic, hematologic, or cardiovascular diseases or disorders.

The present invention also provides compounds that are useful in inhibiting of zinc-dependent HDAC enzymes, and in particular HDAC6 or HDAC11. These compounds can also be useful in the treatment of diseases including cancer.

The present invention further provides compounds that can inhibit HDAC6 or HDAC11. In some embodiments, the efficacy-safety profile of the compounds of the current invention can be improved relative to other known HDAC (e.g. HDAC6 or HDAC11) inhibitors. Additionally, the present technology also has the advantage of being able to be used for a number of different types of diseases, including cancer and non-cancer indications. Additional features and advantages of the present technology will be apparent to one of skill in the art upon reading the Detailed Description of the Invention, below.

BRIEF DESCRIPTION OF THE DRAWINGS

FIG. 1 shows an X-ray crystal structure of methyl (R)-1'-[(4-methanesulfonylphenyl)methyl]-2'-oxo-3,4-dihydro-1H-spiro[naphthalene-2,3'-pyrrolidine]-7-carboxylate.

DETAILED DESCRIPTION OF THE INVENTION

HDAC6 is a zinc-dependent histone deacetylase that has two catalytic domains. HDAC6 can interact with and deacetylate non-histone proteins, including HSP90 and α-tubulin. Acetylation of HSP90 is associated with loss of function of HSP90. HDAC6 is also implicated in the degradation of misfolded proteins as part of the aggresome. HDAC11 is reported to interact with or deacetylate RNA splicing-related proteins in the survival of motor neuron complex and cell cycle-related proteins including Cdt1, BubR1, and Cdc25. Accordingly, inhibition of HDAC6 or HDAC11 can have downstream effects that can play a role in the development of certain diseases such as cancer. The present invention provides inhibitors of HDAC6 or HDAC11 and methods for using the same to treat disease.

In a first aspect of the invention, compounds of the Formula I are described:

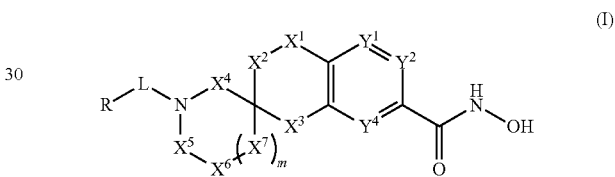

(I)

and pharmaceutically acceptable salts, prodrugs, solvates, hydrates, tautomers, and isomers thereof, wherein m, R, L, X$^1$, X$^2$, X$^3$, X$^4$, X$^5$, X$^6$, X$^7$, Y$^1$, Y$^2$, and Y$^4$ are described as above.

In a second aspect of the invention, compounds of the Formula II are described:

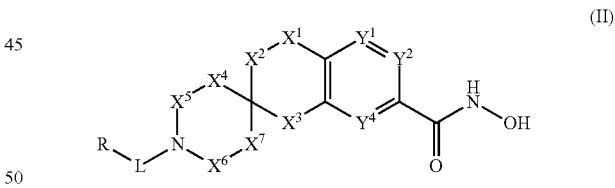

(II)

and pharmaceutically acceptable salts, prodrugs, solvates, hydrates, tautomers, and isomers thereof, wherein R, L, X$^1$, X$^2$, X$^3$, X$^4$, X$^5$, X$^6$, X$^7$, Y$^1$, Y$^2$, and Y$^4$ are described as above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, —$C_1$-$C_6$alkyl, —$OC_2$-$C_6$alkenyl, —$OC_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —$NH_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 24 ring atoms or a polycyclic aromatic radical, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

"Alkyl" refers to a straight or branched chain saturated hydrocarbon. $C_1$-$C_6$alkyl groups contain 1 to 6 carbon atoms. Examples of a $C_1$-$C_6$alkyl group include, but are not limited to, methyl, ethyl, propyl, butyl, pentyl, isopropyl, isobutyl, sec-butyl and tert-butyl, isopentyl and neopentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$cycloalkenyl is a cycloalkenyl group containing between 4 and 8 carbon atoms.

The terms "heterocyclyl" or "heterocycloalkyl" or "heterocycle" refer to monocyclic or polycyclic 3 to 24-membered rings containing carbon and heteroatoms taken from oxygen, nitrogen, or sulfur and wherein there is not delocalized πt electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocycloalkyl ring can also be fused or bridged, e.g., can be a bicyclic ring.

As used herein, the term "halo" or "halogen" means a fluoro, chloro, bromo, or iodo group.

The term "carbonyl" refers to a functional group composing a carbon atom double-bonded to an oxygen atom. It can be abbreviated herein as "oxo", as C(O), or as C=O.

"Spirocycle" or "spirocyclic" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another carbocyclic, heterocyclic, aromatic, or heteroaromatic ring. One or more of the carbon atoms in the spirocycle can be substituted with a heteroatom (e.g., O, N, S, or P). A $C_5$-$C_{12}$ spirocycle is a spirocycle containing between 5 and 12 carbon atoms. One or more of the carbon atoms can be substituted with a heteroatom.

The term "spirocyclic heterocycle" or "spiroheterocycle" is understood to mean a spirocycle wherein at least one of the rings is a heterocycle (e.g., at least one of the rings is furanyl, morpholinyl, or piperadinyl).

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "stereoisomers" refers to the set of compounds which have the same number and type of atoms and share the same bond connectivity between those atoms, but differ in three dimensional structure. The term "stereoisomer" refers to any member of this set of compounds.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. In some cases these diastereomers were separated and in other cases a wavy bond is used to indicate the structural element where configuration is variable.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the invention.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula I or Formula II may have one or more asymmetric carbon atom and may occur as racemates, racemic mixtures and as individual enantiomers or diastereomers.

A "patient" or "subject" is a mammal, e.g., a human, mouse, rat, guinea pig, dog, cat, horse, cow, pig, or non-human primate, such as a monkey, chimpanzee, baboon or rhesus.

In one embodiments of the compounds of Formula I or Formula II, $X^4$ is —C(O)—.

In one or more embodiments of the compounds of Formula I, m is 0 or 1.

In one embodiment of the compound of Formula I, the compound is of the Formula I-a, I-b, I-c, I-d I-e, I-f, I-g, I-h, I-j, or I-k:

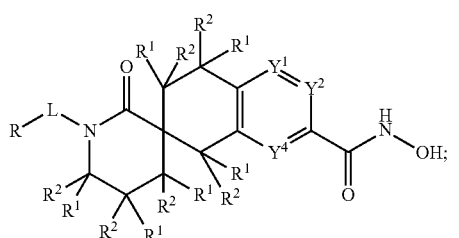
(I-a)

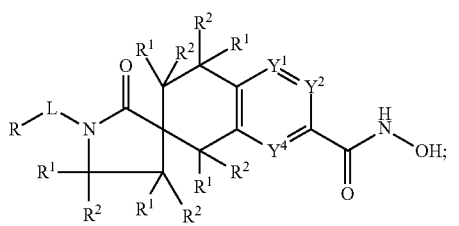
(I-b)

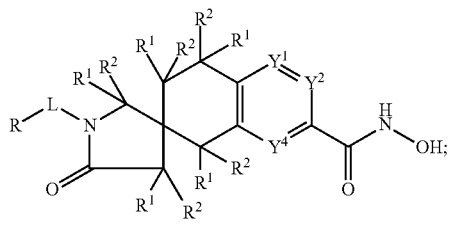
(I-c)

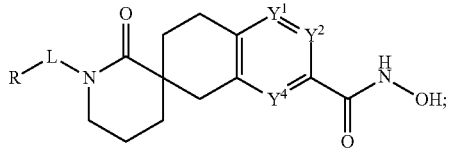
(I-d)

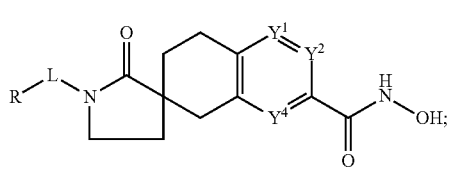
(I-e)

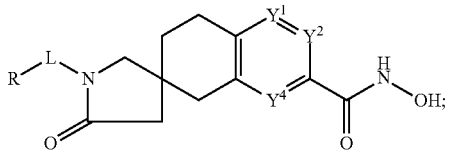
(I-f)

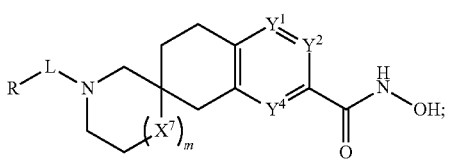
(I-g)

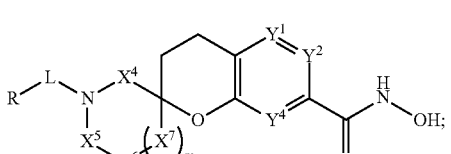
(I-h)

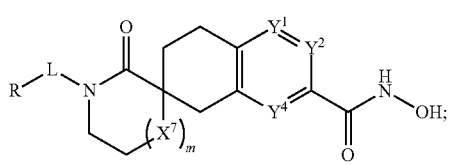
(I-j)

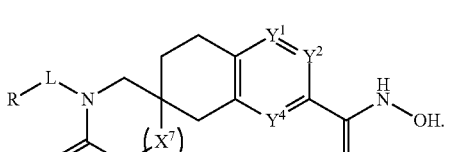
(I-k)

In one embodiment of the compound of Formula II, the compound is of the Formula II-a, II-b, II-c, or II-d:

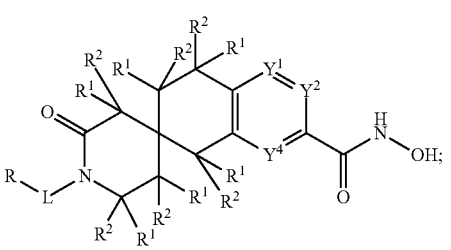
(II-a)

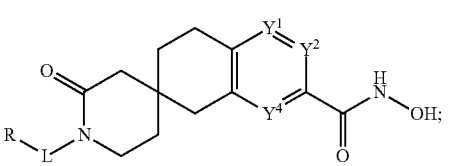
(II-b)

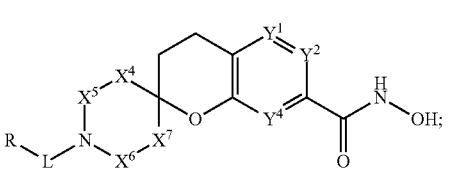
(II-c)

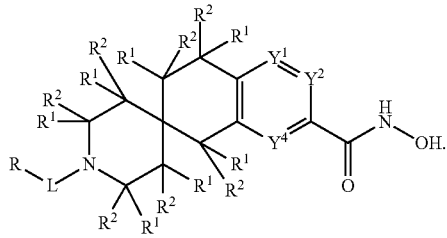

(II-d)

In one or more embodiments, the compounds of Formula I are:

N-hydroxy-1'-(4-methoxybenzoyl)-3,4-dihydro-1H-spiro[naphthalene-2,3'-pyrrolidine]-7-carboxamide (I-1);
N-hydroxy-1'-((4-methoxyphenyl)sulfonyl)-3,4-dihydro-H-spiro[naphthalene-2,3'-pyrrolidine]-7-carboxamide (I-2);
N-hydroxy-1'-(4-methoxybenzyl)-3,4-dihydro-1H-spiro[naphthalene-2,3'-pyrrolidine]-7-carboxamide (I-3);
1'-(cyclohexanecarbonyl)-N-hydroxy-3,4-dihydro-1H-spiro[naphthalene-2,3'-pyrrolidine]-7-carboxamide (I-4);
1'-cyclohexyl-N-hydroxy-3,4-dihydro-1H-spiro[naphthalene-2,3'-pyrrolidine]-7-carboxamide (I-5);
N7-hydroxy-N'-phenyl-3,4-dihydro-1H-spiro[naphthalene-2,3'-pyrrolidine]-1',7-dicarboxamide (I-6);
1'-(cyclohexylsulfonyl)-N-hydroxy-3,4-dihydro-1H-spiro[naphthalene-2,3'-pyrrolidine]-7-carboxamide (I-7);
N-hydroxy-3,4-dihydro-1H-spiro[naphthalene-2,3'-pyrrolidine]-7-carboxamide (I-8);
N-hydroxy-1'-methyl-3,4-dihydro-1H-spiro[naphthalene-2,3'-pyrrolidine]-7-carboxamide (I-9);
1'-formyl-N-hydroxy-3,4-dihydro-1H-spiro[naphthalene-2,3'-pyrrolidine]-7-carboxamide (I-10);
N-hydroxy-1'-isopropyl-3,4-dihydro-1H-spiro[naphthalene-2,3'-pyrrolidine]-7-carboxamide (I-11);
1'-acetyl-N-hydroxy-3,4-dihydro-1H-spiro[naphthalene-2,3'-pyrrolidine]-7-carboxamide (I-12);
N-hydroxy-1'-(methyl sulfonyl)-3,4-dihydro-1H-spiro[naphthalene-2,3'-pyrrolidine]-7-carboxamide (I-13);
N-hydroxy-1'-(3-methoxybenzyl)-3,4-dihydro-1H-spiro[naphthalene-2,3'-pyrrolidine]-7-carboxamide (I-14);
N-hydroxy-1'-(2-methoxybenzyl)-3,4-dihydro-1H-spiro[naphthalene-2,3'-pyrrolidine]-7-carboxamide (I-15);
(S)—N-hydroxy-1'-phenyl-3,4-dihydro-1H-spiro[naphthalene-2,3'-pyrrolidine]-7-carboxamide (I-16);
(R)—N-hydroxy-1'-phenyl-3,4-dihydro-1H-spiro[naphthalene-2,3'-pyrrolidine]-7-carboxamide (I-17);
(S)—N-hydroxy-1'-methyl-3,4-dihydro-1H-spiro[naphthalene-2,3'-pyrrolidine]-7-carboxamide (I-18);
(R)—N-hydroxy-1'-methyl-3,4-dihydro-1H-spiro[naphthalene-2,3'-pyrrolidine]-7-carboxamide (I-19);
N-hydroxy-1'-(4-methoxyphenethyl)-2'-oxo-3,4-dihydro-1H-spiro[naphthalene-2,3'-pyrrolidine]-7-carboxamide (I-20);
1'-(3,4-dichlorobenzyl)-N-hydroxy-2'-oxo-3,4-dihydro-1H-spiro[naphthalene-2,3'-pyrrolidine]-7-carboxamide (I-21);
N-hydroxy-2'-oxo-1'-(pyridin-4-ylmethyl)-3,4-dihydro-1H-spiro[naphthalene-2,3'-pyrrolidine]-7-carboxamide (I-22);
1'-(cyclohexylmethyl)-N-hydroxy-2'-oxo-3,4-dihydro-1H-spiro[naphthalene-2,3'-pyrrolidine]-7-carboxamide (I-23);
N-hydroxy-1'-isopropyl-2'-oxo-3,4-dihydro-1H-spiro[naphthalene-2, 3'-pyrrolidine]-7-carboxamide (I-24);
1'-(3-(dimethylamino)propyl)-N-hydroxy-2'-oxo-3,4-dihydro-1H-spiro[naphthalene-2,3'-pyrrolidine]-7-carboxamide (I-25);
N-hydroxy-2'-oxo-1'-phenyl-3,4-dihydro-H-spiro[naphthalene-2,3'-pyrrolidine]-7-carboxamide (I-26);
1'-(4-chloro-3-(trifluoromethyl)benzyl)-N-hydroxy-2'-oxo-3,4-dihydro-1H-spiro[naphthalene-2,3'-pyrrolidine]-7-carboxamide (I-27);
(S)—N-hydroxy-2'-oxo-1'-(pyridin-3-yl)-3,4-dihydro-1H-spiro[naphthalene-2,3'-pyrrolidine]-7-carboxamide (I-28);
(R)—N-hydroxy-2'-oxo-1'-(pyridin-3-yl)-3,4-dihydro-1H-spiro[naphthalene-2,3'-pyrrolidine]-7-carboxamide (I-29);
N-hydroxy-2'-oxo-1'-(pyridin-4-yl)-3,4-dihydro-1H-spiro[naphthalene-2,3'-pyrrolidine]-7-carboxamide (I-30);
(S)-1'-(1H-benzo[d]imidazol-2-yl)-N-hydroxy-2'-oxo-3,4-dihydro-1H-spiro[naphthalene-2,3'-pyrrolidine]-7-carboxamide (I-31);
(R)-1'-(1H-benzo[d]imidazol-2-yl)-N-hydroxy-2'-oxo-3,4-dihydro-1H-spiro[naphthalene-2,3'-pyrrolidine]-7-carboxamide (I-32);
(S)—N-hydroxy-1'-(1-(2-methoxyethyl)-1H-benzo[d]imidazol-2-yl)-2'-oxo-3,4-dihydro-1H-spiro[naphthalene-2,3'-pyrrolidine]-7-carboxamide (I-33);
(R)—N-hydroxy-1'-(1-(2-methoxyethyl)-1H-benzo[d]imidazol-2-yl)-2'-oxo-3,4-dihydro-1H-spiro[naphthalene-2,3'-pyrrolidine]-7-carboxamide (I-34);
(S)-1'-benzyl-N-hydroxy-2'-oxo-3,4-dihydro-1H-spiro[naphthalene-2,3'-pyrrolidine]-7-carboxamide (I-35);
(R)-1'-benzyl-N-hydroxy-2'-oxo-3,4-dihydro-1H-spiro[naphthalene-2,3'-pyrrolidine]-7-carboxamide (I-36);
(S)-1'-(4-chlorobenzyl)-N-hydroxy-2'-oxo-3,4-dihydro-1H-spiro[naphthalene-2,3'-pyrrolidine]-7-carboxamide (I-37);
(R)-1'-(4-chlorobenzyl)-N-hydroxy-2'-oxo-3,4-dihydro-1H-spiro[naphthalene-2,3'-pyrrolidine]-7-carboxamide (I-38);
(S)-1'-((5-chloropyridin-2-yl)methyl)-N-hydroxy-2'-oxo-3,4-dihydro-1H-spiro[naphthalene-2,3'-pyrrolidine]-7-carboxamide (I-39);
(R)-1'-((5-chloropyridin-2-yl)methyl)-N-hydroxy-2'-oxo-3,4-dihydro-1H-spiro[naphthalene-2,3'-pyrrolidine]-7-carboxamide (I-40);
(S)-1'-(4-fluorobenzyl)-N-hydroxy-2'-oxo-3,4-dihydro-1H-spiro[naphthalene-2,3'-pyrrolidine]-7-carboxamide (I-41);
(R)-1'-(4-fluorobenzyl)-N-hydroxy-2'-oxo-3,4-dihydro-1H-spiro[naphthalene-2,3'-pyrrolidine]-7-carboxamide (I-42);
(R)—N-hydroxy-2'-oxo-1'-(pyridin-2-yl)-3,4-dihydro-1H-spiro[naphthalene-2,3'-pyrrolidine]-7-carboxamide (I-43);
(S)—N-hydroxy-2'-oxo-1'-(pyridin-2-yl)-3,4-dihydro-1H-spiro[naphthalene-2,3'-pyrrolidine]-7-carboxamide (I-44);
(S)—N-hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-7-carboxamide (I-45);
(R)—N-hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-7-carboxamide (I-46);
(S)—N-hydroxy-2'-oxo-3,4-dihydro-1H-spiro[naphthalene-2,3'-pyrrolidine]-7-carboxamide (I-47);
(R)—N-hydroxy-2'-oxo-3,4-dihydro-1H-spiro[naphthalene-2,3'-pyrrolidine]-7-carboxamide (I-48);

(S)-1'-((2-chlorothiazol-5-yl)methyl)-N-hydroxy-2'-oxo-3,4-dihydro-1H-spiro[naphthalene-2,3'-pyrrolidine]-7-carboxamide (I-49);

(S)—N-hydroxy-1'-((2-hydroxythiazol-5-yl)methyl)-2'-oxo-3,4-dihydro-1H-spiro[naphthalene-2,3'-pyrrolidine]-7-carboxamide (I-50);

(R)—N-hydroxy-1'-(4-(methylsulfonyl)benzyl)-2'-oxo-3,4-dihydro-1H-spiro[naphthalene-2,3'-pyrrolidine]-7-carboxamide (I-51);

(S)—N-hydroxy-2'-oxo-1'-propyl-3,4-dihydro-1H-spiro[naphthalene-2,3'-pyrrolidine]-7-carboxamide (I-52);

(S)-1'-(cyclobutylmethyl)-N-hydroxy-2'-oxo-3,4-dihydro-1H-spiro[naphthalene-2,3'-pyrrolidine]-7-carboxamide (I-53);

(S)—N-hydroxy-1'-isopentyl-2'-oxo-3,4-dihydro-1H-spiro[naphthalene-2,3'-pyrrolidine]-7-carboxamide (I-54);

(S)-1'-(but-2-yn-1-yl)-N-hydroxy-2'-oxo-3,4-dihydro-1H-spiro[naphthalene-2,3'-pyrrolidine]-7-carboxamide (I-55);

(S)—N-hydroxy-1'-(2-methoxyethyl)-2'-oxo-3,4-dihydro-1H-spiro[naphthalene-2,3'-pyrrolidine]-7-carboxamide (I-56);

(S)—N-hydroxy-2'-oxo-1'-((tetrahydro-2H-pyran-4-yl)methyl)-3,4-dihydro-1H-spiro[naphthalene-2,3'-pyrrolidine]-7-carboxamide (I-57);

(S)-1'-cinnamyl-N-hydroxy-2'-oxo-3,4-dihydro-1H-spiro[naphthalene-2,3'-pyrrolidine]-7-carboxamide (I-58);

(S)—N-hydroxy-1'-(2-methylbenzyl)-2'-oxo-3,4-dihydro-1H-spiro[naphthalene-2,3'-pyrrolidine]-7-carboxamide (I-59);

(S)—N-hydroxy-2'-oxo-1'-(2-(trifluoromethyl)benzyl)-3,4-dihydro-1H-spiro[naphthalene-2,3'-pyrrolidine]-7-carboxamide (I-60);

(S)-1'-(2-chlorobenzyl)-N-hydroxy-2'-oxo-3,4-dihydro-1H-spiro[naphthalene-2,3'-pyrrolidine]-7-carboxamide (I-61);

(S)—N-hydroxy-2'-oxo-1'-(2-(trifluoromethoxy)benzyl)-3,4-dihydro-1H-spiro[naphthalene-2,3'-pyrrolidine]-7-carboxamide (I-62);

(S)-1'-(benzo[c][1,2,5]oxadiazol-5-ylmethyl)-N-hydroxy-2'-oxo-3,4-dihydro-1H-spiro[naphthalene-2,3'-pyrrolidine]-7-carboxamide (I-63);

(S)—N-hydroxy-1'-(2-morpholino-2-oxoethyl)-2'-oxo-3,4-dihydro-1H-spiro[naphthalene-2,3'-pyrrolidine]-7-carboxamide (I-64);

(S)—N-hydroxy-1'-(2-methoxybenzyl)-2'-oxo-3,4-dihydro-1H-spiro[naphthalene-2,3'-pyrrolidine]-7-carboxamide (I-65);

(S)—N-hydroxy-1'-((1-isopropyl-1H-benzo[d]imidazol-2-yl)methyl)-2'-oxo-3,4-dihydro-1H-spiro[naphthalene-2,3'-pyrrolidine]-7-carboxamide (I-66);

(S)-1'-(2,5-dichlorobenzyl)-N-hydroxy-2'-oxo-3,4-dihydro-1H-spiro[naphthalene-2,3'-pyrrolidine]-7-carboxamide (I-67);

(S)-1'-(2,6-dichlorobenzyl)-N-hydroxy-2'-oxo-3,4-dihydro-1H-spiro[naphthalene-2,3'-pyrrolidine]-7-carboxamide (I-68);

(S)—N-hydroxy-1'-(3-methoxybenzyl)-2'-oxo-3,4-dihydro-1H-spiro[naphthalene-2,3'-pyrrolidine]-7-carboxamide (I-69);

(S)—N-hydroxy-2'-oxo-1'-(pyridin-3-ylmethyl)-3,4-dihydro-1H-spiro[naphthalene-2,3'-pyrrolidine]-7-carboxamide (I-70);

(S)—N-hydroxy-2'-oxo-1'-(pyridin-2-ylmethyl)-3,4-dihydro-1H-spiro[naphthalene-2,3'-pyrrolidine]-7-carboxamide (I-71);

(S)-1'-(3-fluorobenzyl)-N-hydroxy-2'-oxo-3,4-dihydro-1H-spiro[naphthalene-2,3'-pyrrolidine]-7-carboxamide (I-72);

(S)—N-hydroxy-2'-oxo-1'-(4-(trifluoromethoxy)benzyl)-3,4-dihydro-1H-spiro[naphthalene-2,3'-pyrrolidine]-7-carboxamide (I-73);

(S)-1'-(3-chlorobenzyl)-N-hydroxy-2'-oxo-3,4-dihydro-1H-spiro[naphthalene-2,3'-pyrrolidine]-7-carboxamide (I-74);

(S)—N-hydroxy-1'-(4-methoxybenzyl)-2'-oxo-3,4-dihydro-1H-spiro[naphthalene-2,3'-pyrrolidine]-7-carboxamide (I-75);

(S)-1'-(2-fluorobenzyl)-N-hydroxy-2'-oxo-3,4-dihydro-1H-spiro[naphthalene-2,3'-pyrrolidine]-7-carboxamide (I-76);

(S)—N-hydroxy-1'-(naphthalen-2-ylmethyl)-2'-oxo-3,4-dihydro-1H-spiro[naphthalene-2,3'-pyrrolidine]-7-carboxamide (I-77);

(S)-1'-(2-(difluoromethoxy)benzyl)-N-hydroxy-2'-oxo-3,4-dihydro-1H-spiro[naphthalene-2,3'-pyrrolidine]-7-carboxamide (I-78);

(R)—N-hydroxy-2'-oxo-1'-propyl-3,4-dihydro-1H-spiro[naphthalene-2,3'-pyrrolidine]-7-carboxamide (I-79);

(R)—N-hydroxy-1'-(3-hydroxypropyl)-2'-oxo-3,4-dihydro-1H-spiro[naphthalene-2,3'-pyrrolidine]-7-carboxamide (I-80);

(R)-1'-(cyclobutylmethyl)-N-hydroxy-2'-oxo-3,4-dihydro-1H-spiro[naphthalene-2,3'-pyrrolidine]-7-carboxamide (I-81);

(R)—N-hydroxy-1'-isopentyl-2'-oxo-3,4-dihydro-1H-spiro[naphthalene-2,3'-pyrrolidine]-7-carboxamide (I-82);

(R)-1'-(but-2-yn-1-yl)-N-hydroxy-2'-oxo-3,4-dihydro-1H-spiro[naphthalene-2,3'-pyrrolidine]-7-carboxamide (I-83);

(R)—N-hydroxy-1'-(2-methoxyethyl)-2'-oxo-3,4-dihydro-1H-spiro[naphthalene-2,3'-pyrrolidine]-7-carboxamide (I-84);

(R)—N-hydroxy-2'-oxo-1'-((tetrahydro-2H-pyran-4-yl)methyl)-3,4-dihydro-1H-spiro[naphthalene-2,3'-pyrrolidine]-7-carboxamide (I-85);

(R)-1'-cinnamyl-N-hydroxy-2'-oxo-3,4-dihydro-1H-spiro[naphthalene-2,3'-pyrrolidine]-7-carboxamide (I-86);

(R)—N-hydroxy-1'-(2-methylbenzyl)-2'-oxo-3,4-dihydro-1H-spiro[naphthalene-2,3'-pyrrolidine]-7-carboxamide (I-87);

(R)—N-hydroxy-2'-oxo-1'-(2-(trifluoromethyl)benzyl)-3,4-dihydro-1H-spiro[naphthalene-2,3'-pyrrolidine]-7-carboxamide (I-88);

(R)-1'-(2-chlorobenzyl)-N-hydroxy-2'-oxo-3,4-dihydro-1H-spiro[naphthalene-2,3'-pyrrolidine]-7-carboxamide (I-89);

(R)—N-hydroxy-2'-oxo-1'-(2-(trifluoromethoxy)benzyl)-3,4-dihydro-1H-spiro[naphthalene-2,3'-pyrrolidine]-7-carboxamide (I-90);

(R)-1'-(benzo[c][1,2,5]oxadiazol-5-ylmethyl)-N-hydroxy-2'-oxo-3,4-dihydro-1H-spiro[naphthalene-2,3'-pyrrolidine]-7-carboxamide (I-91);

(R)—N-hydroxy-1'-(2-morpholino-2-oxoethyl)-2'-oxo-3,4-dihydro-1H-spiro[naphthalene-2,3'-pyrrolidine]-7-carboxamide (I-92);

(R)—N-hydroxy-1'-(2-methoxybenzyl)-2'-oxo-3,4-dihydro-1H-spiro[naphthalene-2,3'-pyrrolidine]-7-carboxamide (I-93);

(R)-1'-(2,5-dichlorobenzyl)-N-hydroxy-2'-oxo-3,4-dihydro-1H-spiro[naphthalene-2,3'-pyrrolidine]-7-carboxamide (I-94);

(R)-1'-(2,6-dichlorobenzyl)-N-hydroxy-2'-oxo-3,4-dihydro-1H-spiro[naphthalene-2,3'-pyrrolidine]-7-carboxamide (I-95);
(R)—N-hydroxy-1'-(3-methoxybenzyl)-2'-oxo-3,4-dihydro-1H-spiro[naphthalene-2,3'-pyrrolidine]-7-carboxamide (I-96);
(R)—N-hydroxy-2'-oxo-1'-(pyridin-3-ylmethyl)-3,4-dihydro-1H-spiro[naphthalene-2,3'-pyrrolidine]-7-carboxamide (I-97);
(R)—N-hydroxy-2'-oxo-1'-(pyridin-2-ylmethyl)-3,4-dihydro-1H-spiro[naphthalene-2,3'-pyrrolidine]-7-carboxamide (I-98);
(R)-1'-(3-fluorobenzyl)-N-hydroxy-2'-oxo-3,4-dihydro-1H-spiro[naphthal ene-2,3'-pyrrolidine]-7-carboxamide (I-99);
(R)—N-hydroxy-2'-oxo-1'-(4-(trifluoromethoxy)benzyl)-3,4-dihydro-1H-spiro[naphthalene-2,3'-pyrrolidine]-7-carboxamide (I-100);
(R)-1'-(3-chlorobenzyl)-N-hydroxy-2'-oxo-3,4-dihydro-1H-spiro[naphthalene-2,3'-pyrrolidine]-7-carboxamide (I-101);
(R)—N-hydroxy-1'-(4-methoxybenzyl)-2'-oxo-3,4-dihydro-1H-spiro[naphthalene-2,3'-pyrrolidine]-7-carboxamide (I-102);
(R)-1'-(2-fluorobenzyl)-N-hydroxy-2'-oxo-3,4-dihydro-1H-spiro[naphthalene-2,3'-pyrrolidine]-7-carboxamide (I-103);
(R)—N-hydroxy-1'-(naphthalen-2-ylmethyl)-2'-oxo-3,4-dihydro-1H-spiro[naphthalene-2,3'-pyrrolidine]-7-carboxamide (I-104);
(R)-1'-(2-(difluoromethoxy)benzyl)-N-hydroxy-2'-oxo-3,4-dihydro-1H-spiro[naphthalene-2,3'-pyrrolidine]-7-carboxamide (I-105);
(R)—N-hydroxy-2'-oxo-1'-(4-phenoxyphenyl)-3,4-dihydro-1H-spiro[naphthalene-2,3'-pyrrolidine]-7-carboxamide (I-106);
(R)—N-hydroxy-2'-oxo-1'-(quinolin-3-yl)-3,4-dihydro-1H-spiro[naphthalene-2, 3'-pyrrolidine]-7-carboxamide (I-107);
(R)-1'-(2,3-dihydrobenzofuran-7-yl)-N-hydroxy-2'-oxo-3,4-dihydro-1H-spiro[naphthalene-2,3'-pyrrolidine]-7-carboxamide (I-108);
(R)-1'-(1,3-dimethyl-1H-pyrazol-4-yl)-N-hydroxy-2'-oxo-3,4-dihydro-1H-spiro[naphthalene-2,3'-pyrrolidine]-7-carboxamide (I-109);
(R)—N-hydroxy-1'-(imidazo[1,2-a]pyridin-6-yl)-2'-oxo-3,4-dihydro-1H-spiro[naphthalene-2,3'-pyrrolidine]-7-carboxamide (I-110);
(R)—N-hydroxy-1'-(imidazo[1,2-a]pyridin-3-yl)-2'-oxo-3,4-dihydro-1H-spiro[naphthalene-2,3'-pyrrolidine]-7-carboxamide (I-111);
(S)-1'-(3,4-dichlorophenyl)-N-hydroxy-2'-oxo-3,4-dihydro-1H-spiro[naphthalene-2,3'-pyrrolidine]-7-carboxamide (I-112);
(S)-1'-(2,4-dimethylphenyl)-N-hydroxy-2'-oxo-3,4-dihydro-H-spiro[naphthalene-2,3'-pyrrolidine]-7-carboxamide (I-113);
(S)—N-hydroxy-1'-(2-methoxyphenyl)-2'-oxo-3,4-dihydro-1H-spiro[naphthalene-2,3'-pyrrolidine]-7-carboxamide (I-114);
(S)-1'-(benzo[d][1,3]dioxol-5-yl)-N-hydroxy-2'-oxo-3,4-dihydro-1H-spiro[naphthalene-2,3'-pyrrolidine]-7-carboxamide (I-115);
(S)—N-hydroxy-2'-oxo-1'-(4-phenoxyphenyl)-3,4-dihydro-1H-spiro[naphthalene-2,3'-pyrrolidine]-7-carboxamide (I-116);
(R)—N-hydroxy-1'-(3-(2-morpholinoethoxy)phenyl)-2'-oxo-3,4-dihydro-1H-spiro[naphthalene-2,3'-pyrrolidine]-7-carboxamide (I-117);
(S)—N-hydroxy-2'-oxo-1'-(quinolin-3-yl)-3,4-dihydro-1H-spiro[naphthalene-2,3'-pyrrolidine]-7-carboxamide (I-118);
(S)-1'-(4-(2-(dimethylamino)ethyl)phenyl)-N-hydroxy-2'-oxo-3,4-dihydro-1H-spiro[naphthalene-2,3'-pyrrolidine]-7-carboxamide (I-119);
(R)—N-hydroxy-1'-methyl-2'-oxo-3,4-dihydro-1H-spiro[naphthalene-2,3'-pyrrolidine]-7-carboxamide (I-120);
(S)—N-hydroxy-1'-methyl-2'-oxo-3,4-dihydro-1H-spiro[naphthalene-2,3'-pyrrolidine]-7-carboxamide (I-121);
(S)—N-hydroxy-1'-(4-methylbenzyl)-2'-oxo-3,4-dihydro-1H-spiro[naphthalene-2,3'-pyrrolidine]-7-carboxamide (I-122);
(R)—N-hydroxy-1'-(4-methylbenzyl)-2'-oxo-3,4-dihydro-1H-spiro[naphthalene-2,3'-pyrrolidine]-7-carboxamide (I-123);
(S)-1'-(3-fluoro-4-(trifluoromethyl)benzyl)-N-hydroxy-2'-oxo-3,4-dihydro-1H-spiro[naphthalene-2,3'-pyrrolidine]-7-carboxamide (I-124);
(R)-1'-(3-fluoro-4-(trifluoromethyl)benzyl)-N-hydroxy-2'-oxo-3,4-dihydro-1H-spiro[naphthalene-2,3'-pyrrolidine]-7-carboxamide (I-125);
(S)—N-hydroxy-2'-oxo-1'-(4-(trifluoromethyl)benzyl)-3,4-dihydro-1H-spiro[naphthalene-2,3'-pyrrolidine]-7-carboxamide (I-126);
(R)—N-hydroxy-2'-oxo-1'-(4-(trifluoromethyl)benzyl)-3,4-dihydro-1H-spiro[naphthalene-2,3'-pyrrolidine]-7-carboxamide (I-127);
(R)-1'-(4-fluorobenzyl)-N-hydroxy-5'-oxo-3,4-dihydro-1H-spiro[naphthalene-2,3'-pyrrolidine]-7-carboxamide (I-128);
(S)-1'-(4-fluorobenzyl)-N-hydroxy-5'-oxo-3,4-dihydro-1H-spiro[naphthalene-2,3'-pyrrolidine]-7-carboxamide (I-129);
(R)—N-hydroxy-1'-methyl-5'-oxo-3,4-dihydro-1H-spiro[naphthalene-2,3'-pyrrolidine]-7-carboxamide (I-130);
(S)—N-hydroxy-1'-methyl-5'-oxo-3,4-dihydro-1H-spiro[naphthalene-2,3'-pyrrolidine]-7-carboxamide (I-131);
(S)—N-hydroxy-5'-oxo-1'-phenyl-3,4-dihydro-1H-spiro[naphthalene-2,3'-pyrrolidine]-7-carboxamide (I-132);
(R)-1'-(cyclobutylmethyl)-N-hydroxy-5'-oxo-3,4-dihydro-1H-spiro[naphthalene-2,3'-pyrrolidine]-7-carboxamide (I-133);
(S)-1'-(cyclobutylmethyl)-N-hydroxy-5'-oxo-3,4-dihydro-1H-spiro[naphthalene-2,3'-pyrrolidine]-7-carboxamide (I-134);
(R)—N-hydroxy-1'-(3-methoxypropyl)-5'-oxo-3,4-dihydro-1H-spiro[naphthalene-2,3'-pyrrolidine]-7-carboxamide (I-135);
(S)—N-hydroxy-1'-(3-methoxypropyl)-5'-oxo-3,4-dihydro-1H-spiro[naphthalene-2,3'-pyrrolidine]-7-carboxamide (I-136);
(R)—N-hydroxy-1'-isobutyl-5'-oxo-3,4-dihydro-1H-spiro[naphthalene-2,3'-pyrrolidine]-7-carboxamide (I-137);
(S)—N-hydroxy-1'-isobutyl-5'-oxo-3,4-dihydro-1H-spiro[naphthalene-2,3'-pyrrolidine]-7-carboxamide (I-138);
(R)—N-hydroxy-1'-isopropyl-5'-oxo-3,4-dihydro-1H-spiro[naphthalene-2,3'-pyrrolidine]-7-carboxamide (I-139);
(S)—N-hydroxy-1'-isopropyl-5'-oxo-3,4-dihydro-1H-spiro[naphthalene-2,3'-pyrrolidine]-7-carboxamide (I-140);
(S)-1'-cyclopropyl-N-hydroxy-5'-oxo-3,4-dihydro-1H-spiro[naphthalene-2,3'-pyrrolidine]-7-carboxamide (I-141);
(R)-1'-ethyl-N-hydroxy-5'-oxo-3,4-dihydro-1H-spiro[naphthalene-2,3'-pyrrolidine]-7-carboxamide (I-142);

(S)-1'-ethyl-N-hydroxy-5'-oxo-3,4-dihydro-1H-spiro[naphthalene-2,3'-pyrrolidine]-7-carboxamide (I-143);

(S)—N-hydroxy-5'-oxo-1'-(2,2,2-trifluoroethyl)-3,4-dihydro-1H-spiro[naphthalene-2,3'-pyrrolidine]-7-carboxamide (I-144);

(R)—N-hydroxy-5'-oxo-1'-phenyl-3,4-dihydro-1H-spiro[naphthalene-2,3'-pyrrolidine]-7-carboxamide (I-145);

(R)—N-hydroxy-1'-(oxetan-3-ylmethyl)-5'-oxo-3,4-dihydro-H-spiro[naphthalene-2,3'-pyrrolidine]-7-carboxamide (I-146);

(S)—N-hydroxy-1'-(oxetan-3-ylmethyl)-5'-oxo-3,4-dihydro-1H-spiro[naphthalene-2,3'-pyrrolidine]-7-carboxamide (I-147);

(R)-1'-cyclopropyl-N-hydroxy-5'-oxo-3,4-dihydro-H-spiro[naphthalene-2,3'-pyrrolidine]-7-carboxamide (I-148);

(R)—N-hydroxy-5'-oxo-1'-(2,2,2-trifluoroethyl)-3,4-dihydro-1H-spiro[naphthalene-2,3'-pyrrolidine]-7-carboxamide (I-149);

(R)-1'-cyclobutyl-N-hydroxy-5'-oxo-3,4-dihydro-1H-spiro[naphthalene-2,3'-pyrrolidine]-7-carboxamide (I-150);

(S)-1'-cyclobutyl-N-hydroxy-5'-oxo-3,4-dihydro-1H-spiro[naphthalene-2,3'-pyrrolidine]-7-carboxamide (I-151);

(R)-1'-cyclopentyl-N-hydroxy-5'-oxo-3,4-dihydro-1H-spiro[naphthalene-2,3'-pyrrolidine]-7-carboxamide (I-152); or (S)-1'-cyclopentyl-N-hydroxy-5'-oxo-3,4-dihydro-1H-spiro[naphthalene-2,3'-pyrrolidine]-7-carboxamide (I-153).

In one or more embodiments, the compounds of Formula II are:

N-hydroxy-1'-(4-methoxybenzoyl)spiro[chromane-2,4'-piperidine]-7-carboxamide (II-1);

N-hydroxy-1'-((4-methoxyphenyl)sulfonyl)spiro[chromane-2,4'-piperidine]-7-carboxamide (II-2);

1'-(cyclohexylsulfonyl)-N-hydroxyspiro[chromane-2,4'-piperidine]-7-carboxamide (II-3);

N7-hydroxy-N1'-phenylspiro[chromane-2,4'-piperidine]-1',7-dicarboxamide (II-4);

1'-(cyclohexanecarbonyl)-N-hydroxyspiro[chromane-2,4'-piperidine]-7-carboxamide (II-5);

1'-cyclohexyl-N-hydroxyspiro[chromane-2,4'-piperidine]-7-carboxamide (II-6); or

N-hydroxy-1'-(4-methoxybenzyl)spiro[chromane-2,4'-piperidine]-7-carboxamide (II-7).

In one or more embodiments, the compounds of Formula I are:

N-hydroxy-1'-methyl-3,4-dihydro-1H-spiro[naphthalene-2,3'-piperidine]-7-carboxamide (I-154);

N-hydroxy-1-methyl-3',4'-dihydro-1'H-spiro[azepane-3,2'-naphthalene]-7'-carboxamide (I-155);

N-hydroxy-1-methyl-3',4'-dihydro-1'H-spiro[azocane-3,2'-naphthalene]-7'-carboxamide (I-156);

N-hydroxy-1'-methyl-2'-oxo-3,4-dihydro-1H-spiro[naphthalene-2,3'-piperidine]-7-carboxamide (I-157);

N-hydroxy-1-methyl-2-oxo-3',4'-dihydro-1'H-spiro[azepane-3,2'-naphthalene]-7'-carboxamide (I-158);

N-hydroxy-1-methyl-2-oxo-3',4'-dihydro-1'H-spiro[azocane-3,2'-naphthalene]-7'-carboxamide (I-159);

N-hydroxy-1'-methyl-6'-oxo-3,4-dihydro-1H-spiro[naphthalene-2,3'-piperidine]-7-carboxamide (I-160);

N-hydroxy-1-methyl-7-oxo-3',4'-dihydro-1'H-spiro[azepane-3,2'-naphthalene]-7'-carboxamide (I-161); or N-hydroxy-1-methyl-8-oxo-3',4'-dihydro-1'H-spiro[azocane-3,2'-naphthalene]-7'-carboxamide (I-162).

In one embodiment of the compounds of Formulae I and II, $Y^1$, $Y^2$, and $Y^4$ are each $CR^1$. In other embodiments, $Y^1$ is N and $Y^2$ and $Y^4$ are each $CR^1$. In other embodiments, $Y^2$ is N and $Y^1$ and $Y^4$ are each $CR^1$. In other embodiments, $Y^4$ is N and $Y^1$ and $Y^2$ are each $CR^1$.

In some embodiments of the compounds of Formulae I and II, $Y^1$, $Y^3$, and $Y^4$ are each $CR^1$ and $X^1$, $X^2$, $X^3$, $X^4$, $X^5$, $X^6$, and $X^7$ are each independently —$CR^1R^2$—. In some embodiments, $X^1$ is —C(O)—, and $X^2$, $X^3$, $X^4$, $X^5$, $X^6$, and $X^7$ are each independently —$CR^1R^2$—. In some embodiments, $X^2$ is —C(O)—, and $X^2$, $X^3$, $X^4$, $X^5$, $X^6$, and $X^7$ are each independently —$CR^1R^2$—. In some embodiments, $X^3$ is —C(O)—, and $X^1$, $X^2$, $X^4$, $X^5$, $X^6$, and $X^7$ are each independently —$CR^1R^2$—. In some embodiments, $X^4$ is —C(O)—, and $X^1$, $X^2$, $X^3$, $X^5$, $X^6$, and $X^7$ are each independently —$CR^1R^2$—. In some embodiments, $X^5$ is —C(O)—, and $X^1$, $X^2$, $X^3$, $X^4$, $X^6$, and $X^7$ are each independently —$CR^1R^2$—. In some embodiments, $X^6$ is —C(O)—, and $X^1$, $X^2$, $X^3$, $X^4$, $X^5$, and $X^7$ are each independently —$CR^1R^2$—. In some embodiments, $X^7$ is —C(O)—, and $X^1$, $X^2$, $X^3$, $X^5$, $X^5$, and $X^6$ are each independently —$CR^1R^2$—.

In other embodiments of the compounds of Formulae I and II, $X^1$ is —$NR^3$—, and $X^2$, $X^3$, $X^4$, $X^5$, $X^6$, and $X^7$ are each independently —$CR^1R^2$—. In some embodiments, $X^2$ is —$NR^3$—, and $X^1$, $X^3$, $X^4$, $X^5$, $X^6$, and $X^7$ are each independently —$CRR^1R^2$—. In some embodiments, $X^3$ is —$NR^3$—, and $X^1$, $X^2$, $X^4$, $X^5$, $X^6$, and $X^7$ are each independently —$CR^1R^2$—. In some embodiments, $X^4$ is —$NR^3$—, and $X^1$, $X^2$, $X^3$, $X^5$, $X^6$, and $X^7$ are each independently —$CR^1R^2$—. In some embodiments, $X^5$ is —$NR^3$—, and $X^1$, $X^2$, $X^3$, $X^4$, $X^6$, and $X^7$ are each independently —$CR^1R^2$—. In some embodiments, $X^6$ is —$NR^3$—, and $X^1$, $X^2$, $X^3$, $X^4$, $X^5$, and $X^7$ are each independently —$CR^1R^2$—. In some embodiments, $X^7$ is —$NR^3$—, and $X^1$, $X^2$, $X^3$, $X^4$, $X^5$, and $X^6$ are each independently —$CR^1R^2$—.

In other embodiments of the compounds of Formula I, $X^1$ is —O—, —$SO_2$—, —S(O)—, or —S—, and $X^2$, $X^3$, $X^4$, $X^5$, $X^6$, and $X^7$ are each independently —$CR^1R^2$—. In some embodiments, $X^2$ is —O—, —$SO_2$—, —S(O)—, or —S—, and $X^1$, $X^3$, $X^4$, $X^5$, $X^6$, and $X^7$ are each independently —$CR^1R^2$—. In some embodiments, $X^3$ is —O—, —$SO_2$—, —S(O)—, or —S—, and $X^1$, $X^2$, $X^4$, $X^5$, $X^6$, and $X^7$ are each independently —$CR^1R^2$—. In some embodiments, $X^4$ is —S—, —$SO_2$— or —S(O)—, and $X^1$, $X^2$, $X^3$, $X^5$, $X^6$, and $X^7$ are each independently —$CR^1R^2$—. In some embodiments, $X^5$ is —S—, —$SO_2$— or —S(O)—, and $X^1$, $X^2$, $X^3$, $X^4$, $X^6$, and $X^7$ are each independently —$CR^1R^2$—. In some embodiments, $X^6$ is —O—, —$SO_2$—, —S(O)—, or —S—, and $X^1$, $X^2$, $X^3$, $X^4$, $X^5$, and $X^7$ are each independently —$CR^1R^2$—. In some embodiments, $X^7$ is —O—, —$SO_2$—, —S(O)—, or —S—, and $X^1$, $X^2$, $X^3$, $X^4$, $X^5$, and $X^6$ are each independently —$CR^1R^2$—.

In other embodiments of the compounds of Formula II, $X^1$ is —O—, —$SO_2$—, —S(O)—, or —S—, and $X^2$, $X^3$, $X^4$, $X^5$, $X^6$, and $X^7$ are each independently —$CR^1R^2$—. In some embodiments, $X^2$ is —O—, —$SO_2$—, —S(O)—, or —S—, and $X^1$, $X^3$, $X^4$, $X^5$, $X^6$, and $X^7$ are each independently —$CR^1R^2$—. In some embodiments, $X^3$ is —O—, —$SO_2$—, —S(O)—, or —S—, and $X^1$, $X^2$, $X^4$, $X^5$, $X^6$, and $X^7$ are each independently —$CR^1R^2$—. In some embodiments, $X^4$ is —O—, —$SO_2$—, —S(O)—, or —S—, and $X^1$, $X^2$, $X^3$, $X^5$, $X^6$, and $X^7$ are each independently —$CR^1R^2$—. In some embodiments, $X^5$ is —S—, —$SO_2$— or —S(O)—, and $X^1$, $X^2$, $X^3$, $X^4$, $X^6$, and $X^7$ are each independently —$CR^1R^2$—. In some embodiments, $X^6$ is —S—, —$SO_2$— or —S(O)—, and $X^1$, $X^2$, $X^3$, $X^4$, $X^5$, and $X^7$ are each independently —$CR^1R^2$—. In some embodiments, $X^7$ is —O—, —$SO_2$—, —S(O)—, or —S—, and $X^1$, $X^2$, $X^3$, $X^4$, $X^5$, and $X^6$ are each independently —$CR^1R^2$—.

In other embodiments of the compounds of Formulae I and II, L is a bond. In other embodiments, L is —(CR$^1$R$^2$)$_n$—. In other embodiments, L is —S(O)$_2$—. In other embodiments, L is —S(O)$_2$NR$^3$—, —S(O)—, or —S(O)NR$^3$—. In other embodiments, L is —C(O)(CR$^1$R$^2$)$_n$O—. In other embodiments, L is —C(O)(CR$^1$R$^2$)$_n$— and n is 0. In other embodiments, L is —C(O)NR$^3$—.

In other embodiments of the compounds of Formulae I and II, R is —C$_1$-C$_6$alkyl optionally substituted with one or more —OH, halogen, oxo, —NO$_2$, —CN, —R$^1$, —R$^2$, —SR$^3$, —OR$^3$, —NHR$^3$, —NR$^3$R$^4$, —S(O)$_2$NR$^3$R$^4$, —S(O)$_2$R$^1$, —C(O)R$^1$, —CO$_2$R$^1$, —NR$^3$S(O)$_2$R$^1$, —S(O)R$^1$, —S(O)NR$^3$R$^4$, —NR$^3$S(O)R$^1$, heterocycle, aryl, or heteroaryl. In other embodiments, R is —C$_2$-C$_6$alkenyl or —C$_2$-C$_6$alkynyl optionally substituted with one or more —OH, halogen, oxo, —NO$_2$, —CN, —R$^1$, —R$^2$, —SR$^3$, —OR$^3$, —NHR$^3$, —NR$^3$R$^4$, —S(O)$_2$NR$^3$R$^4$, —S(O)$_2$R$^1$, —C(O)R$^1$, —CO$_2$R$^1$, —NR$^3$S(O)$_2$R$^1$, —S(O)R$^1$, —S(O)NR$^3$R$^4$, —NR$^3$S(O)R$^1$, heterocycle, aryl, or heteroaryl. In other embodiments, R is aryl or heteroaryl optionally substituted with one or more —OH, halogen, oxo, —NO$_2$, —CN, —R$^1$, —R$^2$, —SR$^3$, —OR$^3$, —NHR$^3$, —NR$^3$R$^4$, —S(O)$_2$NR$^3$R$^4$, —S(O)$_2$R$^1$, —C(O)R$^1$, —CO$_2$R$^1$, —NR$^3$S(O)$_2$R$^1$, —S(O)R$^1$, —S(O)NR$^3$R$^4$, —NR$^3$S(O)R$^1$, heterocycle, aryl, or heteroaryl. In other embodiments, R is —C$_4$-C$_8$cycloalkenyl, —C$_3$-C$_8$cycloalkyl, —C$_5$-C$_{12}$spirocycle, heterocyclyl, or spiroheterocyclyl, optionally substituted with one or more —OH, halogen, oxo, —NO$_2$, —CN, —R$^1$, —R$^2$, —SR$^3$, —OR$^3$, —NHR$^3$, —NR$^3$R$^4$, —S(O)$_2$NR$^3$R$^4$, —S(O)$_2$R$^1$, —C(O)R$^1$, —CO$_2$R$^1$, —NR$^3$S(O)$_2$R$^1$, —S(O)R$^1$, —S(O)NR$^3$R$^4$, —NR$^3$S(O)R$^1$, heterocycle, aryl, or heteroaryl.

In other embodiments of the compounds of Formula I, m is 0, 1, 2, or 3. In another embodiment m is 0. In yet another embodiment, m is 1. In yet another embodiment, m is 2. In yet another embodiment, m is 3.

In another embodiment of the invention, the compounds of Formula I or Formula II are enantiomers. In some embodiments the compounds are the (S)-enantiomer. In other embodiments the compounds are the (R)-enantiomer. In yet other embodiments, the compounds of Formula I or Formula II may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Methods of Synthesizing the Disclosed Compounds

The compounds of the present invention may be made by a variety of methods, including standard chemistry. Suitable synthetic routes are depicted in the schemes given below.

The compounds of Formula I or Formula II may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, N.Y. 1999). These groups are removed at a convenient stage of the compound synthesis using methods that are readily apparent to those skilled in the art. The selection processes, as well as the reaction conditions and order of their execution, shall be consistent with the preparation of compounds of Formula I or Formula II.

Those skilled in the art will recognize if a stereocenter exists in the compounds of Formula I or Formula II. Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below.

Scheme 1. General synthesis of compounds of the Formula (I-h) and (I-j).

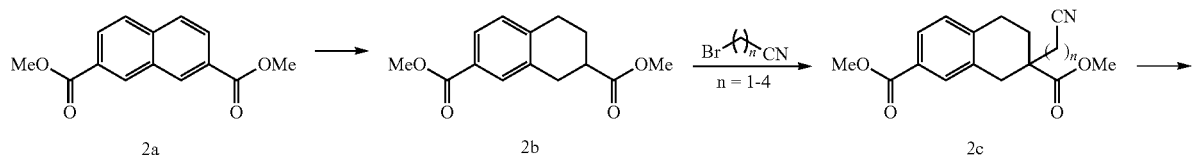

2a       2b       2c

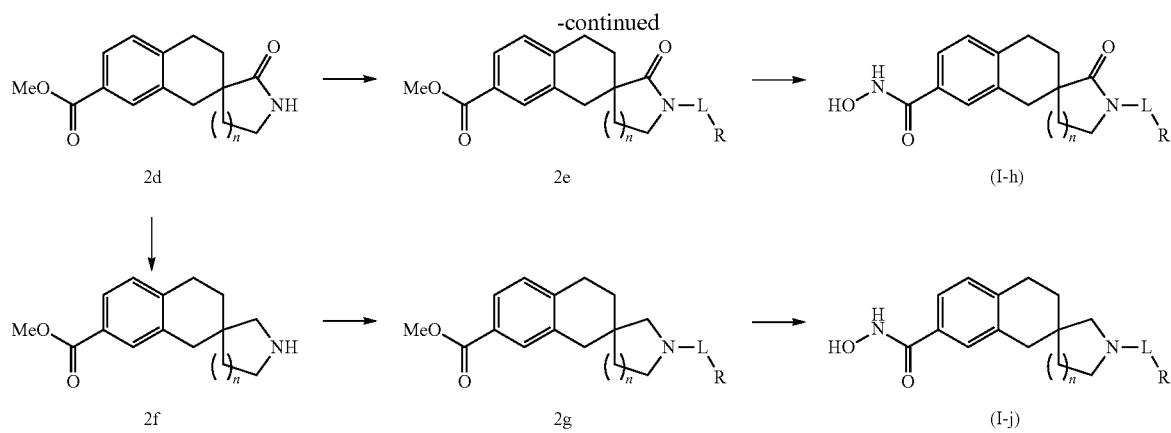

wherein L and R are defined as in Formula (I).

The general way of preparing target molecules of Formula (I-h) by using intermediates 2a, 2b, 2c, 2d, and 2e is outlined in General Scheme 1. Hydrogenation of dimethyl naphthalene-2,7-dicarboxylate (2a) in the presence of palladium on carbon under standard conditions affords 2b. Deprotonation of 2b with a base, followed by alkylation with a halo-nitrile provides Intermediates 2c. Spiro-lactams 2d can be obtained by treatment of 2c with platinum (IV) oxide ($PtO_2$) in the presence of hydrogen ($H_2$) gas, followed by treatment with ammonia ($NH_3$). Addition of the R-L moiety can be achieved via standard methods of alkylation or arylation. For example, alkylation of 2d with an alkyl halide in the presence of a base, e.g. sodium hydride, can provide compounds such as Intermediate 2e. Alternatively, arylation of 2d with an aryl bromide or aryl iodide in the presence of a metal catalyst, e.g. copper (I) iodide (CuI), a diamine ligand, and a base, e.g. cesium carbonate ($Cs_2CO_3$), can also provide compounds such as Intermediate 2e. Treatment of 2e with hydroxylamine and a base, e.g, sodium hydroxide, provides compounds of Formula (I-h).

The general way of preparing target molecules of Formula (I-j) by using intermediates 2a, 2b, 2c, 2d, 2f, and 2g is also outlined in General Scheme 1. Spiro-amines 2f can be obtained by reduction of 2d, for example, by conversion to its thioamide and treatment with nickel (II) chloride hexahydrate and sodium borohydride. Addition of the R-L moiety can be achieved via standard methods of alkylation, arylation, acylation, urea formation, or sulfonation. Treatment of 2g with hydroxylamine and a base, e.g, sodium hydroxide, provides compounds of Formula (I-j).

Scheme 2. General synthesis of amide compounds of the Formula (I-k).

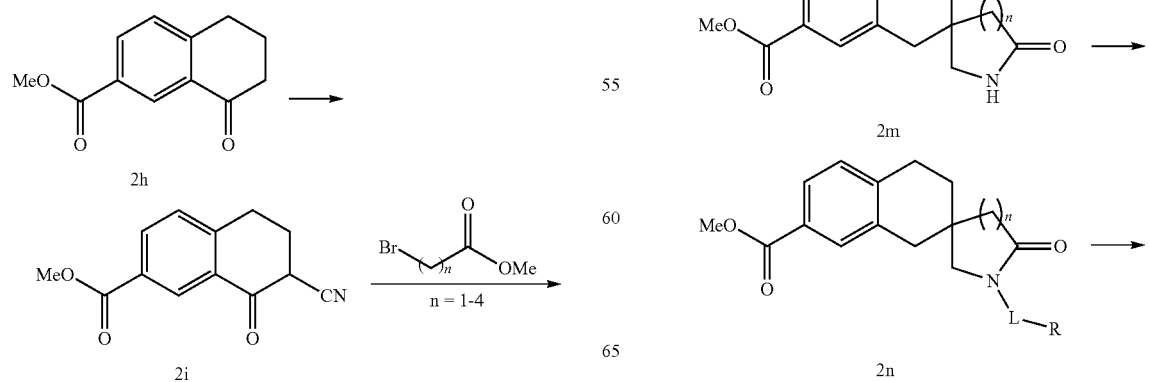

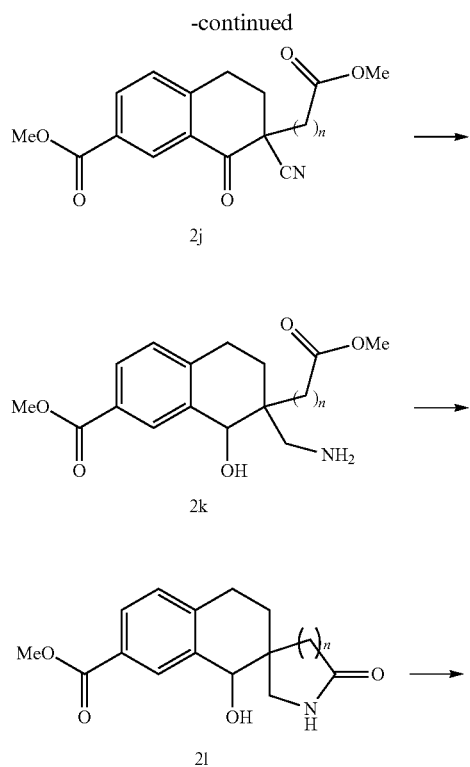

-continued

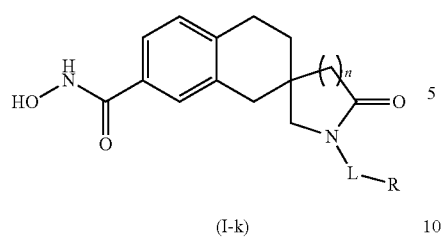

(I-k)

wherein L and R are defined as in Formula (I).

The general way of preparing target molecules of Formula (I-k) by using intermediates 2h, 2i, 2j, 2k, 2l, 2m, and 2n is outlined in General Scheme 2. Nitrile addition to methyl 8-oxo-5,6,7,8-tetrahydronaphthalene-2-carboxylate (2h) provides 2i. Deprotonation of 2i with a base, followed by alkylation with a halo-ester can provide Intermediates 2j. Spiro-lactams 2l can be obtained by treatment of 2j with $PtO_2$ in the presence of hydrogen ($H_2$) gas to provide 2k, followed by treatment with $NH_3$. Dehydroxylation of 2l affords 2m. Addition of the R-L moiety can be achieved via standard methods of alkylation or arylation. For example, alkylation of 2m with an alkyl halide in the presence of a base, e.g. sodium hydride, can provide compounds of Intermediates 2n. Alternatively, coupling of 2m with an aryl boronic acid in the presence of a metal catalyst, e.g. copper (II) acetate ($Cu(OAc)_2$), and a base, e.g. triethylamine, can also provide compounds of Intermediates 2n. Treatment of 2n with hydroxylamine and a base, e.g, sodium hydroxide, provides compounds of Formula (I-k).

Scheme 3. General synthesis of compounds of the Formula (II-e).

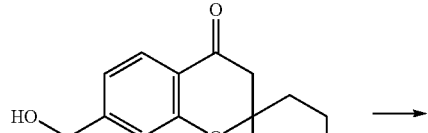

2o

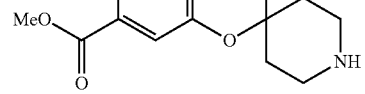

2p

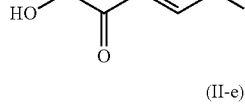

2q

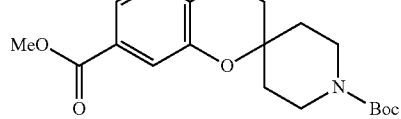

2r

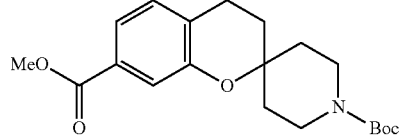

2s

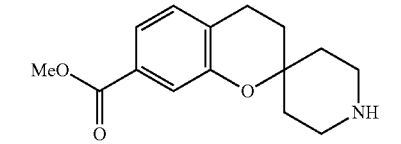

2t

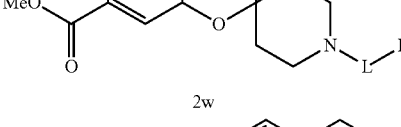

2u

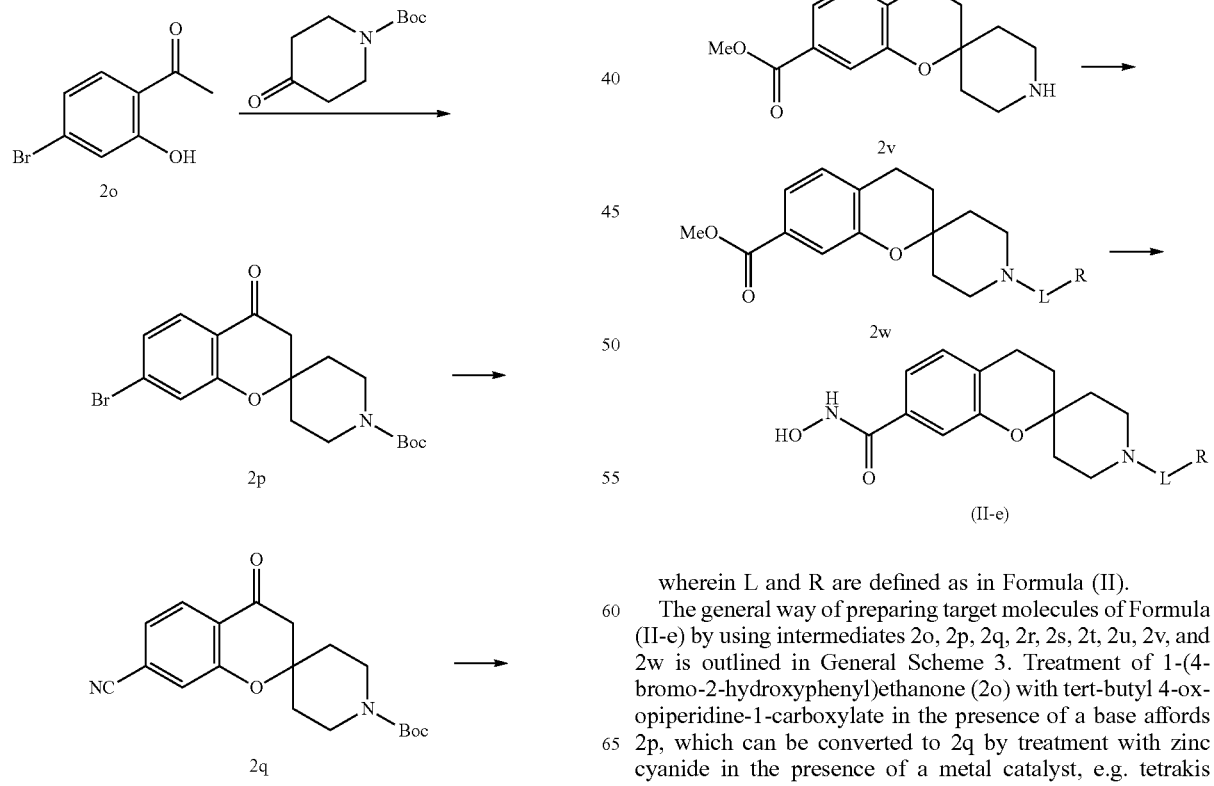

2v

2w (II-e)

wherein L and R are defined as in Formula (II).

The general way of preparing target molecules of Formula (II-e) by using intermediates 2o, 2p, 2q, 2r, 2s, 2t, 2u, 2v, and 2w is outlined in General Scheme 3. Treatment of 1-(4-bromo-2-hydroxyphenyl)ethanone (2o) with tert-butyl 4-oxopiperidine-1-carboxylate in the presence of a base affords 2p, which can be converted to 2q by treatment with zinc cyanide in the presence of a metal catalyst, e.g. tetrakis(triphenylphosphine)palladium(0) ($Pd(PPh_3)4$). Hydrolysis of 2q, followed by esterification and Boc protection under standard conditions provides 2t, which can be reduced by stepwise treatment using sodium borohydride followed by triethylsilane and trifluroacetic acid to afford 2v. Addition of the R-L moiety can be achieved via standard methods of alkylation, arylation, acylation, urea formation, or sulfonation. Treatment of 2w with hydroxylamine and a base, e.g, sodium hydroxide, provides compounds of Formula (II-e).

Methods of Using the Disclosed Compounds

Another aspect of the invention relates to a method of treating a disease associated with HDAC6 or HDAC11 modulation in a subject in need thereof. The method involves administering to a patient in need of treatment for diseases or disorders associated with HDAC6or HDAC11 modulation an effective amount of a compound of Formula I or Formula II. In an embodiment, the disease can be, but is not limited to, cancer, neurodegenerative disease, neurodevelopmental disease, inflammatory or autoimmune disease, infection, metabolic disease, hematologic disease, or cardiovascular disease.

Another aspect of the invention is directed to a method of inhibiting HDAC6 or HDAC11. The method involves administering to a patient in need thereof an effective amount of Formula I or Formula II.

The present invention relates to compositions capable of modulating the activity of (e.g., inhibiting) HDACs, and in particular HDAC6 or HDAC11. The present invention also relates to the therapeutic use of such compounds.

One therapeutic use of the compounds of the present invention is to treat proliferative diseases or disorders such as cancer. Cancer can be understood as abnormal or unregulated cell growth within a patient and can include but is not limited to lung cancer, ovarian cancer, breast cancer, prostate cancer, pancreatic cancer, hepatocellular cancer, renal cancer and leukemias such as acute myeloid leukemia and acute lymphoblastic leukemia. Additional cancer types include T-cell lymphoma (e.g., cutaneous T-cell lymphoma, peripheral T-cell lymphoma), Hodgkin lymphoma, melanoma, and multiple myeloma. In other embodiments, treating proliferative diseases or disorders can include any cancer where there is evidence of an increase in Treg/effector T cell ratio or in an absolute Treg number, either in the periphery or in the tumor microenvironment or tertiary lymphoid structures, or increased expression of T cell tolerance-related genes. Such proliferative diseases or disorders can include but are not limited to: any Kras mutant carrying tumor (http://cancerimmunolres.aacrjournals.org/content/early/2016/02/13/2326-6066.CIR-15-0241.long); renal cell carcinoma; lung carcinoma; cervical cancer; prostate cancer; ovarian cancer; head and neck cancer; lymphoma; colorectal cancer, non-small cell lung carcinoma; breast cancers (Gobert, M. et al. (2009) Cancer Res. 69, 2000-2009); and bladder cancer.

One therapeutic use of the compounds of the present disclosure is to treat neurological diseases or disorders or neurodegeneration. Neurological disorders are understood as disorders of the nervous system (e.g., the brain and spinal cord). Neurological disorders or neurodegenerative diseases can include but are not limited to epilepsy, attention deficit disorder (ADD), Alzheimer's disease, Parkinson's Disease, Huntington's Disease, amyotrophic lateral sclerosis, spinal muscular atrophy, essential tremor, central nervous system trauma caused by tissue injury, oxidative stress-induced neuronal or axonal degeneration, and multiple sclerosis.

Another therapeutic use of the compounds of the present disclosure is to treat neurodevelopmental disorders. Neurodevelopmental disorders can include, but are not limited to, Rett syndrome, intellectual disability, intellectual and developmental disability, autism spectrum disorder, fetal alcohol syndrome, developmental coordination disorder, stereotypic movement disorder, Tourette syndrome, cerebral palsy, fragile X syndrome, attention deficit hyperactivity disorder, and Mendelsohnn's syndrome.

Another therapeutic use of the compounds of the present invention is also to treat inflammatory diseases or disorders. Inflammation can be understood as a host's response to an initial injury or infection. Symptoms of inflammation can include but are not limited to redness, swelling, pain, heat and loss of function. Inflammation may be caused by the upregulation of pro-inflammatory cytokines such as IL-1β, and increased expression of the FOXP3 transcription factor. In some embodiments, the inflammatory diseases include fibrosis or fibrotic diseases. Types of fibrotic diseases include but are not limited to lung fibrosis or pulmonary fibrosis, Liver fibrosis; Heart fibrosis; Mediastinal fibrosis; Retroperitoneal cavity fibrosis; Bone marrow fibrosis; Skin fibrosis; and Scleroderma or systemic sclerosis.

Another therapeutic use of the compounds of the present invention is also to treat autoimmune diseases or disorders. Autoimmune disorders are understood as disorders wherein a host's own immune system responds to tissues and substances occurring naturally in the host's body. Autoimmune diseases can include but are not limited to rheumatoid arthritis, Crohn's disease, type-1 diabetes, systemic juvenile idiopathic arthritis; inflammatory bowel disease; allograft transplantation; eczema, psoriasis, idiopathic thrombocytopenic purpra, autoimmune thrombocytopenia, acquired immune thrombocytopenia, autoimmune neutropenia, autoimmune hemolyitic anemia, parvovirus B19-associated red cell aplasia, acquired antifactor VIII autoimmunity, acquired von Willebrand disease, monoclonal gammopathy, aplastic anemia, pure red cell aplasia, Diamond-Blackfan anemia, hemolytic disease of the newborn, immune mediated-refractoriness to platelet transfusion, hemolytic uremic syndrome, Evan's syndrome, Guillain-Barre syndrome, chronic demyelinating polyradiculoneuropathy, paraproteinemic IgM demyelinating polyneuropathy, Lambert-Eaton myasthenic syndrome, myasthenia gravis, multifocal motor neuropathy, stiff man syndrome, paraneoplastic encephalomyelitis, sensory neuropathy with anti-Hu antibodies, myelitis, autoimmune diabetic neuropathy, acute idiopathic neuropathy, toxic epidermal necrolysis, gangrene, granuloma, pemphigus vulgaris, bullous pemphigoid, vitiligo, scleroderma, atomic dermatitis, systemic and diffuse sclerosis, primary biliary cirrhosis, Celiac disease, dermatitis herpetiformis, cryptogenic cirrhosis, reactive arthritis, Hashimoto's thryroditis, Wegner's granulomoatosis, micropolyarterits, Churg-Strauss syndrome Type I and Type II autoimmune polygalndular syndromes, linear IgA disease, epidermolysis bullosa acquisita, erythema nodosa, pemphigoid gestationis, cicatricial pemphigoid, mixed essential cryoglobulinemia, chronic bullous disease of childhood, Goodpasture's syndrome, sclerosis cholangitis, ankylosing spondylitis, Bechet's syndrome temporal arteritis, Takayasu's arteritis, autoimmune urticaria, and Kawasaki's disease.

Another therapeutic use of the compounds of the present invention is also to treat infectious diseases or disorders. Infections or infectious diseases are caused by the invasion of a foreign pathogen. The infection may be caused by, for instance, a bacteria, a fungus, or virus. Bacterial infections include, but are not limited to *streptococcus* infections, mycobacterial infections, *bacillus* infections, *Salmonella* infections, *Vibrio* infections, spirochete infections, and *Neisseria* infections. Viral infections include, but are not limited to herpes virus infections, hepatitis virus infections, west nile virus infections, flavivirus infections, influenza virus infections, rhinovirus infections, papillomavirus infections, paramyxovirus infections, parainfluenza virus infections, and retrovirus infections. In particular embodiments, the compounds of the present invention are useful for treating infections which result in an inflammatory cytokine burst. Non-limiting examples of such infections include Ebola and other viral hemorrhagic fever-causing viruses, and Malaria.

Another therapeutic use of the compounds of the present invention is also to treat and/or prevent allergy and unwanted immune responses associated with allergy. A non-limiting list of allergies and related conditions includes, pollen allergy (e.g. Japanese Cedar Pollen), mold allergy, food allergies (including, but not limited to peanut, tree nut, milk, soy, gluten, and egg allergies), animal allergies (e.g. allergies to dogs, cats, rabbits), dust mite allergy, atopic dermatitis, allergic rhinitis, allergic otitis, allergic asthma, dry eye, ocular allergy, allergic urticaria, contact dermatitis, anaphylaxis, eosinophilic esophagitis.

Yet another therapeutic use of the compounds of the present invention is also to treat metabolic diseases or disorders. Metabolic diseases can be characterized as abnormalities in the way that a subject stores energy. Metabolic disorders can include but are not limited to metabolic syndrome, diabetes, obesity, high blood pressure, non-alcoholic fatty liver disease and heart failure.

Yet another therapeutic use of the compounds of the present invention is also to treat hematologic disorders. Hematologic diseases primarily affect the blood. Hematologic disorders can include but are not limited to anemia, multiple myeloma, lymphoma, and leukemia.

Yet another therapeutic use of the compounds of the present invention is also to prevent and/or treat transplant rejection. Tissues that are transplanted include (but are not limited to) whole organs such as kidney, liver, heart, lung; organ components such as skin grafts and the cornea of the eye; and cell suspensions such as bone marrow cells and cultures of cells selected and expanded from bone marrow or circulating blood, and whole blood transfusions.

Yet another therapeutic use of the compounds of the present invention is also to treat cardiovascular diseases or disorders. Cardiovascular diseases affect the heart and blood vessels of a patient. Exemplary conditions include but are not limited to cardiovascular stress, pressure overload, chronic ischemia, infarction-reperfusion injury, hypertension, Brain infarct after cerebral artery occlusion; atherosclerosis, peripheral artery disease, cardiac hypertrophy, cardiac arrhythmias, stroke, and heart failure.

Another therapeutic use of the compounds of the present invention is for purging the reservoir of latently infected memory CD4+T cells in HIV+ patients (Matalon, et al., Mol Med. 2011; 17(5-6): 466-472).

The disclosed compound can be administered in effective amounts to treat or prevent a disorder and/or prevent the development thereof in subjects.

Another aspect of the present disclosure relates to a compound of Formula I or Formula II, or a pharmaceutically acceptable salt, hydrate, solvate, prodrug, stereoisomer, or tautomer thereof, for use in treating or preventing a disease associated with HDAC6 or HDAC11modulation. In some embodiments, the disease is cancer, neurodegenerative disease, neurodevelopmental disorder, inflammatory or autoimmune disease, infection, metabolic disease, hematologic disease, or cardiovascular disease. In some embodiments, the compound inhibits a histone deacetylase. In another embodiment, the compound inhibits a zinc-dependent histone deacetylase. In another embodiment, the compound inhibits the HDAC6 isozyme zinc-dependent histone deacetylase. In another embodiment, the compound inhibits the HDAC11 isozyme zinc-dependent histone deacetylase.

In another aspect, the present disclosure relates to the use of a compound of Formula (I), or a pharmaceutically acceptable salt, hydrate, solvate, prodrug, stereoisomer, or tautomer thereof, in the manufacture of a medicament for treating or preventing a disease associated with HDAC6 or HDAC11 modulation. In some embodiments, the disease is cancer, neurodegenerative disease, neurodevelopmental disorder, inflammatory or autoimmune disease, infection, metabolic disease, hematologic disease, or cardiovascular disease. In some embodiments, the compound inhibits a histone deacetylase. In another embodiment, the compound inhibits a zinc-dependent histone deacetylase. In another embodiment, the compound inhibits the HDAC6 isozyme zinc-dependent histone deacetylase.

In some embodiments, the cancer is melanoma, cutaneous T-cell lymphoma, peripheral T-cell lymphoma, Hodgkin lymphoma, multiple myeloma, leukemia, lung, ovarian, breast, prostate, pancreatic, hepatocellular or renal cancer. In other embodiments, the neurodegenerative disease is Alzheimer's, Huntington's, Parkinson's, Amyotrophic Lateral Sclerosis, or spinal muscular atrophy. In other embodiments, the neurodevelopmental disorder is Rett syndrome. In yet other embodiments, the inflammatory or autoimmune disease is rheumatoid arthritis, spondylitis arthritis, psoriatic arthritis, psoriasis, multiple sclerosis, systemic lupus erythematosus, inflammatory bowel diseases, graft versus host disease, transplant rejection or fibrotic disease.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e)

absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanami dephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention relates to a pharmaceutical composition comprising a compound of Formula I or Formula II and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Without wishing to be bound by any particular theory, the compounds of the present invention can inhibit HDACs such as HDAC6 or HDAC11 by interacting with the zinc ($Zn^{2+}$) ion in the protein's active site via the hydroxamic acid group bound to the aromatic ring of the compound. The binding can prevent the zinc ion from interacting with its natural substrates, thus inhibiting the enzyme.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The present invention includes a number of unique features and advantages compared with other inhibitors of HDAC enzymes, for instance HDAC6 or HDAC11. For instance, the present invention features a unique class of small molecule therapeutic agents of Formula I or Formula II. The compounds were designed by using crystal structure information of HDAC ligand-protein complexes as well as advanced computational chemistry tools. These techniques led to the development of new chemical scaffolds that were iteratively refined to optimize key recognition features between the ligand and receptor known to be necessary for potency.

Definitions used in the following examples and elsewhere herein are:

Boc tert-Butoxy carbamate
$CDCl_3$ Deuterated chloroform
$CH_2Cl_2$ Methylene chloride, Dichloromethane
$CH_3CN$ Acetonitrile
$CH_3I$ Iodomethane
CO (g) Carbon monoxide (gas)
$CO_2$ Carbon dioxide
$Cs_2CO_3$ Cesium carbonate
$Cu(OAc)_2$ Copper (II) acetate
CuBr Copper (I) bromide
CuI Copper (I) iodide
$D_2O$ Deuterated water
DCE 1,2-Dichloroethane
DIEA Diisopropylethylamine
DMA Dimethylacetamide
DMF N,N-Dimethylformamide
DMSO Dimethylsulfoxide
ES Electrospray ionization Et₂O Diethyl ether
Et₃N Triethylamine
Et₃SiH triethylsilane
EtOAc Ethyl acetate
EtOH Ethanol
h hours
H₂ (g) Hydrogen (gas)
H₂O Water
HBTU N,N,N',N'-Tetramethyl-O-(1H-benzotriazol-1-yl) uronium hexafluorophosphate
HCl Hydrochloric acid
K₂CO₃ Potassium carbonate
K₃PO₄ Potassium phosphate tribasic
MeOH Methanol
MgSO₄ Magnesium sulfate
min minutes
MS Mass spectrometry
Na₂CO₃ Sodium carbonate
Na₂SO₄ Sodium sulfate
NaBH(OAc)₃ Sodium triacetoxyborohydride
NaBH₃CN Sodium cyanoborohydride
NaBH₄ Sodium borohydride
NaH Sodium hydride
NaHCO₃ Sodium bicarbonate
NaI Sodium iodide
NaOH Sodium hydroxide
NH₂OH Hydroxylamine
NH₃ Ammonia
NH₄Cl Ammonium chloride
NH₄HCO₃ Ammonium bicarbonate
NiCl₂.6H₂O Nickel(II) chloride hexahydrate
NMM 4-Methylmorpholine
NMR Nuclear magnetic resonance
Pd(dppf)Cl₂ [1,1'-Bis(diphenylphosphino)ferrocene]dichloropalladium(II)
Pd(OAc)₂ Palladium (II) acetate
Pd(PPh₃)₄ Tetrakis(triphenylphosphine)palladium(0)
Pd₂(dba)₃ Tris(dibenzylideneacetone)dipalladium(0)
ppm Parts per million
PtO₂ Platinum (IV) oxide
TFA Trifluoroacetic acid
THF Tetrahydrofuran
XantPhos 4,5-Bis(diphenylphosphino)-9,9-dimethylxanthene
Zn(CN)₂ Zinc cyanide Example 1

Preparation of N-hydroxy-2'-oxo-1'-phenyl-3,4-dihydro-1H-spiro[naphthalene-2,3'-pyrrolidine]-7-carboxamide (I-26)

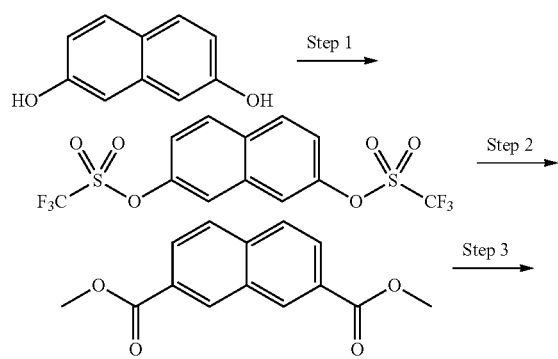

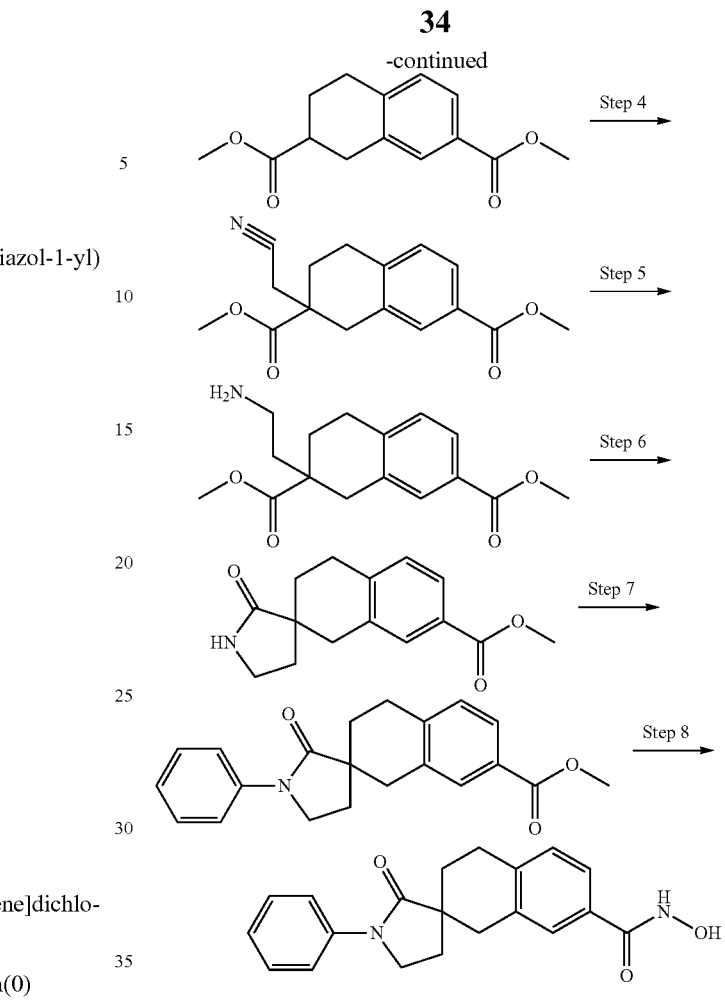

Step-1: Naphthalene-2,7-diyl bis(trifluoromethanesulfonate)

Into a 1-L round-bottom flask was placed naphthalene-2,7-diol (60 g, 374.6 mmol, 1equiv) in THF (600 mL), trifluoromethanesulfonic anhydride (127 g, 1.2 equiv) and 2,6-dichloropyridine (250 mL). The resulting solution was stirred overnight at room temperature and then concentrated under vacuum. The residue was diluted with 500 mL of EtOAc, washed with 5×100 mL of water and concentrated under vacuum to give 120 g (75% yield) of the title compound as a yellow solid. MS: (ES, m/z): 425 [M+H]⁺.

Step-2: Dimethyl naphthalene-2,7-dicarboxylate

Into a 1-L round-bottom flask was placed naphthalene-2,7-diyl bis(trifluoromethanesulfonate) (80 g, 188.55 mmol, 1 equiv) in MeOH (600 mL), Pd(dppf)Cl₂ (6g, 8.20 mmol, 0.04 equiv) and Et₃N (79 mL, 3 equiv). The resulting mixture was stirred overnight at 70° C. under CO (g) (20 psi). The solids were filtered and the filtrate was concentrated under vacuum. The residue was purified by normal phase chromatography on silica gel with EtOAc/petroleum ether (1:2). The collected fractions were concentrated to give 40 g (87% yield) of the title compound as a white solid. MS: (ES, m/z): 245 [M+H]⁺.

Step-3: Dimethyl 1,2,3,4-tetrahydronaphthalene-2,7-dicarboxylate

Into a 1-L round-bottom flask was placed dimethyl naphthalene-2,7-dicarboxylate (20g, 81.89 mmol, 1 equiv) in isopropanol (600 mL) and palladium on carbon (6 g, 0.3 equiv). The resulting solution was stirred for 30 h at 40° C. under H₂ (g) (50 psi). The solids were filtered out. The filtrate was concentrated under vacuum to give 15 g (74% yield) of the title compound as an oil. MS: (ES, m/z): 249 [M+H]⁺.

Step-4: Dimethyl 2-(cyanomethyl)-1,2,3,4-tetrahydronaphthalene-2,7-dicarboxylate Into a 500-mL round-bottom flask maintained with nitrogen, was placed dimethyl 1,2,3,4-tetrahydronaphthalene-2,7-dicarboxylate (15 g, 60.42 mmol, 1 equiv) in THF (100 mL). lithium diisopropylamide (2M in heptane, 89.29 mmol, 44.65 mL, 1.5 equiv) was added dropwise at −78° C. to the above solution. Next, a solution of 2-bromoacetonitrile (10.71 g, 89.29mmol, 1.5 equiv) in THF (100 mL) was added dropwise with stirring at −78° C. The resulting solution was stirred for additional 1 h at −78° C. The reaction was then quenched by the addition of 50 mL of water and extracted with 3×100 mL of EtOAc. The organic layers were combined and concentrated under vacuum. The residue was purified by normal phase chromatography on silica gel with EtOAc/petroleum ether (1:5). The collected fractions were concentrated to give 8.6 g (50% yield) of the title compound as a white solid. MS: (ES, m/z): 288 [M+H]⁺.

Step-5: Dimethyl 2-(2-aminoethyl)-1,2,3,4-tetrahydronaphthalene-2,7-dicarboxylate Into a 500-mL round-bottom flask was placed dimethyl 2-(cyanomethyl)-1,2,3,4-tetrahydronaphthalene-2,7-dicarboxylate (8.6 g, 29.93 mmol, 1 equiv) in MeOH (300 mL), PtO₂(3.4 g, 0.5 equiv) and acetic acid (30 mL). The resulting mixture was stirred overnight at room temperature with a H₂ (g) balloon. The solids were filtered out. The filtrate was concentrated under vacuum. The residue was dissolved in EtOAc (200 mL), washed with 3×50 mL of sat. aq. NaHCO₃, and concentrated to give 6.1 g (70% yield) of the title compound as an oil. MS: (ES, m/z): 292 [M+H]⁺.

Step-6: Methyl 2'-oxo-3,4-dihydro-1H-spiro[naphthalene-2,3'-pyrrolidine]-7-carboxylate Into a 500-mL round-bottom flask was placed dimethyl 2-(2-aminoethyl)-1,2,3,4-tetrahydronaphthalene-2,7-dicarboxylate (6.1 g, 20.94 mmol, 1 equiv) in MeOH (250 mL) and NH₃/MeOH (28 mL). The resulting solution was stirred overnight at room temperature. The resulting mixture was concentrated under vacuum to give 5.68 g (100% yield) of the title compound as a white solid. ¹H NMR (300 MHz, CDCl₃) δ (ppm): 7.82-7.79 (t, 2H), 7.18-7.27 (t, 1H), 5.94 (s, 1H), 3.91 (s, 3H), 3.42-3.39 (t, 2H), 3.15-2.67 (t, 4H), 2.17-1.62 (t, 4H). MS: (ES, m/z): 260 [M+H]⁺.

Step-7: Methyl 2'-oxo-1'-phenyl-3,4-dihydro-1H-spiro[naphthalene-2,3'-pyrrolidine]-7-carboxylate Into a 100-mL round-bottom flask was placed methyl 2'-oxo-3,4-dihydro-1H-spiro[naphthalene-2,3'-pyrrolidine]-7-carboxylate (150 mg, 0.58 mmol, 1 equiv) in DMF (3 mL), CuI (11 mg, 0.06 mmol, 0.1 equiv), K₃PO₄ (307 mg, 1.45 mmol, 2.5 equiv) and bromobenzene (108mg, 0.69 mmol, 1.2 equiv) and 1-N, 2-N-dimethylcyclohexane-1,2-diamine (8 mg, 0.06 mmol, 0.1 equiv). The resulting mixture was stirred overnight at 101° C. in an oil bath. The resulting mixture was diluted with 30 mL of water and extracted with 3×30 mL of EtOAc. The organic layers were combined and concentrated under vacuum. The residue was purified by normal phase chromatography on silica gel with EtOAc/petroleum ether (1:5). The collected fractions were concentrated to give 120 mg (62% yield) of the title compound as a white solid. MS: (ES, m/z): 336 [M+H]⁺.

Step-8: N-Hydroxy-2'-oxo-1'-phenyl-3,4-dihydro-1H-spiro[naphthalene-2,3'-pyrrolidine]-7-carboxamide Into a 100-mL round-bottom flask was placed methyl 2'-oxo-1'-phenyl-3,4-dihydro-1H-spiro[naphthalene-2,3'-pyrrolidine]-7-carboxylate (120 mg, 0.36 mmol, 1 equiv) in THF/MeOH (4:1, 2 mL), NH₂OH (50% in water, 1 mL, 42 equiv) and aq. 1N NaOH (1 mL, 2.7equiv). The resulting solution was stirred overnight at 40° C. in an oil bath. The crude product was purified by Prep-HPLC with the following conditions: Column: SunFire Prep C18, 5 μm, 19×150 mm; Mobile Phase A: Water/0.05% Formic Acid; Mobile Phase B: CH₃CN/0.05% Formic Acid; Gradient: 5% B to 56% B in 9 min; Detector: UV 220 nm, 254 nm. The collected fractions were lyophilized to give 36.2 mg (30% yield) of the title compound as a pink solid. ¹H NMR (300 MHz, DMSO-d6) δ (ppm): 11.09 (s, 1H), 8.96 (s, 1H), 7.74-7.71 (m, 2H), 7.51-7.49 (m, 2H), 7.42-7.37 (m, 2H), 7.21-7.13 (m, 2H), 3.88-3.83 (t, 2H), 2.98-2.75 (m, 4H), 2.06-1.81 (m, 4H). MS: (ES, m/z): 337 [M+H]⁺.

Example 2

Preparation of 1'-(3,4-dichlorobenzyl)-N-hydroxy-2'-oxo-3,4-dihydro-1H-spiro[naphthalene-2,3'-pyrrolidine]-7-carboxamide (I-21)

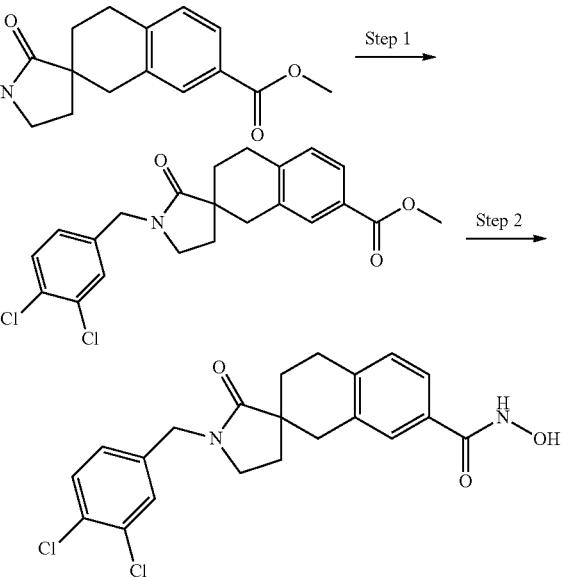

Step-1: Methyl 1'-(3,4-dichlorobenzyl)-2'-oxo-3,4-dihydro-1H-spiro[naphthalene-2,3'-pyrrolidine]-7-carboxylate Into a 25-mL round-bottom flask was placed methyl 2'-oxo-3,4-dihydro-1H-spiro[naphthalene-2,3'-pyrrolidine]-

7-carboxylate (150 mg, 0.58 mmol, 1 equiv) in DMF (5 mL), NaH (60% dispersion in oil, 42 mg, 1.75 mmol, 3 equiv) and 4-(bromomethyl)-1,2-dichlorobenzene (208 mg, 0.87 mmol, 1.5 equiv). The resulting mixture was stirred for 1 h at room temperature. The reaction was then quenched by the addition of 20 mL of water. The resulting solution was extracted with 3×50 mL of EtOAc. The organic layers were combined and concentrated under vacuum to give 190 mg (79% yield) of the title compound as a colorless oil. MS: (ES, m/z): 418 [M+H]$^+$.

Step-2: 1'-(3,4-Dichlorobenzyl)-N-hydroxy-2'-oxo-3,4-dihydro-1H-spiro[naphthalene-2,3'-pyrrolidine]-7-carboxamide Into a 100-mL round-bottom flask was placed methyl 1'-(3,4-dichlorobenzyl)-2'-oxo-3,4-dihydro-1H-spiro[naphthalene-2,3'-pyrrolidine]-7-carboxylate (190 mg, 0.45 mmol, 1 equiv) in THF/MeOH (4:1, 2 mL), NH$_2$OH (50% in water, 1 mL, 33.6 equiv), and aq. 1N NaOH (1 mL, 2.2 equiv). The resulting solution was stirred overnight at 40° C. in an oil bath. The crude product was purified by Prep-HPLC with the following conditions: Column: SunFire Prep C18, 5 μm, 19×150 mm; Mobile Phase A: Water/0.05% Formic Acid; Mobile Phase B: CH$_3$CN/0.05% Formic Acid; Gradient: 5% B to 56% B in 9 min; Detector: UV 220 nm, 254 nm. The collected fractions were lyophilized to give 20.9 mg (11% yield) of the title compound as a pink solid. $^1$H NMR (300 MHz, DMSO-d6) δ (ppm): 11.05 (s, 1H), 8.95 (s, 1H), 7.63-7.63 (t, 1H), 7.51-7.49 (m, 3H), 7.25-7.15 (m, 2H), 4.43 (s, 2H), 3.34-3.22 (t, 2H), 2.93-2.51 (m, 4H), 1.95-1.64 (m, 4H). MS: (ES, m/z): 419 [M+H]$^+$.

TABLE 1

The following compounds were prepared according to the method of Example 2.

| Ex. | Structure | $^1$H NMR δ (ppm) | Found (ES, m/z) [M + H]$^+$ |
|---|---|---|---|
| I-22 | 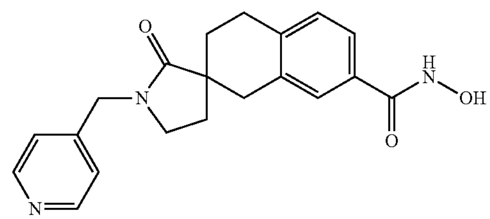 [SMILES: O=C(NO)c1ccc2c(c1)CC1(CC2)CCN(Cc2ccncc2)C1=O] | (400 MHz, DMSO-d6): 11.09 (s, 1H), 8.73-8.81 (m, 2H), 7.42-7.64 (m, 4H), 7.17-7.19 (d, J = 10.4 Hz, 1H), 4.62 (s, 2H), 3.23-3.26 (m, 2H), 2.75-2.96 (m, 3H), 2.63-2.70 (m, 1H), 1.76-1.98 (m, 4H) | 352 |
| I-23 | | (400 MHz, DMSO-d6): 11.07 (s, 1H), 8.96 (s, 1H), 7.49-7.47 (t, 2H), 7.16-7.15 (t, H), 3.31-3.29 (t, 2H), 3.07-3.05 (t, 2H), 2.88-2.67 (t, 3H), 2.61-2.57 (t, 1H), 1.91-1.60 (t, 10H), 1.30-1.06 (t, 3H), 0.99-0.80 (t, 2H) | 357 |
| I-24 | 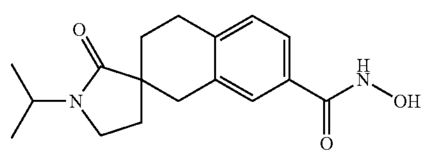 [SMILES: CC(C)N1CCC2(CCc3ccc(C(=O)NO)cc3C2)C1=O] | (400 MHz, DMSO-d6): 11.09 (s, 1H), 8.94 (s, 1H), 7.48-7.46 (t, 2H), 7.17-7.15 (t, H), 4.16-4.13 (t, 2H), 3.33-3.26 (t, 3H), 2.87-2.63 (t, 3H), 2.59-2.509 (t, 1H), 1.90-1.50 (t, 4H), 1.14-1.09 (t, 6H) | 303 |
| I-25 | 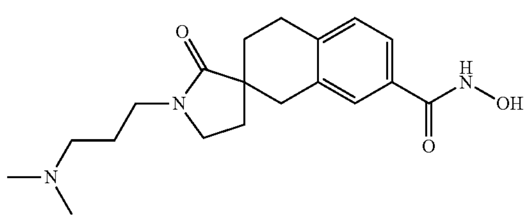 [SMILES: CN(C)CCCN1CCC2(CCc3ccc(C(=O)NO)cc3C2)C1=O] | (300 MHz, DMSO-d6): 11.01 (s, 1H), 8.22 (s, 1H), 7.49-7.46 (t, 2H), 7.17-7.15 (t, H), 3.36-3.20 (t, 4H), 2.96-2.75 (t, 3H), 2.65-2.51 (t, 1H), 2.36-2.21 (t, 8H), 1.96-1.51 (t, 6H) | 346 |
| I-27 | 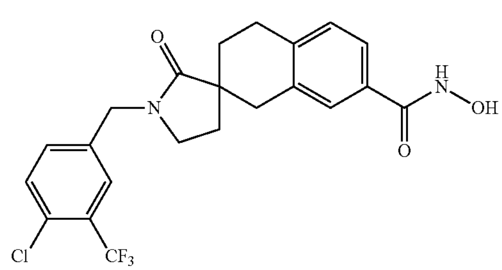 [SMILES: O=C(NO)c1ccc2c(c1)CC1(CC2)CCN(Cc2ccc(Cl)c(C(F)(F)F)c2)C1=O] | (300 MHz, DMSO-d6): 11.08 (s, 1H), 7.76-7.73 (m, 2H), 7.56-7.47 (m, 3H), 7.17 (d, J = 8.4 Hz, 1H), 4.52 (s, 2H), 3.26 (t, J = 6.6 Hz, 2H), 2.94-2.75 (m, 3H), 2.67-2.62 (m, 1H), 1.96-1.82 (m, 2H), 1.76-1.64 (m, 2H) | 453 |

Example 3

Preparation of N-hydroxy-2'-oxo-1'-(pyridin-4-yl)-3,4-dihydro-1H-spiro[naphthalene-2,3'-pyrrolidine]-7-carboxamide (I-30)

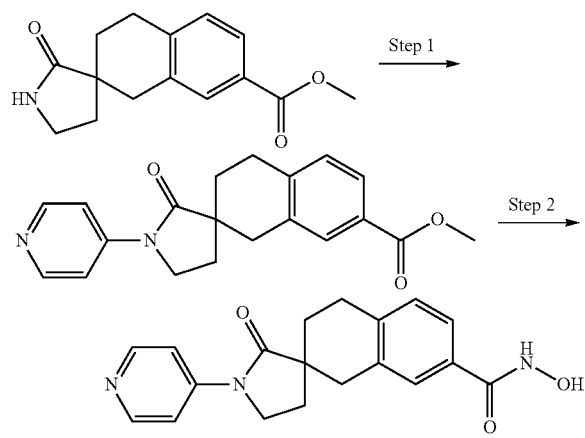

Step-1: Methyl 2'-oxo-1'-(pyridin-4-yl)-3,4-dihydro-1H-spiro[naphthalene-2,3'-pyrrolidine]-7-carboxylate Into a 100-mL round-bottom flask was placed methyl 2'-oxo-3,4-dihydro-1H-spiro[naphthalene-2,3'-pyrrolidine]-7-carboxylate (100 mg, 0.39 mmol, 1 equiv) in 1,4-dioxane (5 mL), 4-bromopyridine hydrochloride (73 mg, 0.38 mmol, 0.97 equiv), Pd(OAc)$_2$ (8.5 mg, 0.04mmol, 0.1 equiv), XantPhos (70 mg, 0.12 mmol, 0.3 equiv) and Cs$_2$CO$_3$ (190 mg, 0.58 mmol, 1.5equiv). The resulting mixture was stirred overnight at 101° C. The solids were filtered out. The filtrate was concentrated and purified by normal phase chromatography on silica gel with EtOAc/petroleum ether (2:1). The collected fractions were concentrated to give 90 mg (69% yield) of the title compound as a solid. MS: (ES, m/z): 337 [M+H]$^+$.

Step-2: N-Hydroxy-2'-oxo-1'-(pyridin-4-yl)-3,4-dihydro-1H-spiro[naphthalene-2,3'-pyrrolidine]-7-carboxamide Into a 10-mL round-bottom flask was placed methyl 2'-oxo-1'-(pyridin-4-yl)-3,4-dihydro-1H-spiro[naphthalene-2,3'-pyrrolidine]-7-carboxylate (90 mg, 0.27 mmol, 1 equiv) in THF/MeOH (4:1, 1.25 mL), NH$_2$OH (50% in water, 1.767 g, 26.77 mmol, 99 equiv), and aq. 1N NaOH (0.5 mL, 2 equiv). The resulting solution was stirred for 1.5 h at room temperature. 6N HCl was added to the resulting mixture to adjust to pH 3. The crude product was purified by Prep-HPLC with the following conditions: Column: Waters HSS C18, 2.1×50 mm, 1.8 μm; Mobile Phase A: Water/0.05% TFA; Mobile Phase B: CH$_3$CN/0.05% TFA; Flow rate: 0.7mL/min; Gradient: 5% B to 95% B in 2.0 min, hold 0.6 min; Detector: UV 254 nm. Collected fractions were lyophilized to afford 17.3 mg (19% yield) of the title compound as an off-white solid. $^1$H NMR (400 MHz, DMSO-d6) δ (ppm): 11.12 (s, 1H), 8.51-8.36 (m, 2H), 7.75-7.73 (d, J =7.0 Hz, 2H), 7.51-7.49 (d, J =7.6 Hz, 2H), 7.20-7.18 (d, J=8.0 Hz, 1H), 3.89-3.85 (t, J=6.8Hz, 2H), 2.97-2.79 (m, 4H), 2.10-1.84 (m, 4H). MS: (ES, m/z): 338 [M+H]$^+$.

Example 4

Preparation of N-hydroxy-1'-(4-methoxyphenethyl)-2'-oxo-3,4-dihydro-1H-spiro[naphthalene-2,3'-pyrrolidine]-7-carboxamide (I-20)

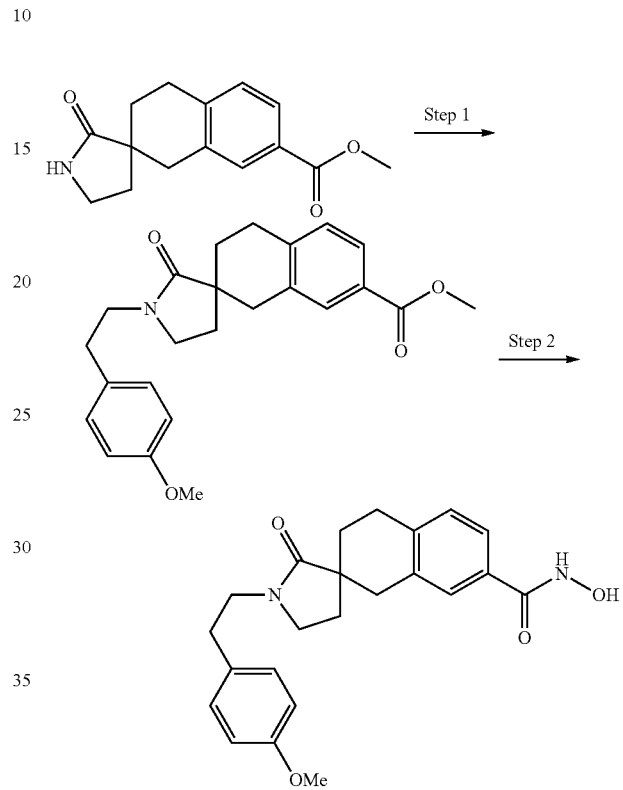

Step-1: Methyl 1'-(4-methoxyphenethyl)-2'-oxo-3,4-dihydro-1H-spiro[naphthalene-2,3'-pyrrolidine]-7-carboxylate A solution of methyl 2'-oxo-3,4-dihydro-1H-spiro[naphthalene-2,3'-pyrrolidine]-7-carboxylate (5.1 mg, 0.197 mmol, 1 equiv) in DMF (1.5 mL) was cooled to 0° C. n an ice-water bath. Next, NaH (60% dispersion in oil, 10 mg, 0.237 mmol 1.2 equiv) was added and the mixture was allowed to stir at 0° C. for 10 min. 1-(2-Bromoethyl)-4-methoxybenzene (49 mg, 0.227 mmol, 1.15 equiv) was added, followed by addition of NaI (3 mg, 0.020 mmol, 0.1 equiv). The reaction was heated at 70° C. for 18 h. The reaction was purified by column chromatography on silica gel (10-50% EtOAc/hexanes) to afford 20 mg (26% yield) of the title compound as a white solid. MS: (ES, m/z): 394 [M+H]$^+$.

Step-2: N-Hydroxy-1'-(4-methoxyphenethyl)-2'-oxo-3,4-dihydro-1H-spiro[naphthalene-2,3'-pyrrolidine]-7-carboxamide Methyl 1'-(4-methoxyphenethyl)-2'-oxo-3,4-dihydro-1H-spiro[naphthalene-2,3'-pyrrolidine]-7-carboxylate (20 mg, 0.051 mmol, 1 equiv) was dissolved in a solution of THF/MeOH (4:1, 1.38 mL). NH$_2$OH (50% in water, 0.279 mL, 4.6 mmol, 90 equiv) was added, followed by aq. 2N NaOH (0.076 mL, 3 equiv). The reaction was allowed to stir at room temperature for 48 h and was purified directly by reverse-phase chromatography using the following conditions: Column: XTerra Prep MS C18 OBD 5 μm, 19×100 mm; Mobile Phase A: Water/0.05% Formic Acid, Mobile Phase B: CH$_3$CN/0.05% Formic Acid; Flow rate: 20 mL/min; Gradient: 15% B to 85% B in 10 min; Detector: UV 220 nm and 254 nm. Combined fractions were lyophilized to afford 4 mg (22% yield) of the title compound. $^1$H NMR (300 MHz, DMSO-d6) δ (ppm): 8.37 (s, 1H), 7.39-7.53 (m, 2H), 7.10-7.23 (m, 3H), 6.81-6.95 (m, 2H), 3.66-3.89(m, 3H), 3.34-3.50 (m, 2H), 3.09-3.32 (m, 4H), 2.67-2.86 (m, 4H), 1.46-1.84 (m, 4H). MS: (ES, m/z): 395 [M+H]$^+$.

Example 5

Preparation of (S)-1'-(4-chlorobenzyl)-N-hydroxy-2'-oxo-3,4-dihydro-1H-spiro[naphthalene-2,3'-pyrrolidine]-7-carboxamide (I-37) and (R)-1'-(4-chlorobenzyl)-N-hydroxy-2'-oxo-3,4-dihydro-1H-spiro[naphthalene-2,3'-pyrrolidine]-7-carboxamide (I-38)

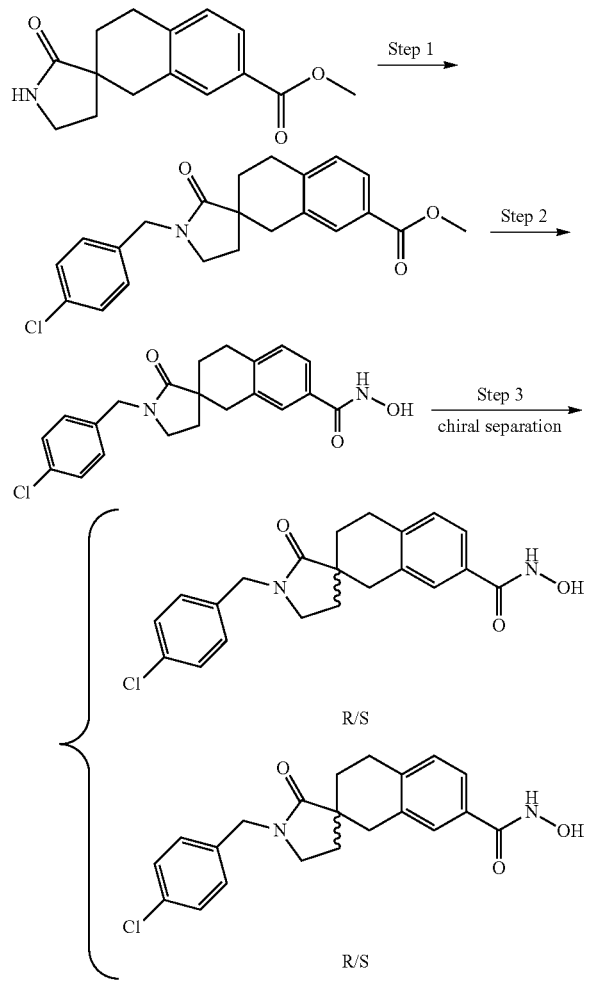

Step-1: Methyl 1'-(4-chlorobenzyl)-2'-oxo-3,4-dihydro-1H-spiro[naphthalene-2,3'-pyrrolidine]-7-carboxylate Into a 25-mL round-bottom flask was placed methyl 2'-oxo-3,4-dihydro-1H-spiro[naphthalene-2,3'-pyrrolidine]-7-carboxylate (150 mg, 0.58 mmol, 1 equiv) in DMF (5 mL), NaH (42 mg, 1.75 mmol, 3 equiv) and 1-(bromomethyl)-4-chlorobenzene (177 mg, 0.86 mmol, 1.5 equiv). The resulting mixture was stirred for 1 h at room temperature. The reaction was then quenched by the addition of 20 mL of water. The resulting solution was extracted with 3×50 mL of EtOAc. The combined organics were concentrated under vacuum to give 175 mg (79% yield) of the title compound as an oil. MS: (ES, m/z): 384 [M+H]$^+$.

Step-2: 1'-(4-Chlorobenzyl)-N-hydroxy-2'-oxo-3,4-dihydro-1H-spiro[naphthalene-2,3'-pyrrolidine]-7-carboxamide Into a 100-mL round-bottom flask was placed methyl 1'-(4-chlorobenzyl)-2'-oxo-3,4-dihydro-1H-spiro[naphthalene-2,3'-pyrrolidine]-7-carboxylate (175 mg, 0.46 mmol, 1 equiv) in THF/MeOH (4:1, 2.5 mL), NH$_2$OH (50% in water, 1 mL, 33 equiv), and aq. 1N NaOH (1 mL, 2.2 equiv). The resulting solution was stirred overnight at 50° C. in an oil bath. The solids were filtered out. The crude product was purified by Prep-HPLC with the following conditions: Column: SunFire Prep C18, 5 μm, 19×150 mm; Mobile Phase A: Water/0.05% Formic Acid; Mobile Phase B: CH$_3$CN/0.05% Formic Acid; Gradient: 5% B to 65% B in 10 min; Detector: UV 220 nm, 254 nm. The collected fractions were lyophilized to give 31.8 mg (18% yield) of the title compound as a pink solid. $^1$H NMR (300 MHz, DMSO-d6) δ (ppm): 11.08 (s, 1H), 8.94 (s, 1H), 7.49-7.42 (m, 4H), 7.28-7.15 (m, 3H), 4.42 (s, 2H), 3.32-3.19 (t, 2H), 2.94-2.60 (m, 4H), 1.92-1.63 (m, 4H). MS: (ES, m/z): 385 [M+H]+.

Step-3: Chiral separation of (S)-1'-(4-chlorobenzyl)-N-hydroxy-2'-oxo-3,4-dihydro-1H-spiro[naphthalene-2,3'-pyrrolidine]-7-carboxamide and (R)-1'-(4-chlorobenzyl)-N-hydroxy-2'-oxo-3,4-dihydro-1H-spiro[naphthalene-2,3'-pyrrolidine]-7-carboxamide The racemate of 1'-(4-chlorobenzyl)-N-hydroxy-2'-oxo-3,4-dihydro-1H-spiro[naphthalene-2,3'-pyrrolidine]-7-carboxamide (10 mg, 0.03 mmol) was purified by Chiral-Prep-HPLC with the following conditions: Column: Chiralpak IB 0.46×25 cm, 5 μm; Mobile Phase: hexanes/isopropanol (hold 50% isopropanol for 40 min); Detector: UV 254 nm. The first eluting isomer (Rt 21.32 min) was collected and concentrated to give 1.2 mg (12% yield) of an off-white solid which was assigned as the S isomer of 1'-(4-chlorobenzyl)-N-hydroxy-2'-oxo-3,4-dihydro-1H-spiro[naphthalene-2,3'-pyrrolidine]-7-carboxamide. $^1$H NMR (400 MHz, DMSO-d6) δ (ppm): 11.09 (s, 1H), 8.95 (s, 1H), 7.50-7.42 (m, 4H), 7.28-7.25 (d, J=8.4 Hz, 2H), 7.17-7.16(d, J=8.0 Hz, 2H), 4.42 (s, 2H), 3.23-3.19 (t, J=6.8 Hz, 2H), 2.93-2.61 (m, 4H), 1.93-1.66 (m, 4H). MS: (ES, m/z): 385 [M+H]$^+$. The second eluting isomer (Rt 37.5 min) was collected and concentrated to give 1.2 mg (12% yield) of an off-white solid which was assigned as the R isomer of 1'-(4-chlorobenzyl)-N-hydroxy-2'-oxo-3,4-dihydro-1H-spiro[naphthalene-2,3'-pyrrolidine]-7-carboxamide as an off-white solid. $^1$H NMR (400 MHz, DMSO-d6) δ (ppm): 11.09 (s, 1H), 8.95 (s, 1H), 7.50-7.42 (m, 4H), 7.28-7.25 (d, J=8.4 Hz, 2H), 7.17-7.16 (d, J=8.0 Hz, 2H), 4.42 (s, 2H), 3.23-3.19 (t, J=6.8 Hz, 2H), 2.93-2.61 (m, 4H), 1.93-1.66 (m, 4H). MS: (ES, m/z): 385 [M+H]$^+$.

Example 6

Preparation of (S)—N-hydroxy-2'-oxo-1'-(pyridin-3-yl)-3,4-dihydro-1H-spiro[naphthalene-2,3'-pyrrolidine]-7-carboxamide (I-28) and (R)—N-hydroxy-2'-oxo-1'-(pyridin-3-yl)-3,4-dihydro-1H-spiro[naphthalene-2,3'-pyrrolidine]-7-carboxamide (I-29)

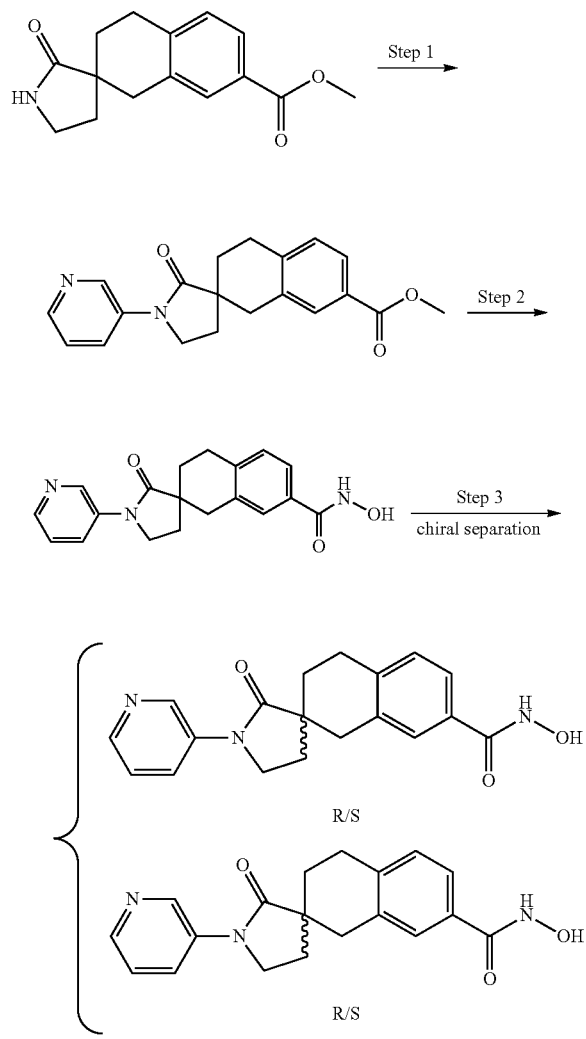

Step-1: Methyl 2'-oxo-1'-(pyridin-3-yl)-3,4-dihydro-1H-spiro[naphthalene-2,3'-pyrrolidine]-7-carboxylate Into a 100-mL round-bottom flask was placed methyl 2'-oxo-3,4-dihydro-1H-spiro[naphthalene-2,3'-pyrrolidine]-7-carboxylate (100 mg, 0.39 mmol, 1 equiv) in 1,4-dioxane (5 mL), 3-bromopyridine (60 mg, 0.38 mmol, 0.98 equiv), Pd(OAc)$_2$ (8.5 mg, 0.04 mmol, 0.1equiv), XantPhos (70 mg, 0.12 mmol, 0.3 equiv) and Cs$_2$CO$_3$ (190 mg, 0.58 mmol, 1.5 equiv). The resulting mixture was stirred overnight at 101° C. The solids were filtered out. The filtrate was concentrated and the residue was purified by column chromatography on silica gel with EtOAc/petroleum ether (1:1). The collected fractions were concentrated to give 70 mg (54% yield) of the title compound as a solid. MS: (ES, m/z): 337 [M+H]$^+$.

Step-2: N-Hydroxy-2'-oxo-1'-(pyridin-3-yl)-3,4-dihydro-1H-spiro[naphthalene-2,3'-pyrrolidine]-7-carboxamide Into a 100-mL round-bottom flask was placed methyl 2'-oxo-1'-(pyridin-3-yl)-3,4-dihydro-1H-spiro[naphthalene-2,3'-pyrrolidine]-7-carboxylate (70 mg, 0.21 mmol, 1 equiv), THF/MeOH (4:1, 1.25 mL), NH$_2$OH (50% in water, 1.375 g, 41.63 mmol, 200 equiv), and aq. 1N NaOH (0.4 mL, 2 equiv). The resulting solution was stirred for 1 h at room temperature. 6N HCl was added to the resulting mixture to adjust to pH 3. The crude product was purified by Prep-HPLC with the following conditions: Column: Waters HSS C18, 2.1×50 mm, 1.8 μm, Mobile Phase A: Water/0.05% TFA; Mobile Phase B: CH$_3$CN/0.05% TFA; Flow rate: 0.7mL/min; Gradient: 5% B to 95% B in 2.0 min, hold 0.6 min; Detector: UV 254 nm. The collected fractions were lyophilized to give 25 mg (35% yield) of the title compound as a white solid. MS: (ES, m/z): 338 [M+H]$^+$.

Step-3: Chiral separation of (S)—N-hydroxy-2'-oxo-1'-(pyridin-3-yl)-3,4-dihydro-1H-spiro[naphthalene-2,3'-pyrrolidine]-7-carboxamide and (R)—N-hydroxy-2'-oxo-1'-(pyridin-3-yl)-3,4-dihydro-1H-spiro[naphthalene-2,3'-pyrrolidine]-7-carboxamide The racemate of N-hydroxy-2'-oxo-1'-(pyridin-3-yl)-3,4-dihydro-1H-spiro[naphthalene-2,3'-pyrrolidine]-7-carboxamide (25 mg, 0.074 mmol) was purified by Chiral-Prep-HPLC with the following conditions: Column: Chiralpak AS-H, 2×25 cm; Mobile Phase: hexanes/EtOH (hold 50% EtOH for 27 min); Detector: UV 254, 220 nm. The first eluting isomer (Rt 10.72 min) was collected and lyophilized to give 9.6 mg of an off-white solid which was assigned as the S isomer of N-hydroxy-2'-oxo-1'-(pyridin-3-yl)-3,4-dihydro-1H-spiro[naphthalene-2,3'-pyrrolidine]-7-carboxamide. $^1$H NMR (400 MHz, DMSO-d6) δ (ppm): 11.11 (s, 1H), 8.94 (d, J=2.8 Hz, 2H), 8.37-8.35 (m, 1H), 8.18-8.15 (m, 1H), 7.51-7.49 (d, J=8.4 Hz, 2H), 7.45-7.42 (m, 1H), 7.20 (d, J=8.0 Hz, 1H), 3.92-3.88 (t, J=6.8 Hz, 2H), 2.98-2.78(m, 4H), 2.11-1.80 (m, 4H). MS: (ES, m/z): 338 [M+H]$^+$. The second eluting isomer (Rt 17.49min) was collected and lyophilized to give 8.9 mg of an off-white solid which was assigned as the R isomer of N-hydroxy-2'-oxo-1'-(pyridin-3-yl)-3,4-dihydro-1H-spiro[naphthalene-2,3'-pyrrolidine]-7-carboxamide. $^1$H NMR (400 MHz, DMSO-d6) δ (ppm): 11.11 (s, 1H), 8.94 (d, J=2.8 Hz, 2H), 8.37-8.35 (m, 1H), 8.18-8.15 (m, 1H), 7.51-7.49 (d, J=8.4 Hz, 2H), 7.45-7.42 (m, 1H), 7.20 (d, J=8.0 Hz, 1H), 3.92-3.88 (t, J=6.8 Hz, 2H), 2.98-2.78 (m, 4H), 2.11-1.80 (m, 4H). MS: (ES, m/z): 338 [M+H]$^+$.

Example 7

Preparation of (S)-1'-(4-fluorobenzyl)-N-hydroxy-2'-oxo-3,4-dihydro-1H-spiro[naphthalene-2,3'-pyrrolidine]-7-carboxamide (I-41) and (R)-1'-(4-fluorobenzyl)-N-hydroxy-2'-oxo-3,4-dihydro-1H-spiro[naphthalene-2,3'-pyrrolidine]-7-carboxamide (I-42)

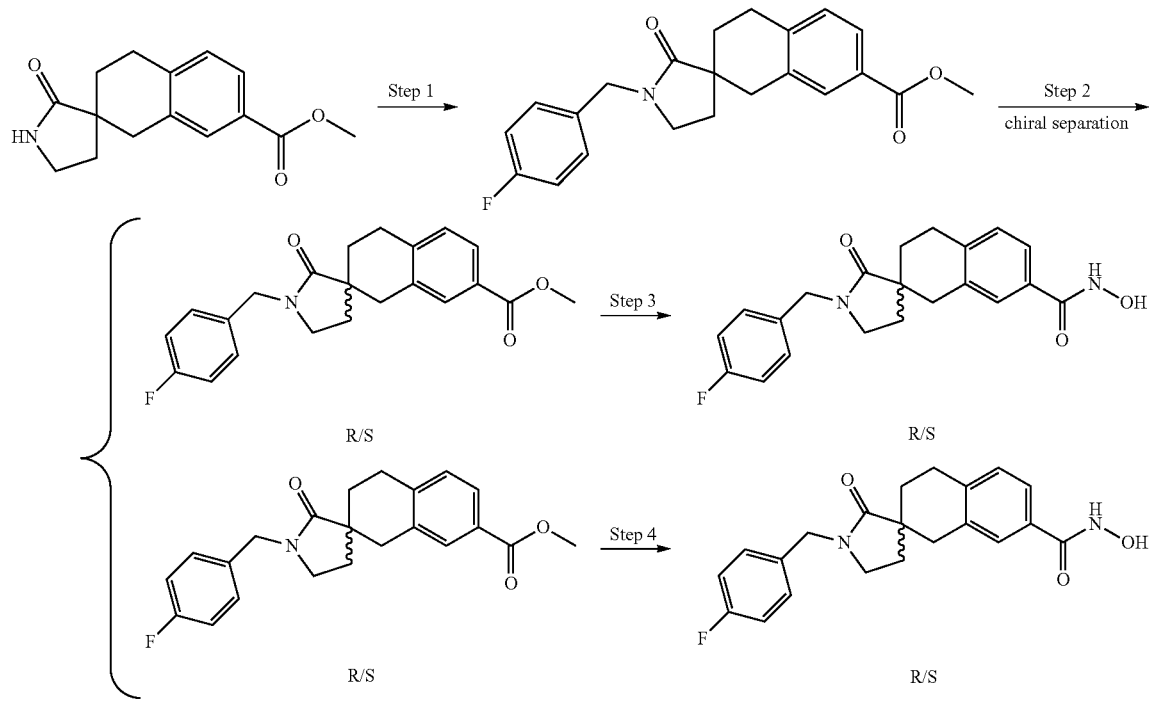

Step-1: Methyl 1'-(4-fluorobenzyl)-2'-oxo-3,4-dihydro-1H-spiro[naphthalene-2,3'-pyrrolidine]-7-carboxylate Into a 50-mL round-bottom flask purged and maintained with an inert atmosphere of nitrogen, was placed methyl 2'-oxo-3,4-dihydro-1H-spiro[naphthalene-2,3'-pyrrolidine]-7-carboxylate (100 mg, 0.39 mmol, 1 equiv) in DMF (5 mL). This was followed by the addition of NaH (60% dispersion in oil, 38 mg, 1.58 mmol, 2.5 equiv). The resulted mixture was stirred for 20 min at room temperature. To this mixture was added 1-(bromomethyl)-4-fluorobenzene (109mg, 0.58 mmol, 1.5 equiv). The resulting mixture was stirred for 3 h at room temperature. The reaction mixture was cooled to 0° C. in an ice-water bath and quenched by the addition of 10 mL of water. The resulting solution was extracted with 3×10 mL of EtOAc. The organic layers were combined and dried over anhydrous Na$_2$SO$_4$, filtered and concentrated under vacuum. The residue was purified by normal phase chromatography on silica gel with EtOAc/petroleum ether (1:3). The collected fractions were concentrated to give 105 mg (74% yield) of the title compound as a colorless oil. MS: (ES, m/z): 368 [M+H]$^+$.

Step-2: Chiral separation of (S)-methyl 1'-(4-fluorobenzyl)-2'-oxo-3,4-dihydro-1H-spiro[naphthalene-2,3'-pyrrolidine]-7-carboxylate and (R)-methyl 1'-(4-fluorobenzyl)-2'-oxo-3,4-dihydro-1H-spiro[naphthalene-2,3'-pyrrolidine]-7-carboxylate The racemate of methyl 1'-(4-fluorobenzyl)-2'-oxo-3,4-dihydro-1H-spiro[naphthalene-2,3'-pyrrolidine]-7-carboxylate (105 mg, 0.28 mmol) was purified by Chiral-Prep-HPLC with the following conditions: Column: Chiralpak IB, 2×25 cm; Mobile Phase: hexanes/isopropanol (hold 50% isopropanol for 18 min); Detector: UV 254, 220 nm. The first eluting isomer (Rt 7.86 min) was collected and concentrated to give 27 mg of an off-white solid which was assigned as the S isomer of methyl 1'-(4-fluorobenzyl)-2'-oxo-3,4-dihydro-1H-spiro[naphthalene-2,3'-pyrrolidine]-7-carboxylate. MS: (ES, m/z): 368 [M+H]$^+$. The second eluting isomer (Rt 13.22 min) was collected and concentrated to give 31 mg of an off-white solid which was assigned as the R isomer of methyl 1'-(4-fluorobenzyl)-2'-oxo-3,4-dihydro-1H-spiro[naphthalene-2,3'-pyrrolidine]-7-carboxylate as an off-white solid. MS: (ES, m/z): 368[M+H]$^+$.

Step-3: (S)-1'-(4-Fluorobenzyl)-N-hydroxy-2'-oxo-3,4-dihydro-1H-spiro[naphthalene-2,3'-pyrrolidine]-7-carboxamide Into a 10-mL round-bottom flask was placed the first eluted isomer from Step 2, which was assigned as (S)- methyl 1'-(4-fluorobenzyl)-2'-oxo-3,4-dihydro-1H-spiro[naphthalene-2,3'-pyrrolidine]-7-carboxylate as described above, (42 mg, 0.11 mmol, 1 equiv), THF/MeOH (4:1, 2.5 mL), NH$_2$OH (50% in water, 0.5 mL, 69 equiv), and aq. 1N NaOH (0.3 mL, 2.7 equiv). The resulting solution was stirred for 3 h at room temperature. The reaction mixture was cooled to 0° C. in an ice-water bath and the pH value of the solution was adjusted to 7.0 with 1N HCl. The solids were filtered out. The crude product was purified by Prep-HPLC with the following conditions: Column: XBridge C18, 19×150 mm, 5 μm; Mobile Phase A: Water/0.05% TFA, Mobile Phase B: CH$_3$CN/0.05% TFA; Flow rate: 25 mL/min; Gradient: 5% B to 60% B in 7.0min; Detector: 254 nm. The collected fractions were lyophilized to give 27 mg (49% yield) of the title compound as an off-white solid. $^1$H NMR (400 MHz, DMSO-d6) δ (ppm): 11.10 (s, 1H), 7.49-7.47 (m, 2H), 7.30-7.20 (m, 2H), 7.18-7.16 (m, 3H), 4.45 (s, 2H), 3.20 (t, J=7.2 Hz, 2H), 2.93-2.76 (m, 3H), 2.67-2.54 (m, 1H), 1.92-1.82 (m, 2H), 1.72-1.63 (m, 2H). MS: (ES, m/z): 369[M+H]$^+$.

Example 8

Preparation of intermediates methyl (S)-2'-oxo-3,4-dihydro-1H-spiro[naphthalene-2,3'-pyrrolidine]-7-carboxylate and methyl (R)-2'-oxo-3,4-dihydro-1H-spiro[naphthalene-2,3'-pyrrolidine]-7-carboxylate

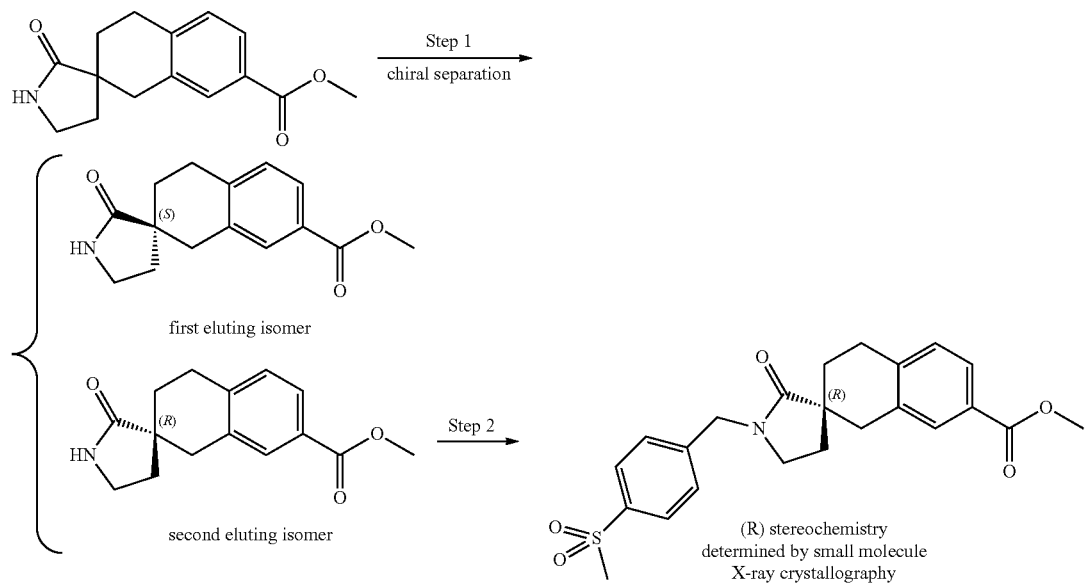

NMR (400 MHz, DMSO-d6) δ (ppm): 11.10 (s, 1H), 7.49-7.47 (m, 2H), 7.30-7.20 (m, 2H), 7.18-7.16 (m, 3H), 4.45 (s, 2H), 3.20 (t, J=7.2 Hz, 2H), 2.93-2.76 (m, 3H), 2.67-2.54 (m, 1H), 1.92-1.82 (m, 2H), 1.72-1.63 (m, 2H). MS: (ES, m/z): 369[M+H]$^+$.

Step-4: (R)-1'-(4-Fluorobenzyl)-N-hydroxy-2'-oxo-3,4-dihydro-1H-spiro[naphthalene-2,3'-pyrrolidine]-7-carboxamide Into a 10-mL round-bottom flask was placed the first eluted isomer from Step 2, which was assigned as (R)-methyl 1'-(4-fluorobenzyl)-2'-oxo-3,4-dihydro-1H-spiro[naphthalene-2,3'-pyrrolidine]-7-carboxylate as described above, (57 mg, 0.16 mmol, 1 equiv), THF/MeOH (4:1, 2.5 mL), NH$_2$OH (50% in water, 0.5 mL, 47 equiv), and aq. 1N NaOH (0.3 mL, 2 equiv). The resulting solution was stirred for 3 h at room temperature. The reaction mixture was cooled to 0° C. in an ice-water bath and the pH value of the solution was adjusted to 7.0 with 1N HCl. The solids were filtered out. The crude product was purified by Prep-HPLC with the following conditions: Column: XBridge C18, 19×150 mm, 5 μm; Mobile Phase A: Water/0.05% TFA, Mobile Phase B: CH$_3$CN/0.05% TFA; Flow rate: 25 mL/min; Gradient: 5% B to 60% B in 7.0min; Detector: 254 nm. The collected fractions were lyophilized to give 31 mg (41% yield) of the title compound as an off-white solid. $^1$H NMR (400 MHz, DMSO-d6) δ (ppm): 11.10 (s, 1H), 7.49-7.47 (m, 2H), 7.30-7.20 (m, 2H), 7.18-7.16 (m, 3H), 4.45 (s, 2H), 3.20 (t, J=7.2 Hz, 2H), 2.93-2.76 (m, 3H), 2.67-2.54 (m, 1H), 1.92-1.82 (m, 2H), 1.72-1.63 (m, 2H). MS: (ES, m/z): 369[M+H]$^+$.

Step-1: Chiral separation of methyl (S)-2'-oxo-3,4-dihydro-1H-spiro[naphthalene-2,3'-pyrrolidine]-7-carboxylate and methyl (R)-2'-oxo-3,4-dihydro-1H-spiro[naphthalene-2,3'-pyrrolidine]-7-carboxylate The racemate of methyl 2'-oxo-3,4-dihydro-1H-spiro[naphthalene-2,3'-pyrrolidine]-7-carboxylate (32 g) was purified by Prep-SFC with the following conditions: Column: Chiralpak AS-H, 5×25 cm, 5 μm; Mobile Phase A: CO$_2$, Mobile Phase B: isopropanol; Flow rate: 200mL/min; Detector: UV 220 nm. The first eluting isomer (Rt 6.47 min) was collected and concentrated to give 11 g (34% yield) of an off-white solid. $^1$H NMR (400 MHz, DMSO-d6) δ (ppm): 7.70-7.67 (m, 3H), 7.26-7.24 (d, J=8.0 Hz, 1H), 3.82 (s, 3H), 3.29-3.22 (m, 2H), 2.94-2.65 (m, 4H), 1.94-1.73 (m, 4H). MS: (ES, m/z): 260 [M+H]$^+$. The second eluting isomer (Rt 10.21 min) was collected and concentrated to give 11 g (34% yield) of an off-white solid. $^1$H NMR (400 MHz, DMSO-d6) δ(ppm): 7.70-7.67 (m, 3H), 7.26-7.24 (d, J=8.0 Hz, 1H), 3.82 (s, 3H), 3.29-3.22 (m, 2H), 2.94-2.65 (m, 4H), 1.94-1.73 (m, 4H). MS: (ES, m/z): 260 [M+H]$^+$.

Step-2: Determination of the absolute stereochemistry of methyl (R)-2'-oxo-3,4-dihydro-1H-spiro[naphthalene-2,3'-pyrrolidine]-7-carboxylate Into a 50-mL round-bottom flask, was placed a solution of the second eluting isomer from Step 1 (700 mg, 2.70 mmol, 1 equiv) in DMF (5 mL). This was followed by the addition of NaH (130 mg, 5.40 mmol, 2 equiv) at 0° C. The resulting solution was stirred for 30 min at room temperature. To this solution was added 1-(bromomethyl)-4-methanesulfonyl-benzene (1.01 g, 4.05 mmol, 1.5 equiv). The resulting solution was stirred for 12 h at room temperature. The reaction was then quenched by the addition of 20 mL of aq. NH$_4$Cl and further diluted with 100 mL of EtOAC. The resulting solution was washed with 5×50 mL of water. The combined aqueous layers were extracted with 2×50 mL of EtOAc and the combined organic layers were dried over anhydrous MgSO$_4$ and concentrated to afford 0.44 g (39% yield) of a single isomer of 1'-(4-(methylsulfonyl)benzyl)-2'-oxo-3,4-dihydro-1H-spiro[naphthalene-2,3'-pyrrolidine]-7-carboxylic acid as a white solid. MS: (ES, m/z): 414 [M+H]$^+$.

Into a 25-mL round-bottom flask, were placed 1'-[(4-methanesulfonylphenyl)methyl]-2'-oxo-3,4-dihydro-1H-spiro[naphthalene-2,3'-pyrrolidine]-7-carboxylic acid (440 mg, 1.06mmol, 1 equiv) and MeOH (5 mL). This was followed by the addition of sulfuric acid (1 mL) dropwise with stirring at 0° C. The resulting solution was stirred for 18 h at 60° C. in an oil bath. The resulting mixture was concentrated under vacuum. The residue was dissolved in 20 mL of H$_2$O. The resulting solution was extracted with 50 mL of EtOAc and the combined organic layers were dried over anhydrous MgSO$_4$. The residue was purified on a C$_{18}$ column eluting with CH$_3$CN/water (2:3) to afford 466 mg (81% yield) of a single isomer of methyl 1'-[(4-methanesulfonylphenyl)methyl]-2'-oxo-3,4-dihydro-1H-spiro[naphthalene-2,3'-pyrrolidine]-7-carboxylate as a white solid. $^1$H NMR (400 MHz, DMSO-d6) δ (ppm): 8.00-7.98 (d, J=8.0 Hz, 2H), 7.80-7.76 (m, 2H), 7.55-7.57 (d, J=8.4 Hz, 2H), 7.26-7.24 (d, J=8.0 Hz, 1H), 4.64 (s, 2H), 3.89 (s, 3H), 3.35-3.33 (m, 2H), 3.15 (s, 3H), 3.10-3.02 (m, 3H), 2.79-2.75 (d, J=16.4 Hz, 1H), 2.12-2 (m, 2H), 1.92-1.78 (m, 2H). MS: (ES, m/z): 428 [M+H]$^+$. A sample was recrystallized from EtOAc/hexanes (~1:1) and submitted for small molecule X-ray crystallography, which showed the material to be methyl (R)-1'-[(4-methanesulfonylphenyl)methyl]-2'-oxo-3,4-dihydro-1H-spiro[naphthalene-2,3'-pyrrolidine]-7-carboxylate (see Example 44). Thus, the first eluting isomer of Step 1 was assigned as methyl (S)-2'-oxo-3,4-dihydro-1H-spiro[naphthalene-2,3'-pyrrolidine]-7-carboxylate and the second eluting isomer of Step 1 was assigned as methyl (R)-2'-oxo-3,4-dihydro-1H-spiro[naphthalene-2,3'-pyrrolidine]-7-carboxylate.

Example 9

Preparation of (S)-1'-(1H-benzo[d]imidazol-2-yl)-N-hydroxy-2'-oxo-3,4-dihydro-1H-spiro[naphthalene-2,3'-pyrrolidine]-7-carboxamide (II-31)

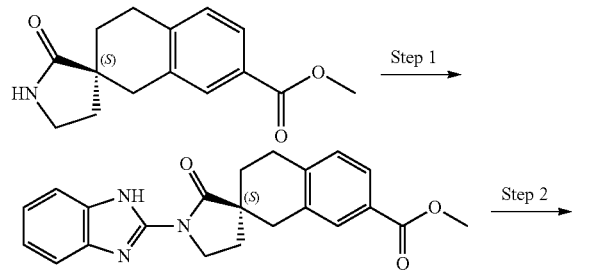

Step-1: (S)-Methyl 1'-(1H-benzo[d]imidazol-2-yl)-2'-oxo-3,4-dihydro-H-spiro[naphthalene-2,3'-pyrrolidine]-7-carboxylate Into a 10-mL sealed tube purged and maintained with an inert atmosphere of nitrogen, was placed 2-bromo-1H-1,3-benzodiazole (48 mg, 0.24 mmol, 1 equiv), (S)-methyl 2'-oxo-3,4-dihydro-1H-spiro[naphthalene-2,3'-pyrrolidine]-7-carboxylate (73 mg, 0.28 mmol, 2 equiv), Pd$_2$(dba)$_3$ (10 mg, 0.01 mmol, 0.05 equiv), XantPhos (10 mg, 0.02 mmol, 0.10 equiv), Cs$_2$CO$_3$(180 mg, 0.55 mmol, 3 equiv), and toluene (3 mL). The resulting mixture was stirred for 10 h at 110° C. in an oil bath. The reaction mixture was cooled to 20° C. with an ice-water bath. The solids were filtered out. The filtrate was concentrated and the residue was purified by normal phase chromatography on silica gel with EtOAc/petroleum ether (1:1). The collected fractions were concentrated to give 37 mg (40% yield) of the title compound as a colorless oil. MS: (ES, m/z): 376 [M+H]$^+$.

Step-2: (S)-1'-(1H-Benzo[d]imidazol-2-yl)-N-hydroxy-2'-oxo-3,4-dihydro-1H-spiro[naphthalene-2,3'-pyrrolidine]-7-carboxamide Into a 10-mL round-bottom flask was placed (S)-methyl 1'-(1H-benzo[d]imidazol-2-yl)-2'-oxo-3,4-dihydro-1H-spiro[naphthalene-2,3'-pyrrolidine]-7-carboxylate (37 mg, 0.10 mmol, 1 equiv), THF/MeOH (4:1, 2.5 mL), NH$_2$OH (50% in water, 0.5 mL, 75 equiv), and aq. 1N NaOH (0.3 mL, 3 equiv). The resulting solution was stirred for 3 h at room temperature. The reaction mixture was cooled to 0° C. with an ice-water bath. The pH value of the solution was adjusted to 7.0 with 1N HCl. The solids were filtered out. The crude product was purified by Prep-HPLC with the following conditions: Column: XBridge C18, 19×150 mm, 5 μm; Mobile Phase A: Water/0.05% TFA, Mobile Phase B: CH$_3$CN/0.05% TFA; Flow rate: 25 mL/min; Gradient: 5% B to 37% B in 7.0 min; Detector: 254 nm. The collected fractions were lyophilized to give 9.5 mg (20% yield) of the title compound as an off-white solid. $^1$H NMR (400 MHz, DMSO-d6) δ (ppm): 11.14 (s, 1H), 7.55-7.51 (m, 4H), 7.22-7.17 (m, 3H), 4.09-4.00 (m, 2H), 3.05-2.85 (m, 4H), 2.19-2.14 (m, 1H), 2.04-1.89 (m, 3H). MS: (ES, m/z): 377 [M+H]$^+$.

Example 10

Preparation of (S)—N-hydroxy-1'-(1-(2-methoxyethyl)-1H-benzo[d]imidazol-2-yl)-2'-oxo-3,4-dihydro-1H-spiro[naphthalene-2,3'-pyrrolidine]-7-carboxamide (I-33)

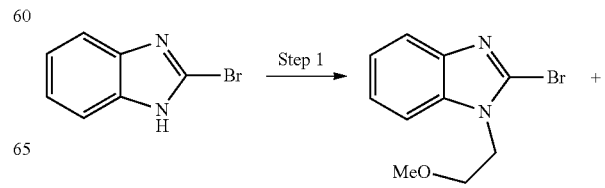

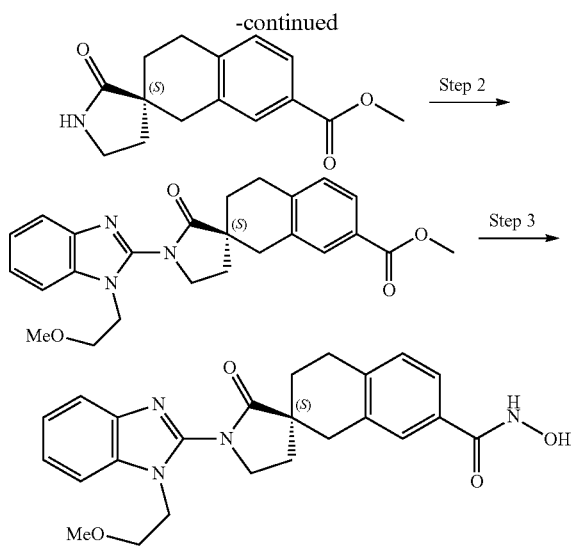

Step-1:
2-Bromo-1-(2-methoxyethyl)-1H-1,3-benzodiazole

Into a 250-mL round-bottom flask purged and maintained with an inert atmosphere of nitrogen, was placed 2-bromo-1H-1,3-benzodiazole (4.0 g, 20.30 mmol, 1 equiv) in DMF (100mL). This was followed by the addition of NaH (60% dispersion in oil, 1.6 g, 40 mmol, 2 equiv). The resulting mixture was stirred for 20 min at room temperature. To this mixture was added 1-bromo-2-methoxyethane (4.2 g, 30.22 mmol, 1.5 equiv). The reaction was stirred for 10 h at room temperature. The reaction mixture was cooled to 0° C. with an ice-water bath and quenched by the addition of 100 mL of water. The resulting solution was extracted with 3×100 mL of $CH_2Cl_2$. The combined organics were dried over anhydrous $Na_2SO_4$, filtered and concentrated under vacuum. The residue was purified by column chromatography on silica gel with EtOAc/petroleum ether (1:1). The collected fractions were concentrated to give 4.2 g (81% yield) of the title compound as a brown oil. MS: (ES, m/z): 255, 257 [M+H]$^+$.

Step-2: (S)-Methyl 1'-(1-(2-methoxyethyl)-1H-benzo[d]imidazol-2-yl)-2'-oxo-3,4-dihydro-1H-spiro[naphthalene-2,3'-pyrrolidine]-7-carboxylate Into a 10-mL sealed tube purged and maintained with an inert atmosphere of nitrogen, was placed (S)-methyl 72'-oxo-3,4-dihydro-1H-spiro[naphthalene-2,3'-pyrrolidine]-7-carboxylate (48 mg, 0.19 mmol, 1 equiv) in toluene (2 mL), 2-bromo-1-(2-methoxyethyl)-1H-1,3-benzodiazole (94 mg, 0.37 mmol, 2 equiv), CuI (3.5 mg, 0.02 mmol, 0.1 equiv), $Cs_2CO_3$ (182 mg, 0.56 mmol, 3 equiv) and (1R,2R)-1-N,2-N-dimethylcyclohexane-1,2-diamine (5 mg, 0.04 mmol, 0.2 equiv). The resulting mixture was stirred for 10 h at 110° C. in an oil bath. The solids were filtered out and the filtrate was concentrated. The residue was purified by column chromatography on silica gel with EtOAc/petroleum ether (1:1). The collected fractions were concentrated to give 52 mg (65% yield) of the title compound as a colorless oil. MS: (ES, m/z): 434 [M+H]$^+$.

Step-3: (S)—N-Hydroxy-1'-(1-(2-methoxyethyl)-1H-benzo[d]imidazol-2-yl)-2'-oxo-3,4-dihydro-1H-spiro[naphthalene-2,3'-pyrrolidine]-7-carboxamide Into a 10-mL round-bottom flask was placed (S)-methyl 1'-(1-(2-methoxyethyl)-1H-benzo[d]imidazol-2-yl)-2'-oxo-3,4-dihydro-1H-spiro[naphthalene-2,3'-pyrrolidine]-7-carboxylate (52 mg, 0.12 mmol, 1 equiv), THF/MeOH (4:1, 2.5 mL), $NH_2OH$ (50% in water, 0.5 mL, 63equiv), and aq. 1N NaOH (0.3 mL, 2.5 equiv). The resulting solution was stirred for 3 h at room temperature. The reaction mixture was cooled to 0° C. with an ice-water bath. The pH of the solution was adjusted to 7.0 with 1N HCl. The solids were filtered out. The crude product was purified by Prep-HPLC with the following conditions: Column: XBridge C18, 19×150 mm, 5μm; Mobile Phase A: Water/0.05% TFA, Mobile Phase B: $CH_3CN$/0.05% TFA; Flow rate: 25mL/min; Gradient: 5% B to 46% B in 7.0 min; Detector: 254 nm. The collected fractions were lyophilized to give 35 mg (66% yield) of the title as an off-white solid. $^1$H NMR (400 MHz, DMSO-d6) δ (ppm): 11.14 (s, 1H), 7.65-7.51 (m, 4H), 7.31-7.20 (m, 3H), 4.34 (t, J=5.2 Hz, 2H), 3.99-3.89 (m, 2H), 3.61 (t, J=5.2 Hz, 2H), 3.20 (s, 3H), 3.01-2.86 (m, 4H), 2.22-2.15 (m, 1H), 2.03-1.96 (m, 3H). MS: (ES, m/z): 435 [M+H]$^+$.

Example 11

Preparation of (S)-1'-benzyl-N-hydroxy-2'-oxo-3,4-dihydro-1H-spiro[naphthalene-2,3'-pyrrolidine]-7-carboxamide (I-35)

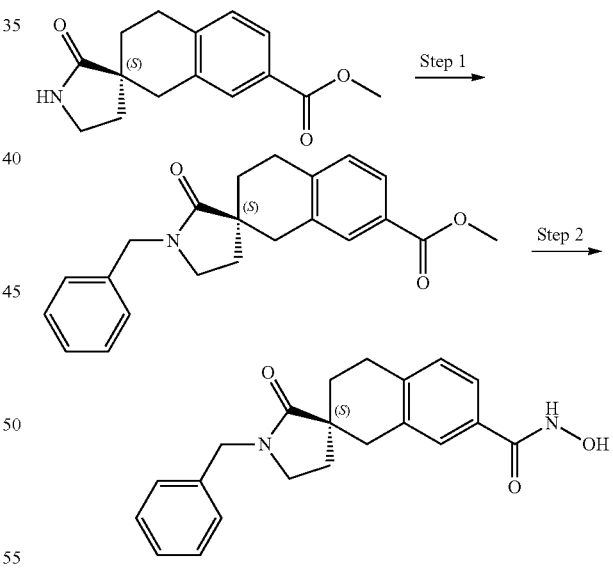

Step-1: Methyl (S)-1'-benzyl-2'-oxo-3,4-dihydro-1H-spiro[naphthalene-2,3'-pyrrolidine]-7-carboxylate Into a 25-mL round-bottom flask was placed methyl (S)-2'-oxo-3,4-dihydro-1H-spiro[naphthalene-2,3'-pyrrolidine]-7-carboxylate (40 mg, 0.15 mmol, 1 equiv) in DMF (4 mL), (bromomethyl)benzene (41 mg, 0.24 mmol, 1.5 equiv), and NaH (9.26 mg, 0.39 mmol, 2.5equiv). The resulting mixture was stirred for 3 h at room temperature. The reaction mixture was cooled to 0° C. in an ice-water bath and then quenched by the addition of 25 mL of water. The resulting solution was extracted with 3×50 mL of EtOAc. The combined organics were washed with 2×50 mL of water and 1×50 mL of brine. The organic layer was dried over anhydrous Na$_2$SO$_4$, filtered and concentrated under vacuum. The residue was purified by normal phase chromatography on silica gel with CH$_2$Cl$_2$/MeOH (20:1). The collected fractions were concentrated to give 58 mg of the title compound as a light yellow solid. MS: (ES, m/z): 350[M+H]$^+$.

Step-2: (S)-1'-Benzyl-N-hydroxy-2'-oxo-3,4-dihydro-1H-spiro[naphthalene-2,3'-pyrrolidine]-7-carboxamide Into a 25-mL round-bottom flask was placed methyl (S)-1'-benzyl-2'-oxo-3,4-dihydro-1H-spiro[naphthalene-2,3'-pyrrolidine]-7-carboxylate (58 mg, 0.17 mmol, 1 equiv), THF/MeOH (4:1, 2 mL), NH$_2$OH (50% in water, 329 mg, 9.96 mmol, 30 equiv), and aq. 1N NaOH (0.33 mL, 2 equiv). The resulting solution was stirred for 1.5 h at room temperature. The reaction mixture was cooled to 0° C. with an ice-water bath. The pH of the solution was adjusted to 6 with 1N HCl. The crude product was purified by Prep-HPLC with the following conditions: Column: XBridge C18, 19×150 mm, 5 μm; Mobile Phase A: Water/0.05% TFA, Mobile Phase B: CH$_3$CN/0.05% TFA; Flow rate: 25 mL/min; Gradient: 5% B to 54% B in 7.0 min; Detector: 254 nm. The collected fractions were lyophilized to give 24.3 mg (42% yield) of the title compound as a pink solid. $^1$H NMR (400 MHz, DMSO-d6) δ (ppm): 11.10 (s, 1H), 7.50-7.47 (d, 2H), 7.40-7.36 (m, 2H), 7.32-7.22 (m, 3H), 7.18-7.15 (d, J=7.8 Hz, 2H), 4.43 (s, 1H), 3.23-3.19(m, 2H), 2.95-2.73 (m, 3H), 2.66-2.60 (d, J=16.5 Hz, 1H), 1.94-1.82 (m, 2H), 1.74-1.63 (m, 2H). MS: (ES, m/z): 351 [M+H]$^+$.

TABLE 2

The following compounds were prepared according to the method of Example 11, with the following modification:
In Step 1, the halide can be a chloride or a bromide.

| Ex. | Structure | $^1$H NMR δ (ppm) | Found (ES, m/z) [M + H]$^+$ |
|---|---|---|---|
| I-122 | 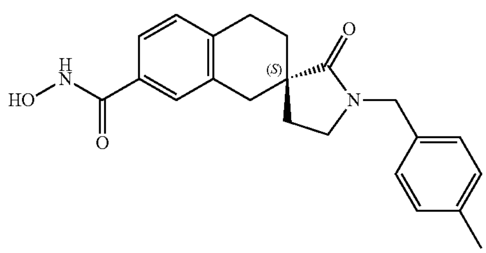 | (400 MHz, DMSO-d6): 11.08 (s, 1H), 8.96-8.95 (br s, 1H), 8.39 (s, 0.04H), 7.49-7.47 (d, J = 8.0 Hz, 2H), 7.19-7.11 (m, 5H), 4.37 (s, 2H), 3.22-3.16 (m, 2H), 2.93-2.75 (m, 3H), 2.63-2.59 (m, 1H), 2.33-2.29 (s, 3H), 1.90-1.84 (m, 2H), 1.69-1.61 (m, 2H) | 365 |
| I-71 | 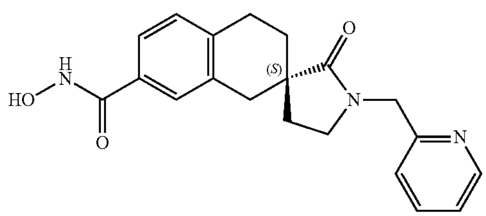 | (400 MHz, DMSO-d6): 11.11 (s, 1H), 8.61-8.59 (d, J = 8.0 Hz, 1H), 7.95-7.91 (m, 1H), 7.51-7.43 (m, 2H), 7.42-7.40 (m, 1H), 7.35-7.33 (m, 1H), 7.18-7.16 (m, 1H), 4.57 (s, 2H), 3.37-3.34 (m, 2H), 2.94-2.82 (m, 3H), 2.71-2.67 (m, 1H), 1.98-1.84 (m, 2H), 1.78-1.69 (m, 2H) | 352 |
| I-70 | 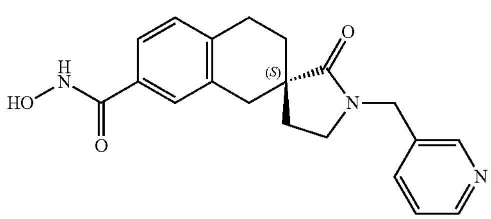 | (400 MHz, DMSO-d6): 11.20 (s, 1H), 8.69-8.66 (m, 2H), 8.05-7.96 (m, 1H), 7.72-7.71 (m, 1H), 7.50-7.47 (m, 2H), 7.18-7.16 (m, 1H), 4.56 (s, 2H), 3.31-3.28 (m, 2H), 2.93-2.76 (m, 3H), 2.68-2.64 (m, 1H), 1.96-1.85 (m, 2H), 1.79-1.67 (m, 2H) | 352 |
| I-124 | 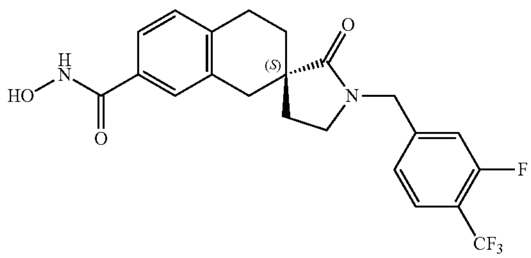 | (400 MHz, DMSO-d6): 11.16-11.09 (br s, 1H), 8.97-8.96 (br s, 1H), 7.83-7.79 (m, 1H), 7.51-7.48 (m, 2H), 7.38-7.35 (d, J = 12.0 Hz, 1H), 7.30-7.28 (d, J = 8.0 Hz, 1H), 7.19-7.17 (d, J = 8.0 Hz, 1H), 4.54 (s, 2H), 3.32-3.27 (m, 2H), 2.94-2.78 (m, 3H), 2.71-2.67 (d, J = 16.0 Hz, 1H), 1.98-1.84 (m, 2H), 1.77-1.71 (m, 2H) | 437 |

TABLE 2-continued

The following compounds were prepared according to the method of Example 11, with the following modification:
In Step 1, the halide can be a chloride or a bromide.

| Ex. | Structure | ¹H NMR δ (ppm) | Found (ES, m/z) [M + H]⁺ |
|---|---|---|---|
| I-39 | 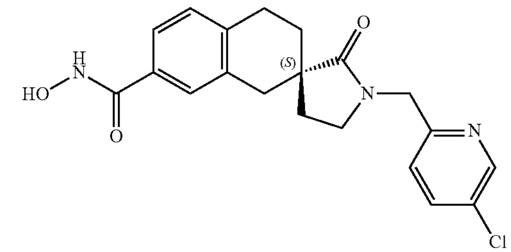 | (300 MHz, DMSO-d6): 11.09 (s, 1H), 8.84 (s, 1H), 7.94 (d, J = 6.9 Hz, 1H), 7.50-7.47 (m, 2H), 7.31 (d, J = 8.4 Hz, 1H), 7.71 (d, J = 8.4 Hz, 1H), 4.53 (s, 2H), 3.34 (t, J = 6.6 Hz, 2H), 2.94-2.79 (m, 3H), 2.72-2.50 (m, 1H), 1.98-1.91 (m, 2H), 1.89-1.81 (m, 2H) | 386 |
| I-49 | 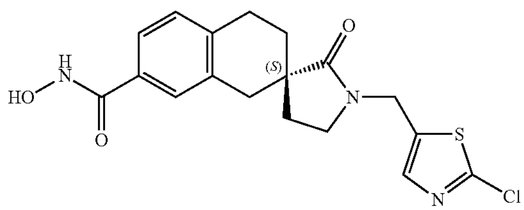 | (400 MHz, DMSO-d6): 11.08 (s, 1H), 7.64 (s, 1H), 7.46-7.48 (m, 2H), 7.15-7.17 (dd, J = 8 Hz, 1H), 4.60 (s, 2H), 3.29-3.32 (t, J = 6.8 Hz, 2H), 2.79-2.90 (m, 3H), 2.50-2.58 (m, 1H), 1.80-1.90 (m, 2H), 1.77-1.80 (m, 2H) | 392 |
| I-50 | 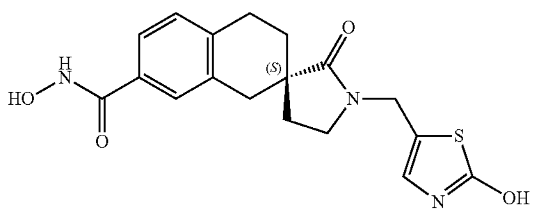 | (400 MHz, DMSO-d6): 11.02-11.09 (m, 2H), 8.94 (s, 1H), 7.49-7.47 (m, 2H), 7.14-7.16 (d, J = 8 Hz, 1H), 6.83-6.85 (d, J = 8 Hz, 1H), 4.27 (s, 2H), 3.23-3.26 (t, J = 7.2 Hz, 2H), 2.80-2.89 (m, 3H), 2.57-2.66 (m, 1H), 1.80-1.92 (m, 2H), 1.70-1.79 (m, 1H), 1.63-1.69 (m, 1H) | 374 |
| I-45 | 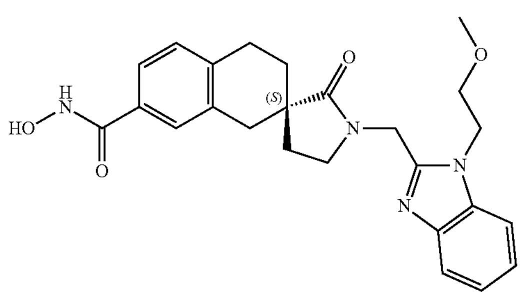 | (400 MHz, DMSO-d6): 11.10 (s, 1H), 7.83-7.76 (m, 2H), 7.51-7.45 (m, 4H), 7.19 (d, J = 8.4 Hz, 1H), 4.93 (s, 2H), 4.63 (s, 2H), 3.72 (s, 2H), 3.46 (s, 2H), 3.24 (s, 3H), 2.94-2.70 (m, 4H), 2.01-1.87 (m, 4H) | 449 |

Example 12

Preparation of (S)-1'-(benzo[c][1,2,5]oxadiazol-5-ylmethyl)-N-hydroxy-2'-oxo-3,4-dihydro-1H-spiro[naphthalene-2,3'-pyrrolidine]-7-carboxamide (I-63)

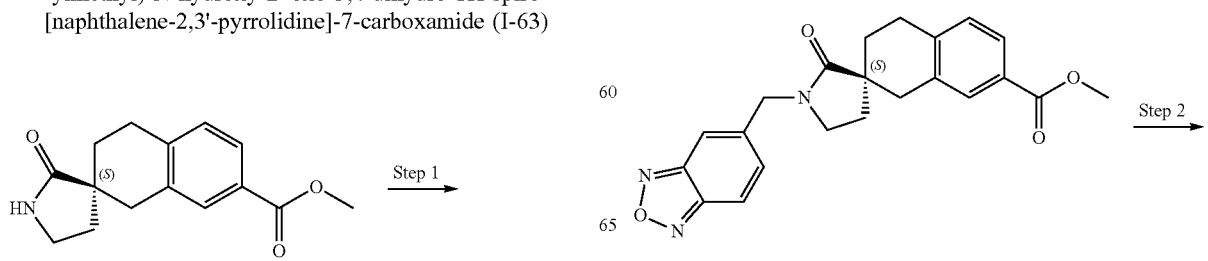

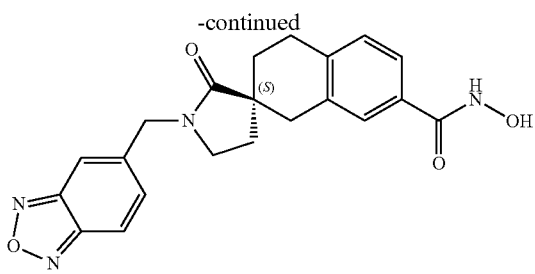

Step-1: (S)-1'-(Benzo[c][1,2,5]oxadiazol-5-ylmethyl)-2'-oxo-3,4-dihydro-1H-spiro[naphthalene-2,3'-pyrrolidine]-7-carboxylic acid Into a 25-mL 3-necked round-bottom flask purged and maintained with an inert atmosphere of nitrogen, was placed a solution of methyl (S)-2'-oxo-3,4-dihydro-1H-spiro[naphthalene-2,3'-pyrrolidine]-7-carboxylate (330 mg, 1.27 mmol, 1 equiv) in DMF (4 mL). This was followed by the portion wise addition of NaH (60% dispersion in oil, 127 mg, 5.29mmol, 2.5 equiv) at −5° C. with stirring for 30 min. To this mixture was added a solution of 5-(bromomethyl)-2,1,3-benzoxadiazole (405 mg, 1.90 mmol, 1.5 equiv) in DMF (0.5 mL). The resulting mixture was stirred for 5 h at room temperature. The reaction was then quenched by the addition of 2 mL of aq. NH$_4$Cl at 0° C. and diluted with 30 mL of H$_2$O. The resulting solution was extracted with 30 mL of EtOAc and the aqueous layers were combined. The pH value of the solution was adjusted to 3 with 3N HCl. The resulting solution was extracted with 3×25 mL of EtOAc. The organics were combined and dried over anhydrous Na$_2$SO$_4$, filtered and concentrated under vacuum. The residue was purified by normal phase column chromatography on silica gel with CH$_2$Cl$_2$/MeOH (18:1). The collected fractions were concentrated to give 97 mg (20% yield) of the title compound as a brown solid. MS: (ES, m/z): 378 [M+H]$^+$.

Step-2: (S)-1'-(Benzo[c][1,2,5]oxadiazol-5-ylmethyl)-N-hydroxy-2'-oxo-3,4-dihydro-1H-spiro[naphthalene-2,3'-pyrrolidine]-7-carboxamide Into an 8-mL vial, was placed a solution of (S)-1'-(benzo[c][1,2,5]oxadiazol-5-ylmethyl)-2'-oxo-3,4-dihydro-1H-spiro[naphthalene-2,3'-pyrrolidine]-7-carboxylic acid (97 mg, 0.26 mmol, 1 equiv) in DMA (3 mL). This was followed by the addition of isopropyl chloroformate (162 mg, 1.32 mmol, 5 equiv), and the dropwise addition of NMM (130 mg, 1.29mmol, 5 equiv) with stirring at 0° C. To the mixture was added dropwise a solution of NH$_2$OH*HCl (90 mg, 1.29 mmol, 5 equiv) in DMA (0.5 mL) with stirring at 0° C. The resulting solution was stirred for 22 h at room temperature. The crude product was purified by Prep-HPLC with the following conditions: Column: Sunfire C18 5 µm, 19×150 mm; Mobile Phase A: Water/0.1% TFA, Mobile Phase B: CH$_3$CN/0.1% TFA, Gradient: 20% B to 38% B in 10 min; Flow rate: 25 mL/min; Detector: UV 254, 220 nm. The collected fractions were lyophilized to give 27 mg (27% yield) of the title compound as an off-white solid. $^1$H NMR (400 MHz, DMSO-d6) δ (ppm): 11.21 (br s, 1H), 8.10-8.07 (d, J=12.0 Hz, 1H), 7.85 (s, 1H), 7.51-7.43 (m, 3H), 7.19-7.17 (d, J=8.0 Hz, 1H), 4.57 (s, 2H), 3.35-3.31 (m, 2H), 2.96-2.81 (m, 3H), 2.80-2.69 (m, 1H), 1.99-1.85 (m, 2H), 1.79-1.71 (m, 2H). MS: (ES, m/z): 393 [M+H]$^+$.

TABLE 3

The following compound was prepared according to the method of Example 12.

| Ex. | Structure | $^1$H NMR δ (ppm) | Found (ES, m/z) [M + H]$^+$ |
|---|---|---|---|
| I-126 | (structure shown) | (400 MHz, DMSO-d6): 11.18-10.98 (br s, 1H), 9.04-8.88 (br s, 1H), 7.81-7.74 (d, J = 28 Hz, 2H), 7.51-7.43 (m, 4H), 7.18-7.13 (d, J = 20 Hz, 1H), 4.53-4.49 (s, 2H), 3.32-3.21 (m, 2H), 2.95-2.77 (m, 3H), 2.69-2.65 (d, J = 16 Hz, 1H), 1.96-1.84 (m, 2H), 1.76-1.67 (m, 2H) | 419 |

Example 13

Preparation of (S)—N-hydroxy-2'-oxo-1'-(pyridin-2-yl)-3,4-dihydro-1H-spiro[naphthalene-2,3'-pyrrolidine]-7-carboxamide (I-44)

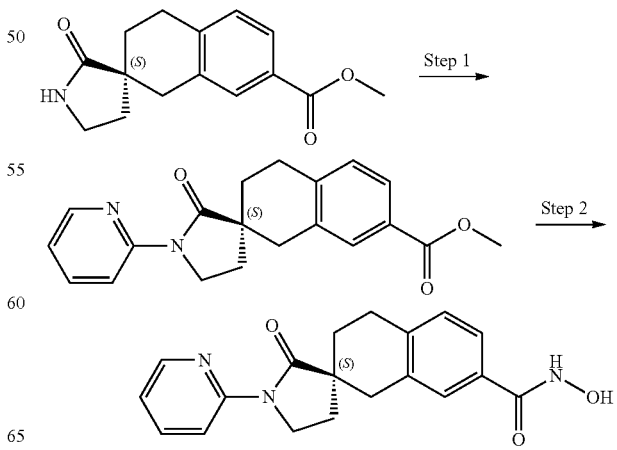

Step-1: Methyl (S)-2'-oxo-1'-(pyridin-2-yl)-3,4-dihydro-1H-spiro[naphthalene-2,3'-pyrrolidine]-7-carboxylate Into a 100-mL round-bottom flask was placed methyl (S)-2'-oxo-3,4-dihydro-1H-spiro[naphthalene-2,3'-pyrrolidine]-7-carboxylate (100 mg, 0.39 mmol, 1 equiv) in 1,4-dioxane (6 mL), Pd(OAc)$_2$ (40 mg, 0.18 mmol, 0.5 equiv), XantPhos (70 mg, 0.12 mmol, 0.3 equiv), Cs$_2$CO$_3$ (190 mg, 0.58 mmol, 1.5 equiv) and 2-bromopyridine (91 mg, 0.58 mmol, 1.5 equiv). The resulting mixture was stirred overnight at 101° C. The solids were filtered out. The filtrate was concentrated and the residue was purified by normal phase chromatography on silica gel with EtOAc/petroleum ether (1:6). The collected fractions were concentrated to give 80 mg (62% yield) of the title compound as a white solid. MS: (ES, m/z): 337 [M+H]$^+$.

Step-2: (S)—N-Hydroxy-2'-oxo-1'-(pyridin-2-yl)-3,4-dihydro-1H-spiro[naphthalene-2,3'-pyrrolidine]-7-carboxamide Into a 100-mL round-bottom flask was placed methyl (S)-2'-oxo-1'-(pyridin-2-yl)-3,4-dihydro-1H-spiro[naphthalene-2,3'-pyrrolidine]-7-carboxylate (80 mg, 0.24 mmol, 1 equiv) in THF/MeOH (4:1, 1.25 mL), NH$_2$OH (50% in water, 1.53 g, 46.26 mmol, 96 equiv), and aq. 1N NaOH (0.5 mL, 2 equiv). The resulting solution was stirred for 3 h at room temperature. 1N HCl was added to adjust to pH 4. The crude product was purified by Prep-HPLC with the following conditions: Column: Waters HSS C18, 2.1×50 mm, 1.8 μm; Mobile Phase A: Water/0.05% TFA, Mobile Phase B: CH$_3$CN/0.05% TFA; Flow rate: 0.7 mL/min; Gradient: 5% B to 95% B in 2.0 min, hold 0.6 min; Detector: UV 254 nm. The collected fractions were lyophilized to give 25mg (23% yield) of the title compound as a pink solid. $^1$H NMR (400 MHz, DMSO-d6) δ (ppm): 11.10 (s, 1H), 8.42-8.41 (d, J=4 Hz, 1H), 8.36-8.34 (d, J=8.4 Hz, 1H), 7.86-7.82 (m, 1H), 7.51-7.49 (d, J=8.8 Hz, 2H), 7.23-7.15 (m, 2H), 4.03-3.99 (t, J=6.4 Hz, 2H), 2.99-2.80 (m, 4H), 2.06-1.81 (m, 4H). MS: (ES, m/z): 338 [M+H]$^+$.

Example 14

Preparation of (S)—N-hydroxy-2'-oxo-3,4-dihydro-1H-spiro[naphthalene-2,3'-pyrrolidine]-7-carboxamide (I-47)

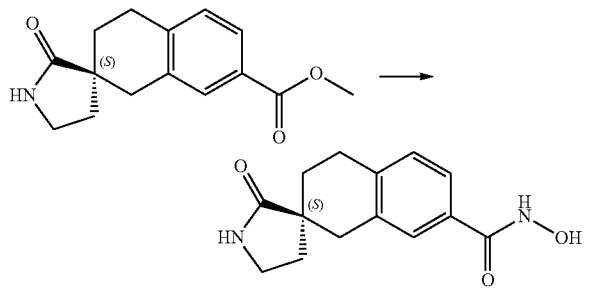

A mixture of methyl (S)-2'-oxo-3,4-dihydro-1H-spiro[naphthalene-2,3'-pyrrolidine]-7-carboxylate (100 mg, 0.39 mmol, 1 equiv) in THF/MeOH (4:1, 2.5 mL), NH$_2$OH (50% in water, 1.52 mL, 60 equiv), and aq. 1N NaOH (0.77 mL, 2 equiv) was stirred for 1.5 h at room temperature. The crude product was purified by Prep-HPLC with the following conditions: Column: Waters HSS C18, 2.1×50 mm, 1.8 μm; Mobile Phase A: Water/0.05% Formic Acid, Mobile Phase B: CH$_3$CN/0.05% Formic Acid; Flow rate: 0.7 mL/min; Gradient: 5% B to 95% B in 2.0 min, hold 0.6 min; Detector: UV 254 nm. The collected fractions were lyophilized to give 46.9 mg (40% yield) of the title compound as a pink solid. $^1$H NMR (400 MHz, DMSO-d6) δ (ppm): 11.09 (s, 1H), 8.95 (s, 1H), 7.66 (s, 1H), 7.46-7.49 (m, 2H), 7.15-7.16 (d, J=8 Hz, 1H), 3.19-3.22 (t, J=6 Hz, 2H), 2.74-2.90 (m, 3H), 2.58-2.67 (m, 1H), 1.91-1.95 (m, 1H), 1.80-1.90(m, 2H), 1.72-1.79 (m, 1H). MS: (ES, m/z): 261 [M+H]$^+$.

Example 15

Preparation of (S)—N-hydroxy-1'-methyl-2'-oxo-3,4-dihydro-1H-spiro[naphthalene-2,3'-pyrrolidine]-7-carboxamide (I-121)

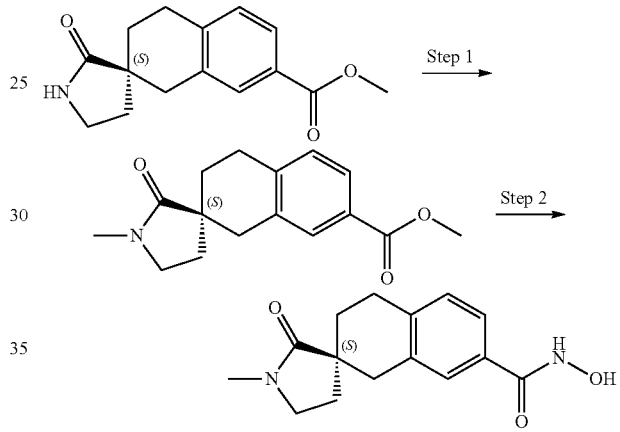

Step-1: Methyl (S)-1'-methyl-2'-oxo-3,4-dihydro-1H-spiro[naphthalene-2,3'-pyrrolidine]-7-carboxylate Into a 10-mL round-bottom flask was placed a solution of methyl (S)-2'-oxo-3,4-dihydro-1H-spiro[naphthalene-2,3'-pyrrolidine]-7-carboxylate (100 mg, 0.39 mmol, 1 equiv) in DMF (4 mL). This was followed by the addition of NaH (60% dispersion in oil, 50 mg, 2.08mmol, 3 equiv) at 0° C. The resulting mixture stirred at room temperature for 10 min. CH$_3$I (80mg, 0.56 mmol, 1.5 equiv) was added at 0° C. and the reaction was stirred for 3 h at room temperature. The reaction was then quenched by the addition of 3 mL of H$_2$O. The resulting solution was extracted with 3×10 ml of EtOAc. The organic layers were combined and concentrated under vacuum. The residue was purified by normal phase chromatography on silica gel with EtOAc/petroleum ether (1:1). The collected fractions were concentrated to give 80 mg (76% yield) of the title compound as a light yellow solid. MS: (ES, m/z): 274 [M+H]$^+$.

Step-2: (S)—N-Hydroxy-1'-methyl-2'-oxo-3,4-dihydro-1H-spiro[naphthalene-2,3'-pyrrolidine]-7-carboxamide Into a 10-mL vial, was placed a solution of methyl (S)-1'-methyl-2'-oxo-3,4-dihydro-1H-spiro[naphthalene-2, 3'-pyrrolidine]-7-carboxylate (80 mg, 0.29 mmol, 1 equiv) in THF/MeOH (4:1, 3 mL). This was followed by the addition of NH$_2$OH (50% in water, 0.58 mL, 30 equiv) and aq. 1N NaOH (0.58 mL, 2 equiv). The resulting solution was stirred for 3 h at room temperature. The mixture was purified by Prep-HPLC using the following conditions: Column: XBridge C18, 19×150 mm, 5 μm; Mobile Phase A: Water/0.05% TFA, Mobile Phase B: CH$_3$CN/0.05% TFA; Gradient: 17% B to 35% B in 8 min; Detector: UV 254 nm, 220 nm. Fractions were combine and the solvent was lyophilized to give 27.6 mg (34% yield) of the title compound as a purple solid. $^1$H NMR (400 MHz, DMSO-d6) δ (ppm): 11.80 (s, 1H), 8.94 (s, 1H), 7.47-7.46 (m, 2H), 7.16-7.14 (m, 1H), 3.32-3.29 (m, 2H), 2.91-2.80 (m, 3H), 2.79 (s, 3H), 2.60-2.56 (m, 1H), 1.91-1.81 (m, 2H), 1.70-1.52 (m, 2H). MS: (ES, m/z): 275 [M+H]$^+$.

Example 16

Preparation of (R)—N-hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-7-carboxamide (I-46)

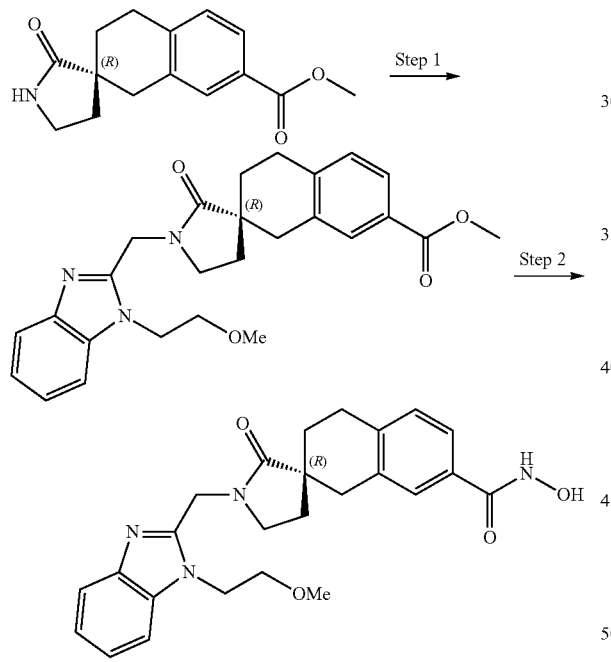

Step-1: Methyl (R)-1'-((1-(2-methoxyethyl)-1H-benzo[d]imidazol-2-yl)methyl)-2'-oxo-3,4-dihydro-1H-spiro[naphthalene-2,3'-pyrrolidine]-7-carboxylate Into a 50-mL round-bottom flask was placed methyl (R)-2'-oxo-3,4-dihydro-1H-spiro[naphthalene-2,3'-pyrrolidine]-7-carboxylate (200 mg, 0.77 mmol, 1 equiv) in DMF (5 mL). This was followed by the addition of NaH (60% dispersion in oil, 37 mg, 1.54 mmol, 2 equiv) at 0° C. over 30 min. 2-(Chloromethyl)-1-(2-methoxyethyl)-1H-1,3-benzodiazole (207 mg, 0.92mmol, 1.2 equiv) was added to the stirring solution at 0° C. The resulting solution was stirred for 2 h at 0° C. The reaction was then quenched by the addition of 50 mL of water and extracted with 3×100 mL of EtOAc. The organic layers were combined and dried over anhydrous Na$_2$SO$_4$, filtered and concentrated under vacuum. The residue was purified by normal phase chromatography on silica gel with EtOAc/petroleum ether (1:2). The collected fractions were concentrated to give 200 mg (58% yield) of the title compound as a yellow oil. MS: (ES, m/z): 448 [M+H]+.

Step-2: (R)—N-Hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-7-carboxamide Into a 50-mL round-bottom flask was placed methyl (R)-1'-((1-(2-methoxyethyl)-1H-benzo [d]imidazol-2-yl)methyl)-2'-oxo-3,4-dihydro-1H-spiro[naphthalene-2,3'-pyrrolidine]-7-carboxylate (80 mg, 0.18 mmol, 1 equiv) in THF/MeOH (4:1, 1.5 mL), NH$_2$OH (50% in water, 0.6 g, 50 equiv), and aq. 1N NaOH (0.36 mL, 2 equiv). The resulting solution was stirred for 1 h at room temperature. The crude product was purified with the following conditions: Column: Waters HSS C18, 2.1×50 mm, 1.8 μm; Mobile Phase A: Water/0.05% TFA, Mobile Phase B: CH$_3$CN/0.05% TFA; Flow rate: 0.7 mL/min; Gradient: 5% B to 95% B in 2.0 min, hold 0.6 min; Detector: UV 254 nm. The collected fractions were lyophilized to give 22 mg (22% yield) of the title compound as a white solid. $^1$H NMR (400 MHz, DMSO-d6) δ (ppm): 11.11 (s, 1H), 7.80-7.74 (m, 2H), 7.51-7.38 (m, 4H), 7.19 (d, J=8.4 Hz, 1H), 4.90 (s, 2H), 4.61 (s, 2H), 3.71 (s, 2H), 3.45-3.41 (m, 2H), 3.24 (s, 3H), 2.94-2.69 (m, 4H), 2.0-1.86 (m, 4H). MS: (ES, m/z): 449[M+H]$^+$.

Example 17

Preparation of (R)-1'-(1H-benzo[d]imidazol-2-yl)-N-hydroxy-2'-oxo-3,4-dihydro-1H-spiro[naphthalene-2,3'-pyrrolidine]-7-carboxamide (I-32)

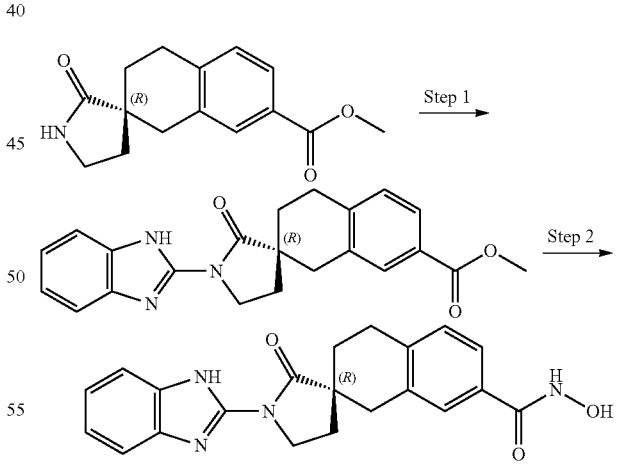

Step-1: Methyl (R)-1'-(1H-benzo[d]imidazol-2-yl)-2'-oxo-3,4-dihydro-1H-spiro[naphthalene-2,3'-pyrrolidine]-7-carboxylate Into a 10-mL sealed tube purged and maintained with an inert atmosphere of nitrogen, was placed 2-bromo-1H-1,3-benzodiazole (73 mg, 0.37 mmol, 2 equiv), methyl (R)-2'-oxo-3,4-dihydro-1H-spiro[naphthalene-2,3'-pyrrolidine]-7- carboxylate (48 mg, 0.19 mmol, 1 equiv), Pd$_2$(dba)$_3$ (10 mg, 0.01 mmol, 0.05 equiv), XantPhos (10 mg, 0.02 mmol, 0.10 equiv), Cs$_2$CO$_3$ (180 mg, 0.55 mmol, 3 equiv), and toluene (3 mL). The resulting mixture was stirred for 10 h at 110° C. in an oil bath. The reaction mixture was cooled to 20° C. with an ice-water bath. The solids were filtered out. The filtrate was concentrated and the residue was purified by normal phase chromatography on silica gel with EtOAc/petroleum ether (1:1). The collected fractions were concentrated to give 42 mg (60% yield) of the title compound as a colorless oil. MS: (ES, m/z): 376 [M+H]$^+$.

Step-2: (R)-1'-(1H-benzo[d]imidazol-2-yl)-N-hydroxy-2'-oxo-3,4-dihydro-1H-spiro[naphthalene-2,3'-pyrrolidine]-7-carboxamide Into a 10-mL round-bottom flask was placed methyl (R)-1'-(1H-benzo[d]imidazol-2-yl)-2'-oxo-3,4-dihydro-1H-spiro[naphthalene-2,3'-pyrrolidine]-7-carboxylate (42 mg, 0.11 mmol, 1 equiv), THF/MeOH (4:1, 2.5 mL), NH$_2$OH (50% in water, 0.5 mL, 70 equiv), and aq. 1N NaOH (0.3 mL, 2.7 equiv). The resulting solution was stirred for 3 h at room temperature. The reaction mixture was cooled to 0° C. with an ice-water bath. The pH value of the solution was adjusted to 7.0 with 1N HCl. The solids were filtered out. The crude product was purified by Prep-HPLC with the following conditions: Column: XBridge C18, 19×150 mm, 5 µm; Mobile Phase A: Water/0.05% TFA, Mobile Phase B: CH$_3$CN/0.05% TFA; Flow rate: 25 mL/min; Gradient: 5% B to 37% B in 7.0 min; Detector: UV 254 nm. The collected fractions were lyophilized to give 3.4 mg (6% yield) of the title compound as an off-white solid. $^1$H NMR (400MHz, DMSO-d6) δ (ppm): 11.14 (s, 1H), 7.55-7.51 (m, 4H), 7.22-7.17 (m, 3H), 4.09-4.00 (m, 2H), 3.05-2.85 (m, 4H), 2.19-2.14 (m, 1H), 2.04-1.89 (m, 3H). MS: (ES, m/z): 377 [M+H]$^+$.

Example 18

Preparation of (R)—N-hydroxy-1'-(1-(2-methoxyethyl)-1H-benzo[d]imidazol-2-yl)-2'-oxo-3,4-dihydro-1H-spiro[naphthalene-2,3'-pyrrolidine]-7-carboxamide (I-34)

Step-1: Methyl (R)-1'-(1-(2-methoxyethyl)-1H-benzo[d]imidazol-2-yl)-2'-oxo-3,4-dihydro-1H-spiro[naphthalene-2,3'-pyrrolidine]-7-carboxylate Into a 10-mL sealed tube purged and maintained with an inert atmosphere of nitrogen, was placed methyl (R)-2'-oxo-3,4-dihydro-1H-spiro[naphthalene-2,3'-pyrrolidine]-7-carboxylate (48 mg, 0.19 mmol, 1 equiv) in toluene (2 mL), 2-bromo-1-(2-methoxyethyl)-1H-1,3-benzodiazole (94 mg, 0.37 mmol, 2 equiv), CuI (3.5 mg, 0.02 mmol, 0.10 equiv), Cs$_2$CO$_3$ (182mg, 0.56 mmol, 3 equiv) and (1R,2R)-1-N,2-N-dimethylcyclohexane-1,2-diamine (5 mg, 0.04mmol, 0.2 equiv). The resulting mixture was stirred for 10 h at 110° C. in an oil bath. The solids were filtered out. The filtrate was concentrated and the residue was purified by column chromatography on silica gel with EtOAc:petroleum ether (1:1). The collected fractions were concentrated to give 30 mg (37% yield) of the title compound as a colorless oil. MS: (ES, m/z): 434 [M+H]$^+$.

Step-2: (R)—N-Hydroxy-1'-(1-(2-methoxyethyl)-1H-benzo[d]imidazol-2-yl)-2'-oxo-3,4-dihydro-1H-spiro[naphthalene-2,3'-pyrrolidine]-7-carboxamide Into a 10-mL round-bottom flask was placed methyl (R)-1'-(1-(2-methoxyethyl)-1H-benzo[d]imidazol-2-yl)-2'-oxo-3,4-dihydro-1H-spiro[naphthalene-2,3'-pyrrolidine]-7-carboxylate (30 mg, 0.07 mmol, 1 equiv), THF/MeOH (4:1, 2.5 mL), NH$_2$OH (50% in water, 0.5 mL, 108equiv), and aq. 1N NaOH (0.3 mL, 4.2 equiv). The resulting solution was stirred for 3 h at room temperature. The reaction mixture was cooled to 0° C. with an ice-water bath. The pH value of the solution was adjusted to 7 with 1N HCl. The solids were filtered out. The crude product was purified by Prep-HPLC with the following conditions: Column: XBridge C18, 19×150 mm, 5µm; Mobile Phase A: Water/0.05% TFA, Mobile Phase B: CH$_3$CN/0.05% TFA; Flow rate: 25mL/min; Gradient: 5% B to 46% B in 7.0 min; Detector: UV 254 nm. The collected fractions were lyophilized to give 11.5 mg (30% yield) of the title compound as an off-white solid. $^1$H NMR (400 MHz, DMSO-d6) δ (ppm): 11.14 (s, 1H), 7.65-7.51 (m, 4H), 7.31-7.20 (m, 3H), 4.34 (t, J=5.2 Hz, 2H), 3.99-3.89 (m, 2H), 3.61 (t, J=5.2 Hz, 2H), 3.20 (s, 3H), 3.01-2.86 (m, 4H), 2.22-2.15 (m, 1H), 2.03-1.96 (m, 3H). MS: (ES, m/z): 435 [M+H]$^+$.

Example 19

Preparation of (R)-1'-benzyl-N-hydroxy-2'-oxo-3,4-dihydro-1H-spiro[naphthalene-2,3'-pyrrolidine]-7-carboxamide (I-36)

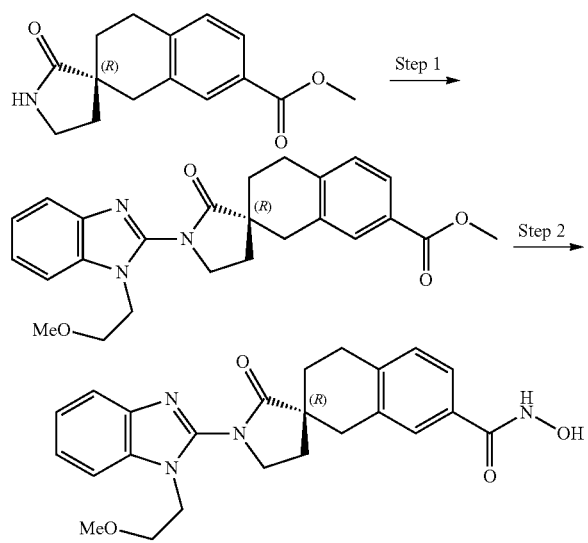

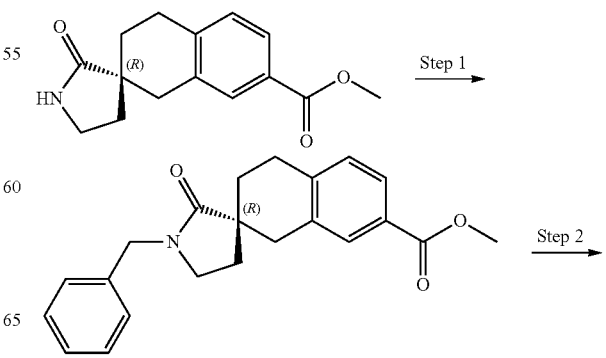

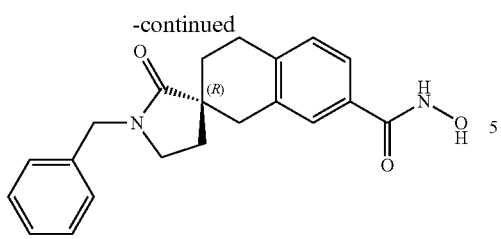

Step-1: Methyl (R)-1'-benzyl-2'-oxo-3,4-dihydro-1H-spiro[naphthalene-2,3'-pyrrolidine]-7-carboxylate Into a 25-mL round-bottom flask was placed methyl (R)-2'-oxo-3,4-dihydro-1H-spiro[naphthalene-2,3'-pyrrolidine]-7-carboxylate (40 mg, 0.15 mmol, 1 equiv) in DMF (4 mL), (bromomethyl)benzene (41 mg, 0.24 mmol, 1.5 equiv) and NaH (9.26 mg, 0.39 mmol, 2.5equiv). The resulting mixture was stirred for 3 h at room temperature. The reaction mixture was cooled to 0° C. in an ice-water bath and then quenched by the addition of 25 mL of water. The resulting solution was extracted with 3×50 mL of EtOAc. The combined organics were washed with 2×50 mL of water and 50 mL of brine. The organics were dried over anhydrous $Na_2SO_4$, filtered and concentrated under vacuum. The residue was purified by normal phase chromatography on silica gel with $CH_2Cl_2$/MeOH (20:1). The collected fractions were concentrated to give 46 mg (85% yield) of the title compound as a light yellow solid. MS: (ES, m/z): 350 [M+H]$^+$.

Step-2: (R)-1'-Benzyl-N-hydroxy-2'-oxo-3,4-dihydro-1H-spiro[naphthalene-2,3'-pyrrolidine]-7-carboxamide Into a 25-mL round-bottom flask was placed methyl (R)-1'-benzyl-2'-oxo-3,4-dihydro-1H-spiro[naphthalene-2,3'-pyrrolidine]-7-carboxylate (46 mg, 0.13 mmol, 1 equiv), THF/MeOH (4:1, 2 mL), $NH_2OH$ (50% in water, 261 mg, 7.90 mmol, 30 equiv), and aq. 1N NaOH (0.26 mL, 2 equiv). The resulting solution was stirred for 15 h at room temperature. The reaction mixture was cooled to 0° C. in an ice-water bath. The pH of the solution was adjusted to 6 with 1N HCl. The crude product was purified by Prep-HPLC with the following conditions: Column, XBridge C18, 19×150 mm, 5 μm; Mobile Phase A: Water/0.05% TFA, Mobile Phase B: $CH_3CN$/0.05% TFA; Flow rate: 25 mL/min; Gradient: 5% B to 54% B in 7.0 min; Detector: UV 254 nm. The collected fractions were lyophilized to give 15.7 mg (34% yield) of the title compound as a pink solid. $^1$H NMR (400 MHz, DMSO-d6) δ (ppm): 11.10 (s, 1H), 7.50-7.47 (d, 2H), 7.40-7.36 (m, 2H), 7.32-7.22 (m, 3H), 7.18-7.15 (d, J=7.8 Hz, 2H), 4.43 (s, 1H), 3.23-3.19(m, 2H), 2.95-2.73 (m, 3H), 2.66-2.60 (d, J=16.5 Hz, 1H), 1.94-1.82 (m, 2H), 1.74-1.63 (m, 2H). MS: (ES, m/z): 351 [M+H]$^+$.

TABLE 4

The following compounds were prepared according to the method of Example 19, with the following modification: In Step 1, the halide can be a chloride or a bromide.

| Ex. | Structure | $^1$H NMR δ (ppm) | Found (ES, m/z) [M + H]$^+$ |
|---|---|---|---|
| I-123 | 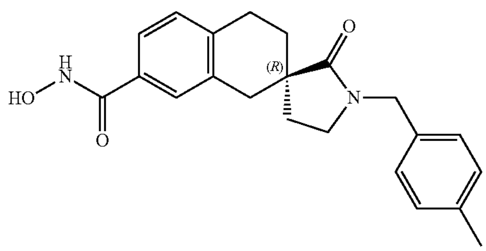 | (400 MHz, DMSO-d6): 11.08 (s, 1H), 8.96-8.95 (br s, 1H), 8.39 (s, 0.04H), 7.49-7.47 (d, J = 8.0 Hz, 2H), 7.19-7.11 (m, 5H), 4.37 (s, 2H), 3.22-3.16 (m, 2H), 2.93-2.75 (m, 3H), 2.63-2.59 (m, 1H), 2.33-2.29 (s, 3H), 1.90-1.84 (m, 2H), 1.69-1.61 (m, 2H) | 365 |
| I-98 | 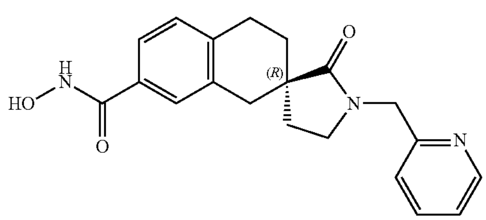 | (400 MHz, DMSO-d6): 11.11 (s, 1H), 8.61-8.59 (d, J = 8.0 Hz, 1H), 7.95-7.91 (m, 1H), 7.51-7.43 (m, 2H), 7.42-7.40 (m, 1H), 7.35-7.33 (m, 1H), 7.18-7.16 (m, 1H), 4.57 (s, 2H), 3.37-3.34 (m, 2H), 2.94-2.82 (m, 3H), 2.71-2.67 (m, 1H), 1.98-1.84 (m, 2H), 1.78-1.69 (m, 2H) | 352 |
| I-97 | 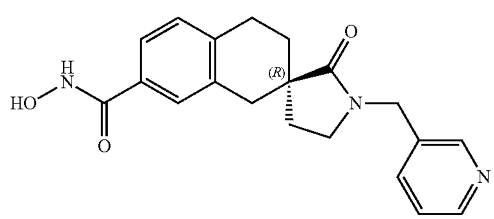 | (400 MHz, DMSO-d6): 11.20 (s, 1H), 8.69-8.66 (m, 2H), 8.05-7.96 (m, 1H), 7.72-7.71 (m, 1h), 7.50-7.47 (m, 2H), 7.18-7.16 (m, 1H), 4.56 (s, 2H), 3.31-3.28 (m, 2H), 2.93-2.76 (m, 3H), 2.68-2.64 (m, 1H), 1.96-1.85 (m, 2H), 1.79-1.67 (m, 2H) | 352 |

TABLE 4-continued

The following compounds were prepared according to the method of Example 19, with the following modification:
In Step 1, the halide can be a chloride or a bromide.

| Ex. | Structure | $^1$H NMR δ (ppm) | Found (ES, m/z) [M + H]$^+$ |
|---|---|---|---|
| I-40 | 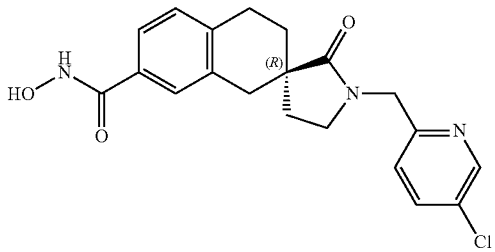 | (400 MHz, DMSO-d6): 11.09 (s, 1H), 8.84 (s, 1H), 7.94 (d, J = 6.9 Hz, 1H), 7.50-7.47 (m, 2H), 7.31 (d, J = 8.4 Hz, 1H), 7.17 (d, J = 8.4 Hz, 1H), 4.53 (s, 2H), 3.34 (t, J = 6.6 Hz, 2H), 2.94-2.79 (m, 3H), 2.72-2.50 (m, 1H), 1.98-1.91 (m, 2H), 1.89-1.81 (m, 2H) | 386 |
| I-51 | 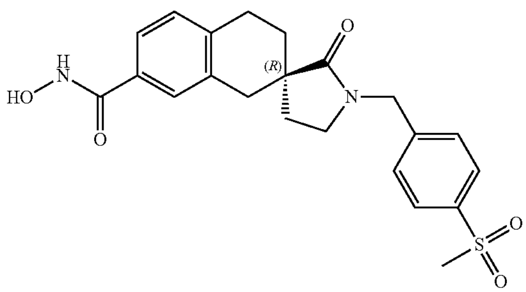 | (300 MHz, DMSO-d6): 11.08 (s, 1H), 7.94-7.92 (d, 2H, J = 8.4 Hz), 7.51-7.47 (m, 4H), 7.18-7.16 (d, 1H, J = 8.0 Hz), 4.53 (s, 2H), 3.33-3.26 (m, 2H), 3.23 (s, 3H), 2.98-2.89 (m, 3H), 2.69-2.65 (m, 1H), 1.96-1.74 (m, 2H), 1.72-1.67 (m, 2H) | 429 |
| I-91 | 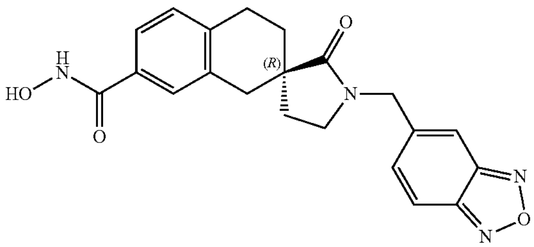 | (400 MHz, DMSO-d6): 11.10 (s, 1H), 8.95 (s, 1H), 8.10-8.08 (d, J = 8 Hz, 1H), 7.85 (s, 1H), 7.51-7.43 (m, 3H), 7.19-7.17 (d, J = 8 Hz, 1H), 4.57 (s, 2H), 3.34-3.31 (m, 2H), 2.96-2.82 (m, 3H), 2.73-2.69 (m, 1H), 1.99-1.79 (m, 2H), 1.77-1.72 (m, 2H) | 393 |

Example 20

Preparation of (R)-1'-(3-fluoro-4-(trifluoromethyl)benzyl)-N-hydroxy-2'-oxo-3,4-dihydro-1H-spiro[naphthalene-2,3'-pyrrolidine]-7-carboxamide (I-125)

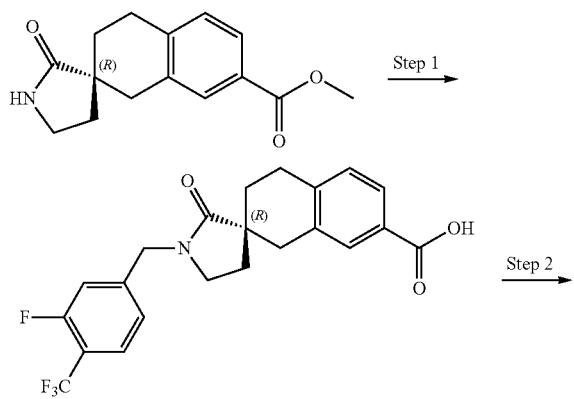

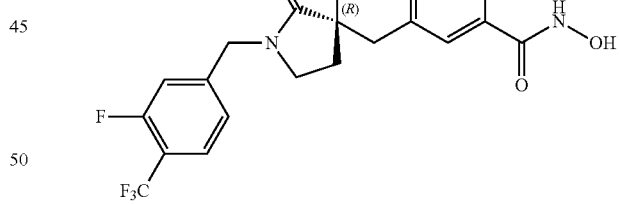

Step-1: (R)-1'-(3-Fluoro-4-(trifluoromethyl)benzyl)-2'-oxo-3,4-dihydro-1H-spiro[naphthalene-2,3'-pyrrolidine]-7-carboxylic acid Into an 8-mL vial, was placed a solution of methyl (R)-2'-oxo-3,4-dihydro-1H-spiro[naphthalene-2,3'-pyrrolidine]-7-carboxylate (100 mg, 0.39 mmol, 1 equiv) in DMF (2 mL). This was followed by the portion-wise addition of NaH (60% dispersion in oil, 38 mg, 1.58mmol, 2.5 equiv) at 0° C. over 1 h. To this mixture was added 4-(bromomethyl)-2-fluoro-1-(trifluoromethyl)benzene (149 mg, 0.58 mmol, 1.5 equiv). The resulting mixture was stirred for 2h at room temperature. The reaction was then quenched by the addition of 25 mL of H$_2$O. The resulting solution was extracted with 2×20 mL of EtOAc. The pH value of the solution was adjusted to 3 with 2N HCl. The resulting solution was extracted with 2×25 mL of EtOAc. The organic layers were combined, dried over anhydrous Na$_2$SO$_4$, filtered, and concentrated under vacuum. The residue was purified by normal phase chromatography on silica gel with CH$_2$Cl$_2$/MeOH (18:1). The collected fractions were concentrated to give 50 mg (31% yield) of the title compound as a colorless oil. MS: (ES, m/z): 422 [M+H]$^+$.

Step-2: (R)-1'-(3-Fluoro-4-(trifluoromethyl)benzyl)-N-hydroxy-2'-oxo-3,4-dihydro-1H-spiro[naphthalene-2,3'-pyrrolidine]-7-carboxamide Into an 8-mL vial, was placed a solution of (R)-1'-(3-fluoro-4-(trifluoromethyl)benzyl)-2'-oxo-3,4-dihydro-1H-spiro[naphthalene-2,3'-pyrrolidine]-7-carboxylic acid (50 mg, 0.12 mmol, 1 equiv) in DMA (2 mL). This was followed by the dropwise addition of isopropylchloroformate (102 mg, 0.83 mmol, 7 equiv) with stirring at 0° C. NMM (84 mg, 0.83 mmol, 7 equiv) was added dropwise with stirring at 0° C. A solution of NH$_2$OH.HCl (58mg, 0.83 mmol, 7 equiv) in DMA (0.5 mL) was added to the resulting mixture at 0° C. The reaction was stirred for 20 h at room temperature. The crude product was purified by Prep-HPLC with the following conditions: Column: Sunfire C18, 19×150 mm, 5 µm; Mobile Phase A: Water/0.05% Formic Acid, Mobile Phase B: CH$_3$CN/0.05% Formic Acid; Flow rate: 25 mL/min; Gradient: 25% B to 60% B in 7 min; Detector: UV 254 nm, 220 nm. The collected fractions were lyophilized to give 9.5 mg (18% yield) of the title compound as an off-white solid. $^1$H NMR (400MHz, DMSO-d6) δ (ppm): 11.16-11.09 (s, 1H), 8.97-8.96 (s, 1H), 7.83-7.79 (m, 1H), 7.51-7.48 (m, 2H), 7.38-7.35 (d, J=12.0 Hz, 1H), 7.30-7.28 (d, J=8.0 Hz, 1H), 7.19-7.17 (d, J=8.0 Hz, 1H), 4.54 (s, 2H), 3.32-3.27 (m, 2H), 2.94-2.78 (m, 3H), 2.71-2.67 (d, J=16.0 Hz, 1H), 1.98-1.84 (m, 2H), 1.77-1.71 (m, 2H). MS: (ES, m/z): 437 [M+H]$^+$.

Example 21

Preparation of (R)—N-hydroxy-2'-oxo-3,4-dihydro-1H-spiro[naphthalene-2,3'-pyrrolidine]-7-carboxamide (I-48)

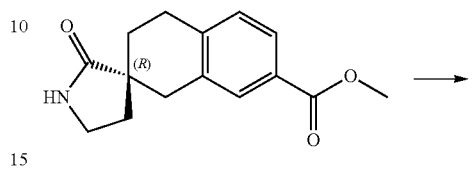

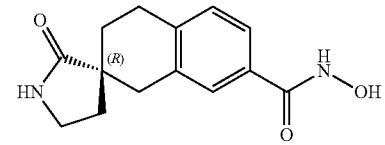

Into a 50-mL round-bottom flask was placed a solution of methyl (R)-2'-oxo-3,4-dihydro-1H-spiro[naphthalene-2,3'-pyrrolidine]-7-carboxylate (100 mg, 0.39 mmol, 1 equiv) in THF/MeOH (4:1, 2.5 mL), NH$_2$OH (50% aqueous solution, 1.52 mL, 60 equiv), and aq. 1N NaOH (0.77 mL, 2 equiv). The resulting solution was stirred for 1.5 h at room temperature. The crude product was purified by Prep-HPLC with the following conditions: Column: Waters HSS C18, 2.1×50 mm, 1.8 µm; Mobile Phase A: Water/0.05% Formic Acid, Mobile Phase B: CH$_3$CN/0.05% Formic Acid; Flow rate: 0.7 mL/min; Gradient: 5% B to 95% B in 2.0 min, hold 0.6 min; Detector: UV 254 nm. The collected fractions were lyophilized to give 50.1 mg (42% yield) of the title compound as a pink solid. $^1$H NMR (400 MHz, DMSO-d6) δ (ppm): 11.09 (s, 1H), 8.95 (s, 1H), 7.66 (s, 1H), 7.46-7.49 (m, 2H), 7.15-7.17 (d, J=8 Hz, 1H), 3.19-3.22 (t, J=6Hz, 2H), 2.74-2.90 (m, 3H), 2.58-2.67 (m, 1H), 1.91-1.95 (m, 1H), 1.80-1.90 (m, 2H), 1.72-1.79(m, 1H). MS: (ES, m/z): 261 [M+H]$^+$.

TABLE 5

The following compound was prepared according to the method of Example 20.

| Ex. | Structure | $^1$H NMR δ (ppm) | Found (ES, m/z) [M + H]$^+$ |
|---|---|---|---|
| I-127 | ![structure] | (400 MHz, DMSO-d6): 11.18-10.98 (br s, 1H), 9.04-8.88 (br s, 1H), 7.81-7.74 (d, J = 28 Hz, 2H), 7.51-7.43 (m, 4H), 7.18-7.13 (d, J = 20 Hz, 1H), 4.53-4.49 (s, 2H), 3.32-3.21 (m, 2H), 2.95-2.77 (m, 3H), 2.69-2.65 (d, J = 16 Hz, 1H), 1.96-1.84 (m, 2H), 1.76-1.67 (m, 2H) | 419 |

Example 22

Preparation of (R)—N-hydroxy-1'-methyl-2'-oxo-3,4-dihydro-1H-spiro[naphthalene-2,3'-pyrrolidine]-7-carboxamide (I-120)

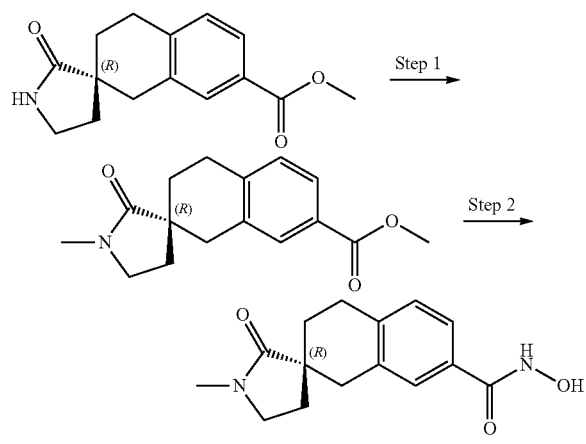

Step-1: Methyl (R)-1'-methyl-2'-oxo-3,4-dihydro-1H-spiro[naphthalene-2,3'-pyrrolidine]-7-carboxylate Into a 25-mL round-bottom flask was placed methyl (R)-2'-oxo-3,4-dihydro-1H-spiro[naphthalene-2,3'-pyrrolidine]-7-carboxylate (100 mg, 0.39 mmol, 1 equiv) in DMF (2 mL). This was followed by the addition of NaH (18.7 mg, 0.78 mmol, 2 equiv) at 0° C. The resulting solution was stirred for 1h at 0° C. in an ice-water bath. To this solution was added $CH_3I$ (110mg, 0.77 mmol, 2 equiv). The reaction was allowed to stir for an additional 16 h at room temperature. The resulting solution was diluted with 30 mL of EtOAc and washed with 5×15 mL of $H_2O$. The organic layer was separated, dried over anhydrous $MgSO_4$, filtered and concentrated under vacuum. The residue was purified by normal phase chromatography on silica gel with EtOAc/petroleum ether (1:1). The collected fractions were concentrated to give 90 mg (85% yield) of the title compound as a yellow solid. MS: (ES, m/z): 274 $[M+H]^+$.

Step-2: (R)—N-Hydroxy-1'-methyl-2'-oxo-3,4-dihydro-1H-spiro[naphthalene-2,3'-pyrrolidine]-7-carboxamide Into an 8-mL vial, was placed methyl (R)-1'-methyl-2'-oxo-3,4-dihydro-1H-spiro[naphthalene-2,3'-pyrrolidine]-7-carboxylate (90 mg, 0.33 mmol, 1 equiv), THF/MeOH (4:1, 2 mL), $NH_2OH$ (50% in water, 326 mg, 9.87 mmol, 30 equiv), and aq. 1N NaOH (26.4 mg, 0.66 mmol, 2 equiv). The resulting solution was stirred for 1.5 h at room temperature. The crude product was purified by Prep-HPLC with the following conditions. Conditions: Column: Xbridge C18, 19×150 mm, 5 μm; Mobile Phase A: Water/0.05% TFA, Mobile Phase B: $CH_3CN$/0.05% TFA; Flow rate: 25 mL/min; 4% B to 55% B in 6 min; Detector: UV 254 nm, 220 nm. The collected fractions were lyophilized to give 30.6 mg (24% yield) of the title compound as a white solid. $^1$H NMR (400 MHz, DMSO-d6) δ (ppm): 11.08 (s, 1H), 7.47-7.46 (d, J=3.6 Hz, 2H), 7.16-7.14 (m, 1H), 3.32-3.28 (m, 2H), 2.91-2.74 (m, 6H), 2.60-2.53 (m, 1H), 1.91-1.76 (m, 2H), 1.70-1.69 (m, 2H). MS: (ES, m/z): 275 $[M+H]^+$.

Example 23

Preparation of (R)—N-hydroxy-2'-oxo-1'-(pyridin-2-yl)-3,4-dihydro-1H-spiro[naphthalene-2,3'-pyrrolidine]-7-carboxamide (I-43)

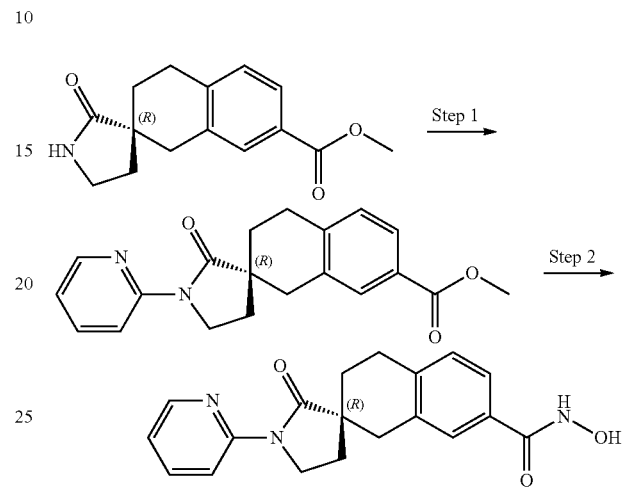

Step-1: Methyl (R)-2'-oxo-1'-(pyridin-2-yl)-3,4-dihydro-1H-spiro[naphthalene-2,3'-pyrrolidine]-7-carboxylate Into a 100 mL round-bottom flask, was placed methyl (R)-2'-oxo-3,4-dihydro-1H-spiro[naphthalene-2,3'-pyrrolidine]-7-carboxylate (100 mg, 0.39 mmol, 1 equiv) in 1,4-dioxane (6 mL), $Pd(OAc)_2$ (40 mg, 0.18 mmol, 0.46 equiv), XantPhos (70 mg, 0.12 mmol, 0.3 equiv), $Cs_2CO_3$ (190 mg, 0.58 mmol, 1.5 equiv) and 2-bromopyridine (91 mg, 0.58 mmol, 1.5 equiv). The resulting mixture was stirred overnight at 101° C. The solids were filtered out and the filtrate was concentrated under vacuum. The residue was purified by normal phase column chromatography on silica gel with EtOAc/petroleum ether (1:6). The collected fractions were concentrated to give 80 mg (62% yield) of the title compound as a white solid. MS: (ES, m/z): 337 $[M+H]^+$.

Step-2: (R)—N-Hydroxy-2'-oxo-1'-(pyridin-2-yl)-3,4-dihydro-1H-spiro[naphthalene-2,3'-pyrrolidine]-7-carboxamide Into a 100 mL round-bottom flask, was placed (R)-2'-oxo-1'-(pyridin-2-yl)-3,4-dihydro-1H-spiro[naphthalene-2,3'-pyrrolidine]-7-carboxylate (80 mg, 0.24 mmol, 1 equiv), THF/MeOH (4:1, 1.25 mL), $NH_2OH$ (50% in water, 1.52 mL, 46.02 mmol, 194 equiv), and aq. 1N NaOH (1 mol/L, 0.48 mL, 2 equiv). The resulting solution was stirred for 1.5 h at room temperature. The crude product was purified by Prep-HPLC with the following conditions: Column: Waters HSS C18, 2.1×50 mm, 1.8 μm; Mobile Phase A: Water/0.05% TFA, Mobile Phase B: $CH_3CN$/0.05% TFA; Flow rate: 0.7 mL/min; Gradient: 5% B to 95% B in 2.0 min, hold 0.6 min; Detector: UV 254 nm. The collected fractions were lyophilized to give 12 mg (11% yield) of the title compound as a pink solid. $^1$H NMR (400 MHz, DMSO-d6) δ (ppm): 11.10 (s, 1H), 8.42-8.41 (d, J=4 Hz, 1H), 8.36-8.34 (d, J=8.4

Hz, 1H), 7.86-7.82 (m, 1H), 7.51-7.49 (d, J=8.8 Hz, 2H), 7.23-7.15 (m, 2H), 4.03-3.99 (m, 2H), 2.99-2.80 (m, 4H), 2.06-1.81 (m, 4H). MS: (ES, m/z): 338 [M+H]+.

Example 24

Preparation of (S)—N-hydroxy-2'-oxo-1'-propyl-3,4-dihydro-1H-spiro[naphthalene-2,3'-pyrrolidine]-7-carboxamide (I-52)

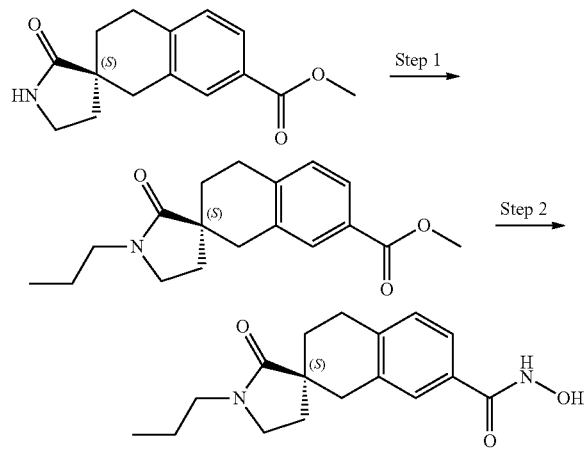

Step-1: Methyl (S)-2'-oxo-1'-propyl-3,4-dihydro-1H-spiro[naphthalene-2,3'-pyrrolidine]-7-carboxylate A solution of methyl (S)-2'-oxo-3,4-dihydro-1H-spiro[naphthalene-2,3'-pyrrolidine]-7-carboxylate (350 mg, 1.35 mmol, 1 equiv) in anhydrous DMF (6.75 mL) was deprotonated with NaH (60% dispersion in oil, 54 mg, 1.35 mmol, 1 equiv). This solution (0.15 mL, 0.30 mmol) was added to a solution of 1-iodopropane (0.2M in CH₃CN, 0.30 mL, 0.06 mmol, 2equiv) in a 2 dram vial. NaI (18 mg, 0.12 mmol, 4.00 equiv) was added and the vial was sealed and shaken at 80° C. for 48 h. The solvent was removed and the residue was diluted with brine (0.5 mL) and extracted with EtOAc (2×0.5 mL). The combined organic layers were concentrated under vacuum.

Step-2: (S)—N-Hydroxy-2'-oxo-1'-propyl-3,4-dihydro-1H-spiro[naphthalene-2,3'-pyrrolidine]-7-carboxamide The residue from Step 1 was dissolved in a solution of THF/MeOH (3:1, 0.2 mL). NH$_2$OH (50% in water, 0.15 mL, 76 equiv) was added, followed by addition of aq. 1N NaOH (0.10 mL, 3.3 equiv). The mixture was sealed and shaken at room temperature for 18 h. The reaction mixture was concentrated and purified by Prep-HPLC with the following conditions: Column: Waters Sunfire C18, 5 μm, 19×50 mm; Mobile Phase A: Water/0.1% formic acid, Mobile Phase B: CH₃CN/0.1% formic acid; Gradient: 15% B to 100% B in 6 min; Flow rate: 23mL/min; Detector: UV 254 nm, 220 nm. The product-containing fractions were combined and concentrated to afford 3 mg (33% yield) of the title compound. MS: (ES, m/z): 303 [M+H]+.

TABLE 6

The following compounds were prepared according to the synthetic method of Example 24 and suitable reagents.

| Ex. | Name | Structure | Found (ES, m/z) [M + H]+ |
|---|---|---|---|
| I-53 | (S)-1'-(cyclobutylmethyl)-N-hydroxy-2'-oxo-3,4-dihydro-1H-spiro[napthalene-2,3'-pyrrolidine]-7-carboxamide | 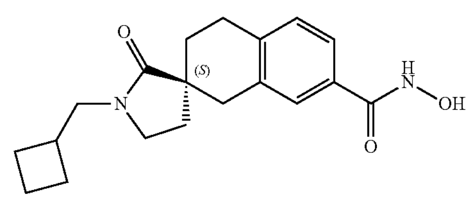 | 329 |
| I-54 | (S)-N-hydroxy-1'-isopentyl-2'-oxo-3,4-dihydro-1H-spiro[naphthalene-2,3'-pyrrolidine]-7-carboxamide | 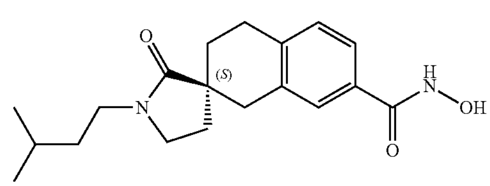 | 331 |
| I-55 | (S)-1'-(but-2-yn-1-yl)-N-hydroxy-2'-oxo-3,4-dihydro-1H-spiro[naphthalene-2,3'-pyrrolidine]-7-carboxamide | 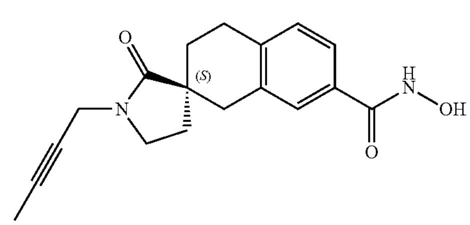 | 313 |

TABLE 6-continued

The following compounds were prepared according to the synthetic method of Example 24 and suitable reagents.

| Ex. | Name | Structure | Found (ES, m/z) [M + H]+ |
|---|---|---|---|
| I-56 | (S)-N-hydroxy-1'-(2-methoxyethyl)-2'-oxo-3,4-dihydro-1H-spiro[naphthalene-2,3'-pyrrolidine]-7-carboxamide | 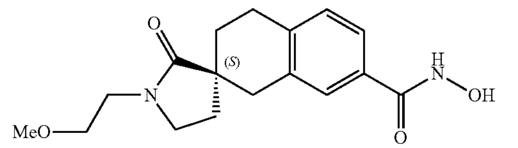 | 319 |
| I-57 | (S)-N-hydroxy-2'-oxo-1'-((tetrahydro-2H-pyran-4-yl)methyl)-3,4-dihydro-1H-spiro[naphthalene-2,3'-pyrrolidine]-7-carboxamide | 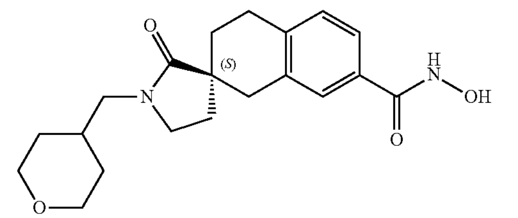 | 359 |
| I-58 | (S)-1'-cinnamyl-N-hydroxy-2'-oxo-3,4-dihydro-1H-spiro[naphthalene-2,3'-pyrrolidine]-7-carboxamide | 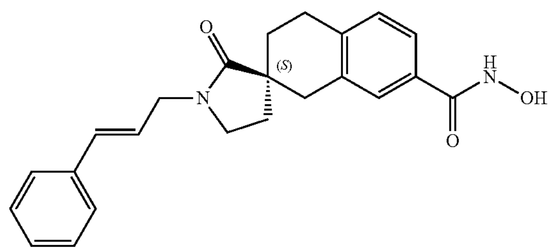 | 377 |
| I-59 | (S)-N-hydroxy-1'-(2-methylbenzyl)-2'-oxo-3,4-dihydro-1H-spiro[naphthalene-2,3'-pyrrolidine]-7-carboxamide | 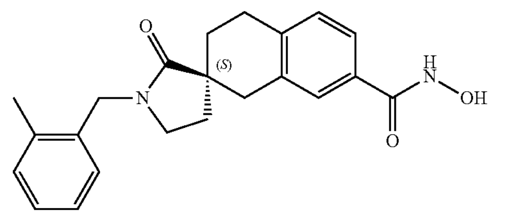 | 365 |
| I-60 | (S)-N-hydroxy-2'-oxo-1'-(2-(trifluoromethyl)benzyl)-3,4-dihydro-1H-spiro[naphthalene-2,3'-pyrrolidine]-7-carboxamide | 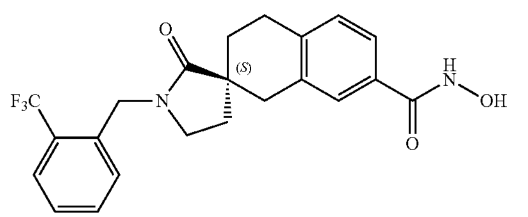 | 419 |
| I-61 | (S)-1'-(2-chlorobenzyl)-N-hydroxy-2'-oxo-3,4-dihydro-1H-spiro[naphthalene-2,3'-pyrrolidine]-7-carboxamide | 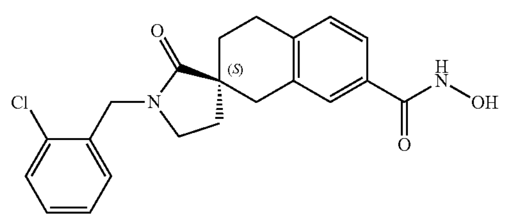 | 385 |
| I-62 | (S)-N-hydroxy-2'-oxo-1'-(2-(trifluoromethoxy)benzyl)-3,4-dihydro-1H-spiro[naphthalene-2,3'-pyrrolidine]-7-carboxamide | 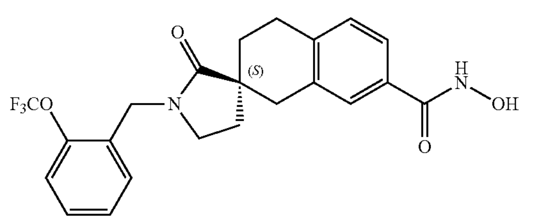 | 435 |

TABLE 6-continued

The following compounds were prepared according to the synthetic method of Example 24 and suitable reagents.

| Ex. | Name | Structure | Found (ES, m/z) [M + H]+ |
|---|---|---|---|
| I-64 | (S)-N-hydroxy-1'-(2-morpholino-2-oxoethyl)-2'-oxo-3,4-dihydro-1H-spiro[naphthalene-2,3'-pyrrolidine]-7-carboxamide | 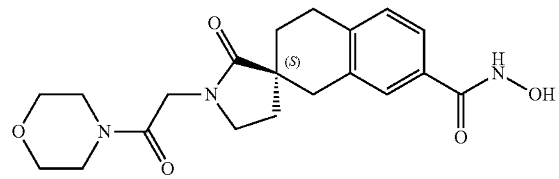 | 388 |
| I-65 | (S)-N-hydroxy-1'-(2-methoxybenzyl)-2'-oxo-3,4-dihydro-1H-spiro[naphthalene-2,3'-pyrrolidine]-7-carboxamide | 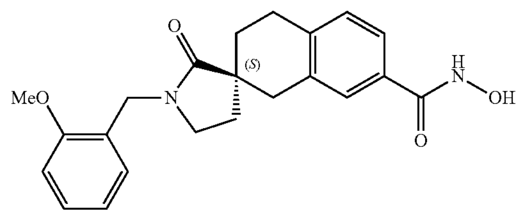 | 381 |
| I-66 | (S)-N-hydroxy-1'-((1-isopropyl-1H-benzo[d]imidazol-2-yl)methyl)-2'-oxo-3,4-dihydro-1H-spiro[naphthalene-2,3'-pyrrolidine]-7-carboxamide | 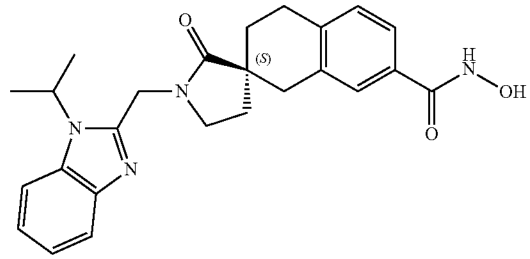 | 433 |
| I-67 | (S)-1'-(2,5-dichlorobenzyl)-N-hydroxy-2'-oxo-3,4-dihydro-1H-spiro[naphthalene-2,3'-pyrrolidine]-7-carboxamide | 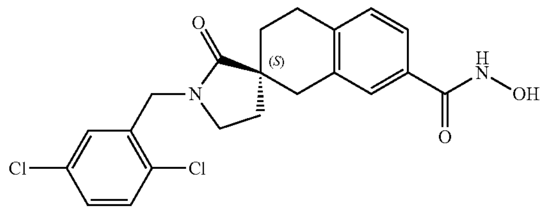 | 419 |
| I-68 | (S)-1'-(2,6-dichlorobenzyl)-N-hydroxy-2'-oxo-3,4-dihydro-1H-spiro[naphthalene-2,3'-pyrrolidine]-7-carboxamide | 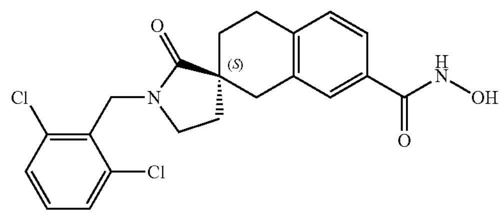 | 419 |
| I-69 | (S)-N-hydroxy-1'-(3-methoxybenzyl)-2'-oxo-3,4-dihydro-1H-spiro[naphthalene-2,3'-pyrrolidine]-7-carboxamide | 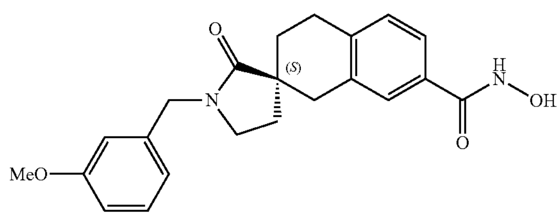 | 381 |

TABLE 6-continued

The following compounds were prepared according to the synthetic method of Example 24 and suitable reagents.

| Ex. | Name | Structure | Found (ES, m/z) [M + H]+ |
|---|---|---|---|
| I-72 | (S)-1'-(3-fluorobenzyl)-N-hydroxy-2'-oxo-3,4-dihydro-1H-spiro[naphthalene-2,3'-pyrrolidine]-7-carboxamide | 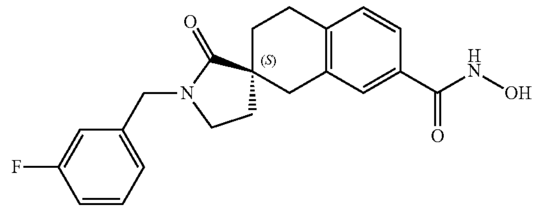 | 369 |
| I-73 | (S)-N-hydroxy-2'-oxo-1'-(4-(trifluoromethoxy)benzyl)-3,4-dihydro-1H-spiro[naphthalene-2,3'-pyrrolidine]-7-carboxamide | 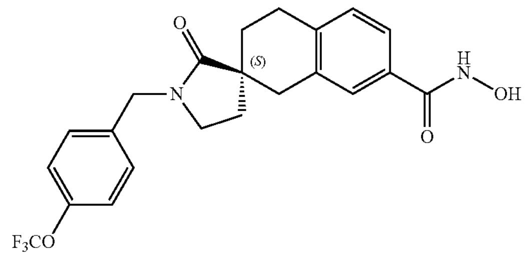 | 435 |
| I-74 | (S)-1'-(3-chlorobenzyl)-N-hydroxy-2'-oxo-3,4-dihydro-1H-spiro[naphthalene-2,3'-pyrrolidine]-7-carboxamide | 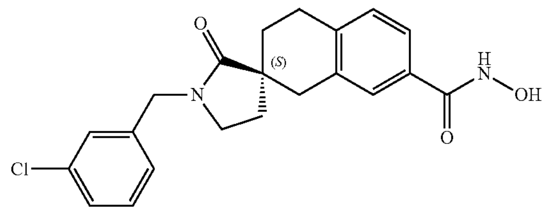 | 385 |
| I-75 | (S)-N-hydroxy-1'-(4-methoxybenzyl)-2'-oxo-3,4-dihydro-1H-spiro[naphthalene-2,3'-pyrrolidine]-7-carboxamide | 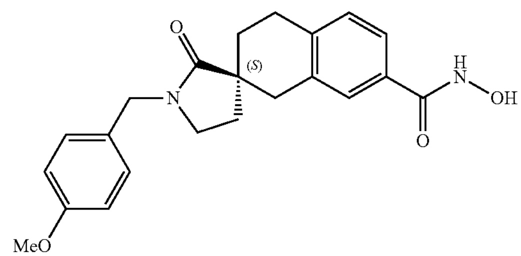 | 381 |
| I-76 | (S)-1'-(2-fluorobenzyl)-N-hydroxy-2'-oxo-3,4-dihydro-1H-spiro[naphthalene-2,3'-pyrrolidine]-7-carboxamide | 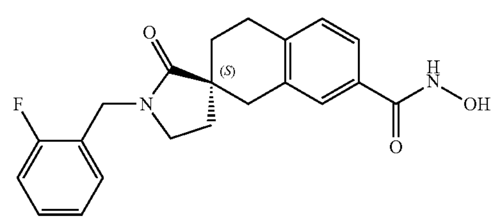 | 369 |
| I-77 | (S)-N-hydroxy-1'-(naphthalen-2-ylmethyl)-2'-oxo-3,4-dihydro-1H-spiro[naphthalene-2,3'-pyrrolidine]-7-carboxamide | 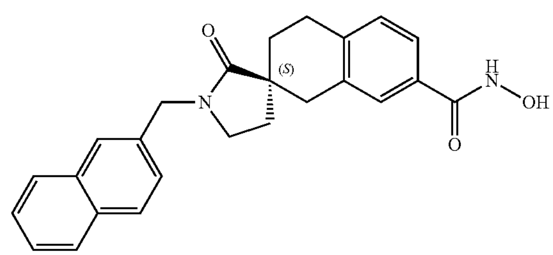 | 401 |

TABLE 6-continued

The following compounds were prepared according to the synthetic method of Example 24 and suitable reagents.

| Ex. | Name | Structure | Found (ES, m/z) [M + H]+ |
|---|---|---|---|
| I-78 | (S)-1'-(2-(difluoromethoxy)benzyl)-N-hydroxy-2'-oxo-3,4-dihydro-1H-spiro[napthalene-2,3'-pyrrolidine]-7-carboxamide | 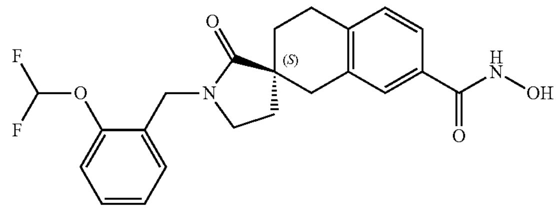 | 417 |

TABLE 7

The following compounds were prepared according to the synthetic method of Example 24, using methyl (R)-2'-oxo-3,4-dihydro-1H-spiro[naphthalene-2,3'-pyrrolidine]-7-carboxylate in Step 1 and other suitable reactants.

| Ex. | Name | Structure | Found (ES, m/z) [M + H]+ |
|---|---|---|---|
| I-79 | (R)-N-hydroxy-2'-oxo-1'-propyl-3,4-dihydro-1H-spiro[naphthalene-2,3'-pyrrolidine]-7-carboxamide | 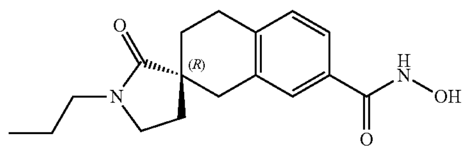 | 303 |
| I-80 | (R)-N-hydroxy-1'-(3-hydroxypropyl)-2'-oxo-3,4-dihydro-1H-spiro[naphthalene-2,3'-pyrrolidine]-7-carboxamide | 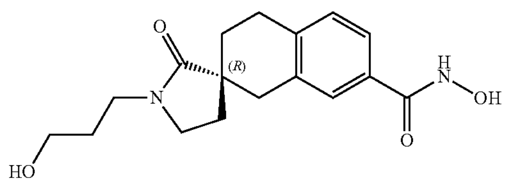 | 319 |
| I-81 | (R)-1'-(cyclobutylmethyl)-N-hydroxy-2'-oxo-3,4-dihydro-1H-spiro[naphthalene-2,3'-pyrrolidine]-7-carboxamide | 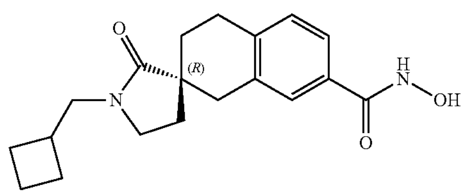 | 329 |
| I-82 | (R)-N-hydroxy-1'-isopentyl-2'-oxo-3,4-dihydro-1H-spiro[naphthalene-2,3'-pyrrolidine]-7-carboxamide | 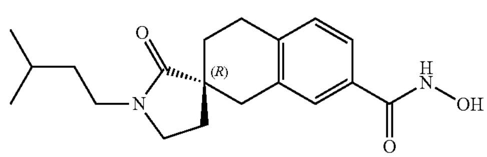 | 331 |
| I-83 | (R)-1'-(but-2-yn-1-yl)-N-hydroxy-2'-oxo-3,4-dihydro-1H-spiro[naphthalene-2,3'-pyrrolidine]-7-carboxamide | 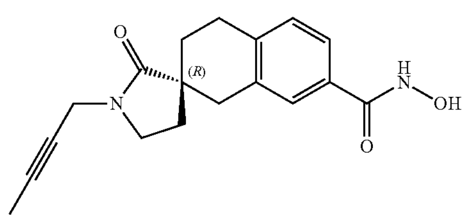 | 313 |
| I-84 | (R)-N-hydroxy-1'-(2-methoxyethyl)-2'-oxo-3,4-dihydro-1H-spiro[naphthalene-2,3'-pyrrolidine]-7-carboxamide | 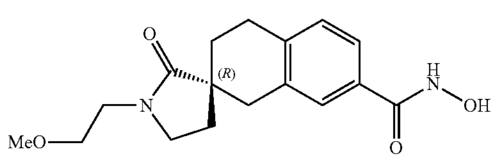 | 319 |

TABLE 7-continued

The following compounds were prepared according to the synthetic method of Example 24, using methyl (R)-2'-oxo-3,4-dihydro-1H-spiro[naphthalene-2,3'-pyrrolidine]-7-carboxylate in Step 1 and other suitable reactants.

| Ex. | Name | Structure | Found (ES, m/z) [M + H]+ |
|---|---|---|---|
| I-85 | (R)-N-hydroxy-2'-oxo-1'-((tetrahydro-2H-pyran-4-yl)methyl)-3,4-dihydro-1H-spiro[naphthalene-2,3'-pyrrolidine]-7-carboxamide | 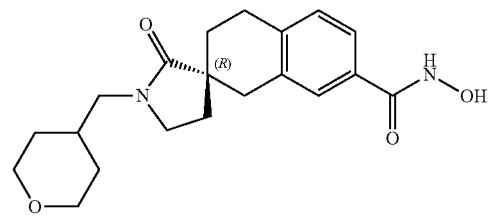 | 359 |
| I-86 | (R)-1'-cinnamyl-N-hydroxy-2'-oxo-3,4-dihydro-1H-spiro[naphthalene-2,3'-pyrrolidine]-7-carboxamide | 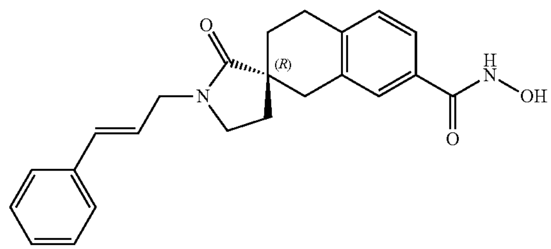 | 377 |
| I-87 | (R)-N-hydroxy-1'-(2-methylbenzyl)-2'-oxo-3,4-dihydro-1H-spiro[naphthalene-2,3'-pyrrolidine]-7-carboxamide | 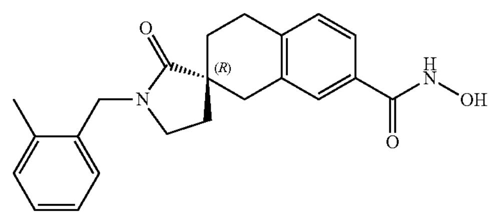 | 365 |
| I-88 | (R)-N-hydroxy-2'-oxo-1'-(2-(trifluoromethyl)benzyl)-3,4-dihydro-1H-spiro[naphthalene-2,3'-pyrrolidine]-7-carboxamide | 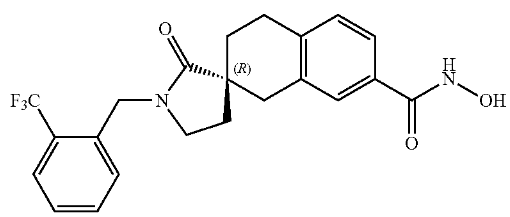 | 419 |
| I-89 | (R)-1'-(2-chlorobenzyl)-N-hydroxy-2'-oxo-3,4-dihydro-1H-spiro[naphthalene-2,3'-pyrrolidine]-7-carboxamide | 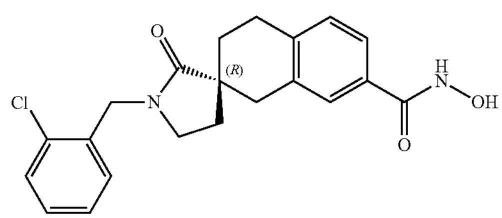 | 385 |
| I-90 | (R)-N-hydroxy-2'-oxo-1'-(2-(trifluoromethoxy)benzyl)-3,4-dihydro-1H-spiro[naphthalene-2,3'-pyrrolidine]-7-carboxamide | 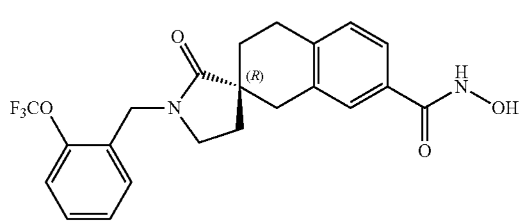 | 435 |

TABLE 7-continued

The following compounds were prepared according to the synthetic method of Example 24, using methyl (R)-2'-oxo-3,4-dihydro-1H-spiro[naphthalene-2,3'-pyrrolidine]-7-carboxylate in Step 1 and other suitable reactants.

| Ex. | Name | Structure | Found (ES, m/z) [M + H]+ |
|---|---|---|---|
| I-92 | (R)-N-hydroxy-1'-(2-morpholino-2-oxoethyl)-2'-oxo-3,4-dihydro-1H-spiro[naphthalene-2,3'-pyrrolidine]-7-carboxamide | 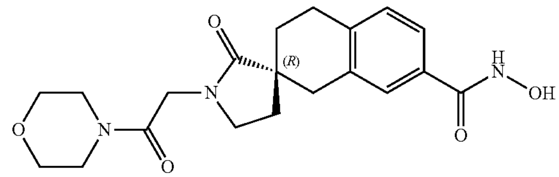 | 388 |
| I-93 | (R)-N-hydroxy-1'-(2-methoxybenzyl)-2'-oxo-3,4-dihydro-1H-spiro[naphthalene-2,3'-pyrrolidine]-7-carboxamide | 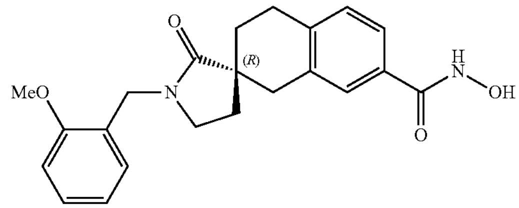 | 381 |
| I-94 | (R)-1'-(2,5-dichlorobenzyl)-N-hydroxy-2'-oxo-3,4-dihydro-1H-spiro[naphthalene-2,3'-pyrrolidine]-7-carboxamide | 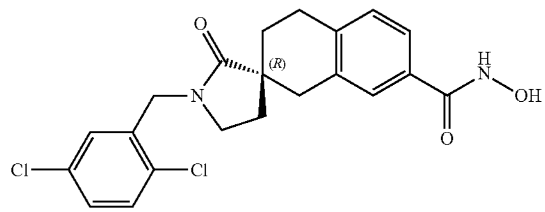 | 419 |
| I-95 | (R)-1'-(2,6-dichlorobenzyl)-N-hydroxy-2'-oxo-3,4-dihydro-1H-spiro[naphthalene-2,3'-pyrrolidine]-7-carboxamide | 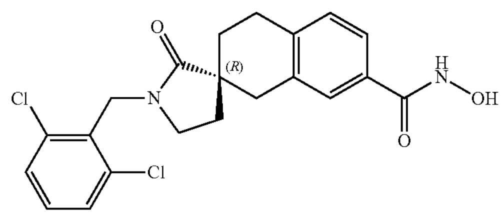 | 419 |
| I-96 | (R)-N-hydroxy-1'-(3-methoxybenzyl)-2'-oxo-3,4-dihydro-1H-spiro[naphthalene-2,3'-pyrrolidine]-7-carboxamide | 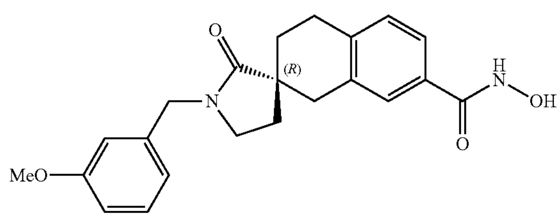 | 381 |
| I-99 | (R)-1'-(3-fluorobenzyl)-N-hydroxy-2'-oxo-3,4-dihydro-1H-spiro[naphthalene-2,3'-pyrrolidine]-7-carboxamide | 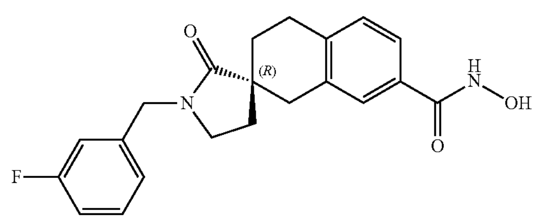 | 369 |

TABLE 7-continued

The following compounds were prepared according to the synthetic method of Example 24, using methyl (R)-2'-oxo-3,4-dihydro-1H-spiro[naphthalene-2,3'-pyrrolidine]-7-carboxylate in Step 1 and other suitable reactants.

| Ex. | Name | Structure | Found (ES, m/z) [M + H]+ |
|---|---|---|---|
| I-100 | (R)-N-hydroxy-2'-oxo-1'-(4-(trifluoromethoxy)benzyl)-3,4-dihydro-1H-spiro[naphthalene-2,3'-pyrrolidine]-7-carboxamide | 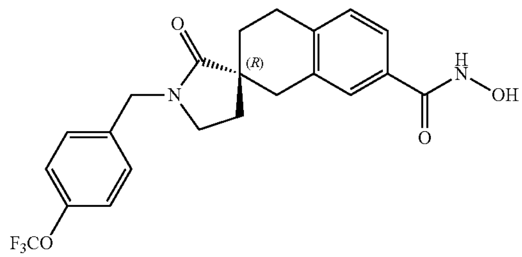 | 435 |
| I-101 | (R)-1'-(3-chlorobenzyl)-N-hydroxy-2'-oxo-3,4-dihydro-1H-spiro[naphthalene-2,3'-pyrrolidine]-7-carboxamide | 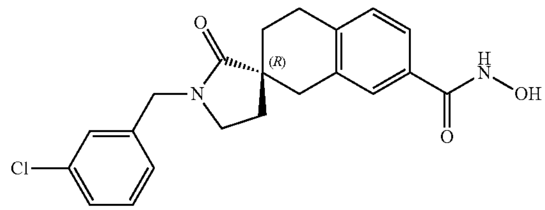 | 385 |
| I-102 | (R)-N-hydroxy-1'-(4-methoxybenzyl)-2'-oxo-3,4-dihydro-1H-spiro[naphthalene-2,3'-pyrrolidine]-7-carboxamide | 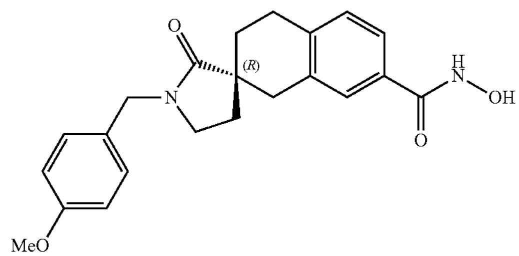 | 381 |
| I-103 | (R)-1'-(2-fluorobenzyl)-N-hydroxy-2'-oxo-3,4-dihydro-1H-spiro[naphthalene-2,3'-pyrrolidine]-7-carboxamide | 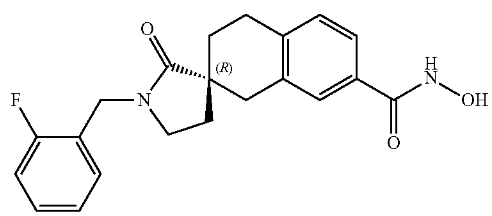 | 369 |
| I-104 | (R)-N-hydroxy-1'-(naphthalen-2-ylmethyl)-2'-oxo-3,4-dihydro-1H-spiro[naphthalene-2,3'-pyrrolidine]-7-carboxamide | 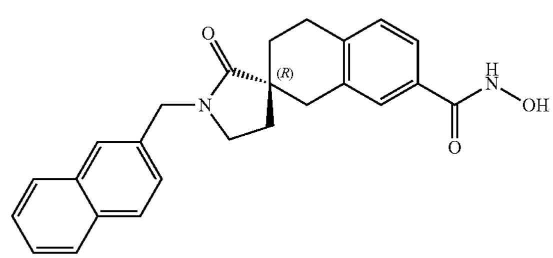 | 401 |
| I-105 | (R)-1'-(2-(difluoromethoxy)benzyl)-N-hydroxy-2'-oxo-3,4-dihydro-1H-spiro[naphthalene-2,3'-pyrrolidine]-7-carboxamide | 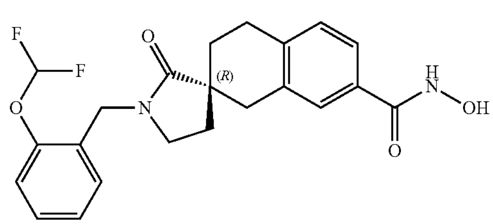 | 417 |

Example 25

Preparation of (R)—N-hydroxy-2'-oxo-1'-(4-phenoxyphenyl)-3,4-dihydro-1H-spiro[naphthalene-2,3'-pyrrolidine]-7-carboxamide (I-106)

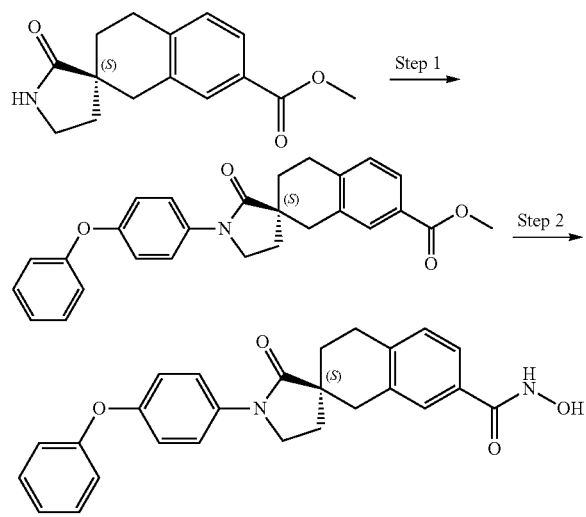

Step-1: Methyl (S)-2'-oxo-1'-(4-phenoxyphenyl)-3,4-dihydro-1H-spiro[naphthalene-2,3'-pyrrolidine]-7-carboxylate A 2-mL vial was charged with methyl (R)-2'-oxo-3,4-dihydro-1H-spiro[naphthalene-2,3'-pyrrolidine]-7-carboxylate (0.2M in 1,4-dioxane, 0.150 mL, 0.03 mmol, 1 equiv) and $Cs_2CO_3$ (39 mg, 0.12 mmol, 4 equiv). Then a solution of 1-bromo-4-phenoxybenzene (0.2M in 1,4-dioxane, 0.30 mL, 0.06 mmol, 2 equiv) was added. The vial was sealed and brought into a glovebox. A degassed solution of CuBr (10 mol % yield) and N,N-dimethylethane-1,2-diamine (20 mol %, 0.02M in DMA, 0.15 mL, 0.003 mmol) was added. The vial was sealed and heated at 110° C. for 18 h. The solvent was removed and the residue was diluted with brine (0.5 mL) and extracted with EtOAc (2×0.5 mL). The combined organic layers were concentrated under vacuum.

Step-2: (R)—N-Hydroxy-2'-oxo-1'-(4-phenoxyphenyl)-3,4-dihydro-1H-spiro[naphthalene-2,3'-pyrrolidine]-7-carboxamide The residue from Step 1 was dissolved in THF/MeOH (3:1, 0.2 mL) and $NH_2OH$ (50% in water, 0.15 mL, 76 equiv) was added, followed by addition of aq. 1N NaOH (0.1 mL, 3.3 equiv). The mixture was sealed and then shaken at room temperature for 18 h. The reaction mixture was concentrated and purified by Prep-HPLC using the following conditions: Column: Waters Sunfire C18, 5 μm, 19×50 mm; Mobile Phase A: Water/0.1% formic acid, Mobile Phase B: $CH_3CN$/0.1% formic acid; Gradient: 15% B to 100% B in 6 min; Flow rate: 23 mL/min; Detector: UV 254 nm/220 nm. The product-containing fractions were combined and concentrated to afford 1 mg (8.6% yield) of the title compound. MS: (ES, m/z): 429 $[M+H]^+$.

TABLE 8

The following compounds were prepared according to the synthetic method of Example 25, using suitable reactants.

| Ex. | Name | Structure | Found (ES, m/z) $[M + H]^+$ |
|---|---|---|---|
| I-107 | (R)-N-hydroxy-2'-oxo-1'-(quinolin-3-yl)-3,4-dihydro-1H-spiro[naphthalene-2,3'-pyrrolidine]-7-carboxamide | 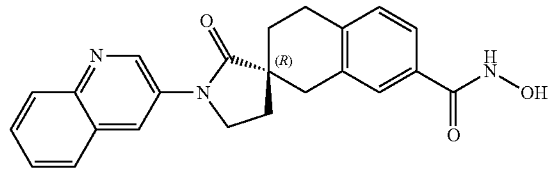 | 388 |
| I-108 | (R)-1'-(2,3-dihydrobenzofuran-7-yl)-N-hydroxy-2'-oxo-3,4-dihydro-1H-spiro[naphthalene-2,3'-pyrrolidine]-7-carboxamide | 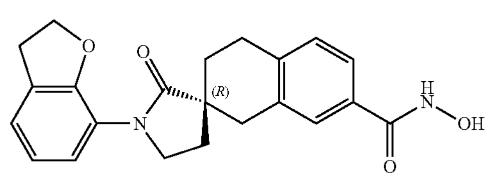 | 379 |
| I-109 | (R)-1'-(1,3-dimethyl-1H-pyrazol-4-yl)-N-hydroxy-2'-oxo-3,4-dihydro-1H-spiro[naphthalene-2,3'-pyrrolidine]-7-carboxamide | 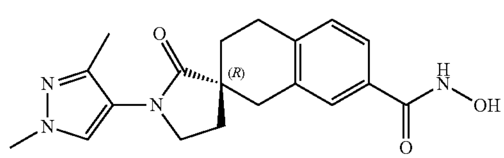 | 355 |

TABLE 8-continued

The following compounds were prepared according to the synthetic method of Example 25, using suitable reactants.

| Ex. | Name | Structure | Found (ES, m/z) [M + H]+ |
|---|---|---|---|
| I-110 | (R)-N-hydroxy-1'-(imidazo[1,2-a]pyridin-6-yl)-2'-oxo-3,4-dihydro-1H-spiro[naphthalene-2,3'-pyrrolidine]-7-carboxamide | 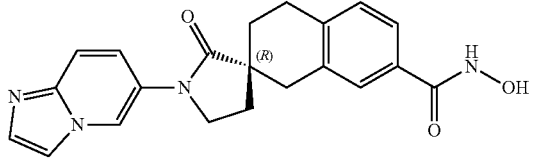 | 377 |
| I-111 | (R)-N-hydroxy-1'-(imidazo[1,2-a]pyridin-3-yl)-2'-oxo-3,4-dihydro-1H-spiro[naphthalene-2,3'-pyrrolidine]-7-carboxamide | 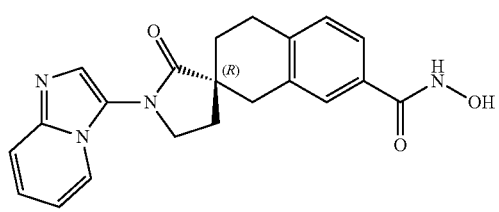 | 377 |
| I-117 | (R)-N-hydroxy-1'-(3-(2-morpholinoethoxy)phenyl)-2'-oxo-3,4-dihydro-1H-spiro[naphthalene-2,3'-pyrrolidine]-7-carboxamide | 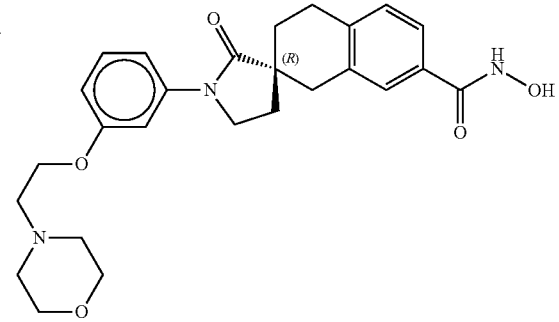 | 466 |

TABLE 9

The following compounds were prepared according to the synthetic method of Example 25, using methyl (S)-2'-oxo-3,4-dihydro-1H-spiro[naphthalene-2,3'-pyrrolidine]-7-carboxylate in Step 1 and suitable reagents.

| Ex. | Name | Structure | Found (ES, m/z) [M + H]+ |
|---|---|---|---|
| I-112 | (S)-1'-(3,4-dichlorophenyl)-N-hydroxy-2'-oxo-3,4-dihydro-1H-spiro[naphthalene-2,3'-pyrrolidine]-7-carboxamide | 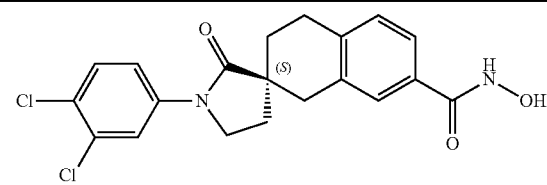 | 405 |
| I-113 | (S)-1'-(2,4-dimethylphenyl)-N-hydroxy-2'-oxo-3,4-dihydro-1H-spiro[naphthalene-2,3'-pyrrolidine]-7-carboxamide | 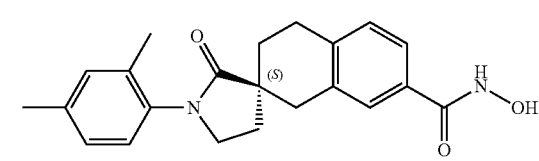 | 365 |
| I-114 | (S)-N-hydroxy-1'-(2-methoxyphenyl)-2'-oxo-3,4-dihydro-1H-spiro[naphthalene-2,3'-pyrrolidine]-7-carboxamide | 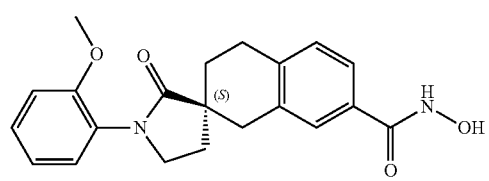 | 367 |

TABLE 9-continued

The following compounds were prepared according to the synthetic method of Example 25, using methyl (S)-2'-oxo-3,4-dihydro-1H-spiro[naphthalene-2,3'-pyrrolidine]-7-carboxylate in Step 1 and suitable reagents.

| Ex. | Name | Structure | Found (ES, m/z) [M + H]+ |
|---|---|---|---|
| I-115 | (S)-1'-(benzo[d][1,3]dioxol-5-yl)-N-hydroxy-2'-oxo-3,4-dihydro-1H-spiro[naphthalene-2,3'-pyrrolidine]-7-carboxamide | 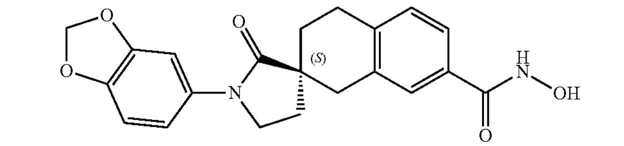 | 381 |
| I-116 | (S)-N-hydroxy-2'-oxo-1'-(4-phenoxyphenyl)-3,4-dihydro-1H-spiro[naphthalene-2,3'-pyrrolidine]-7-carboxamide | 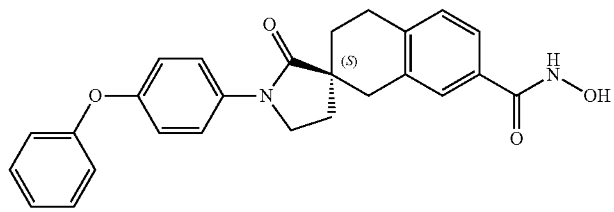 | 429 |
| I-118 | (S)-N-hydroxy-2'-oxo-1'-(quinolin-3-yl)-3,4-dihydro-1H-spiro[naphthalene-2,3'-pyrrolidine]-7-carboxamide | 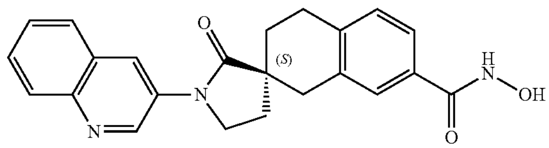 | 388 |
| I-119 | (S)-1'-(4-(2-(dimethylamino)ethyl)phenyl)-N-hydroxy-2'-oxo-3,4-dihydro-1H-spiro[naphthalene-2,3'-pyrrolidine]-7-carboxamide | 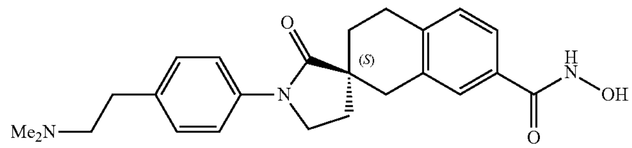 | 408 |

Example 26

Preparation of 1'-(cyclohexanecarbonyl)-N-hydroxy-3,4-dihydro-1H-spiro[naphthalene-2,3'-pyrrolidine]-7-carboxamide (I-4)

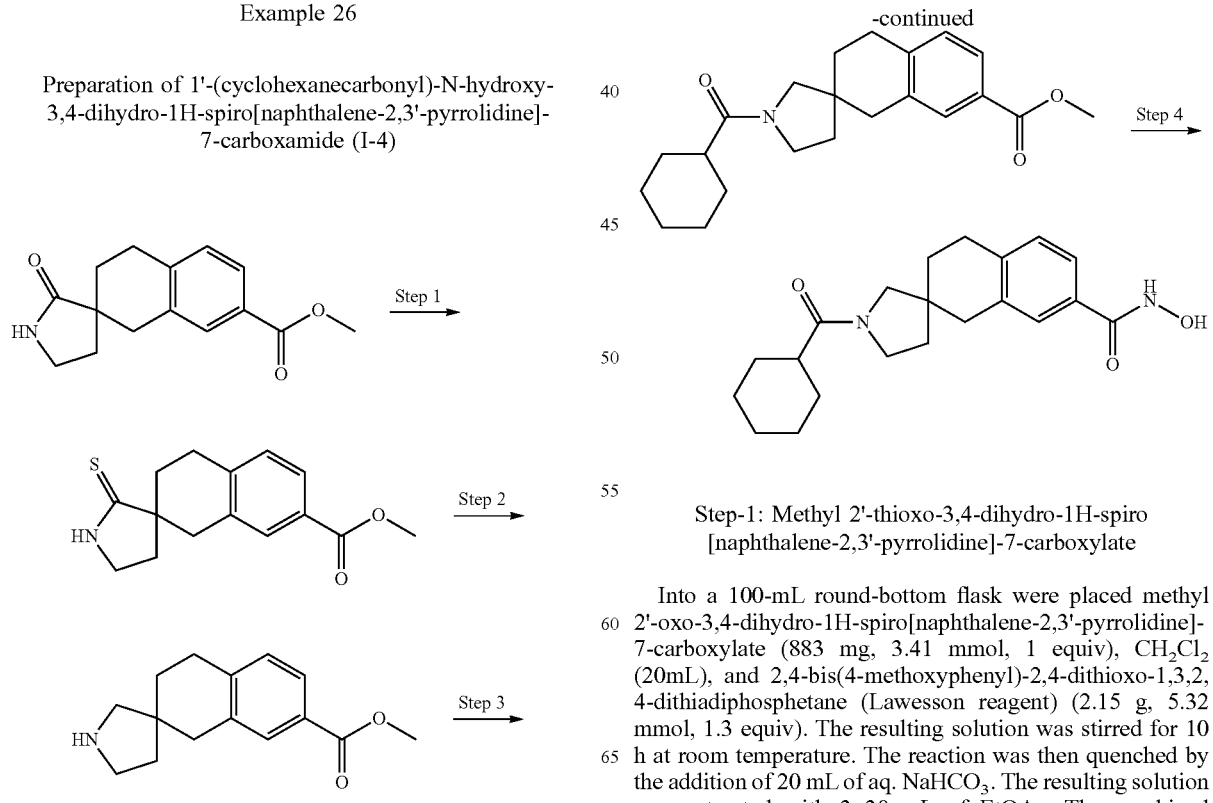

Step-1: Methyl 2'-thioxo-3,4-dihydro-1H-spiro[naphthalene-2,3'-pyrrolidine]-7-carboxylate Into a 100-mL round-bottom flask were placed methyl 2'-oxo-3,4-dihydro-1H-spiro[naphthalene-2,3'-pyrrolidine]-7-carboxylate (883 mg, 3.41 mmol, 1 equiv), CH$_2$Cl$_2$ (20mL), and 2,4-bis(4-methoxyphenyl)-2,4-dithioxo-1,3,2,4-dithiadiphosphetane (Lawesson reagent) (2.15 g, 5.32 mmol, 1.3 equiv). The resulting solution was stirred for 10 h at room temperature. The reaction was then quenched by the addition of 20 mL of aq. NaHCO$_3$. The resulting solution was extracted with 3×30 mL of EtOAc. The combined organic layers were dried over anhydrous Na₂SO₄, filtered and concentrated under vacuum. The residue was purified by normal phase chromatography on silica gel with EtOAc/petroleum ether (1:1). The collected fractions were concentrated under vacuum to give 729 mg (78% yield) of the title compound as a white solid. MS: (ES, m/z): 276 [M+H]⁺.

Step-2: Methyl 3,4-dihydro-1H-spiro[naphthalene-2, 3'-pyrrolidine]-7-carboxylate Into a 100-mL round-bottom flask purged and maintained with an inert atmosphere of nitrogen, were placed methyl 2'-thioxo-3,4-dihydro-1H-spiro[naphthalene-2,3'-pyrrolidine]-7-carboxylate (729 mg, 2.65 mmol, 1 equiv), THF/MeOH (4:1, 10 mL), NiCl₂.6H₂O (3.78 g, 15.90mmol, 6 equiv), and NaBH₄ (301 mg, 7.96 mmol, 3 equiv). The resulting mixture was stirred for 30 min at 0° C. in an ice-water bath. The solids were filtered out, and the filtrate was concentrated under vacuum. The residue was dissolved in 20 mL of THF and the solids were filtered out. The filtrate was concentrated under vacuum to give 370 mg (57% yield) of the title compound as a dark green solid. MS: (ES, m/z): 246 [M+H]⁺.

Step-3: Methyl 1'-(cyclohexanecarbonyl)-3,4-dihydro-1H-spiro[naphthalene-2,3'-pyrrolidine]-7-carboxylate Into a 10-mL round-bottom flask were placed methyl 3,4-dihydro-1H-spiro[naphthalene-2,3'-pyrrolidine]-7-carboxylate (40 mg, 0.16 mmol, 1 equiv), CH₂Cl₂ (2 mL), and Et₃N (64.64 mg, 0.64 mmol, 4 equiv). This was followed by the addition of cyclohexanecarbonyl chloride (28.13 mg, 0.19 mmol, 1.2 equiv) at 0° C. The resulting solution was stirred overnight at room temperature. The reaction was then quenched by the addition of 20mL of water and extracted with 3×20 mL of CH₂Cl₂. The combined organics were washed with 50 mL of brine, dried over anhydrous Na₂SO₄, filtered and concentrated under vacuum. The residue was purified by normal phase chromatography on silica gel with EtOAc/petroleum ether (1:3). The collected fractions were concentrated under vacuum to give 30 mg (52% yield) of title compound as a yellow oil. MS: (ES, m/z): 356[M+H]⁺.

Step-4: 1'-(Cyclohexanecarbonyl)-N-hydroxy-3,4-dihydro-H-spiro[naphthalene-2,3'-pyrrolidine]-7-carboxamide Into a 10-mL round-bottom flask was placed methyl 1'-(cyclohexanecarbonyl)-3,4-dihydro-1H-spiro[naphthalene-2,3'-pyrrolidine]-7-carboxylate (30 mg, 0.08 mmol, 1 equiv), THF/MeOH (4:1, 2 mL), NH₂OH (50% in water, 290.4 mg, 50 equiv), and aq. 1N NaOH (0.176mL, 2 equiv). The resulting solution was stirred for 2 h at room temperature. The pH of the solution was adjusted to 6 with 6N HCl. The crude product was purified by Prep-HPLC with the following conditions: Column: Waters HSS C18, 2.1×50 mm, 1.8 μm; Mobile Phase A: Water/0.05% TFA, Mobile Phase B: CH₃CN/0.05% TFA; Flow rate: 0.7 mL/min; Gradient: 5% B to 95% B in 2 min, hold 0.6 min; Detector: UV 254 nm. The collected fractions were lyophilized to give 2.3 mg (6% yield) of title compound as an off-white solid. ¹H NMR (400MHz, DMSO-d6) δ (ppm): 11.13 (s, 1H), 8.97 (s, 1H), 7.49-7.47 (d, J=3.2 Hz, 2H), 7.18-7.15(m, 1H), 3.63-3.60 (t, J=7.2 Hz, 1H), 3.40-3.34 (m, 1H), 3.18-3.07 (m, 1H), 2.85-2.74 (m, 2H), 2.71-2.67 (m, 2H), 2.33-2.32 (m, 1H), 1.80-1.58 (m, 10H), 1.32-1.15 (m, 6H). MS: (ES, m/z): 357[M+H]⁺.

TABLE 10

The following compounds were prepared according to the method of Example 26.

| Ex. | Structure | ¹H NMR δ (ppm) | Found (ES, m/z) [M + H]⁺ |
|---|---|---|---|
| I-7 | 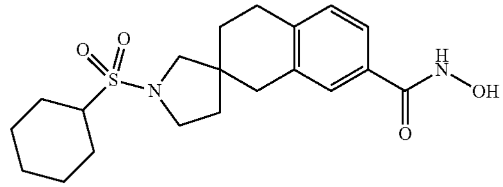 [SMILES: O=C(NO)c1ccc2c(c1)CC1(CC2)CCN(S(=O)(=O)C2CCCCC2)C1] | (400 MHz, DMSO-d6 + D₂O): 7.49-7.47 (d, J = 7.2 Hz, 2H), 7.19-7.17 (d, J = 7.6 Hz, 1H), 3.44-3.40 (t, J = 8.0 Hz, 2H), 3.13-3.11 (m, 3H), 2.76-2.74 (m, 4H), 2.00-1.97 (d, J = 10 Hz, 2H), 1.84-1.73 (m, 6H), 1.64-1.60 (d, J = 13.6 Hz, 1H), 1.39-1.33 (m, 4H), 1.20-1.03 (m, 1H) | 393 |
| I-12 | 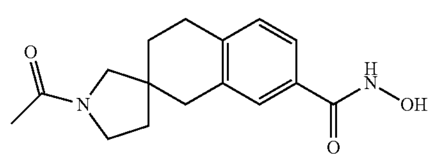 [SMILES: CC(=O)N1CCC2(CCc3ccc(C(=O)NO)cc3C2)C1] | (400 MHz, DMSO-d6): 11.09 (s, 1H), 9.08 (br s, 1H), 7.49-7.46 (t, J = 6.4 Hz, 2H), 7.18-7.16 (d, J = 8.0 Hz, 1H), 3.61-3.55 (m, 1H), 3.44-3.37 (m, 1H), 3.31-3.21 (m, 1H), 3.15-3.08 (m, 1H), 2.88-2.80 (m, 2H), 2.75-2.67 (m, 4H), 1.94-1.89 (d, J = 19.6 Hz, 3H), 1.86-1.65 (m, 4H) | 289 |
| I-13 | 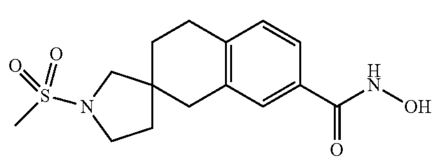 [SMILES: CS(=O)(=O)N1CCC2(CCc3ccc(C(=O)NO)cc3C2)C1] | (400 MHz, DMSO-d6 + D₂O): 7.48-7.47 (d, J = 6.8 Hz, 2H), 7.20-7.18 (d, J = 8.4 Hz, 1H), 3.40-3.36 (t, J = 7.0 Hz, 2H), 3.10-3.01 (m, 2H), 2.91 (s, 3H), 2.84-2.76 (m, 4H), 1.80-1.74 (m, 4H) | 325 |

Example 27

Preparation of 1'-cyclohexyl-N-hydroxy-3,4-dihydro-1H-spiro[naphthalene-2,3'-pyrrolidine]-7-carboxamide (I-5)

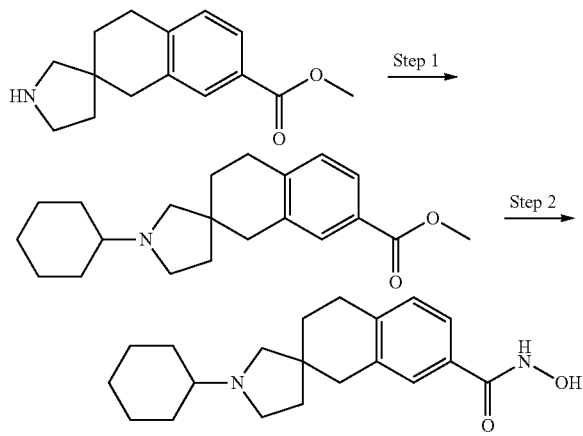

Step-1: Methyl 1'-cyclohexyl-3,4-dihydro-1H-spiro[naphthalene-2,3'-pyrrolidine]-7-carboxylate Into a 25-mL round-bottom flask was placed cyclohexanone (26.4 mg, 0.27 mmol, 1.1 equiv), $CH_2Cl_2$ (5 mL), and methyl 3,4-dihydro-1H-spiro[naphthalene-2,3'-pyrrolidine]-7-carboxylate (60 mg, 0.24 mmol, 1 equiv). The mixture was stirred for 1 h at room temperature. This was followed by the addition of $NaBH(OAc)_3$ (519.4 mg, 2.45 mmol, 10 equiv). The resulting solution was stirred overnight at room temperature. The reaction was then quenched by the addition of 20 mL of water. The resulting solution was extracted with 3×30 mL of $CH_2Cl_2$ and the organic layers combined. The organics were washed with 50 mL of aq. $NaHCO_3$, dried over anhydrous $Na_2SO_4$, filtered and concentrated under vacuum. This afforded 48 mg (60% yield) of title compound as a yellow oil. MS: (ES, m/z): 328 [M+H]$^+$.

Step-1: 1'-Cyclohexyl-N-hydroxy-3,4-dihydro-1H-spiro[naphthalene-2,3'-pyrrolidine]-7-carboxamide Into a 10-mL round-bottom flask was methyl 1'-cyclohexyl-3,4-dihydro-1H-spiro[naphthalene-2,3'-pyrrolidine]-7-carboxylate (48 mg, 0.15 mmol, 1 equiv), THF/MeOH (4:1, 3 mL), $NH_2OH$ (50% in water, 485.1 mg, 50 equiv), and aq. 1N NaOH (0.294 mL, 2equiv). The resulting solution was stirred for 2 h at room temperature. The pH of the solution was adjusted to 6 with 6N HCl. The crude product was purified by Prep-HPLC with the following conditions: Column: SunFire Prep C18 OBD 19×150 mm, 5 μm; Mobile Phase A: Water/0.05% TFA, Mobile Phase B: $CH_3CN$/0.05% TFA; Gradient: 8% B to 32% B in 8 min; Detector: UV 254 nm, 220 nm. The collected fractions were lyophilized to give 13 mg (20% yield) of title compound as an off-white solid. $^1H$ NMR (400 MHz, DMSO-d6) δ (ppm): 11.16(s, 1H), 9.69 (s, 1H), 8.98 (s, 1H), 7.51-7.47 (m, 2H), 7.19-7.17 (d, J=8.0 Hz, 1H), 3.65-3.61(m, 1H), 3.33-3.24 (m, 2H), 3.11-3.02 (m, 2H), 2.88-2.80 (m, 4H), 2.09-2.02 (t, J=14.4 Hz, 2H), 1.94-1.73 (m, 6H), 1.61-1.59 (d, J=11.6 Hz, 1H), 1.34-1.11 (m, 5H). MS: (ES, m/z): 329[M+H]$^+$.

TABLE 11

The following compound was prepared according to the method of Example 27.

| Ex. | Structure | $^1$H NMR δ (ppm) | Found (ES, m/z) [M + H]$^+$ |
|---|---|---|---|
| I-9 | 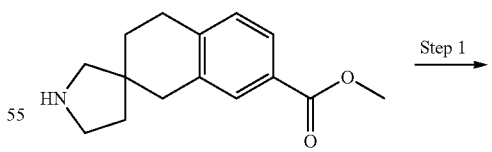 | (400 MHz, DMSO-d6): 11.14 (s, 1H), 9.89 (s, 1H), 8.97 (s, 1H), 7.51-7.48 (t, J = 6.8 Hz, 2H), 7.19-7.17 (d, J = 7.6 Hz, 1H), 3.65 (s, 1H), 3.49-3.46 (d, J = 12.4 Hz, 1H), 3.20 (s, 1H), 2.98-2.79 (m, 8H), 2.20-1.75 (m, 4H) | 261 |

Example 28

Preparation of N-hydroxy-1'-isopropyl-3,4-dihydro-1H-spiro[naphthalene-2,3'-pyrrolidine]-7-carboxamide (I-11)

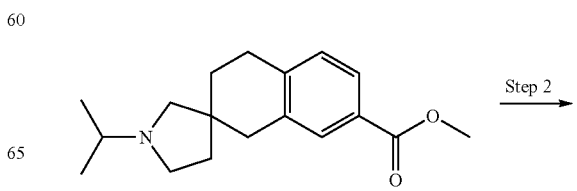

-continued

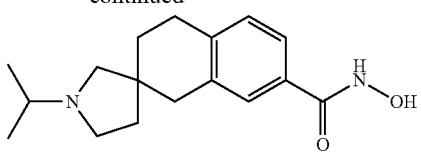

Step-1: Methyl 1'-isopropyl-3,4-dihydro-1H-spiro[naphthalene-2,3'-pyrrolidine]-7-carboxylate Into a 10-mL round-bottom flask was placed methyl 3,4-dihydro-1H-spiro[naphthalene-2,3'-pyrrolidine]-7-car- (135 mg, 0.98 mmol, 3 equiv), and 2-iodopropane (111 mg, 0.65 mmol, 2 equiv). The reaction was stirred overnight at room temperature. The reaction was then quenched by the addition of 50 mL of water. The resulting solution was extracted with 3×50 mL of EtOAc. The combined organics were washed with 3×50 mL of brine, dried over anhydrous $Na_2SO_4$, filtered, and concentrated under vacuum to provide 35 mg (crude) of the title compound as a yellow solid. MS: (ES, m/z): 288 $[M+H]^+$.

Step-2: N-Hydroxy-1'-isopropyl-3,4-dihydro-1H-spiro[naphthalene-2,3'-pyrrolidine]-7-carboxamide Into a 10-mL round-bottom flask was placed methyl 1'-isopropyl-3,4-dihydro-1H-spiro[naphthalene-2,3'-pyrrolidine]-7-carboxylate (35 mg, 0.12 mmol, 1 equiv), THF/ MeOH (4:1, 2 mL), $NH_2OH$ (50% in water, 483 mg, 60 equiv), and aq. 1N NaOH (0.24 mL, 2 equiv). The resulting solution was stirred for 2 h at room temperature. The solids were filtered out. The crude product was purified by Prep-HPLC with the following conditions: Column: SunFire PrepC18, 19×150 mm, 5 μm; Mobile Phase A: Water/0.05% TFA, Mobile Phase B: $CH_3CN$/0.05% TFA; Gradient: 2% B to 8% B in 7 min; Detector: UV 254 nm. The collected fractions were lyophilized to give 3.8 mg (11% yield) of the title compound as a yellow solid. $^1H$ NMR (400 MHz, DMSO-d6) δ (ppm): 11.13 (br s, 1H), 8.25 (s, 1H), 7.47-7.35 (m, 2H), 7.15-7.08 (m, 1H), 2.96-2.66 (m, 7H), 2.46 (s, 2H), 1.77-1.48 (m, 4H), 1.16-1.04 (d, J=6.4 Hz, 6H). MS: (ES, m/z): 289 $[M+H]^+$.

TABLE 12

The following compounds were prepared according to the method of Example 28.

| Ex. | Structure | $^1H$ NMR δ (ppm) | Found (ES, m/z) $[M + H]^+$ |
|---|---|---|---|
| I-14 | 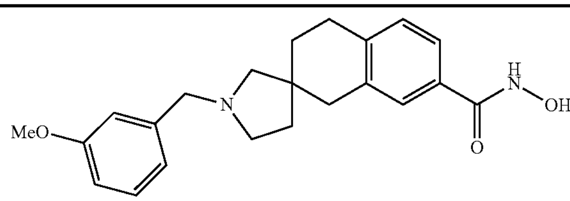 | (300 MHz, DMSO-d6): 11.04 (s, 1H), 8.17 (s, 1H), 7.46-7.44 (d, J = 4.2 Hz, 2H), 7.23-7.18 (t, J = 8.1 Hz, 1H), 7.13-7.10 (d, J = 8.4 Hz, 1H), 6.88-6.87 (d, J = 4.5 Hz, 2H), 6.79-6.76 (m, 1H), 3.72 (s, 3H), 3.56 (s, 2H), 2.86-2.66 (m, 5H), 2.56-5.54 (m, 1H), 2.40-2.28 (m, 2H), 1.76-1.49 (m, 4H) | 367 |
| I-15 | 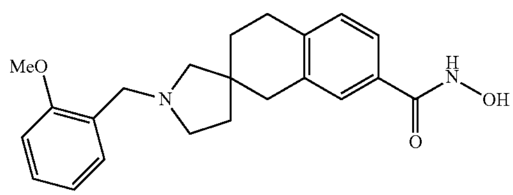 [SMILES: COc1ccccc1CN1CCC2(CCc3ccc(C(=O)NO)cc3C2)C1] | (400 MHz, DMSO-d6): 11.14 (s, 1H), 10.24-10.19 (br s, 1H), 8.97 (s, 1H), 7.55-7.41 (m, 4H), 7.19-7.12 (m, 2H), 7.05-7.01 (t, J = 6.6 Hz, 1H), 4.38-4.35 (t, J = 6.0 Hz, 2H), 3.86-3.83 (d, J = 12.0 Hz, 3H), 3.56-3.50 (m, 2H), 3.24-2.99 (m, 2H), 2.94-2.77 (m, 4H), 2.02-1.83 (m, 4H) | 367 |

Example 29

Preparation of N7-hydroxy-N1'-phenyl-3,4-dihydro-1H-spiro[naphthalene-2,3'-pyrrolidine]-1',7-dicarboxamide (I-6)

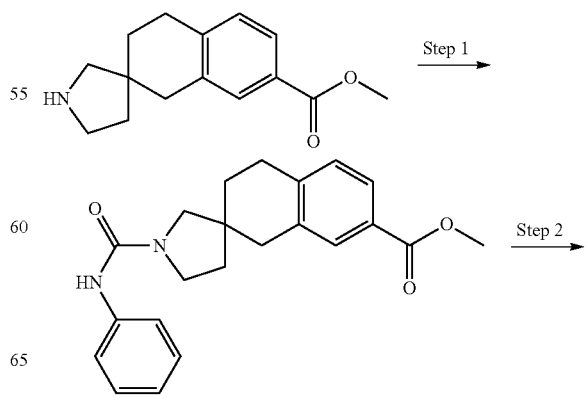

-continued

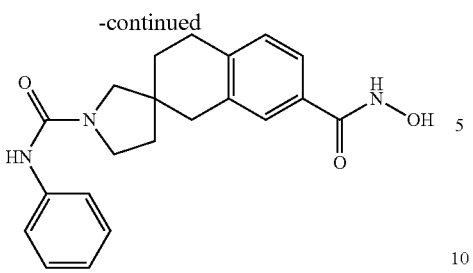

Step-1: Methyl 1'-(phenylcarbamoyl)-3,4-dihydro-1H-spiro[naphthalene-2,3'-pyrrolidine]-7-carboxylate Into a 25-mL round-bottom flask was placed methyl 3,4-dihydro-1H-spiro[naphthalene-2,3'-pyrrolidine]-7-carboxylate (30 mg, 0.12 mmol, 1 equiv), CH$_2$Cl$_2$ (5 mL), and Et$_3$N (24.64 mg, 2 equiv). This was followed by the addition of isocyanatobenzene (21.9 mg, 0.18 mmol, 1.5 equiv) at 0° C. The reaction was stirred overnight at 0° C. in an ice-water bath. The reaction was then quenched by the addition of 20 mL of water. The resulting solution was extracted with 3×20 mL of CH$_2$Cl$_2$. The combined organic layers were washed with 50 mL of brine, dried over anhydrous Na$_2$SO$_4$, filtered and concentrated under vacuum to give 67 mg of the title compound as a yellow solid, which was used without purification. MS: (ES, m/z): 365 [M+H]$^+$.

Step-2: N7-Hydroxy-N1'-phenyl-3,4-dihydro-1H-spiro[naphthalene-2,3'-pyrrolidine]-1',7-dicarboxamide Into a 10-mL round-bottom flask was placed methyl 1'-(phenylcarbamoyl)-3,4-dihydro-1H-spiro[naphthalene-2,3'-pyrrolidine]-7-carboxylate (67 mg, 0.18 mmol, 1 equiv), THF/MeOH (4:1, 2 mL), NH$_2$OH (50% in water, 607.2 mg, 50 equiv), and aq. 1N NaOH (0.368mL, 2 equiv). The resulting solution was stirred for 2 h at room temperature. The pH of the solution was adjusted to 6 with 6N HCl. The crude product was purified by Prep-HPLC with the following conditions: Column: Waters HSS C18, 2.1×50 mm, 1.8 μm; Mobile Phase: A: Water/0.05% TFA, Mobile Phase B: CH$_3$CN/0.05% TFA; Flow rate: 0.7 mL/min; Gradient: 5% B to 95% B in 2 min, hold 0.6 min; Detector: UV 254 nm. The collected fractions were lyophilized to give 32.7 mg (37% yield) of the title compound as a pink solid. $^1$H NMR (400MHz, DMSO-d6) δ (ppm): 11.10 (s, 1H), 8.09 (s, 1H), 7.50-7.49 (d, J=6.8 Hz, 4H), 7.23-7.19(t, J=8.0 Hz, 3H), 6.92-6.89 (t, J=7.4 Hz, 1H), 3.56-3.51 (m, 2H), 3.25 (s, 2H), 2.87-2.76 (m, 4H), 1.82-1.76 (m, 4H). MS: (ES, m/z): 366 [M+H]$^+$.

Example 30

Preparation of N-hydroxy-3,4-dihydro-1H-spiro[naphthalene-2,3'-pyrrolidine]-7-carboxamide (I-8)

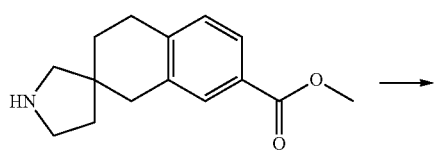 →

-continued

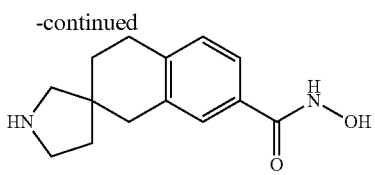

Into a 10-mL round-bottom flask was placed methyl 3,4-dihydro-1H-spiro[naphthalene-2,3'-pyrrolidine]-7-carboxylate (70 mg, 0.29 mmol, 1 equiv), THF/MeOH (4:1, 2 mL), NH$_2$OH (50% in water, 1.13 g, 60 equiv), and aq. 1N NaOH (0.58 mL, 2 equiv). The resulting solution was stirred for 2 h at room temperature. The solids were filtered out. The crude product was purified by Prep-HPLC with the following conditions: Column: Sunfire C18, 19×150 mm, 5 μm; Mobile Phase A: Water/0.05% TFA, Mobile Phase B: CH$_3$CN/0.05% TFA; Gradient: 5% B to 20% B in 6 min; Detector: UV 254 nm. The collected fractions were lyophilized to give 32.4 mg (32% yield) of title compound as an off-white solid. $^1$H NMR (400MHz, DMSO-d6+D$_2$O) δ (ppm): 7.50-7.47 (m, 2H), 7.18-7.16 (d, J=8.0 Hz, 1H), 3.33-3.29 (m, 2H), 3.03-2.93 (m, 2H), 2.83-2.77 (m, 4H), 1.80-1.75 (m, 4H). MS: (ES, m/z): 247 [M+H]$^+$.

Example 31

Preparation of 1'-formyl-N-hydroxy-3,4-dihydro-1H-spiro[naphthalene-2,3'-pyrrolidine]-7-carboxamide (I-10)

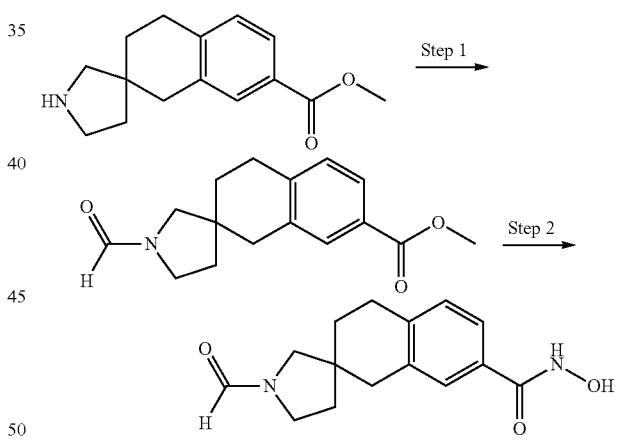

Step-1: Methyl 1'-formyl-3,4-dihydro-1H-spiro[naphthalene-2,3'-pyrrolidine]-7-carboxylate Into a 50-mL round-bottom flask, was placed methyl 3,4-dihydro-1H-spiro[naphthalene-2,3'-pyrrolidine]-7-carboxylate (100 mg, 0.41 mmol, 1 equiv), and ethyl formate (5 mL). The resulting solution was stirred overnight at 60° C. in an oil bath. The resulting mixture was concentrated under vacuum and quenched by the addition of 50 mL of water. The resulting solution was extracted with 3×30 mL of EtOAc. The organic layers were combined, washed with 50 mL of brine and concentrated under vacuum to give 130 mg of the title compound as a yellow oil, which was used without any purification. MS: (ES, m/z): 274 [M+H]$^+$.

Step-2: 1'-Formyl-N-hydroxy-3,4-dihydro-1H-spiro[naphthalene-2,3'-pyrrolidine]-7-carboxamide Into a 10-mL round-bottom flask was placed methyl 1'-formyl-3,4-dihydro-1H-spiro[naphthalene-2,3'-pyrrolidine]-7-carboxylate (65 mg, 0.24 mmol, 1 equiv), THF/MeOH (4:1, 2 mL), NH$_2$OH (50% in water, 943 mg, 60 equiv), and aq. 1N NaOH (0.45 mL, 2 equiv). The resulting solution was stirred for 2 h at room temperature. The solids were filtered out. The crude product was purified by Prep-HPLC with the following conditions: Column: Sunfire C18, 19×150 mm, 5 µm; Mobile Phase A: Water/0.05% TFA, Mobile Phase B: CH$_3$CN/0.05% TFA; Gradient: 7% B to 23% B in 7 min; Detector: UV 254 nm. The collected fractions were lyophilized to give 3.5 mg (4% yield) of the title compound as a pink solid. $^1$H NMR (400 MHz, DMSO-d6) δ (ppm): 11.08 (s, 1H), 8.93 (s, 1H), 8.16-8.14 (d, J=7.2 Hz, 1H), 7.49-7.46 (d, J=8.4 Hz, 2H), 7.17-7.12 (t, J=10.6 Hz, 1H), 3.64-3.61 (t, J=7.2 Hz, 1H), 3.39-3.36 (m, 1H), 3.32-3.26 (m, 1H), 3.13-3.06 (m, 1H), 2.89-2.77 (m, 2H), 2.71-2.65 (m, 2H), 1.81-1.66 (m, 4H). MS: (ES, m/z): 275 [M+H]$^+$.

Example 32

Preparation of N-hydroxy-1'-(4-methoxybenzoyl)-3,4-dihydro-1H-spiro[naphthalene-2,3'-pyrrolidine]-7-carboxamide (I-1)

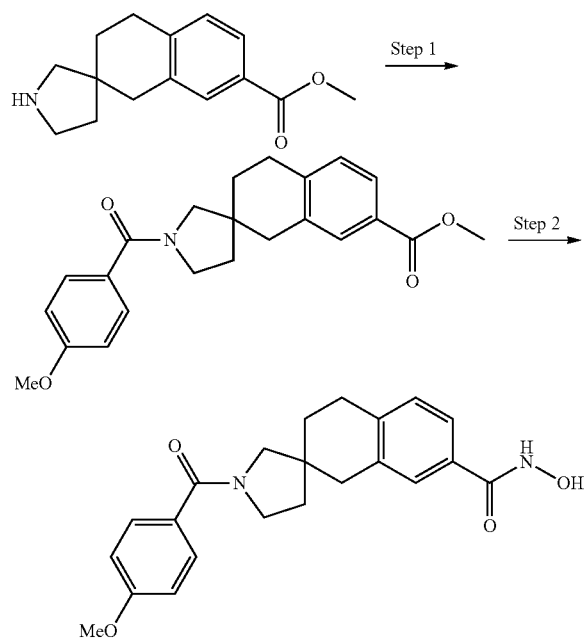

Step-1: Methyl 1'-(4-methoxybenzoyl)-3,4-dihydro-1H-spiro[naphthalene-2,3'-pyrrolidine]-7-carboxylate Methyl 3,4-dihydro-1H-spiro[naphthalene-2,3'-pyrrolidine]-7-carboxylate*TFA (78mg, 0.217 mmol, 1 equiv) was combined in CH$_2$Cl$_2$ (2.0 mL) with 4-methoxybenzoic acid (35mg, 0.228 mmol, 1.05 equiv), DIEA (0.114 mL, 0.651 mmol, 3 equiv), and HBTU (95 mg, 0.250mmol, 1.15 equiv). The resulting mixture was stirred at room temperature for 48 h. The reaction was purified by normal phase chromatography on silica gel (30% EtOAc/hexanes to 100% EtOAc) to afford 57.7 mg (70% yield) of the title compound as a white solid. MS: (ES, m/z): 379[M+H]+.

Step-2: N-Hydroxy-1'-(4-methoxybenzoyl)-3,4-dihydro-1H-spiro[naphthalene-2,3'-pyrrolidine]-7-carboxamide Methyl 1'-(4-methoxybenzoyl)-3,4-dihydro-1H-spiro[naphthalene-2,3'-pyrrolidine]-7-carboxylate (57 mg, 0.152 mmol, 1 equiv) was dissolved in a solution of THF/MeOH (4:1, 1.5mL). NH$_2$OH (50% in water, 0.80 mL, 12.93 mmol, 85 equiv), and aq. 1N NaOH (0.015 mL, 2equiv). The reaction was allowed to stir at room temperature for 1 h and purified directly by Prep-HPLC using the following conditions: Column: XTerra Prep MS C18 OBD 5 am, 19×100 mm; Mobile Phase A: Water/0.05% Formic Acid, Mobile Phase B: CH$_3$CN/0.05% Formic Acid; Flow rate: 20 mL/min; Gradient: 15% B to 85% B in 10 min; Detector: UV 254nm, 220 nm. Combined fractions were lyophilized to afford 21.2 mg (37% yield) of the title compound. $^1$H NMR (300 MHz, DMSO-d6) δ (ppm): 11.07 (br s, 1H), 8.18 (s, 1H), 7.30-7.66(m, 4H), 7.02-7.29 (m, 1H), 6.76-7.02 (m, 2H), 3.70-3.84 (m, 3H), 3.57 (br d, J=7.0 Hz, 2H), 3.15-3.44 (m, 4H), 2.59-2.91 (m, 4H), 2.38-2.56 (m, 8H), 1.60-1.90 (m, 4H). MS: (ES, m/z): 381[M+H]$^+$.

Example 33

Preparation of N-hydroxy-1'-((4-methoxyphenyl)sulfonyl)-3,4-dihydro-1H-spiro[naphthalene-2,3'-pyrrolidine]-7-carboxamide (I-2)

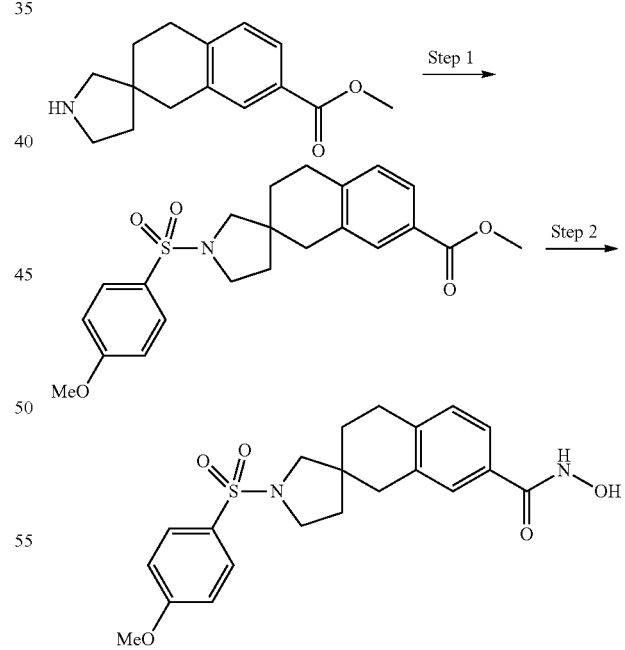

Step-1: Methyl 1'-((4-methoxyphenyl)sulfonyl)-3,4-dihydro-1H-spiro[naphthalene-2,3'-pyrrolidine]-7-carboxylate Methyl 3,4-dihydro-1H-spiro[naphthalene-2,3'-pyrrolidine]-7-carboxylate.TFA (78mg, 0.217 mmol, 1 equiv) was combined with DIEA (0.13 mL, 0.760 mmol, 3.5 equiv) in THF (2.0 mL). After several minutes, 4-methoxybenzene-1-sulfonyl chloride (54 mg, 0.260 mmol, 1.2equiv) was added and the resulting mixture was stirred at room temperature for 16 h. The reaction mixture was partitioned between sat. aq. NaHCO$_3$ and EtOAc. Water was added to dissolve salts. The organic phase was removed and the aqueous layer was extracted with several portions of EtOAc. The combined organic phases were washed with brine, dried over anhydrous Na$_2$SO$_4$, filtered and concentrated. The resulting residue was purified by normal phase chromatography on silica gel to afford 60.2 mg (67% yield) of the title compound as a yellow solid. $^1$H NMR (300 MHz, DMSO-d6) δ (ppm): 11.07 (br s, 1H), 8.95 (br s, 1H), 7.68-7.72 (m, 2H), 7.43 (dd, J=7.9, 1.5 Hz, 1H), 7.25 (s, 1H), 7.03-7.20 (m, 3H), 3.87 (s, 3H), 3.15-3.45 (m, 4H), 2.57-2.81 (m, 2H), 2.34-2.46 (m, 2H), 1.44-1.68 (m, 4H). MS: (ES, m/z): 415 [M+H]+.

Step-2: N-Hydroxy-1'-((4-methoxyphenyl)sulfonyl)-3,4-dihydro-H-spiro[naphthalene-2,3'-pyrrolidine]-7-carboxamide Methyl 1'-((4-methoxyphenyl)sulfonyl)-3,4-dihydro-1H-spiro[naphthalene-2,3'-pyrrolidine]-7-carboxylate (60 mg, 0.145 mmol, 1 equiv) was dissolved in a solution of THF/MeOH (4:1, 1.25 mL). NH$_2$OH (50% in water, 0.76 mL, 12.32 mmol, 85 equiv) was added, followed by aq. 1N NaOH (0.015 mL, 2 equiv). The reaction was allowed to stir at room temperature for 1 h and was purified directly by Prep-HPLC using the following conditions: Column: XTerra Prep MS C18 OBD 5 am, 19×100 mm; Mobile Phase A: Water/0.05% Formic Acid, Mobile Phase B: CH$_3$CN/0.05% Formic Acid; Flow rate: 20 mL/min; Gradient: 15% B to 85% B in 10 min; Detector: UV 254 nm, 220 nm. Combined fractions were lyophilized to afford 19.6 mg (33% yield) of the title compound. MS: (ES, m/z): 416 [M+H]$^+$.

Example 34

Preparation of N-hydroxy-1'-(4-methoxybenzyl)-3,4-dihydro-1H-spiro[naphthalene-2,3'-pyrrolidine]-7-carboxamide (I-3)

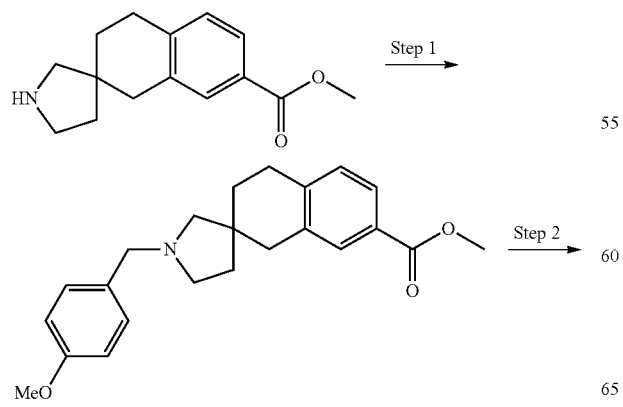

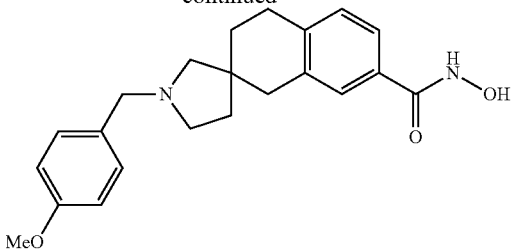

Step-1: Methyl 1'-(4-methoxybenzyl)-3,4-dihydro-1H-spiro[naphthalene-2,3'-pyrrolidine]-7-carboxylate Methyl 3,4-dihydro-1H-spiro[naphthalene-2,3'-pyrrolidine]-7-carboxylate*TFA (78mg, 0.217 mmol, 1 equiv) was combined with Et$_3$N (0.03 mL, 0.217 mmol, 1 equiv) and 4-methoxybenzaldehyde (0.026 mL, 0.217 mmol, 1 equiv) in DCE (2.0 mL). The reaction was stirred at room temperature for 1 h. Then NaBH(OAc)$_3$ (55 mg, 0.260 mmol, 1.2 equiv) was added and the reaction was allowed to stir at room temperature for 48 h. The reaction mixture was directly purified by normal phase chromatography on silica gel (10% EtOAc/hexanes to 100% EtOAc) to afford 46.2 mg (58% yield) of the title compound. MS: (ES, m/z): 366 [M+H]$^+$.

Step-2: N-Hydroxy-1'-(4-methoxybenzyl)-3,4-dihydro-1H-spiro[naphthalene-2,3'-pyrrolidine]-7-carboxamide Methyl 1'-(4-methoxybenzyl)-3,4-dihydro-1H-spiro[naphthalene-2,3'-pyrrolidine]-7-carboxylate (46.2 mg, 0.126 mmol, 1 equiv) was dissolved in a solution of THF/MeOH (4:1 1.25mL). NH$_2$OH (50% in water, 0.66 mL, 10.75 mmol, 85 equiv) was added followed by aq. 1N NaOH (0.013 mL, 2 equiv). The reaction was allowed to stir at room temperature for 1 h and was purified directly by Prep-HPLC using the following conditions: Column: XTerra Prep MS C$_{18}$OBD 5 μm, 19×100 mm; Mobile Phase A: Water/0.05% Formic Acid, Mobile Phase B: CH3CN/0.05% Formic Acid; Flow rate: 20 mL/min; Gradient: 15% B to 85% B in 10 min; Detector: UV 254 nm, 220 nm. Combined fractions were lyophilized to afford 33.9 mg (73% yield) of the title compound. $^1$H NMR (300 MHz, DMSO-d6) δ (ppm): 11.07 (br s, 1H), 8.16 (s, 1H), 7.37-7.53 (m, 2H), 7.16-7.27 (m, 2H), 6.97-7.16 (m, 1H), 6.74-6.89 (m, 2H), 3.70 (s, 3H), 3.54 (s, 2H), 2.54-2.80 (m, 6H), 2.34 (s, 2H), 1.39-1.75 (m, 4H). MS: (ES, m/z): 367 [M+H]$^+$.

Example 35

Preparation of (S)—N-hydroxy-1'-phenyl-3,4-dihydro-1H-spiro[naphthalene-2,3'-pyrrolidine]-7-carboxamide (I-16)

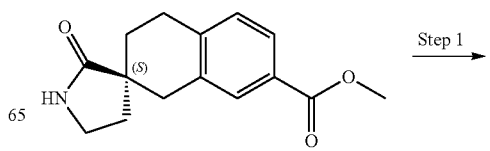

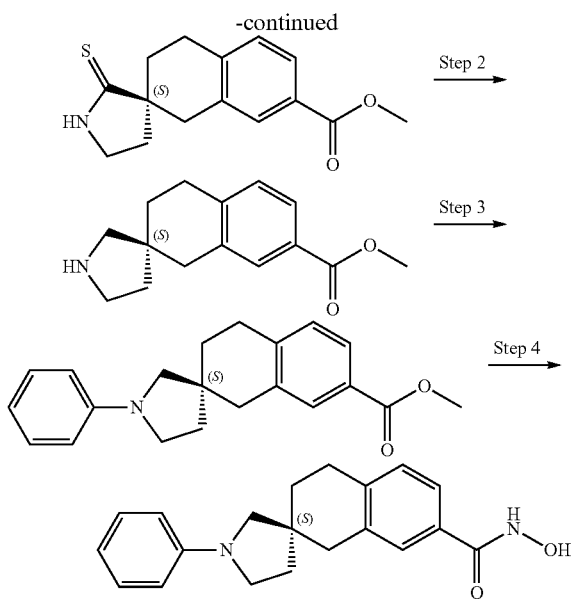

Step-1: Methyl (S)-2'-thioxo-3,4-dihydro-1H-spiro[naphthalene-2,3'-pyrrolidine]-7-carboxylate Into a 50-mL round-bottom flask, was placed methyl (S)-2'-oxo-3,4-dihydro-1H-spiro[naphthalene-2,3'-pyrrolidine]-7-carboxylate (600 mg, 2.31 mmol, 1 equiv) in $CH_2Cl_2$ (15mL) and 2,4-bis(4-methoxyphenyl)-2,4-dithioxo-1,3,2,4-dithiadiphosphetane (Lawesson reagent) (1.4 g, 3.46 mmol, 1.5 equiv). The resulting solution was stirred overnight at room temperature. The reaction was then quenched by the addition of 20 mL of aq. $NaHCO_3$ and extracted with 3×20 mL of $CH_2Cl_2$. The combined organic layers were washed with 30 mL of brine, dried over anhydrous $Na_2SO_4$ and concentrated under vacuum. The residue was purified by normal phase column chromatography on silica gel with EtOAc/petroleum ether (1:1). The collected fractions were concentrated under vacuum to give 530 mg (83% yield) of the title compound as a pink solid. MS: (ES, m/z): 276 [M+H]$^+$.

Step-2: Methyl (S)-3,4-dihydro-1H-spiro[naphthalene-2,3'-pyrrolidine]-7-carboxylate Into a 100-mL 3-necked round-bottom flask purged and maintained with an inert atmosphere of nitrogen, was placed methyl (S)-2'-thioxo-3,4-dihydro-1H-spiro[naphthalene-2,3'-pyrrolidine]-7-carboxylate (530 mg, 1.92 mmol, 1 equiv), THF/MeOH (4:1, 10 mL), and $NiCl_2 \cdot 6H_2O$ (2.7 g, 11.52 mmol, 6 equiv). This was followed by the addition of $NaBH_4$ (220 mg, 5.82 mmol, 3 equiv) in several batches at 0° C. The reaction was stirred overnight at room temperature. The resulting mixture was concentrated under vacuum. The residue was dissolved in THF (5 mL), and the solids were filtered out, the filtrate was concentrated under vacuum. The residue was purified by normal phase column chromatography on silica gel with $CH_2Cl_2$/MeOH (10:1). The collected fractions were concentrated under vacuum to give 1.2 g of the title compound as a green solid, which was used without further purification. MS: (ES, m/z): 246[M+H]$^+$.

Step-3: Methyl (S)-1'-phenyl-3,4-dihydro-1H-spiro[naphthalene-2,3'-pyrrolidine]-7-carboxylate Into a 50-mL round-bottom flask, was placed methyl (S)-3,4-dihydro-1H-spiro[naphthalene-2,3'-pyrrolidine]-7-carboxylate (100 mg, 0.41 mmol, 1 equiv), $CH_2Cl_2$ (5 mL), $Et_3N$ (124 mg, 1.23 mmol, 3 equiv), $PhB(OH)_2$ (100 mg, 0.82 mmol, 2 equiv), and $Cu(OAc)_2$ (38mg, 0.21 mmol, 0.50 equiv). Oxygen gas was introduced to the reaction. The resulting solution was stirred overnight at room temperature. The reaction was then quenched by the addition of 10mL of water and extracted with 3×10 mL of $CH_2Cl_2$. The organic layers were combined and washed with 15 mL of brine, dried over anhydrous $Na_2SO_4$, filtered and concentrated under vacuum. The residue was purified by normal phase column chromatography on silica gel with EtOAc/petroleum ether (1:5). The collected fractions were concentrated under vacuum to give 106 mg (81% yield) of the title compound as a yellow oil. MS: (ES, m/z): 322 [M+H]$^+$.

Step-4: (S)—N-Hydroxy-1'-phenyl-3,4-dihydro-1H-spiro[naphthalene-2,3'-pyrrolidine]-7-carboxamide Into a 10-mL round-bottom flask, was placed methyl (S)-1'-phenyl-3,4-dihydro-1H-spiro[naphthalene-2,3'-pyrrolidine]-7-carboxylate (33 mg, 0.10 mmol, 1 equiv), THF/MeOH (4:1), $NH_2OH$ (50% in water, 407 mg, 60 equiv), and aq. 1N NaOH (0.2 mL, 0.20 mmol, 2equiv). The resulting solution was stirred for 2 h at room temperature. The solids were filtered out. The crude product was purified by Prep-HPLC with the following conditions: Column: XBridge Prep C18 OBD, 5 μm, 19×150 mm; Mobile Phase A: Water/0.1% Formic Acid, Mobile Phase B: $CH_3CN$/0.1% Formic Acid; Flow rate: 20 mL/min; Gradient: 40% B to 48% B in 10 min; Detector: 254 nm, 220 nm. The collected fractions were lyophilized to give 12.2 mg (37% yield) of the title compound as an off-white solid. $^1H$ NMR (300 MHz, DMSO-d6) δ (ppm): 7.50-7.46 (t, J=6.6 Hz, 2H), 7.22-7.17 (t, J=7.8 Hz, 3H), 6.72-6.64 (m, 3H), 3.50-3.40 (m, 2H), 3.21-3.10 (m, 2H), 2.91-2.76 (m, 4H), 1.98-1.82 (m, 4H). MS: (ES, m/z): 323 [M+H]+.

TABLE 13

The following compounds were prepared according to the method of Example 35, using methyl (R)-2'-oxo-3,4-dihydro-1H-spiro[naphthalene-2,3'-pyrrolidine]-7-carboxylate in Step 1.

| Ex. | Structure | $^1H$ NMR δ (ppm) | Found (ES, m/z) [M + H]$^+$ |
|---|---|---|---|
| I-17 | ![structure] | (300 MHz, DMSO-d6): 8.93 (s, 1H), 7.46-7.45 (m, 2H), 7.19-7.09 (m, 3H), 6.55-6.47 (m, 3H), 3.37-3.35 (m, 2H), 3.10-3.07 (m, 2H), 2.87 (s, 2H), 2.78 (s, 2H), 1.88-1.81 (m, 4H) | 323 |

Example 36

Preparation of (S)—N-hydroxy-1'-methyl-3,4-di-hydro-1H-spiro[naphthalene-2,3'-pyrrolidine]-7-carboxamide (I-18)

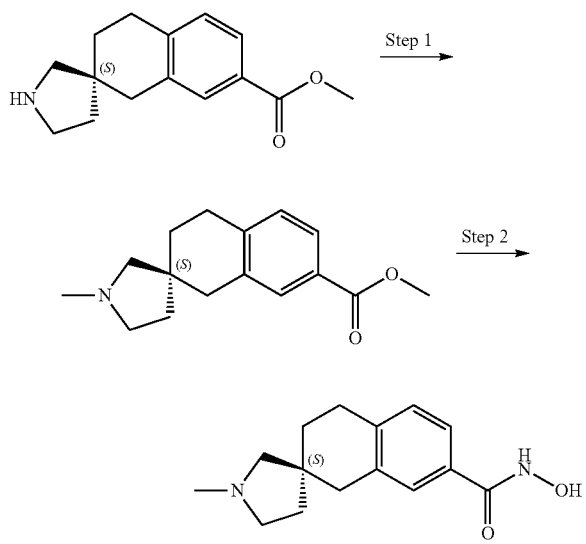

Step-1: Methyl (S)-1'-methyl-3,4-dihydro-1H-spiro[naphthalene-2,3'-pyrrolidine]-7-carboxylate Into a 10-mL round-bottom flask, was placed methyl (S)-3,4-dihydro-1H-spiro[naphthalene-2,3'-pyrrolidine]-7-carboxylate (100 mg, 0.41 mmol, 1 equiv) in $CH_2Cl_2$ (2 mL), and formaldehyde (30% in $H_2O$, 82 mg, 2.73 mmol, 2 equiv). After 1 h, $NaBH_3CN$ (78 mg, 1.24 mmol, 3 equiv) was added at 0° C. The resulting solution was stirred overnight at room temperature. The reaction was then quenched by the addition of 20 mL of water and was extracted with 3×20 mL of $CH_2Cl_2$. The combined organic layers were washed with 15 mL of brine, dried over anhydrous $Na_2SO_4$, filtered and concentrated under vacuum to afford 30 mg (28% yield) of the title compound as a yellow oil. MS: (ES, m/z): 260 $[M+H]^+$.

Step-2: (S)—N-hydroxy-1'-methyl-3,4-dihydro-1H-spiro[naphthalene-2,3'-pyrrolidine]-7-carboxamide Into a 10-mL round-bottom flask, was placed methyl (S)-1'-methyl-3,4-dihydro-1H-spiro[naphthalene-2,3'-pyrrolidine]-7-carboxylate (30 mg, 0.12 mmol, 1 equiv), THF/MeOH (4:1, 1 mL), $NH_2OH$ (50% in water, 459 mg, 60 equiv), and aq. 1N NaOH (0.25 mL, 2 equiv). The resulting solution was stirred for 2 h at room temperature. The solids were filtered out. The crude product was purified by Prep-HPLC with the following conditions: Column: XBridge Prep C18 OBD, 5 μm, 19×150 mm; Mobile Phase A: Water/10 mmol $NH_4HCO_3$, Mobile Phase B: $CH_3CN$/10 mmol $NH_4HCO_3$; Flow rate: 20 mL/min; Gradient: 5% B to 25% B in 8 min; Detector: UV 254 nm, 220 nm. The collected fractions were lyophilized to give 13.5 mg (45% yield) of the title compound as a white solid. $^1$H NMR (300 MHz, DMSO-d6) δ (ppm): 9.11 (s, 1H), 7.47-7.43 (d, J=10.2 Hz, 2H), 7.12-7.09 (d, J=8.1 Hz, 1H), 2.79-2.57 (m, 5H), 2.45-2.37 (m, 1H), 2.29-2.20 (m, 5H), 1.74-1.70 (t, J=6.6 Hz, 2H), 1.65-1.59 (m, 1H), 1.52-1.46 (m, 1H). MS: (ES, m/z): 261 $[M+H]^+$.

TABLE 14

The following compounds were prepared according to the method of Example 36, using methyl (R)-3,4-dihydro-1H-spiro[naphthalene-2,3'-pyrrolidine]-7-carboxylate in Step 1.

| Ex. | Structure | $^1$H NMR δ (ppm) | Found (ES, m/z) $[M + H]^+$ |
|---|---|---|---|
| I-19 | 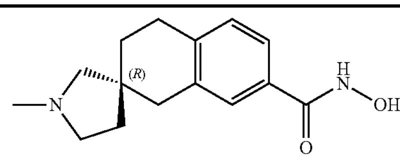 | (400 MHz, DMSO-d6): 7.47-7.43 (m, 2H), 7.09 (s, 1H), 2.79-2.72 (m, 2H), 2.67-2.55 (m, 2H), 2.51-2.50 (m, 1H), 2.44-2.41 (m, 1H), 2.29-2.22 (m, 2H), 2.20 (s, 3H), 1.74-1.70 (m, 2H), 1.64-1.63 (m, 1H), 1.62-1.60 (m, 1H) | 261 |

Example 37

Preparation of (R)-1'-(4-fluorobenzyl)-N-hydroxy-5'-oxo-3,4-dihydro-1H-spiro[naphthalene-2,3'-pyrrolidine]-7-carboxamide (I-128)

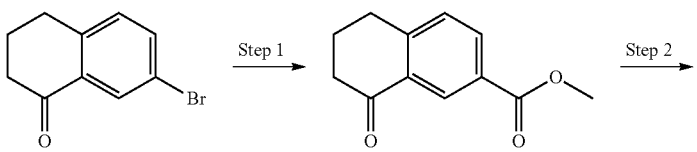

-continued

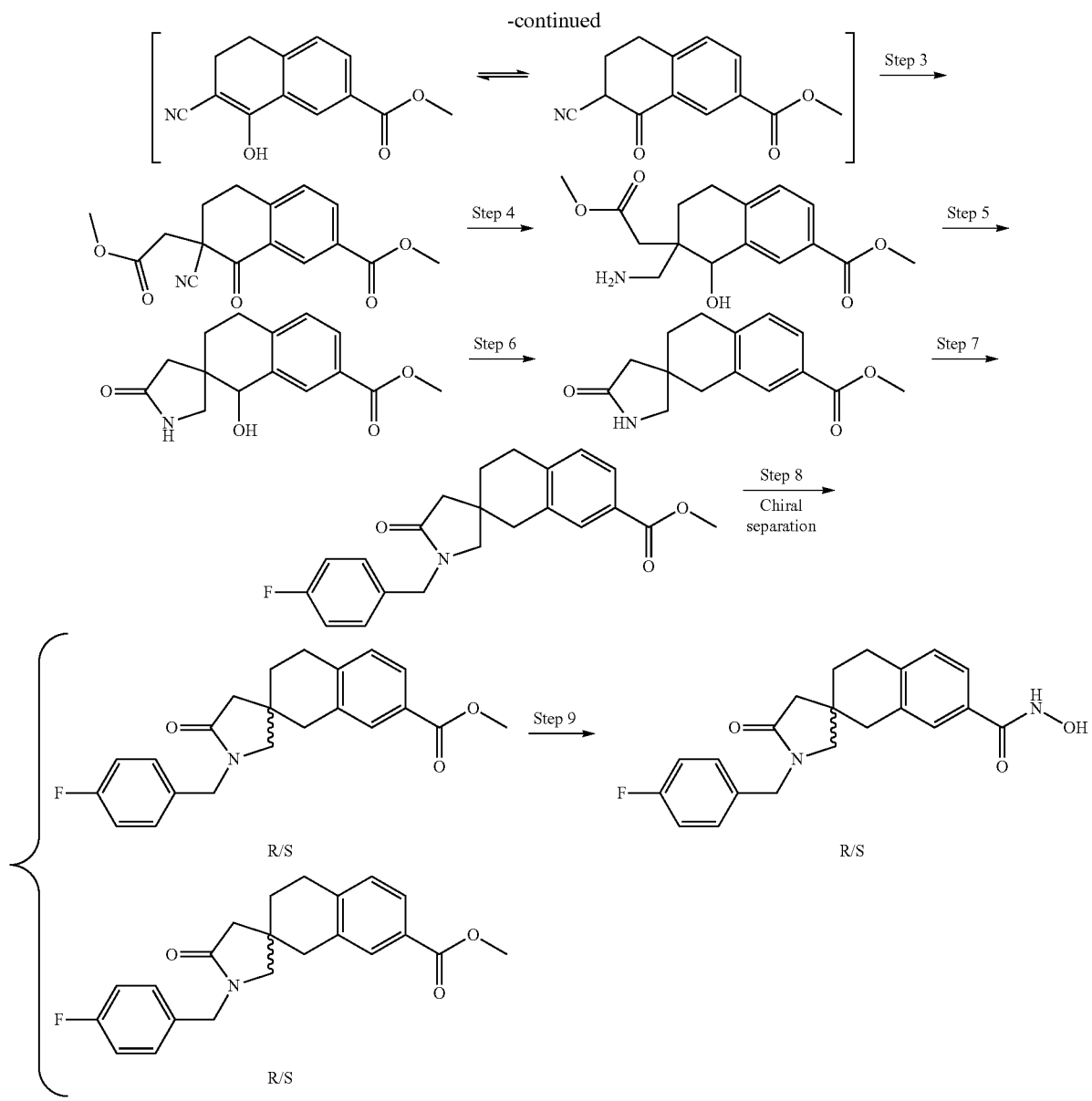

Step-1: Methyl 8-oxo-5,6,7,8-tetrahydronaphthalene-2-carboxylate

Into a 2-L pressure tank reactor (30 atm), was placed 7-bromo-3,4-dihydronaphthalen-1(2H)-one (25 g, 111.07 mmol, 1 equiv), Et$_3$N (33.6 g, 332.05 mmol, 3 equiv), Pd(dppf)Cl$_2$ (8.1 g, 11.07 mmol, 0.10 equiv), and MeOH (1 μL). CO (g) was introduced into the reaction. The resulting solution was stirred overnight at 90° C. at 30 atm. The resulting mixture was concentrated under vacuum. The residue was purified by normal phase chromatography on silica gel with EtOAc/petroleum ether (1:5). The collected fractions were concentrated under vacuum to give 17.7 g (78% yield) of the title compound as a yellow solid. MS: (ES, m/z): 205 [M+H]$^+$.

Step-2: Methyl 7-cyano-8-oxo-5,6,7,8-tetrahydronaphthalene-2-carboxylate

Into a 250-mL 3-necked round-bottom flask purged and maintained with an inert atmosphere of nitrogen, was placed bis(propan-2-yl)amine (17.7 mL, 127.5 mmoL, 1.7 equiv) in THF (50 mL). n-BuLi (2.5M, 57 mL, 142.5 mmoL, 1.9 equiv) was added dropwise at −78° C. The reaction was stirred for an additional 1 h at −78° C. The solution was then slowly added to a solution of methyl 8-oxo-5,6,7,8-tetrahydronaphthalene-2-carboxylate (15 g, 75 mmol, 1 equiv) in THF (800 mL) at −78° C. under an inert atmosphere of nitrogen. After stirring for 30 min at −78° C., a solution of 4-methylbenzene-1-sulfonyl cyanide (25.35 g, 150 mmol, 2 equiv) in THF (300 mL) was added dropwise at −78° C. The reaction was stirred for an additional 30 min at −78° C. The reaction was quenched by the addition of 150 mL sat. aq. NH$_4$Cl and stirred for 1 h at −78° C. The mixture was extracted with EtOAc. The organic layer was separated, dried over anhydrous Na$_2$SO$_4$, filtered, and concentrated under vacuum. The residue was purified by normal phase chromatography on silica gel with EtOAc/petroleum ether (2:5). The collected fractions were concentrated under vacuum to give 8 g of the title compound as a yellow solid. MS: (ES, m/z): 230 [M+H]$^+$.

Step-3: Methyl 7-cyano-7-(2-methoxy-2-oxoethyl)-8-oxo-5,6,7,8-tetrahydronaphthalene-2-carboxylate Into a 250-mL round-bottom flask was placed methyl 7-cyano-8-oxo-5,6,7,8-tetrahydronaphthalene-2-carboxylate (8 g, 34.90 mmol, 1 equiv), K$_2$CO$_3$ (9.6 g, 68.96 mmol, 2 equiv), and DMF (60 mL). Methyl 2-bromoacetate (10.62 g, 68.96 mmol, 2 equiv) was then added at 0° C. The resulting mixture was stirred overnight at room temperature. The reaction was quenched by the addition of 10 mL of H$_2$O. The resulting solution was extracted with 3×15 mL of EtOAc. The combined organic layers were washed with 3×10 mL of brine, dried over anhydrous Na$_2$SO$_4$, filtered and concentrated under vacuum. The residue was purified by Prep-HPLC with the following conditions: Mobile Phase A: H$_2$O/10% NH$_4$HCO$_3$, Mobile Phase B: CH$_3$CN/10% NH$_4$HCO$_3$; Flow rate: 60 mL/min; Gradient: 0% B to 40% B in 60 min; Detector: UV 254 nm. The collected fractions were concentrated under vacuum to give 2 g (19% yield) of the title compound as a white solid. MS: (ES, m/z): 302 [M+H]$^+$.

Step-4: Methyl 7-(aminomethyl)-8-hydroxy-7-(2-methoxy-2-oxoethyl)-5,6,7,8-tetrahydronaphthalene-2-carboxylate Into a 250-mL round-bottom flask was placed methyl 7-cyano-7-(2-methoxy-2-oxoethyl)-8-oxo-5,6,7,8-tetrahydronaphthalene-2-carboxylate (1.3 g, 4.31 mmol, 1 equiv), MeOH (43 mL), acetic acid (26 mL), and PtO$_2$ (0.55 g, 0.56 equiv). H$_2$ (g) was introduced to the flask. The resulting solution was stirred overnight at room temperature. The solids were filtered out. The filtrate was concentrated under vacuum to give 1.6 g of the title compound as a yellow oil, which was used without further purification. MS: (ES, m/z): 308 [M+H]$^+$.

Step-5: Methyl 1-hydroxy-5'-oxo-3,4-dihydro-1H-spiro[naphthalene-2,3'-pyrrolidine]-7-carboxylate Into a 100-mL round-bottom flask was placed methyl 7-(aminomethyl)-8-hydroxy-7-(2-methoxy-2-oxoethyl)-5,6,7,8-tetrahydronaphthalene-2-carboxylate (1.6 g, 5.21 mmol, 1 equiv), MeOH (20 mL), then a solution of 7M NH$_3$ in MeOH (8 mL, 56.00 mmol, 10.7 equiv) was added. The resulting solution was stirred for 1 h at room temperature. The resulting mixture was concentrated under vacuum. The crude product was purified by normal phase chromatography on silica gel with CH$_2$Cl$_2$/MeOH (0% to 40% gradient). The collected fractions were concentrated under vacuum to give 0.56 g (39% yield) of the title compound as a yellow oil. MS: (ES, m/z): 276 [M+H]$^+$.

Step-6: Methyl 5'-oxo-3,4-dihydro-1H-spiro[naphthalene-2,3'-pyrrolidine]-7-carboxylate Into a 100-mL round-bottom flask was placed methyl 1-hydroxy-5'-oxo-3,4-dihydro-1H-spiro[naphthalene-2,3'-pyrrolidine]-7-carboxylate (560 mg, 2.03 mmol, 1 equiv), TFA (5 mL), and Et$_3$SiH (5 mL). The resulting solution was stirred overnight at 80° C. The resulting mixture was concentrated under vacuum. The residue was washed with 3×10 mL of petroleum ether. The combined organics were concentrated to give 0.45 g (85% yield) of the title compound as a white solid. $^1$H NMR (400 MHz, DMSO-d6) δ (ppm): 7.70-7.68 (m, 2H), 7.57 (s, 1H), 7.25-7.23 (d, 1H), 3.82 (s, 3H), 3.13-3.10 (d, 1H), 2.99-2.97 (d, 1H), 2.89-2.81 (m, 4H), 2.17-2.13 (d, 1H), 1.94-1.90 (d, 1H), 1.80-1.76 (m, 2H). MS: (ES, m/z): 260 [M+H]$^+$.

Step-7: Methyl 1'-(4-fluorobenzyl)-5'-oxo-3,4-dihydro-1H-spiro[naphthalene-2,3'-pyrrolidine]-7-carboxylate Into a 25-mL round-bottom flask was placed methyl 5'-oxo-3,4-dihydro-1H-spiro[naphthalene-2,3'-pyrrolidine]-7-carboxylate (180 mg, 0.73 mmol, 1 equiv), DMF (5 mL), NaH (60% dispersion in oil, 27.8 mg, 0.69 mmol, 2.5 equiv) was added at 0° C. After stirring for 30 min at room temperature, 1-(bromomethyl)-4-fluorobenzene (157 mg, 0.83 mmol, 2 equiv) was added dropwise at 0° C. The resulting solution was stirred overnight at room temperature. The reaction was then quenched by the addition of 2 mL of H$_2$O. The crude product was purified by Prep-HPLC with the following conditions: Column: C18 bonded silica gel; Mobile phase A: Water/0.05% TFA, Mobile Phase B: CH$_3$CN/0.05% TFA; Gradient: 0% B to 70% B in 60 min; Detector: UV 254 nm. The collected fractions were concentrated under vacuum to give 130 mg (48% yield) of the title compound as a yellow oil. MS: (ES, m/z): 368 [M+H]$^+$.

Step-8: Chiral separation of methyl (R)-1'-(4-fluorobenzyl)-5'-oxo-3,4-dihydro-1H-spiro[naphthalene-2,3'-pyrrolidine]-7-carboxylate and methyl (S)-1'-(4-fluorobenzyl)-5'-oxo-3,4-dihydro-1H-spiro[naphthalene-2,3'-pyrrolidine]-7-carboxylate Methyl 1'-(4-fluorobenzyl)-5'-oxo-3,4-dihydro-1H-spiro[naphthalene-2,3'-pyrrolidine]-7-carboxylate (130 mg, 0.35 mmol, 1 equiv) was separated by Chiral-Prep-HPLC with the following conditions: Column: Repaired IA, 21.2×150 mm, 5 μm; Mobile Phase A: Hexanes, Mobile Phase B: EtOH; Flow rate: 25 mL/min; Gradient: hold 50% B in 12 min; Detector: UV 254 nm. The first eluting isomer (Rt 5 min) was collected and concentrated under vacuum to give 30 mg (23% yield) of a yellow oil which was assigned as the R isomer of methyl 1'-(4-fluorobenzyl)-5'-oxo-3,4-dihydro-1H-spiro[naphthalene-2,3'-pyrrolidine]-7-carboxylate. MS: (ES, m/z): 368 [M+H]$^+$. The second eluting isomer (Rt 7 min) was collected and concentrated to give 30 mg (23% yield) of a yellow oil which was assigned as the S isomer of methyl 1'-(4-fluorobenzyl)-5'-oxo-3,4-dihydro-1H-spiro[naphthalene-2,3'-pyrrolidine]-7-carboxylate. MS: (ES, m/z): 368 [M+H]$^+$.

Step-9: (R)-1'-(4-Fluorobenzyl)-N-hydroxy-5'-oxo-3,4-dihydro-1H-spiro[naphthalene-2,3'-pyrrolidine]-7-carboxamide Into a 25-mL round-bottom flask was placed the first eluted isomer from Step 8, which was assigned as methyl (R)-1'-(4-fluorobenzyl)-5'-oxo-3,4-dihydro-1H-spiro[naphthalene-2,3'-pyrrolidine]-7-carboxylate as described above, (30 mg, 0.08 mmol, 1 equiv), THF/MeOH (4:1, 1 mL), NH₂OH (50% in water, 326 mg, 4.8 mmoL, 60 equiv), and aq. 1N NaOH (0.16 mL, 0.16 mmoL, 2 equiv). The resulting solution was stirred for 5 h at room temperature. The crude product was purified by Prep-HPLC with the following conditions: Column: SunFire Prep C18 OBD, 5 μm, 19×150 mm; Mobile Phase A: Water/0.1% Formic Acid, Mobile Phase B: CH₃CN/0.1% Formic acid; Gradient: 5% B to 82% B in 8 min; Detector: UV 254 nm, 220 nm. The collected fractions were concentrated under vacuum to give 5.6 mg (19% yield) of the title compound as a light pink solid. ¹H NMR (400 MHz, DMSO-d6) δ (ppm): 11.09 (br s, 1H), 7.48-7.13 (m, 7H), 4.41 (s, 2H), 3.12-3.10 (d, 1H) 3-2.98 (d, 1H), 2.88-2.68 (m, 4H), 2.37-2.33 (d, 1H), 2.16-2.12 (d, 1H), 1.80-1.70 (m, 2H). MS: (ES, m/z): 369 [M+H]⁺.

TABLE 15

The following compound was prepared according to the method of Example 37 using the first eluted isomer from Step 8, with the following modification: In Step 7, the halide can be an iodide.

| Ex. | Structure | ¹H NMR δ (ppm) | Found (ES, m/z) [M + H]⁺ |
|---|---|---|---|
| I-130 | 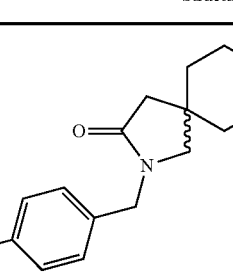 R/S | (400 MHz, DMSO-d6): 11.10 (br s, 1H), 7.50-7.47 (m, 2H), 7.18-7.16 (d, 1H), 3.25-3.22 (d, 1H), 3.10-3.07 (d, 1H), 2.89-2.72 (m, 7H), 2.27-2.23 (d, 1H), 2.08-2.06 (d, 1H), 1.80-1.77 (m, 2H) | 275 |

TABLE 16

The following compounds were prepared according to the method of Example 37, with the following modifications:
(1) In Step 7, the halide can be a bromide or an iodide;
(2) In Step 9, the second eluted isomer from Step 8, which was assigned as methyl (S)-1'-(4-fluorobenzyl)-5'-oxo-3,4-dihydro-1H-spiro[naphthalene-2,3'-pyrrolidine]-7-carboxylate was used.

| Ex. | Structure | ¹H NMR δ (ppm) | Found (ES, m/z) [M + H]⁺ |
|---|---|---|---|
| I-129 | 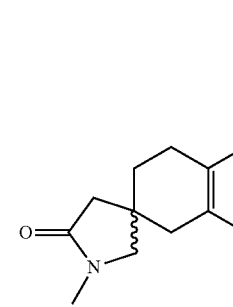 R/S | (400 MHz, DMSO-d6): 11.09 (br s, 1H), 7.48-7.13 (m, 7H), 4.47 (s, 2H), 3.12-3.10 (d, 1H), 3-2.98 (d, 1H), 2.88-2.68 (m, 4H), 2.37-2.33 (d, 1H), 2.16-2.12 (d, 1H), 1.80-1.70 (m, 2H) | 369 |
| I-131 | R/S | (400 MHz, DMSO-d6): 11.10 (br s, 1H), 10.14 (br s, 1H), 7.50-7.46 (m, 2H), 7.13-7.16 (d, 1H), 3.25-3.22 (d, 1H), 3.10-3.07 (d, 1H), 2.87-2.72 (m, 7H), 2.27-2.23 (d, 1H), 2.08-2.06 (d, 1H), 1.81-1.77 (m, 2H) | 275 |

Example 38

Preparation of (S)—N-hydroxy-5'-oxo-1'-phenyl-3,4-dihydro-1H-spiro[naphthalene-2,3'-pyrrolidine]-7-carboxamide (I-132)

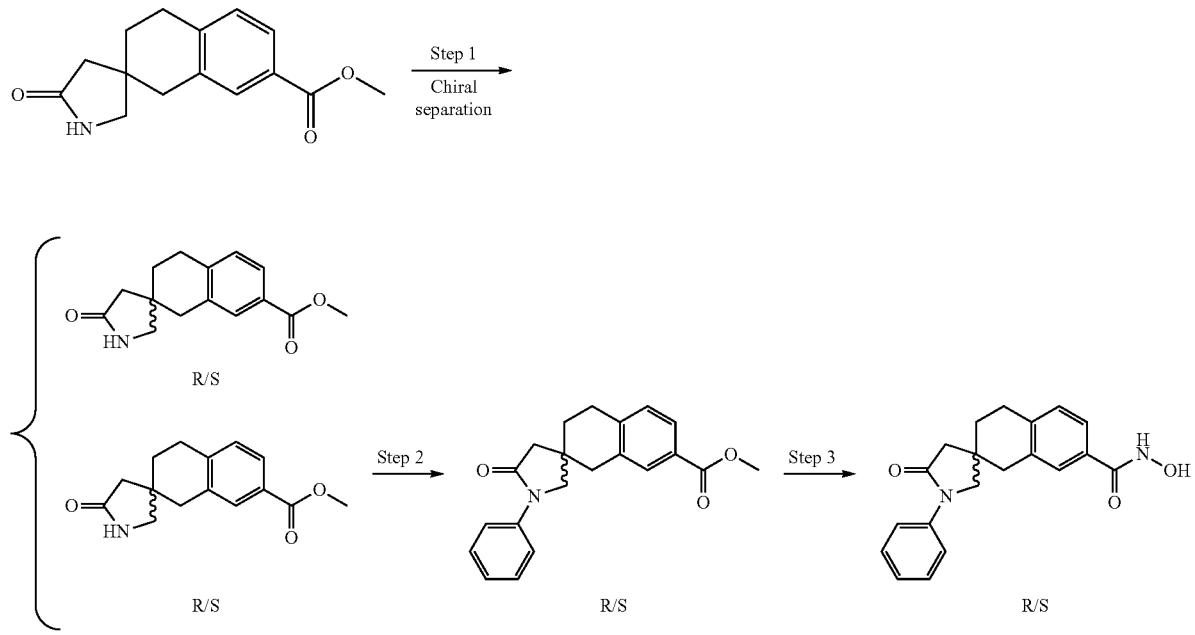

Step-1: Chiral separation of methyl (R)-5'-oxo-3,4-dihydro-1H-spiro[naphthalene-2,3'-pyrrolidine]-7-carboxylate and methyl (S)-5'-oxo-3,4-dihydro-1H-spiro[naphthalene-2,3'-pyrrolidine]-7-carboxylate Methyl 5'-oxo-3,4-dihydro-1H-spiro[naphthalene-2,3'-pyrrolidine]-7-carboxylate (2 g) was separated by Prep-SFC with the following conditions: Column: Chiralpak AS-H, 5×25 cm, 5 μm; Mobile Phase A: $CO_2$ (50%), Mobile Phase B: MeOH (50%); Detector: UV 220 nm. The first eluting isomer (Rt 8.80 min) was collected and concentrated under vacuum to give 1 g (45% yield) of an off-white solid which was assigned as the R isomer of methyl 5'-oxo-3,4-dihydro-1H-spiro[naphthalene-2,3'-pyrrolidine]-7-carboxylate. MS: (ES, m/z): 260 [M+H]$^+$. The second eluting isomer (Rt 16.19 min) was collected and concentrated under vacuum to give 1 g (45% yield) of an off-white solid which was assigned as the S isomer of methyl 5'-oxo-3,4-dihydro-1H-spiro[naphthalene-2,3'-pyrrolidine]-7-carboxylate. MS: (ES, m/z): 260 [M+H]$^+$.

Step-2: Methyl (S)-5'-oxo-1'-phenyl-3,4-dihydro-1H-spiro[naphthalene-2,3'-pyrrolidine]-7-carboxylate Into a 50-mL round-bottom flask, was placed the second eluted isomer from Step 1, which was assigned as methyl (S)-5'-oxo-3,4-dihydro-1H-spiro[naphthalene-2,3'-pyrrolidine]-7-carboxylate as described above, (100 mg, 0.39 mmol, 1 equiv), THF (8 mL), Cu(OAc)$_2$ (70 mg, 0.39 mmol, 1 equiv), Et$_3$N (117 mg, 1.16 mmol, 3 equiv), pyridine (45.7 mg, 0.58 mmol, 1.5 equiv), phenylboronic acid (235.11 mg, 1.93 mmol, 5 equiv) and 4 Å MS (100 mg). Oxygen gas was introduced to the above flask. The resulting mixture was stirred for 24 h at 60° C. The solids were filtered out and the filtrate was concentrated under vacuum. The residue was dissolved in 80 mL of EtOAc and washed with 3×15 mL of H$_2$O. The combined organic layers were dried over anhydrous Na$_2$SO$_4$, filtered and concentrated under vacuum. The residue was purified by normal phase column chromatography on silica gel with EtOAc/petroleum ether (1:2). The collected fractions were concentrated under vacuum to give 77 mg (60% yield) of title compound as a light yellow oil. MS: (ES, m/z): 336 [M+H]$^+$.

Step-3: (S)—N-Hydroxy-5'-oxo-1'-phenyl-3,4-dihydro-1H-spiro[naphthalene-2,3'-pyrrolidine]-7-carboxamide Into an 8-mL vial, was placed a solution of methyl (S)-5'-oxo-1'-phenyl-3,4-dihydro-1H-spiro[naphthalene-2,3'-pyrrolidine]-7-carboxylate (77 mg, 0.23 mmol, 1 equiv) in THF/MeOH (4:1, 2.0 mL), NH$_2$OH (50% in water, 0.46 mL, 30 equiv) and aq. 1N NaOH (0.46 mL, 2 equiv). The resulting solution was stirred for 1 h at 25° C. The crude product was purified by Prep-HPLC with the following conditions: Column: XBridge Prep C18 OBD, 5 μm, 19×150 mm; Mobile Phase A: Water/0.05% TFA, Mobile Phase B: CH$_3$CN/0.05% TFA; Flow rate: 20 mL/min; Gradient: 5% B to 70% B in 7 min; Detector: UV 254 nm, 220 nm. The collected fractions were lyophilized to give 29 mg (38% yield) of the title compound as a white solid. $^1$H NMR (300 MHz, DMSO-d6) δ (ppm): 11.06 (s, 1H), 8.94 (s, 1H), 7.66-7.63 (s, 1H), 7.50-7.47 (m, 2H), 7.38-7.32 (m, 2H), 7.20-7.09 (m, 2H), 3.78-3.75 (m, 1H), 3.60-3.57 (m, 1H), 2.93-2.86 (m, 4H), 2.60-2.54 (m, 1H), 2.36-2.30 (m, 1H), 1.91-1.86 (m, 2H). MS: (ES, m/z): 337 [M+H]$^+$.

TABLE 17

The following compound was prepared according to the method of Example 38 using the first eluted isomer from Step 1.

| Ex. | Structure | ¹H NMR δ (ppm) | Found (ES, m/z) [M + H]⁺ |
|---|---|---|---|
| I-141 | R/S | (300 MHz, DMSO-d6): 11.05 (s, 1H), 8.95 (s, 1H), 7.49-7.45 (m, 2H), 7.16-7.13 (m, 1H), 3.15-3.12 (d, J = 9.6 Hz, 1H), 2.99-2.96 (d, J = 9.6 Hz, 1H), 2.84-2.80 (m, 2H), 2.73-2.71 (m, 2H), 2.67-2.61 (m, 1H), 2.28-2.22 (d, J = 16.5 Hz, 1H), 2.06-2 (d, J = 16.5 Hz, 1H), 1.77-1.72 (m, 2H), 0.69-0.63 (m, 4H) | 301 |

TABLE 18

The following compounds were prepared according to the method of Example 38, with the following modification: In Step 2, the first eluted isomer from Step 1, which was assigned as methyl (R)-5'-oxo-3,4-dihydro-1H-spiro[naphthalene-2,3'-pyrrolidine]-7-carboxylate, was used.

| Ex. | Structure | ¹H NMR δ (ppm) | Found (ES, m/z) [M + H]⁺ |
|---|---|---|---|
| I-145 | R/S | (400 MHz, DMSO-d6): 10.95 (s, 1H), 8.97 (s, 1H), 7.65-7.64 (m, 2H), 7 51-7.47 (m, 2H), 7.37-7.33 (m, 2H), 7.20-7.10 (m, 2H), 3.78-3.76 (d, J = 9.6 Hz, 1H), 3.60-3.57 (d, J = 9.6 Hz, 1H), 2.92-2.82 (m, 4H), 2.60-2.56 (d, J = 16.8 Hz, 1H), 2.36-2.32 (d, J = 16.8 Hz, 1H), 1.90-1.87 (t, J = 6.8 Hz, 2H) | 337 |
| I-148 | R/S | (300 MHz, DMSO-d6): 10.90 (s, 1H), 8.98 (s, 1H), 7.48-7.45 (t, J = 5.7 Hz, 2H), 7.15-7.12 (d, J = 7.8 Hz, 1H), 3.15-3.12 (d, J = 9.6 Hz, 1H), 2.99-2.96 (d, J = 9.6 Hz, 1H), 2.84-2.80 (t, J = 6.5 Hz, 2H), 2.73-2.60 (m, 3H), 2.28-2.22 (d, J = 16.2 Hz, 1H), 2.06-2 (d, J = 16.2 Hz, 1H), 1.76-1.72 (t, J = 6.6 Hz, 2H), 0.66-0.61 (m, 4H) | 301 |

Example 39

Preparation of (R)-1'-(cyclobutylmethyl)-N-hydroxy-5'-oxo-3,4-dihydro-1H-spiro[naphthalene-2,3'-pyrrolidine]-7-carboxamide (I-133)

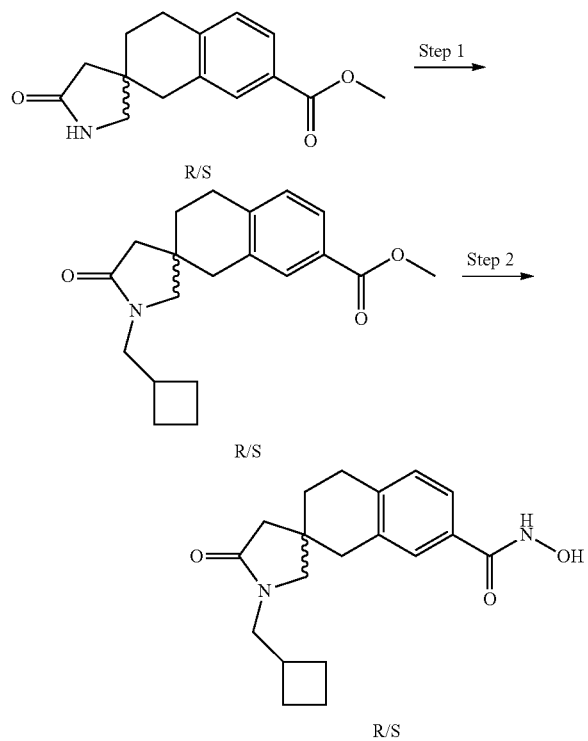

Step-1: Methyl (R)-1'-(cyclobutylmethyl)-5'-oxo-3,4-dihydro-1H-spiro[naphthalene-2,3'-pyrrolidine]-7-carboxylate Into a 10 mL round-bottom flask, was placed the first eluted isomer from Example 38, Step 1, which was assigned as methyl (R)-5'-oxo-3,4-dihydro-1H-spiro[naphthalene-2,3'-pyrrolidine]-7-carboxylate as described above, (100 mg, 0.04 mmol, 1 equiv) in DMF (3 mL). This was followed by the addition of NaH (60% dispersion in oil, 60 mg, 0.25 mmol, 4 equiv), in portions at 0° C. The resulting solution was stirred for 30 min at 25° C. (Bromomethyl)cyclobutane (580 mg, 0.39 mmol, 10 equiv) was then added. The resulting solution was allowed to stir for an additional 4 h at 25° C. The reaction was then quenched by the addition of 15 mL of water. The resulting solution was extracted with 3×50 mL of $CH_2Cl_2$, and the combined organic layers were dried over anhydrous $Na_2SO_4$, filtered and concentrated under vacuum. The residue was purified by normal phase column chromatography on silica gel with $CH_2Cl_2$/MeOH (10:1). The collected fractions were concentrated under vacuum to give 60 mg (50% yield) of title compound as a yellow oil. MS: (ES, m/z): 328 $[M+H]^+$.

Step-2: (R)-1'-(Cyclobutylmethyl)-N-hydroxy-5'-oxo-3,4-dihydro-1H-spiro[naphthalene-2,3'-pyrrolidine]-7-carboxamide Into a 25-mL round-bottom flask, was placed a solution of the product from Step 1, which was assigned as methyl (R)-1'-(cyclobutylmethyl)-5'-oxo-3,4-dihydro-1H-spiro[naphthalene-2,3'-pyrrolidine]-7-carboxylate as described above, (60 mg, 0.18 mmol, 1 equiv) in THF/MeOH (4:1, 3 mL), $NH_2OH$ (50% in water, 1449 mg, 43.87 mmol, 120 equiv), and aq. 1N NaOH (0.4 mL, 2 equiv). The resulting solution was stirred for 2 h at 28° C. The solids were filtered out. The crude product was purified by Prep-HPLC with the following conditions: Column: XBridge Prep C18 OBD, 5 μm, 19×150 mm; Mobile Phase A: Water/0.1% formic acid, Mobile Phase B: $CH_3CN$/0.1% formic acid; Gradient: 5% B to 62% B in 7 min; Detector: UV 254 nm, 220 nm. The collected fractions were lyophilized to give 25.4 mg (42% yield) of title compound as an off-white solid. $^1$H NMR (300 MHz, DMSO-d6) δ (ppm): 11.07 (s, 1H), 8.95 (s, 1H), 7.50-7.48 (m, 2H), 7.17-7.15 (d, J=8.1 Hz, 1H), 3.32-3.17 (m, 3H), 3.07-3.04 (d, J=9.9 Hz, 1H), 2.86-2.74 (m, 4H), 2.47-2.43 (m, 1H), 2.23-2.22 (d, J=16.5 Hz, 1H), 2.06-1.62 (m, 9H). MS: (ES, m/z): 329 $[M+H]^+$.

TABLE 19

The following compounds were prepared according to the method of Example 39 using the first eluted isomer from Example 38 Step 1.

| Ex. | Structure | $^1$H NMR δ (ppm) | Found (ES, m/z) $[M + H]^+$ |
|---|---|---|---|
| I-146 | 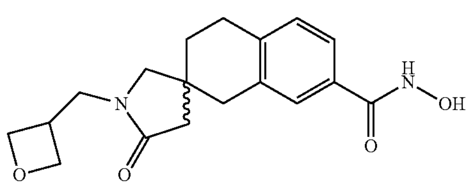 | (300 MHz, DMSO-d6): 9.78-9.14 (m, 1H), 7.49-7.45 (t, J = 11.1 Hz, 2H), 7.16-7.14 (d, J = 7.8 Hz, 1H), 4.64-4.58 (m, 2H), 4.30-4.25 (m, 2H), 3.50-3.40 (t, J = 14.3 Hz, 2H), 3.31-3.03 (m, 3H), 2.85-2.81 (t, J = 6.5 Hz, 2H), 2.73-2.62 (t, J = 16.2 Hz, 2H), 2.28-2.23 (d, J = 16.5 Hz, 1H), 2.07-2.01 (d, J = 16.5 Hz, 1H), 1.78-1.75 (d, J = 6.3 Hz, 2H) | 331 |

TABLE 19-continued

The following compounds were prepared according to the method of Example 39 using the first eluted isomer from Example 38 Step 1.

| Ex. | Structure | ¹H NMR δ (ppm) | Found (ES, m/z) [M + H]⁺ |
|---|---|---|---|
| I-135 | 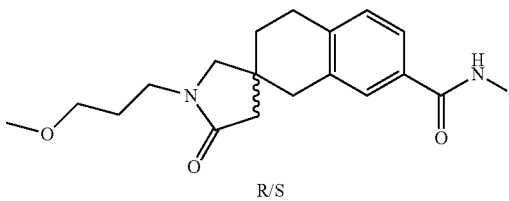 R/S | (300 MHz, DMSO-d6): 11.05 (s, 1H), 8.94 (s, 1H), 7.50-7.47 (d, J = 8.4 Hz, 2H), 7.18-7.15 (d, J = 7.8 Hz, 1H), 3.32-3.20 (m, 5H), 3.19 (s, 2H), 3.16 (s, 1H), 3.10-3.07 (d, J = 9.6 Hz, 1H), 2.87-2.83 (t, J = 6.5 Hz, 2H), 2.77-2.70 (t, J = 9.9 Hz, 2H), 2.29-2.23 (d, J = 16.5 Hz, 1H), 2.07-2.02 (d, J = 16.5 Hz, 1H), 1.81-1.70 (m, 2H), 1.68-1.61 (m, 2H) | 333 |
| I-137 | 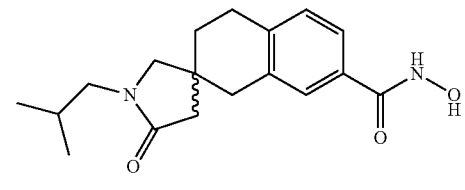 R/S | (400 MHz, DMSO-d6): 11.09 (s, 1H), 8.95 (s, 1H), 7.49-7.46 (m, 2H), 7.17-7.15 (d, J = 8.0 Hz, 1H), 3.23-3.20 (d, J = 9.6 Hz, 1H), 3.10-3.07 (d, J = 10.0 Hz, 1H), 2.99-2.87 (m, 2H), 2.85-2.77 (m, 4H), 2.30-2.26 (d, J = 16.4 Hz, 1H), 2.09-2.05 (d, J = 16.4 Hz, 1H), 1.82-1.78 (m, 3H), 0.84-0.82 (m, 6H) | 317 |
| I-139 | 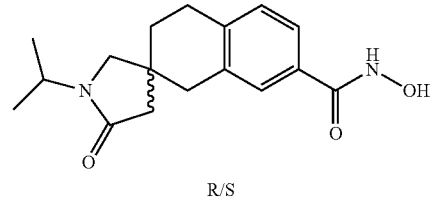 R/S | (300 MHz, DMSO-d6): 7.49-7.46 (d, J = 9.6 Hz, 2H), 7.17-7.15 (d, J = 7.8 Hz, 1H), 4.21-4.12 (m, 1H), 3.16-3.13 (d, J = 9.6 Hz, 1H), 3.05-3.02 (d, J = 9.6 Hz, 1H), 2.87-2.82 (t, J = 6.6 Hz, 2H), 2.74-2.68 (d, J = 18 Hz, 2H), 2.27-2.21 (d, J = 16.2 Hz, 1H), 2.06-2 (d, J = 16.2 Hz, 1H), 1.79-1.75 (t, J = 6.6 Hz, 2H), 1.05-1.02 (m, 6H) | 303 |
| I-142 | 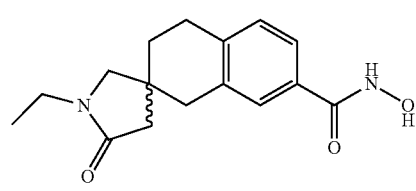 R/S | (300 MHz, DMSO-d6): 11.09 (s, 1H), 8.95 (s, 1H), 7.49-7.46 (m, 2H), 7.17-7.15 (d, J = 7.6 Hz, 1H), 3.24-3.18 (m, 3H), 3.10-3.07 (d, J = 10.0 Hz, 1H), 2.87-2.71 (m, 4H), 2.27-2.23 (d, J = 16.4 Hz, 1H), 2.06-2.02 (d, J = 16.4 Hz, 1H), 1.80-1.77 (t, J = 6.6 Hz, 2H), 1.02-0.98 (t, J = 7.2 Hz, 3H) | 289 |
| I-149 | 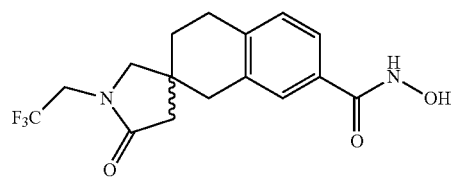 R/S | (400 MHz, DMSO-d6): 11.09 (s, 1H), 8.95 (s, 1H), 7.50-7.47 (m, 2H), 7.18-7.16 (d, J = 8.0 Hz, 1H), 4.10-4.05 (m, 2H), 3.37-3.32 (m, 1H), 3.25-3.23 (d, J = 9.6 Hz, 1H), 2.85-2.77 (m, 4H), 2.38-2.34 (d, J = 16.8 Hz, 1H), 2.17-2.13 (d, J = 16.4 Hz, 1H), 1.82-1.79 (m, 2H) | 343 |

TABLE 20

The following compounds were prepared according to the method of Example 39, with the following modification: In Step 1, the second eluted isomer from Example 38 Step 1, which was assigned as methyl (S)-5'-oxo-3,4-dihydro-1H-spiro[naphthalene-2,3'-pyrrolidine]-7-carboxylate, was used.

| Ex. | Structure | ¹H NMR δ (ppm) | Found (ES, m/z) [M + H]⁺ |
|---|---|---|---|
| I-134 | R/S | (400 MHz, DMSO-d6): 11.09 (br s, 1H), 8.95 (br s, 1H), 7.50-7.46 (m, 2H), 7.17-7.15 (d, J = 8.0 Hz, 1H), 3.25-3.15 (m, 3H), 3.07-3.04 (d, J = 10.0 Hz, 1H), 2.85-2.82 (m, 2H), 2.79-2.69 (m, 2H), 2.50-2.44 (m, 1H), 2.27-2.23 (d, J = 16.4 Hz, 1H), 2.06 (s, 1H), 2.01-1.93 (m, 2H), 1.88-1.75 (m, 4H), 1.70-1.62 (m, 2H) | 329 |
| I-147 | R/S | (400 MHz, DMSO-d6): 8.08-7.89 (m, 2H), 7.48-7.44 (m, 1H), 7.14-7.12 (m, 1H), 4.62-4.57 (m, 2H), 4.28-4.25 (m, 2H), 3.48-3.46 (m, 2H), 3.18-3.12 (m, 2H), 3.10-3.02 (m, 1H), 2.83-2.72 (m, 2H), 2.71-2.67 (m, 2H), 2.49-2.48 (m, 1H), 2.05-2 (m, 1H), 1.76-1.72 (m, 2H) | 331 |
| I-136 | R/S | (400 MHz, DMSO-d6): 11.06 (br s, 1H), 8.95 (br s, 1H), 7.50-7.47 (m, 2H), 7.17-7.15 (d, J = 8.0 Hz, 1H), 3.33-3.28 (m, 2H), 3.24-3.21 (m, 6H), 3.10-3.07 (d, J = 9.6 Hz, 1H), 2.86-2.81 (m, 2H), 2.77-2.76 (d, J = 6.0 Hz, 2H), 2.28-2.24 (d, J = 16.4 Hz, 1H), 2.06-2.02 (d, J = 16.4 Hz, 1H), 1.80-1.77 (m, 2H), 1.69-1.64 (m, 2H) | 333 |
| I-138 | R/S | (400 MHz, DMSO-d6): 11.09 (br s, 1H), 8.96 (br s, 1H), 7.49-7.47 (m, 2H), 7.17-7.15 (d, J = 16.4 Hz, 1H), 3.23-3.21 (d, J = 9.6 Hz, 1H), 3.10-3.07 (d, J = 10.0 Hz, 1H), 3-2.93 (m, 2H), 2.87-2.83 (m, 2H), 2.78-2.73 (m, 2H), 2.30-2.26 (d, J = 16.4 Hz, 1H), 2.09-2.05 (d, J = 16.4 Hz, 1H), 1.86-1.78 (m, 3H), 0.84-0.81 (m, 6H) | 317 |
| I-140 | R/S | (300 MHz, DMSO-d6): 11.08 (s, 1H), 8.94 (s, 1H), 7.49-7.46 (m, 2H), 7.17-7.15 (d, J = 7.8 Hz, 1H), 4.21-4.12 (m, 1H), 3.16-3.12 (d, J = 9.6 Hz, 1H), 3.05-3.02 (d, J = 9.8 Hz, 1H), 2.90-2.65 (m, 4H), 2.26-2.21 (d, J = 16.3 Hz, 1H), 2.07-2.06 (d, J = 16.3 Hz, 1H), 1.77-1.75 (m, 2H), 1.05-1.02 (m, 6H) | 303 |
| I-143 | R/S | (300 MHz, DMSO-d6): 11.07 (s, 1H), 8.95 (s, 1H), 7.49-7.46 (m, 2H), 7.17-7.15 (d, J = 7.8 Hz, 1H), 3.32-3.16-3.03 (m, 3H), 3.10-3.06 (m, 1H ), 2.87-2.82 (m, 2H), 2.76-2.70 (m, 2H), 2.27-2.22 (d, J = 16.4 Hz, 1H), 2.05-2 (d, J = 16.4 Hz, 1H), 1.80-1.75 (m, 2H), 1.02-0.97 (m, 3H) | 289 |

TABLE 20-continued

The following compounds were prepared according to the method of Example 39, with the following modification: In Step 1, the second eluted isomer from Example 38 Step 1, which was assigned as methyl (S)-5'-oxo-3,4-dihydro-1H-spiro[naphthalene-2,3'-pyrrolidine]-7-carboxylate, was used.

| Ex. | Structure | $^1$H NMR δ (ppm) | Found (ES, m/z) [M + H]$^+$ |
|---|---|---|---|
| I-144 | 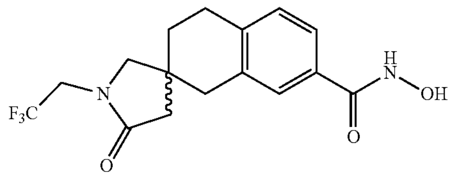 | (400 MHz, DMSO-d6): 11.07 (br s, 1H), 8.90 (br s, 1H), 7.49-7.42 (m, 2H), 7.17-7.09 (m, 1H), 4.12-4.01 (m, 2H), 3.41-3.31 (m, 1H), 3.24-3.22 (m, 1H), 2.92-2.72 (m, 4H), 2.36-2.32 (d, J = 16.8 Hz, 1H), 2.16-2.12 (d, J = 16.8 Hz, 1H), 1.84-1.74 (m, 2H) | 343 |

Example 40

Preparation of (R)-1'-cyclopentyl-N-hydroxy-5'-oxo-3,4-dihydro-1H-spiro[naphthalene-2,3'-pyrrolidine]-7-carboxamide (I-152)

Step-1: Methyl 7-((cyclopentylamino)methyl)-8-hydroxy-7-(2-methoxy-2-oxoethyl)-5,6,7,8-tetrahydronaphthalene-2-carboxylate Into a 50 mL round-bottom flask, was placed a solution of methyl 7-(aminomethyl)-8-hydroxy-7-(2-methoxy-2-oxo-

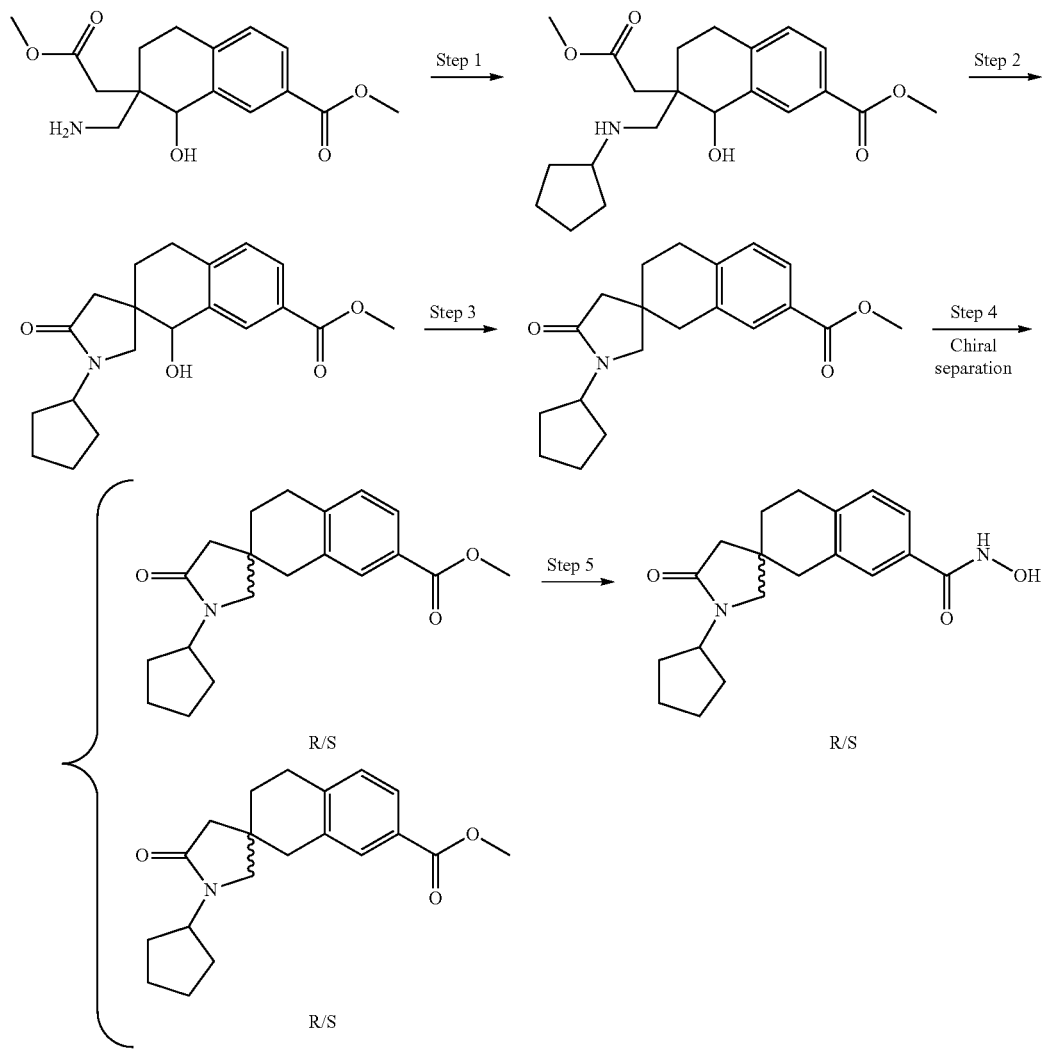

ethyl)-5,6,7,8-tetrahydronaphthalene-2-carboxylate (450 mg, 1.47 mmol, 1 equiv) in MeOH (10 mL) and cyclopentanone (148.77 mg, 1.77 mmol, 1.2 equiv). The resulting solution was stirred for 1h at 25° C. NaBH₃CN (463.09 mg, 7.37 mmol, 5 equiv) was added and the resulting solution was stirred for 3 h at 25° C. The reaction was then quenched by the addition of 20 mL of H₂O and extracted with 3×50 mL of CH₂Cl₂. The combined organic layers were dried over anhydrous Na₂SO₄, filtered and concentrated under vacuum to give 400 mg of the title compound as an oil. MS: (ES, m/z): 376 [M+H]⁺.

Step-2: Methyl 1'-cyclopentyl-1-hydroxy-5'-oxo-3,
4-dihydro-1H-spiro[naphthalene-2,3'-pyrrolidine]-7-
carboxylate Into a 50 mL round-bottom flask, was placed a solution of methyl 7-((cyclopentylamino)methyl)-8-hydroxy-7-(2-methoxy-2-oxoethyl)-5,6,7,8-tetrahydronaphthalene-2-carboxylate (450 mg, 1.20 mmol, 1 equiv) in 20 mL of 7M NH₃ in MeOH. The resulting solution was stirred for 1 h at 25° C. The resulting mixture was concentrated under vacuum. The residue was purified by normal phase column chromatography on silica gel with CH₂Cl₂/MeOH (10:1). The collected fractions were concentrated under vacuum to give 350 mg (85% yield) of the title compound as an oil. MS: (ES, m/z): 344 [M+H]⁺.

Step-3: Methyl 1'-cyclopentyl-5'-oxo-3,4-dihydro-
1H-spiro[naphthalene-2,3'-pyrrolidine]-7-carboxy-
late Into a 50 mL round-bottom flask, was placed a solution of methyl 1'-cyclopentyl-1-hydroxy-5'-oxo-3,4-dihydro-1H-spiro[naphthalene-2,3'-pyrrolidine]-7-carboxylate (400 mg, 1.16 mmol, 1 equiv) in TFA (8 mL), and Et₃SiH (2 mL, 1.45 mmol, 1.25 equiv). The resulting solution was stirred for 2 h at 80° C. in an oil bath. The resulting mixture was concentrated under vacuum. The residue was purified by normal phase column chromatography on silica gel with CH₂Cl₂/MeOH (10:1). The collected fractions were concentrated under vacuum to give 100 mg (26% yield) of the title compound as an oil. MS: (ES, m/z): 328 [M+H]⁺.

Step-4: Chiral separation of methyl (R)-1'-cyclo-
pentyl-5'-oxo-3,4-dihydro-1H-spiro[naphthalene-2,
3'-pyrrolidine]-7-carboxylate and methyl (S)-1'-
cyclopentyl-5'-oxo-3,4-dihydro-1H-spiro
[naphthalene-2,3'-pyrrolidine]-7-carboxylate Methyl 1'-cyclopentyl-5'-oxo-3,4-dihydro-1H-spiro[naphthalene-2,3'-pyrrolidine]-7-carboxylate (100 mg) was separated by Chiral-Prep-HPLC with the following conditions: Column: Chiralpak IC, 2×25 cm, 5 μm; Mobile Phase: hexanes and EtOH; Gradient: hold at 30% EtOH over 30 min; Detector: UV: 254 nm, 220 nm. The first eluting isomer (Rt 3.742 min) was collected and concentrated under vacuum to give 50 mg (50% yield) of an oil which was assigned as the R isomer of methyl 1'-cyclopentyl-5'-oxo-3,4-dihydro-1H-spiro[naphthalene-2,3'-pyrrolidine]-7-carboxylate. MS: (ES, m/z): 328 [M+H]⁺. The second eluting isomer (Rt 4.503 min) was collected and concentrated under vacuum to give 35 mg (35% yield) of an oil which was assigned as the S isomer of methyl 1'-cyclopentyl-5'-oxo-3, 4-dihydro-1H-spiro[naphthalene-2,3'-pyrrolidine]-7-carboxylate. MS: (ES, m/z): 328 [M+H]⁺.

Step-5: (R)-1'-Cyclopentyl-N-hydroxy-5'-oxo-3,4-
dihydro-H-spiro[naphthalene-2,3'-pyrrolidine]-7-
carboxamide Into a 25 mL round-bottom flask, was placed a solution of the first eluted isomer from Step 4, which was assigned as methyl (R)-1'-cyclopentyl-5'-oxo-3,4-dihydro-1H-spiro[naphthalene-2,3'-pyrrolidine]-7-carboxylate as described above, (50 mg, 0.15 mmol, 1 equiv) in THF/MeOH (4:1, 5 mL), NH₂OH (50% in water, 660.68 mg, 9.16 mmol, 60 equiv), and aq. 1N NaOH (0.306 mL, 2 equiv). The resulting solution was stirred for 3 h at 25° C. The solids were filtered out and the crude product was purified by Prep-HPLC with the following conditions: Column: XBridge Prep C18 OBD, 19×150 mm, 5 μm; Mobile Phase A: Water/0.01% NH₄HCO₃, Mobile Phase B: CH₃CN; Gradient: 15% B to 43% B in 8 min; Detector: UV 254 nm, 220 nm. The collected fractions were lyophilized to give 16.4 mg (33% yield) of the title compound as a white solid. ¹H NMR (300 MHz, DMSO-d6) δ (ppm): 10.87 (s, 1H), 8.99 (s, 1H), 7.49-7.45 (m, 2H), 7.16-7.14 (d, J=8.1 Hz, 1H), 4.39-4.34 (m, 1H), 3.19-3.16 (d, J=9.6 Hz, 1H), 3.07-3.03 (d, J=9.6 Hz, 1H), 2.86-2.82 (m, 2H), 2.75-2.73 (m, 2H), 2.27-2.22 (d, J=16.2 Hz, 1H), 2.06-2.01 (d, J=16.5 Hz, 1H), 1.79-1.55 (m, 10H). MS: (ES, m/z): 329 [M+H]⁺.

TABLE 21

The following compound was prepared according to the method of Example 40 using the first eluted isomer from Step 4.

| Ex. | Structure | ¹H NMR δ (ppm) | Found (ES, m/z) [M + H]⁺ |
|---|---|---|---|
| I-150 | 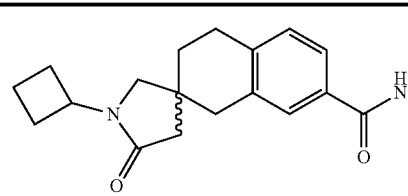 | (400 MHz, DMSO-d6): 11.07 (s, 1H), 8.95 (s, 1H), 7.50-7.46 (m, 2H), 7.18-7.16 (d, J = 7.6 Hz, 1H), 4.52-4.48 (m, 1H), 3.33-3.28 (m, 1H), 3.20-3.18 (d, J = 9.6 Hz, 1H), 2.88-2.74 (m, 4H), 2.29-2.25 (d, J = 16.4 Hz, 1H), 2.15-1.97 (m, 5H), 1.80-1.76 (m, 2H), 1.65-1.50 (m, 2H) | 315 |

TABLE 22

The following compounds were prepared according to the method of Example 40, with the following modification: In Step 5, the second eluted isomer from Step 4, which was assigned as methyl (S)-1'-cyclopentyl-5'-oxo-3,4-dihydro-1H-spiro[naphthalene-2,3'-pyrrolidine]-7-carboxylate, was used.

| Ex. | Structure | ¹H NMR δ (ppm) | Found (ES, m/z) [M + H]⁺ |
|---|---|---|---|
| I-153 | (structure) R/S | (300 MHz, DMSO-d6): 10.75 (s, 1H), 9.01 (s, 1H), 7.49-7.45 (m, 2H), 7.16-7.14 (d, J = 8.1 Hz, 1H), 4.39-4.34 (m, 1H), 3.19-3.16 (d, J = 9.6 Hz, 1H), 3.07-3.04 (d, J = 9.6 Hz, 1H), 2.86-2.82 (m, 2H), 2.75-2.73 (m, 2H), 2.27-2.22 (d, J = 16.2 Hz, 1H), 2.06-2.01 (d, J = 16.5 Hz, 1H), 1.79-1.49 (m, 10H) | 329 |
| I-151 | (structure) R/S | (400 MHz, DMSO-d6): 11.07 (s, 1H), 8.95 (s, 1H), 7.50-7.46 (m, 2H), 7.18-7.16 (d, J = 8.0 Hz, 1H), 4.52-4.48 (m, 1H), 3.33-3.28 (m, 1H), 3.20-3.18 (d, J = 10.0 Hz, 1H), 2.86-2.74 (m, 4H), 2.29-2.25 (d, J = 16.4 Hz, 1H), 2.14-1.97 (m, 5H), 1.80-1.76 (m, 2H), 1.62-1.50 (m, 2H) | 315 |

Example 41

Preparation of N7-hydroxy-N1'-phenylspiro[chroman-2,4'-piperidine]-1',7-dicarboxamide (II-4)

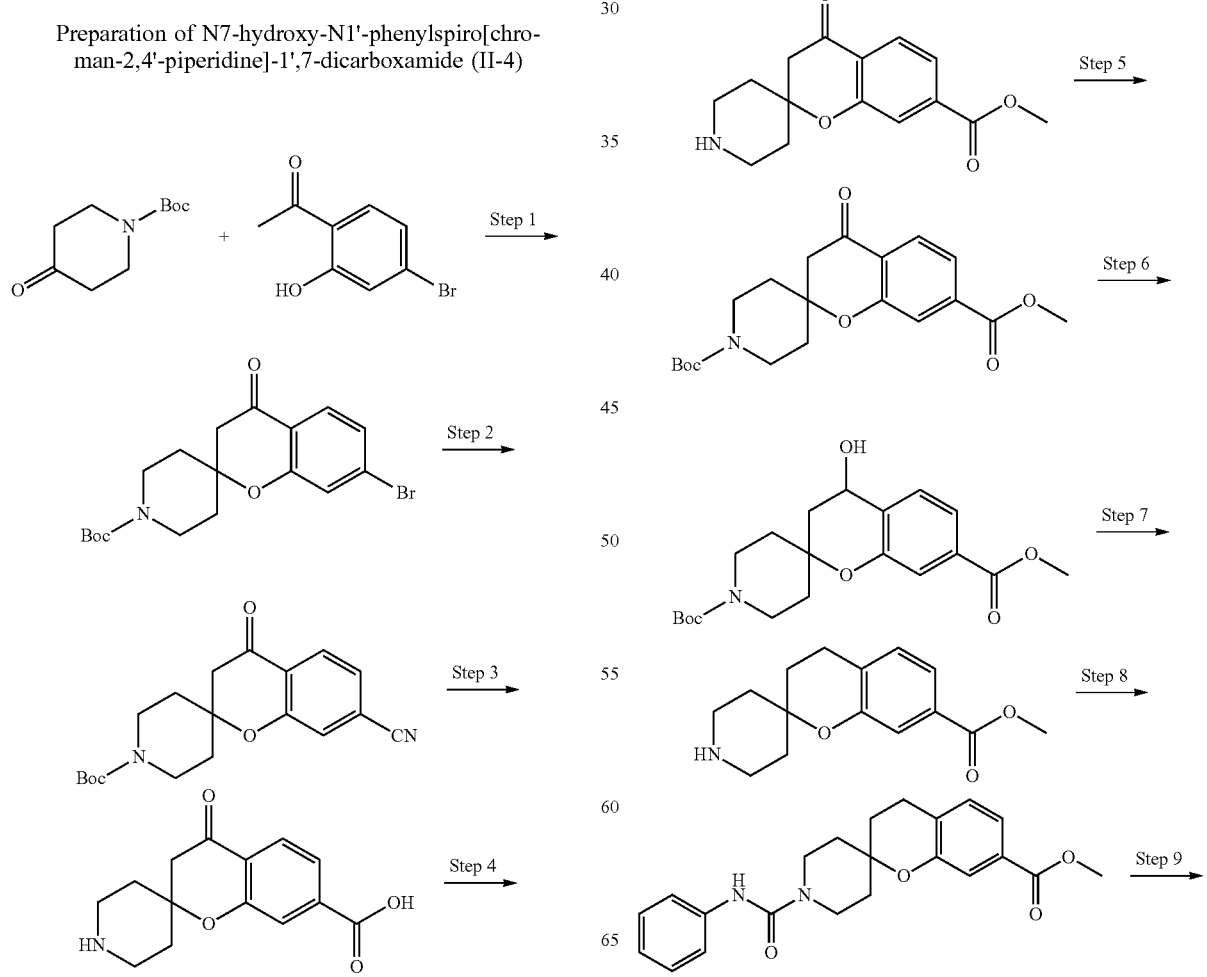

133

-continued

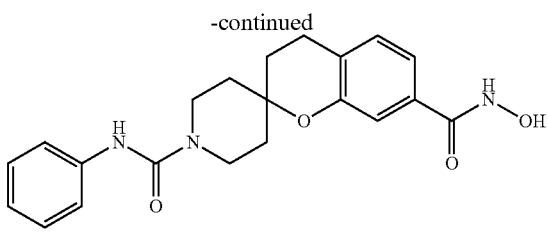

Step-1: tert-Butyl 7-bromo-4-oxospiro[chroman-2,4'-piperidine]-1'-carboxylate 1-(4-bromo-2-hydroxyphenyl)ethanone (2.6 g, 12.1 mmol, 1 equiv), tert-butyl 4-oxopiperidine-1-carboxylate (2.56 g, 21.5 mmol, 1.77 equiv), and pyrrolidine (0.51 mL, 6.2 mmol, 0.5 equiv) were combined in MeOH (21 mL) and refluxed for 12 h. After cooling to room temperature the reaction mixture was concentrated to dryness and purified by normal phase column chromatography on silica gel eluting with a gradient of EtOAc/Hexanes. After purification 3.59 g (75% yield) of the title compound was obtained. $^{1}$H NMR (300 MHz, CDCl$_3$) δ (ppm): 7.70 (d, J=8.5 Hz, 1H), 7.20 (d, J=1.7 Hz, 1H), 7.15 (dd, J$_1$=8.5 Hz, J$_2$=1.65 Hz, 1H), 3.85 (br s, 2H), 3.20-3.10 (m, 2H), 2.70 (s, 2H), 2.05-1.95 (m, 2H), 1.70-1.55 (m, 2H), 1.45 (s, 9H).

Step-2: tert-Butyl 7-cyano-4-oxospiro[chroman-2,4'-piperidine]-1'-carboxylate tert-Butyl 7-bromo-4-oxospiro[chroman-2,4'-piperidine]-1'-carboxylate (3.59 g, 9.1 mmol, 1 equiv) was dissolved in DMF (25 mL) and Zn(CN)$_2$ (2.13 g, 18.2 mmol, 2 equiv) was added. The reaction mixture was evacuated under vacuum and refilled with argon gas several times. Pd(PPh$_3$)$_4$ (550 mg, 0.45 mmol, 0.05 equiv) was added. The reaction mixture was flushed with argon and stirred at 80° C. for 7 h. The mixture was then concentrated to dryness under reduced pressure. The residue was dissolved in EtOAc and sequentially washed with aq. 12-15% NH$_4$OH, water, and brine. The organic layer was dried over Na$_2$SO$_4$, filtered and concentrated. The residue was purified by normal phase chromatography on silica gel with CH$_2$Cl$_2$/EtOAc to provide 2.7 g (87% yield) of the title compound as a light yellow solid. $^{1}$H NMR (300 MHz, CDCl$_3$) δ (ppm): 7.93 (d, J=8.0 Hz, 1H), 7.20 ppm (d, J=0.55 Hz, 1H), 7.25 (dd, J$_1$=8.0 Hz, J$_2$=0.55 Hz, 1H), 3.89 (br s, 2H), 3.24-3.10 (m, 2H), 2.77 (s, 2H), 2.04-1.95 (m, 2H), 1.67-1.55 (m, 2H), 1.45 (s, 9H).

Step-3: 4-Oxospiro[chroman-2,4'-piperidine]-7-carboxylate tert-Butyl 7-cyano-4-oxospiro[chroman-2,4'-piperidine]-1'-carboxylate (2.7 g, 7.9 mmol, 1 equiv) was mixed with 1,4-dioxane (7 mL) and then 6N HCl (28 mL) was added at room temperature. The reaction mixture was stirred at 120° C. for 20 h, then cooled to room temperature and concentrated. After sequential trituration of the crude material in water and MeOH/Et$_2$O, 1.7 g (72% yield) of the title compound was obtained as the HCl salt. $^{1}$H NMR (300 MHz, DMSO-d6) δ (ppm): 9.12 (br s, 2H), 7.84 (d, J=8.25 Hz, 1H), 7.66 (d, J=1.40 Hz, 1H), 7.25 (dd, J$_1$=8.25 Hz, J$_2$=1.40 Hz, 1H), 3.17 (br s, 4H), 2.97 (s, 2H), 2.15-2.05 (m, 2H), 2.00-1.85 (m, 2H).

134

Step-4: Methyl 4-oxospiro[chroman-2,4'-piperidine]-7-carboxylate

4-Oxospiro[chroman-2,4'-piperidine]-7-carboxylate*HCl (1.7 g, 5.7 mmol, 1 equiv) was refluxed in 3N methanolic HCl (80 mL) overnight. The solvent was removed under vacuum. The resulting residue was triturated with MeOH/Et$_2$O and then recrystallized from MeOH to provide 1 g (54% yield) of the title compound as the HCl salt as a white solid. $^{1}$H NMR (300 MHz, DMSO-d6) δ (ppm): 9.04 (br s, 1H), 8.85 (br s, 1H), 7.87 (d, J=8.25 Hz, 1H), 7.71 (s, 1H), 7.61 (J=8.25 Hz, 1H), 3.88 (s, 3H), 3.20-3.15 (m, 4H), 2.99 (m, 2H), 2.15-2.08 (m, 2H), 1.98-1.84 (m, 2H). MS: (ES, m/z): 276 [M+H]$^+$.

Step-5: 1'-tert-Butyl 7-methyl 4-oxospiro[chroman-2,4'-piperidine]-1',7-dicarboxylate Into a 250-mL round-bottom flask was placed methyl 4-oxospiro[chroman-2,4'-piperidine]-7-carboxylate (1.200 g, 4.36 mmol, 1 equiv) in THF (60 mL), di-tert-butyl dicarbonate (1.128 g, 5.17 mmol, 1.2 equiv), Et$_3$N (876 mg, 8.66 mmol, 2 equiv) and 4-dimethylaminopyridine (0.240 g, 1.96 mmol, 0.45 equiv). The reaction was stirred overnight at room temperature. The resulting mixture was concentrated under vacuum. The residue was purified by normal phase chromatography on silica gel with EtOAc/petroleum ether (1:1). The collected fractions were concentrated to give 1.1 g (67% yield) of the title compound as a colorless oil. MS: (ES, m/z): 376 [M+H]$^+$.

Step-6: 1'-tert-Butyl 7-methyl 4-hydroxyspiro[chroman-2,4'-piperidine]-1',7-dicarboxylate Into a 250-mL round-bottom flask was placed 7-methyl 4-oxospiro[chroman-2,4'-piperidine]-1',7-dicarboxylate (1.1 g, 2.88 mmol, 1 equiv) in MeOH (200 mL) and NaBH$_4$ (0.26 g, 6.87 mmol, 2.38 equiv). The resulting mixture was stirred overnight at room temperature and then concentrated under vacuum. The residue was dissolved in CH$_2$Cl$_2$ (150 mL), washed with 3×50 mL of H$_2$O, dried over anhydrous Na$_2$SO$_4$, filtered and concentrated under vacuum to give 1 g (90% yield) of the title compound as a white solid. MS: (ES, m/z): 378 [M+H]$^+$.

Step-7: Methyl spiro[chroman-2,4'-piperidine]-7-carboxylate

Into a 250-mL round-bottom flask was placed 1'-tert-butyl 7-methyl 4-hydroxyspiro[chroman-2,4'-piperidine]-1',7-dicarboxylate (1 g, 2.65 mmol, 1 equiv) in TFA (100 mL), and Et$_3$SiH (20 mL). The resulting solution was stirred overnight at room temperature. The resulting mixture was concentrated under vacuum. The residue was dissolved in CH$_2$Cl$_2$ (200 mL) and washed with aq. Na$_2$CO$_3$. The organic layer was separated and washed with 2×100 mL of H$_2$O, dried over anhydrous Na$_2$SO$_4$, filtered and concentrated under vacuum to give 0.90 g of the title compound as a yellow oil. MS: (ES, m/z): 262 [M+H]$^+$.

Step-8: Methyl 1'-(phenylcarbamoyl)spiro[chroman-2,4'-piperidine]-7-carboxylate Into a 100-mL round-bottom flask was placed methyl spiro[chroman-2,4'-piperidine]-7-carboxylate (100 mg, 0.38 mmol, 1 equiv) in CH$_2$Cl$_2$ (10 mL), isocyanatobenzene (54 mg, 0.45 mmol, 1.18 equiv) and Et$_3$N (0.115 g, 1.14 mmol, 2.97 equiv). The reaction was stirred for 1.5 h at room temperature. The resulting mixture was concentrated under vacuum. The residue was purified by normal phase chromatography on silica gel with EtOAc/petroleum ether (1:1). The collected fractions were concentrated to give 60 mg (41% yield) of the title compound as a yellow oil. MS: (ES, m/z): 381 [M+H]⁺.

Step-9: N7-Hydroxy-N1'-phenylspiro[chroman-2,4'-piperidine]-1',7-dicarboxamide

Into a 50-mL round-bottom flask was placed methyl 1'-(phenylcarbamoyl)spiro[chroman-2,4'-piperidine]-7-carboxylate (60 mg, 0.16 mmol, 1 equiv), THF/MeOH (4:1, 1.25 mL), NH₂OH (50% in water, 0.634 g, 60 equiv), and aq. 1N NaOH (0.3 mL, 1.88 equiv). The reaction was stirred for 5 h at room temperature. The crude product was purified by Prep-HPLC with the following conditions: Column: Waters HSS C18, 1.8 μm, 2.1×50 mm; Mobile Phase, A: Water/0.05% TFA, Mobile Phase B: CH₃CN/0.05% TFA; Flow rate: 0.7 mL/min, Gradient: 5% B to 95% B in 2 min; Detector: UV 254 nm. The collected fractions were lyophilized to give 13.1 mg (17% yield) of the title compound as a pink solid. ¹H NMR (400 MHz, DMSO-d6) δ (ppm): 11.10 (br s, 1H), 8.54 (s, 1H), 7.46 (d, J=7.6 Hz, 2H), 7.24-7.09 (m, 5H), 6.96-6.91 (m, 1H), 3.89 (d, J=13.2 Hz, 2H), 3.27-3.22 (t, J=10.8 Hz, 2H), 2.79-2.76 (t, J=6.4 Hz, 2H), 1.84-1.57 (m, 6H). MS: (ES, m/z): 382 [M+H]⁺.

Example 42

Preparation of 1'-cyclohexyl-N-hydroxyspiro[chroman-2,4'-piperidine]-7-carboxamide (II-6)

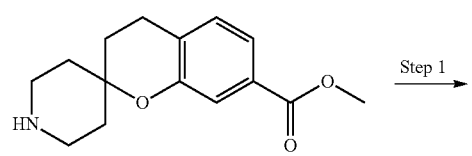

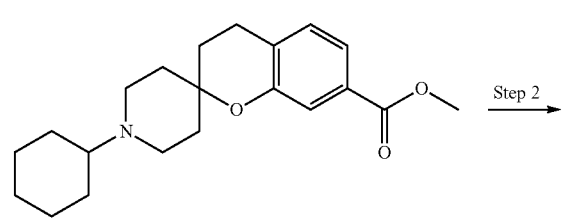

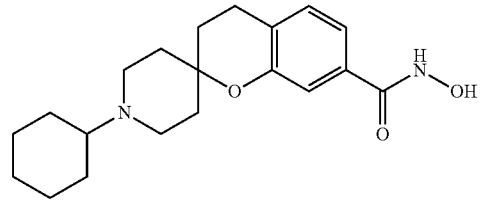

Step-1: Methyl 1'-cyclohexylspiro[chroman-2,4'-piperidine]-7-carboxylate

Into a 100-mL round-bottom flask was placed methyl spiro[chroman-2,4'-piperidine]-7-carboxylate (100 mg, 0.38 mmol, 1 equiv) in CH₂Cl₂ (10 mL), cyclohexanone (112 mg, 1.14 mmol, 3 equiv), and NaBH(OAc)₃ (282 mg, 1.33 mmol, 3.5 equiv). The reaction was stirred overnight at room temperature. The resulting mixture was concentrated under vacuum. The residue was purified by normal phase chromatography on silica gel with EtOAc/petroleum ether (1:1). The collected fractions were concentrated to give 29 mg (22% yield) of the title compound as a yellow oil. MS: (ES, m/z): 344 [M+H]⁺.

Step-1: 1'-Cyclohexyl-N-hydroxyspiro[chroman-2,4'-piperidine]-7-carboxamide

Into a 100-mL round-bottom flask was placed methyl 1'-cyclohexylspiro[chroman-2,4'-piperidine]-7-carboxylate (24.8 mg, 0.07 mmol, 1 equiv), THF/MeOH (4:1, 1.25 mL), NH₂OH (50% in water, 0.239 g, 7.22 mmol, 100 equiv), and aq. 1N NaOH (0.4 mL, 5.7 equiv). The reaction was stirred overnight at room temperature. The crude product was purified by Prep-HPLC with the following conditions: Column: Waters HSS C18, 2.1×50 mm, 1.8 μm; Mobile Phase, A: Water/0.05% TFA, Mobile Phase B: CH₃CN/0.05% TFA; Flow rate: 0.7 mL/min; Gradient: 5% B to 95% B in 2 min; Detector: UV 254 nm. The collected fractions were lyophilized to give 19.9 mg (60% yield) of the title compound as a pink solid. ¹H NMR (400 MHz, DMSO-d6) δ (ppm): 11.12 (br s, 1H), 9.28 (s, 1H), 8.99 (s, 1H), 7.30-7.23 (m, 2H), 7.18-7.13 (m, 1H), 3.39-3.14 (m, 5H), 2.82-2.78 (m, 2H), 2.09-2.06 (d, J=10 Hz, 2H), 2.02-1.96 (m, 2H), 1.92-1.81 (m, 6H), 1.65-1.62 (d, J=12.8 Hz, 1H), 1.53-1.46 (m, 2H), 1.33-1.24 (m, 2H), 1.16-1.03 (m, 1H). MS: (ES, m/z): 345 [M+H]⁺.

TABLE 23

The following compound was prepared according to the method of Example 42, using 4-methoxybenzaldehyde in Step 1.

| Ex. | Structure | $^1$H NMR δ (ppm) | Found (ES, m/z) [M + H]$^+$ |
|---|---|---|---|
| II-7 | 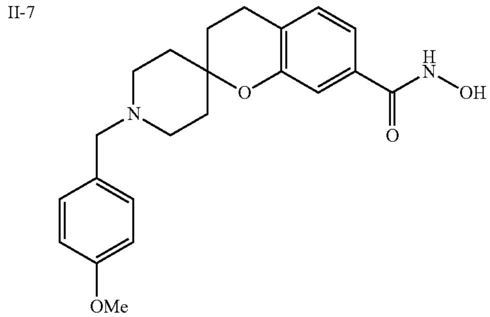 | (400 MHz, DMSO-d6): 11.13 (br s, 1H), 9.65 (s, 1H), 8.99 (s, 1H), 7.47-7.45 (d, J = 8.4 Hz, 2H), 7.28-7.22 (m, 2H), 7.17-7.15 (d, J = 8.4 Hz, 1H), 7.04-7.02 (d, J = 8.4 Hz, 2H), 4.31 (s, 2H), 3.79 (s, 3H), 3.24 (s, 4H), 2.78 (s, 2H), 2.23-1.62 (m, 6H) | 383 |

Example 43

Preparation of N-hydroxy-1'-(4-methoxybenzoyl) spiro[chroman-2,4'-piperidine]-7-carboxamide (II-1)

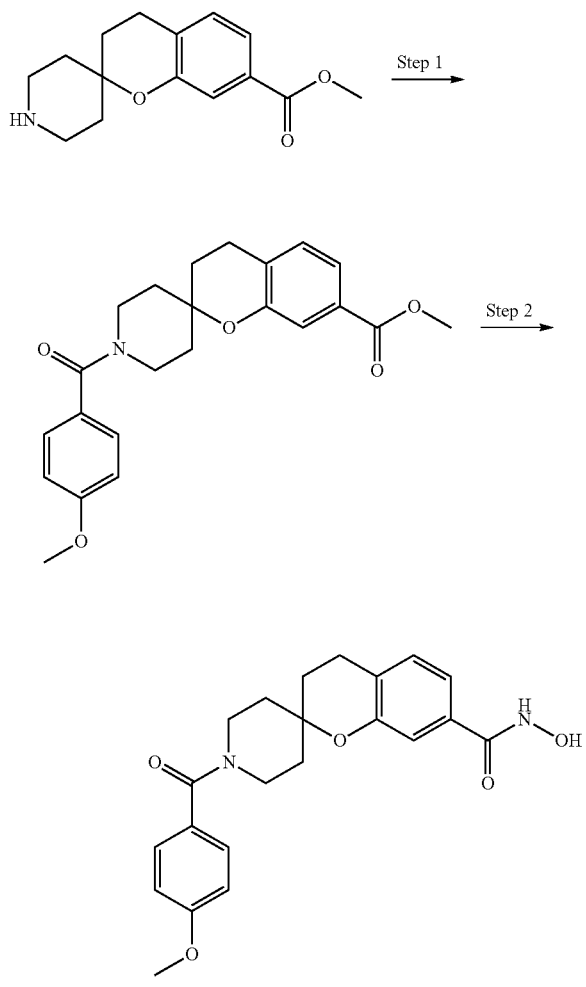

Step-1: Methyl 1'-(4-methoxybenzoyl)spiro[chroman-2,4'-piperidine]-7-carboxylate Into a 100-mL round-bottom flask was placed methyl spiro[chroman-2,4'-piperidine]-7-carboxylate (40 mg, 0.15 mmol, 1 equiv), 4-methoxybenzoyl chloride (0.031 g, 0.18 mmol, 1.2 equiv) in $CH_2Cl_2$ (5 mL) and $Et_3N$ (0.046 g, 0.45 mmol, 3.04 equiv). The reaction was stirred for 3 h at room temperature. The resulting mixture was concentrated under vacuum. The residue was purified by normal phase chromatography on silica gel with EtOAc/petroleum ether (1:1). The collected fractions were concentrated to give 37 mg (62% yield) of the title compound as a yellow oil. MS: (ES, m/z): 396 [M+H]$^+$.

Step-2: N-Hydroxy-1'-(4-methoxybenzoyl)spiro [chroman-2,4'-piperidine]-7-carboxamide Into a 100-mL round-bottom flask was placed methyl 1'-(4-methoxybenzoyl)spiro[chroman-2,4'-piperidine]-7-carboxylate (40 mg, 0.10 mmol, 1 equiv), THF/MeOH (4:1, 1.25 mL), $NH_2OH$ (50% in water, 0.334 g, 10.11 mmol, 100 equiv), and aq. 1N NaOH (0.2 mL, 2 equiv). The resulting solution was stirred for 4 h at room temperature. The crude product was purified by Prep-HPLC with the following conditions: Column: Waters HSS C18, 2.1×50 mm, 1.8 μm; Mobile Phase A: Water/0.05% TFA, Mobile Phase B: $CH_3CN$/0.05% TFA; Flow rate: 0.7 mL/min; Gradient: 5% B to 95% B in 2.0 min; Detector: UV 254 nm. The collected fractions were lyophilized to give 13.1 mg (25% yield) of the title compound as a pink solid. $^1$H NMR (400 MHz, $CD_3OD$) δ (ppm): 7.43 (d, J=8.8 Hz, 2H), 7.25-7.17 (m, 3H), 7.17 (d, J=8.4 Hz, 2H), 4.43 (s, 1H), 3.85 (s, 3H), 3.73-3.40 (m, 3H), 2.90-2.87 (t, J=6.4 Hz, 2H), 1.95-1.68 (m, 6H). MS: (ES, m/z): 397 [M+H]$^+$.

TABLE 24

The following compound was prepared according to the method of Example 43.

| Ex. | Structure | $^1$H NMR δ (ppm) | Found (ES, m/z) [M + H]$^+$ |
|---|---|---|---|
| II-2 | 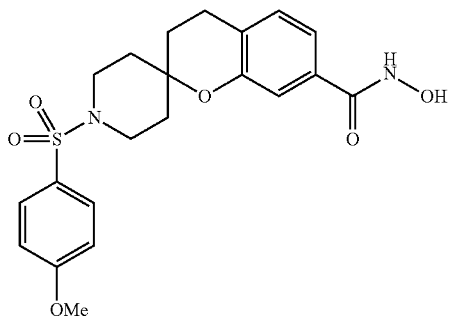 [SMILES: COc1ccc(S(=O)(=O)N2CCC3(CCc4ccc(C(=O)NO)cc4O3)CC2)cc1] | (400 MHz, DMSO-d6): 11.04 (br s, 1H), 7.72-7.69 (m, 2H), 7.20-7.10 (m, 4H), 6.94 (s, 1H), 3.88 (s, 3H), 3.44 (d, J = 11.6 Hz, 2H), 2.74-2.50 (m, 4H), 1.79-1.66 (m, 6H) | 433 |
| II-3 | 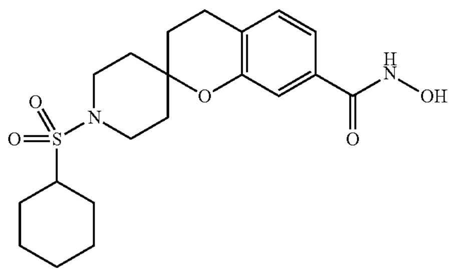 [SMILES: O=C(NO)c1ccc2c(c1)OC1(CC2)CCN(S(=O)(=O)C2CCCCC2)CC1] | (400 MHz, DMSO-d6): 11.08 (br s, 1H), 7.23-7.08 (m, 3H), 3.49 (d, J = 12.4 Hz, 2H), 3.24-3.09 (m, 3H), 2.77-2.74 (t, J = 6.4 Hz, 2H), 2.07-1.12 (m, 16H) | 409 |
| II-5 | 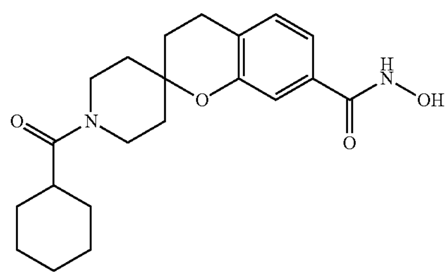 [SMILES: O=C(NO)c1ccc2c(c1)OC1(CC2)CCN(C(=O)C2CCCCC2)CC1] | (400 MHz, DMSO-d6); 11.08 (br s, 1H), 7.22-7.14 (m, 5H), 4.12-4.09 (d, J = 12 Hz, 1H), 3.77-3.73 (d, J = 16 Hz, 1H), 3.38-3.35 (m, 1H), 3.05-2.98 (m, 1H), 2.79-2.76 (m, 2H), 2.59-2.52 (m, 2H), 1.82-1.81 (m, 2H), 1.70-1.62 (m, 8H), 1.40-1.23 (m, 4H), 1.20-1.10 (m, 1H) | 373 |

Example 44

Small Molecule X-ray Crystallography Experiment for methyl (R)-1'-[(4-methanesulfonylphenyl)methyl]-2'-oxo-3,4-dihydro-1H-spiro[naphthalene-2,3'-pyrrolidine]-7-carboxylate Low-temperature diffraction data (ω-scans) were collected on a Rigaku MicroMax-007HF diffractometer coupled to a Saturn994+CCD detector with Cu Kα (λ=1.54178 Å). The structure was solved by direct methods and was refined against F$^2$ on all data by full-matrix least squares. All non-hydrogen atoms were refined anisotropically. Unless otherwise noted, hydrogen atoms were included in the model at geometrically calculated positions and refined using a riding model. The isotropic displacement parameters of all hydrogen atoms were fixed to 1.2 times the U value of the atoms to which they are linked (1.5 times for methyl groups). The overall quality of the data was poor due to crystal quality. The crystal was very small and only provided weak diffraction. This fact resulted in a R$_{int}$ greater than 0.18. All atoms shown are depicted with 50% thermal contours. The hydrogen atoms are shown as spheres. Carbon atoms C11 has R chirality (FIG. 1).

TABLE 25

Crystal data and structure refinement for methyl (R)-1'-[(4-methanesulfonylphenyl)methyl]-2'-oxo-3,4-dihydro-1H-spiro[naphthalene-2,3'-pyrrolidine]-7-carboxylate.

| | | |
|---|---|---|
| Empirical formula | C$_{23}$H$_{25}$NO$_5$S | |
| Formula weight | 427.50 | |
| Temperature | 93(2) K | |
| Wavelength | 1.54187 Å | |
| Crystal system | Monoclinic | |
| Space group | P 2$_1$ | |
| Unit cell dimensions | a = 13.109(2) Å | α = 90°. |
| | b = 5.51280(10) Å | β = 114.104(8)°. |
| | c = 15.6179(11) Å | γ = 90°. |
| Volume | 1030.3(2) Å$^3$ | |
| Z | 2 | |
| Density (calculated) | 1.378 Mg/m$^3$ | |
| Absorption coefficient | 1.698 mm$^{-1}$ | |
| F(000) | 452 | |
| Crystal size | 0.040 × 0.020 × 0.010 mm$^3$ | |
| Crystal color and habit | Colorless Needle | |
| Diffractometer | Rigaku Saturn 944+ CCD | |
| Θ range for data collection | 3.100 to 68.032°. | |
| Index ranges | −15 ≤ h ≤ 15, | |
| | −6 ≤ k ≤ 6, | |
| | −18 ≤ l ≤ 18 | |

TABLE 25-continued

Crystal data and structure refinement for methyl (R)-1'-[(4-methanesulfonylphenyl)methyl]-2'-oxo-3,4-dihydro-1H-spiro[naphthalene-2,3'-pyrrolidine]-7-carboxylate.

| | |
|---|---|
| Reflections collected | 24571 |
| Independent reflections | 3653 [R(int) = 0.1839] |
| Observed reflections (I > 2σ (I)) | 2036 |
| Completeness to θ = 67.687° | 99.9% |
| Absorption correction | Semi-empirical from equivalents |
| Max. and min. transmission | 0.983 and 0.643 |
| Solution method | SHELXT-2014/5 (Sheldrick, 2014) |
| Refinement method | SHELXL-2014/7 (Sheldrick, 2014) |
| Data/restraints/parameters | 3653/1/273 |
| Goodness-of-fit on $F^2$ | 0.896 |
| Final R indices [I > 2σ(I)] | R1 = 0.0503, wR2 = 0.0947 |
| R indices (all data) | R1 = 0.1049, wR2 = 0.1262 |
| Absolute structure parameter | 0.02(3) |
| Largest diff. peak and hole | 0.278 and −0.294 e · Å$^{-3}$ |

Example 45

In vitro Histone Deacetylase Assay

The enzymatic HDAC6 and HDAC11 assays were performed using electrophoretic mobility shift assay. Full length human recombinant HDAC6 and HDAC11 proteins were expressed in baculoviral system and purified by affinity chromatography. The enzymatic reactions were assembled in 384 well plates in a total volume of 25 µL in a reaction buffer composing: 100 mM HEPES, pH 7.5, 25 mM KCl, 0.1% bovine serum albumin, 0.01% Triton X-100, 1% DMSO (from compounds) 2 µM of the fluorescently labeled peptide substrate and enzyme. The enzymes were added at a final concentration of 1 nM for HDAC6, and 10 nM for HDAC11. The peptide substrate FAM-RHKK(Ac)—NH$_2$ was used for HDAC6, and FAM-RHKK(tri-fluor-Ac)—NH$_2$ for HDAC11. The compounds were tested at 12 concentrations spaced by 3× dilution intervals. Negative control samples (0%-inhibition in the absence of inhibitor) and positive control samples (100%-inhibition) were assembled in replicates of four in each assay plate. The reactions were incubated at 25° C. and quenched by the addition of 45 µL of termination buffer (100 mM HEPES, pH 7.5, 0.01% Triton X-100, 0.05% SDS).

The terminated assay plates were analyzed on LabChip® 3000 microfluidic electrophoresis instrument (Perkin Elmer/Caliper Life Sciences). The fluorescence intensity of the electrophoretically separated de-acetylated product and substrate peptide was measured. Activity in each sample was determined as the product to sum ratio (PSR): P/(S+P), where P is the peak height of the product peptide and S is the peak height of the substrate peptide. Percent inhibition ($P_{inh}$) is determined using following equation:

$P_{inh} = (PSR_{0\%} - PSR_{inh})/(PSR_{0\%} - PSR_{100\%})*100$, where $PSR_{inh}$ is the product sum ratio in the presence of inhibitor, $PSR_{0\%}$ is the average product sum ration in the absence of inhibitor and $PSR_{100\%}$ is the average product sum ratio in 100%-inhibition control samples. The IC$_{50}$ values of inhibitors were determined by fitting the %-inhibition curves with 4 parameter dose-response model using XLfit 4 software.

As set forth in Table-26 and Table-27, below, IC$_{50}$ values are defined as follows: IC50≤0.1 µM (+++); IC50>0.1 µM and ≤0.5 µM (++); IC50>0.5 µM (+).

TABLE 26

Inhibitory Concentration (IC50) Values for Representative Compounds against HDAC6

| Reference Number | HDAC6 Activity Range |
|---|---|
| I-1 | +++ |
| I-2 | +++ |
| I-3 | ++ |
| I-4 | +++ |
| I-5 | +++ |
| I-6 | +++ |
| I-7 | +++ |
| I-8 | ++ |
| I-9 | ++ |
| I-10 | +++ |
| I-11 | ++ |
| I-12 | +++ |
| I-13 | +++ |
| I-14 | +++ |
| I-15 | +++ |
| I-16 | +++ |
| I-17 | +++ |
| I-18 | ++ |
| I-19 | ++ |
| I-20 | +++ |
| I-21 | +++ |
| I-22 | +++ |
| I-23 | +++ |
| I-24 | ++ |
| I-25 | +++ |
| I-26 | +++ |
| I-27 | +++ |
| I-28 | +++ |
| I-29 | +++ |
| I-30 | +++ |
| I-31 | +++ |
| I-32 | +++ |
| I-33 | +++ |
| I-34 | +++ |
| I-35 | +++ |
| I-36 | +++ |
| I-37 | +++ |
| I-38 | +++ |
| I-39 | +++ |
| I-40 | +++ |
| I-41 | +++ |
| I-42 | +++ |
| I-43 | +++ |
| I-44 | +++ |
| I-45 | +++ |
| I-46 | +++ |
| I-47 | +++ |
| I-48 | +++ |
| I-49 | +++ |
| I-50 | +++ |
| I-51 | +++ |
| I-52 | +++ |
| I-53 | +++ |
| I-54 | +++ |
| I-55 | +++ |
| I-56 | +++ |
| I-57 | +++ |
| I-58 | +++ |
| I-59 | +++ |
| I-60 | +++ |
| I-61 | +++ |
| I-62 | ++ |
| I-63 | +++ |
| I-64 | +++ |
| I-65 | +++ |
| I-66 | +++ |
| I-67 | ++ |
| I-68 | +++ |

TABLE 26-continued

Inhibitory Concentration (IC50) Values for Representative Compounds against HDAC6

| Reference Number | HDAC6 Activity Range |
|---|---|
| I-69 | +++ |
| I-70 | +++ |
| I-71 | +++ |
| I-72 | +++ |
| I-73 | +++ |
| I-74 | +++ |
| I-75 | +++ |
| I-76 | +++ |
| I-77 | +++ |
| I-78 | +++ |
| I-79 | +++ |
| I-80 | +++ |
| I-81 | +++ |
| I-82 | +++ |
| I-83 | +++ |
| I-84 | +++ |
| I-85 | +++ |
| I-86 | +++ |
| I-87 | +++ |
| I-88 | +++ |
| I-89 | +++ |
| I-90 | +++ |
| I-91 | +++ |
| I-92 | +++ |
| I-93 | +++ |
| I-94 | +++ |
| I-95 | +++ |
| I-96 | +++ |
| I-97 | +++ |
| I-98 | +++ |
| I-99 | +++ |
| I-100 | +++ |
| I-101 | +++ |
| I-102 | +++ |
| I-103 | +++ |
| I-104 | +++ |
| I-105 | +++ |
| I-106 | +++ |
| I-107 | +++ |
| I-108 | +++ |
| I-109 | +++ |
| I-110 | +++ |
| I-111 | +++ |
| I-112 | +++ |
| I-113 | +++ |
| I-114 | +++ |
| I-115 | +++ |
| I-116 | +++ |
| I-117 | +++ |
| I-118 | +++ |
| I-119 | +++ |
| I-120 | +++ |
| I-121 | +++ |
| I-122 | +++ |
| I-123 | +++ |
| I-124 | +++ |
| I-125 | +++ |
| I-126 | +++ |
| I-127 | +++ |
| I-128 | +++ |
| I-129 | +++ |
| I-130 | +++ |
| I-131 | +++ |
| I-132 | +++ |
| I-133 | +++ |
| I-134 | +++ |
| I-135 | +++ |
| I-136 | +++ |
| I-137 | +++ |
| I-138 | +++ |
| I-139 | +++ |
| I-140 | +++ |
| I-141 | +++ |
| I-142 | +++ |
| I-143 | +++ |
| I-144 | +++ |
| I-145 | +++ |
| I-146 | +++ |
| I-147 | +++ |
| I-148 | +++ |
| I-149 | +++ |
| I-150 | +++ |
| I-151 | +++ |
| I-152 | +++ |
| I-153 | +++ |
| II-1 | +++ |
| II-2 | +++ |
| II-3 | +++ |
| II-4 | +++ |
| II-5 | +++ |
| II-6 | ++ |
| II-7 | + |

TABLE 27

Inhibitory Concentration (IC50) Values for Representative Compounds against HDAC11

| Reference Number | HDAC11 Activity Range |
|---|---|
| I-1 | + |
| I-2 | + |
| I-3 | + |
| I-4 | + |
| I-5 | + |
| I-6 | ++ |
| I-7 | + |
| I-8 | + |
| I-9 | + |
| I-10 | + |
| I-11 | + |
| I-12 | + |
| I-13 | + |
| I-14 | + |
| I-15 | + |
| I-16 | + |
| I-17 | + |
| I-18 | + |
| I-19 | + |
| I-20 | ++ |
| I-21 | +++ |
| I-22 | + |
| I-23 | ++ |
| I-24 | + |
| I-25 | + |
| I-26 | ++ |
| I-27 | +++ |
| I-28 | ++ |
| I-29 | + |
| I-30 | + |
| I-31 | + |
| I-32 | + |
| I-33 | + |
| I-34 | +++ |
| I-35 | + |
| I-36 | ++ |
| I-37 | +++ |
| I-38 | + |
| I-39 | + |
| I-40 | +++ |
| I-41 | + |

TABLE 27-continued

Inhibitory Concentration (IC50) Values for Representative Compounds against HDAC11

| Reference Number | HDAC11 Activity Range |
|---|---|
| I-42 | +++ |
| I-43 | + |
| I-44 | + |
| I-45 | + |
| I-46 | ++ |
| I-47 | + |
| I-48 | + |
| I-49 | + |
| I-50 | + |
| I-51 | +++ |
| I-52 | + |
| I-53 | + |
| I-54 | + |
| I-55 | + |
| I-56 | + |
| I-57 | + |
| I-58 | ++ |
| I-59 | + |
| I-60 | + |
| I-61 | + |
| I-62 | + |
| I-63 | + |
| I-64 | + |
| I-65 | + |
| I-66 | + |
| I-67 | + |
| I-68 | + |
| I-69 | + |
| I-70 | + |
| I-71 | + |
| I-72 | + |
| I-73 | + |
| I-74 | + |
| I-75 | + |
| I-76 | + |
| I-77 | ++ |
| I-78 | + |
| I-79 | + |
| I-80 | + |
| I-81 | + |
| I-82 | ++ |
| I-83 | + |
| I-84 | + |
| I-85 | + |
| I-86 | +++ |
| I-87 | +++ |
| I-88 | +++ |
| I-89 | +++ |
| I-90 | +++ |
| I-91 | +++ |
| I-92 | + |
| I-93 | ++ |
| I-94 | +++ |
| I-95 | + |
| I-96 | ++ |
| I-97 | + |
| I-98 | + |
| I-99 | +++ |
| I-100 | +++ |
| I-101 | +++ |
| I-102 | +++ |
| I-103 | +++ |
| I-104 | +++ |
| I-105 | +++ |
| I-106 | +++ |
| I-107 | +++ |
| I-108 | + |
| I-109 | + |
| I-110 | ++ |
| I-111 | ++ |
| I-112 | + |
| I-113 | + |
| I-114 | + |
| I-115 | + |
| I-116 | + |
| I-117 | + |
| I-118 | + |
| I-119 | + |
| I-120 | + |
| I-121 | + |
| I-122 | +++ |
| I-123 | + |
| I-124 | +++ |
| I-125 | ++ |
| I-126 | +++ |
| I-127 | ++ |
| I-128 | + |
| I-129 | + |
| I-130 | + |
| I-131 | + |
| I-132 | + |
| I-133 | + |
| I-134 | + |
| I-135 | + |
| I-136 | + |
| I-137 | + |
| I-138 | + |
| I-139 | + |
| I-140 | + |
| I-141 | + |
| I-142 | + |
| I-143 | + |
| I-144 | + |
| I-145 | + |
| I-146 | + |
| I-147 | + |
| I-148 | + |
| I-149 | + |
| II-1 | + |
| II-2 | + |
| II-3 | +++ |
| II-4 | + |
| II-5 | ++ |
| II-6 | +++ |
| II-7 | + |

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A compound of the Formula I:

$X^1$, $X^2$, $X^3$, $X^6$, and $X^7$ are each independently —$CR^1R^2$—, —$NR^3$—, —O—, —C(O)—, —$SO_2$—, —S(O)—, or —S—;

$X^4$ and $X^5$ are each independently —$CR^1R^2$—, —C(O)—, —$SO_2$—, —S(O)—, or —S—;

$Y^1$, $Y^2$ and $Y^4$ are each independently N or $CR^1$;

L is a bond, —$(CR^1R^2)_n$—, —$C(O)NR^3$—, —$S(O)_2$—, —$S(O)_2NR^3$—, —S(O)—, —$S(O)NR^3$—, —C(O) $(CR^1R^2)_nO$—, or —$C(O)(CR^1R^2)_n$—;

R is independently —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$C_5$-$C_{12}$spirocycle, heterocyclyl, spiroheterocyclyl, aryl, or heteroaryl containing 1-5 heteroatoms selected from the group consisting of N, S, P, or O, wherein each alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —$NO_2$, —CN, —$R^1$, —$R^2$, —$SR^3$, —$OR^3$, —$NHR^3$, —$NR^3R^4$, —$S(O)_2NR^3R^4$, —$S(O)_2R^1$, —$C(O)R^1$, —$CO_2R^1$, —$NR^3S(O)_2R^1$, —$S(O)R^1$, —$S(O)NR^3R^4$, —$NR^3S(O)R^1$, heterocycle, aryl, or heteroaryl;

$R^1$ and $R^2$ are independently, at each occurrence, —H, —$R^3$, —$R^4$, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P and O, —OH, halogen, —$NO_2$, —CN, —$NHC_1$-$C_6$alkyl, —$N(C_1$-$C_6$alkyl$)_2$, —$S(O)_2N(C_1$-$C_6$alkyl$)_2$, —$N(C_1$-$C_6$alkyl)$S(O)_2R^5$, —$S(O)_2(C_1$-$C_6$alkyl), —$(C_1$-$C_6$alkyl)$S(O)_2R^5$, —$C(O)C_1$-$C_6$alkyl, —$CO_2C_1$-$C_6$alkyl, —$N(C_1$-$C_6$alkyl)$S(O)_2C_1$-$C_6$alkyl, or —$(CHR^5)_nNR^3R^4$, wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^3$, —$NHR^3$, $NR^3R^4$, —$S(O)_2N(R^3)_2$—, —$S(O)_2R^5$, —$C(O)R^5$, —$CO_2R^5$, —$NR^3S(O)_2R^5$, —$S(O)R^5$, —$S(O)NR^3R^4$, —$NR^3S(O)R^5$, heterocycle, aryl, or heteroaryl;

or $R^1$ and $R^2$ can combine with the carbon atom to which they are both attached to form a cycloalkyl, heterocycle, spirocycle, spiroheterocycle, or spirocycloalkenyl;

or $R^1$ and $R^2$, when on adjacent or non-adjacent atoms, can combine to form a heterocycle, cycloalkyl, aryl, heteroaryl containing 1-5 heteroatoms selected from the group consisting of N, S, P and O, or cycloalkenyl;

$R^3$ and $R^4$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P, and O, —$S(O)_2N(C_1$-$C_6$alkyl$)_2$, —$S(O)_2(C_1$-$C_6$alkyl), —$(C_1$-$C_6$alkyl)$S(O)_2R^5$, —$C(O)C_1$-$C_6$alkyl, —$CO_2C_1$-$C_6$alkyl, or —$(CHR^5)_nN(C_1$-$C_6$alkyl$)_2$, wherein each alkyl, alkenyl, cycloalkenyl, alkynyl, cycloalkyl, heterocyclyl, aryl, and heteroaryl is optionally substituted with one or more substituents selected from —OH, halogen, —$NO_2$, oxo, —CN, —$R^5$, —$O(C_1$-$C_6)$alkyl, —$NH(C_1$-$C_6)$alkyl, —$N(C_1$-$C_6$alkly$)_2$, —$S(O)_2N(C_1$-$C_6$alkyl$)_2$, —$S(O)_2NHC_1$-$C_6$alkyl, —$C(O)C_1$-$C_6$alkyl, —$CO_2C_1$-$C_6$alkyl, —$N(C_1$-$C_6$alkyl)$S(O)_2C_1$-$C_6$alkyl, —$S(O)R^5$, —$S(O)N(C_1$-$C_6$alkyl$)_2$, —$N(C_1$-$C_6$alkyl)$S(O)R^5$, heterocycle, aryl, or heteroaryl;

$R^5$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from N, S, P and O, —OH, halogen, —$NO_2$, —CN, —$NHC_1$-

$C_6$alkyl, —$N(C_1$-$C_6$alkyl$)_2$, —$S(O)_2NH(C_1$-$C_6$alkyl), —$S(O)_2N(C_1$-$C_6$alkyl$)_2$, —$S(O)_2C_1$-$C_6$alkyl, —$C(O)C_1$-$C_6$alkyl, —$CO_2C_1$-$C_6$alkyl, —$N(C_1$-$C_6$alkyl)$SO_2C_1$-$C_6$alkyl, —$S(O)(C_1$-$C_6$alkyl), —$S(O)N(C_1$-$C_6$alkyl$)_2$, —$N(C_1$-$C_6$alkyl)$S(O)(C_1$-$C_6$alkyl) or —$(CH_2)_nN(C_1$-$C_6$alkyl$)_2$;

n is an integer from 0 to 6; and m is 0, 1, 2 or 3.

2. The compound of claim 1, wherein $X^4$ is —C(O)—.

3. The compound of claim 1, wherein the compound is of the Formula I-a:

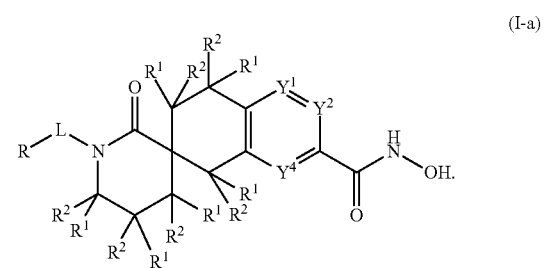

(I-a)

4. The compound of claim 1, wherein the compound is of the Formula I-b:

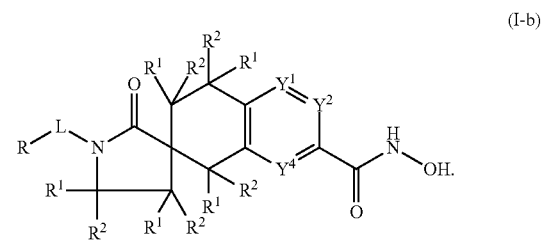

(I-b)

5. The compound of claim 1, wherein the compound is of the Formula I-c:

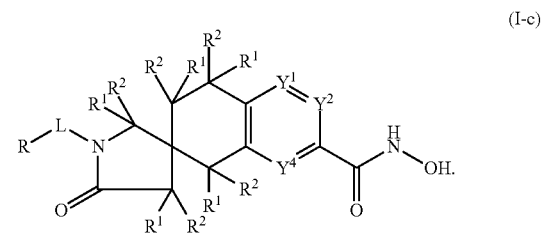

(I-c)

6. The compound of claim 1, wherein the compound is of the Formula I-d:

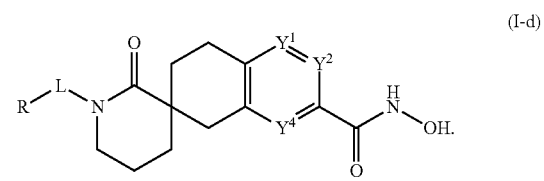

(I-d)

7. The compound of claim 1, wherein the compound is of the Formula I-e:

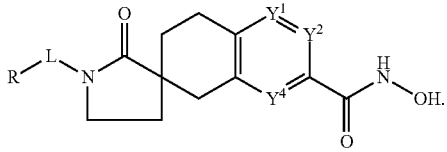

(I-e)

8. The compound of claim 1, wherein the compound is of the Formula I-f:

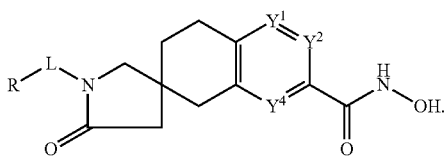

(I-f)

9. The compound of claim 1, wherein the compound is of the Formula I-g:

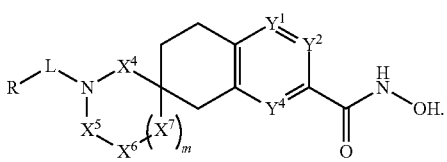

(I-g)

10. The compound of claim 1, wherein the compound is of the Formula I-h:

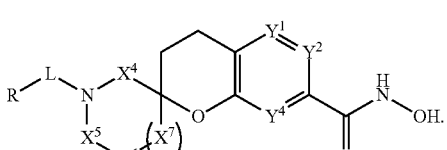

(I-h)

11. The compound of claim 1, wherein the compound is of the Formula I-j:

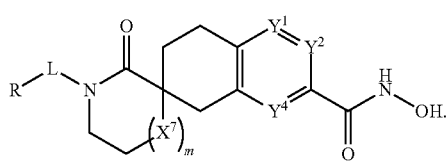

(I-j)

12. The compound of claim 1, wherein the compound is of the Formula I-k:

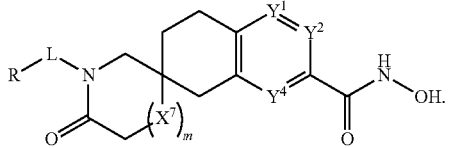

(I-k)

13. A compound of the Formula II:

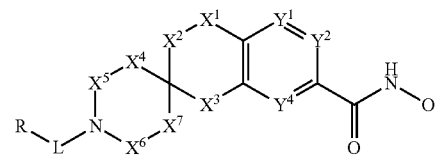

(II)

or a pharmaceutically acceptable salt, prodrug, solvate, hydrate, tautomer, or isomer or thereof, wherein:

$X^1$ is independently —$CR^1R^2$—, —$NR^3$—, —O—, —$SO_2$—, —S(O)—, or —S—;

$X^2$, $X^3$, $X^4$, and $X^7$ are each independently —$CR^1R^2$—, —$NR^3$—, —O—, —C(O)—, —$SO_2$—, —S(O)—, or —S—;

$X^5$ and $X^6$ are each independently —$CR^1R^2$—, —C(O)—, —$SO_2$—, —S(O)—, or —S—;

$Y^1$, $Y^2$ and $Y^4$ are each independently N or $CR^1$;

L is a bond, —$(CR^1R^2)_n$—, —$C(O)NR^3$—, —$S(O)_2$—, —$S(O)_2NR^3$—, —S(O)—, —$S(O)NR^3$—, —$C(O)(CR^1R^2)_nO$—, or —$C(O)(CR^1R^2)_n$—;

R is independently —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$C_5$-$C_{12}$spirocycle, heterocyclyl, spiroheterocyclyl, aryl, or heteroaryl containing 1-5 heteroatoms selected from the group consisting of N, S, P, or O, wherein each -alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —$NO_2$, —CN, —$R^1$, —$R^2$, —$SR^3$, —$OR^3$, —$NHR^3$, —$NR^3R^4$, —$S(O)_2NR^3R^4$, —$S(O)_2R^1$, —$C(O)R^1$, —$CO_2R^1$, —$NR^3S(O)_2R^1$, —$S(O)R^1$, —$S(O)NR^3R^4$, —$NR^3S(O)R^1$, heterocycle, aryl, or heteroaryl;

$R^1$ and $R^2$ are independently, and at each occurrence, —H, —$R^3$, —$R^4$, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, heterocyclyl, aryl, heteroaryl containing 1-5 heteroatoms selected from the group consisting of N, S, P, or O, —OH, halogen, —$NO_2$, —CN, —$NHC_1$-$C_6$alkyl, —$N(C_1$-$C_6$alkyl$)_2$, —$S(O)_2N(C_1$-$C_6$alkyl$)_2$, —$N(C_1$-$C_6$alkyl)$S(O)_2R^5$, —$S(O)_2(C_1$-$C_6$alkyl), —$(C_1$-$C_6$alkyl)$S(O)_2R^5$, —$C(O)C_1$-$C_6$alkyl, —$CO_2C_1$-$C_6$alkyl, —$N(C_1$-$C_6$alkyl)$S(O)_2C_1$-$C_6$alkyl, or —$(CHR^5)_nNR^3R^4$, wherein each alkyl, alkenyl, cycloalkenyl, alkynyl, cycloalkyl, heterocyclyl, aryl, or heteroaryl is optionally substituted with one or more substituents selected from —OH, halogen, —$NO_2$, oxo, —CN, —$R^5$, —$OR^3$, —$NHR^3$, $NR^3R^4$, —$S(O)_2N(R^3)_2$—, —$S(O)_2R^5$, —$C(O)R^5$, —$CO_2R^5$, —$NR^3S(O)_2R^5$, —$S(O)R^5$, —$S(O)NR^3R^4$, —$NR^3S(O)R^5$, heterocycle, aryl, or heteroaryl;

or $R^1$ and $R^2$ can combine with the carbon atom to which they are both attached to form a cycloalkyl, heterocycle, spirocycle, spiroheterocycle, or spirocycloalkenyl;

or R¹ and R², when on adjacent or non-adjacent atoms, can combine to form a heterocycle, cycloalkyl, aryl, heteroaryl containing 1-5 heteroatoms selected from the group consisting of N, S, P and O, or cycloalkenyl;

R³ and R⁴ are independently, at each occurrence, —H, —C₁-C₆alkyl, —C₂-C₆alkenyl, —C₄-C₈cycloalkenyl, —C₂-C₆alkynyl, —C₃-C₈cycloalkyl, heterocyclyl, aryl, heteroaryl containing 1-5 heteroatoms selected from N, S, P and O, —S(O)₂N(C₁-C₆alkyl)₂, —S(O)₂(C₁-C₆alkyl), —(C₁-C₆alkyl)S(O)₂R⁵, —C(O)C₁-C₆alkyl, —CO₂C₁-C₆alkyl, or —(CHR⁵)ₙN(C₁-C₆alkyl)₂, wherein each alkyl, alkenyl, cycloalkenyl, alkynyl, cycloalkyl, heterocyclyl, aryl, and heteroaryl is optionally substituted with one or more substituents selected from —OH, halogen, —NO₂, oxo, —CN, —R⁵, —O(C₁-C₆)alkyl, —NH(C₁-C₆)alkyl, —N(C₁-C₆alkly)₂, —S(O)₂N(C₁-C₆alkyl)₂, —S(O)₂NHC₁-C₆alkyl, —C(O)C₁-C₆alkyl, —CO₂C₁-C₆alkyl, —N(C₁-C₆alkyl)S(O)₂C₁-C₆alkyl, —S(O)R⁵, —S(O)N(C₁-C₆alkyl)₂, —N(C₁-C₆alkyl)S(O)R⁵, heterocycle, aryl, or heteroaryl;

each R⁵ is independently —H, —C₁-C₆alkyl, —C₂-C₆alkenyl, —C₄-C₈cycloalkenyl, —C₂-C₆alkynyl, —C₃-C₈cycloalkyl, heterocyclyl, aryl, heteroaryl containing 1-5 heteroatoms selected from N, S, O and P, —OH, halogen, —NO₂, —CN, —NHC₁-C₆alkyl, —N(C₁-C₆alkyl)₂, —S(O)₂NH(C₁-C₆alkyl), —S(O)₂N(C₁-C₆alkyl)₂, —S(O)₂C₁-C₆alkyl, —C(O)C₁-C₆alkyl, —CO₂C₁-C₆alkyl, —N(C₁-C₆alkyl)SO₂C₁-C₆alkyl, —S(O)(C₁-C₆alkyl), —S(O)N(C₁-C₆alkyl)₂, —N(C₁-C₆alkyl)S(O)(C₁-C₆alkyl) or —(CH₂)ₙN(C₁-C₆alkyl)₂; and n is an integer from 0 to 6.

14. The compound of claim 13, wherein X⁵ is C(O).

15. The compound of claim 13, wherein the compound is of the Formula II-a:

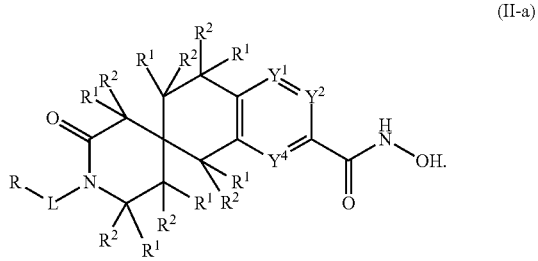

(II-a)

16. The compound of claim 13, wherein the compound is of the Formula II-b:

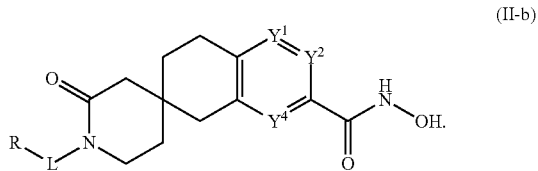

(II-b)

17. The compound of claim 13, wherein the compound is of the Formula II-c:

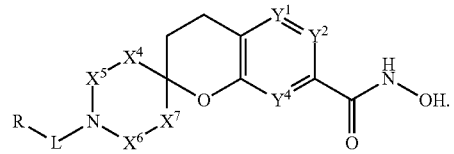

(II-c)

18. The compound of claim 13, wherein the compound is of the Formula II-d:

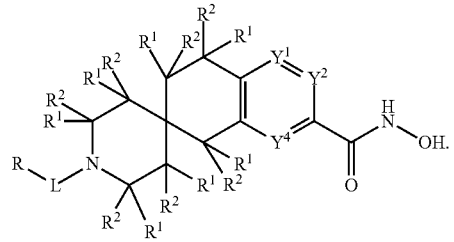

(II-d)

19. A compound of claim 1 selected from:

N-hydroxy-1'-(4-methoxybenzoyl)-3,4-dihydro-1H-spiro[naphthalene-2,3'-pyrrolidine]-7-carboxamide (I-1);

N-hydroxy-1'-((4-methoxyphenyl)sulfonyl)-3,4-dihydro-1H-spiro[naphthalene-2,3'-pyrrolidine]-7-carboxamide (I-2);

N-hydroxy-1'-(4-methoxybenzyl)-3,4-dihydro-1H-spiro[naphthalene-2,3'-pyrrolidine]-7-carboxamide (I-3);

1'-(cyclohexanecarbonyl)-N-hydroxy-3,4-dihydro-1H-spiro[naphthalene-2,3'-pyrrolidine]-7-carboxamide (I-4);

1'-cyclohexyl-N-hydroxy-3,4-dihydro-1H-spiro[naphthalene-2,3'-pyrrolidine]-7-carboxamide (I-5);

N7-hydroxy-N1'-phenyl-3,4-dihydro-1H-spiro[naphthalene-2,3'-pyrrolidine]-1',7-dicarboxamide (I-6);

1'-(cyclohexylsulfonyl)-N-hydroxy-3,4-dihydro-1H-spiro[naphthalene-2,3'-pyrrolidine]-7-carboxamide (I-7);

N-hydroxy-3,4-dihydro-1H-spiro[naphthalene-2,3'-pyrrolidine]-7-carboxamide (I-8);

N-hydroxy-1'-methyl-3,4-dihydro-1H-spiro[naphthalene-2,3'-pyrrolidine]-7-carboxamide (I-9);

1'-formyl-N-hydroxy-3,4-dihydro-1H-spiro[naphthalene-2,3'-pyrrolidine]-7-carboxamide (I-10);

N-hydroxy-1'-isopropyl-3,4-dihydro-1H-spiro[naphthalene-2,3'-pyrrolidine]-7-carboxamide (I-11);

1'-acetyl-N-hydroxy-3,4-dihydro-1H-spiro[naphthalene-2,3'-pyrrolidine]-7-carb oxamide (I-12);

N-hydroxy-1'-(methyl sulfonyl)-3,4-dihydro-1H-spiro[naphthalene-2,3'-pyrrolidine]-7-carboxamide (I-13);

N-hydroxy-1'-(3-methoxybenzyl)-3,4-dihydro-1H-spiro[naphthalene-2,3'-pyrrolidine]-7-carboxamide (I-14);

N-hydroxy-1'-(2-methoxybenzyl)-3,4-dihydro-1H-spiro[naphthalene-2,3'-pyrrolidine]-7-carboxamide (I-15);

(S)—N-hydroxy-1'-phenyl-3,4-dihydro-1H-spiro[naphthalene-2,3'-pyrrolidine]-7-carboxamide (I-16);

(R)—N-hydroxy-1'-phenyl-3,4-dihydro-1H-spiro[naphthalene-2,3'-pyrrolidine]-7-carboxamide (I-17);

(S)—N-hydroxy-1'-methyl-3,4-dihydro-1H-spiro[naphthalene-2,3'-pyrrolidine]-7-carboxamide (I-18);

(R)—N-hydroxy-1'-methyl-3,4-dihydro-1H-spiro[naphthalene-2,3'-pyrrolidine]-7-carboxamide (I-19);

N-hydroxy-1'-(4-methoxyphenethyl)-2'-oxo-3,4-dihydro-1H-spiro[naphthalene-2,3'-pyrrolidine]-7-carboxamide (I-20);

1'-(3,4-dichlorobenzyl)-N-hydroxy-2'-oxo-3,4-dihydro-1H-spiro[naphthalene-2,3'-pyrrolidine]-7-carboxamide (I-21);

N-hydroxy-2'-oxo-1'-(pyridin-4-ylmethyl)-3,4-dihydro-1H-spiro[naphthalene-2,3'-pyrrolidine]-7-carboxamide (I-22);

1'-(cyclohexylmethyl)-N-hydroxy-2'-oxo-3,4-dihydro-1H-spiro[naphthalene-2,3'-pyrrolidine]-7-carboxamide (I-23);

N-hydroxy-1'-isopropyl-2'-oxo-3,4-dihydro-1H-spiro[naphthalene-2,3'-pyrrolidine]-7-carboxamide (I-24);

1'-(3-(dimethylamino)propyl)-N-hydroxy-2'-oxo-3,4-dihydro-1H-spiro[naphthalene-2,3'-pyrrolidine]-7-carboxamide (I-25);

N-hydroxy-2'-oxo-1'-phenyl-3,4-dihydro-1H-spiro[naphthalene-2,3'-pyrrolidine]-7-carboxamide (I-26);

1'-(4-chloro-3-(trifluoromethyl)benzyl)-N-hydroxy-2'-oxo-3,4-dihydro-1H-spiro[naphthalene-2,3'-pyrrolidine]-7-carboxamide (I-27);

(S)—N-hydroxy-2'-oxo-1'-(pyridin-3-yl)-3,4-dihydro-1H-spiro[naphthalene-2,3'-pyrrolidine]-7-carboxamide (I-28);

(R)—N-hydroxy-2'-oxo-1'-(pyridin-3-yl)-3,4-dihydro-1H-spiro[naphthalene-2,3'-pyrrolidine]-7-carboxamide (I-29);

N-hydroxy-2'-oxo-1'-(pyridin-4-yl)-3,4-dihydro-1H-spiro[naphthalene-2,3'-pyrrolidine]-7-carboxamide (I-30);

(S)-1'-(1H-benzo[d]imidazol-2-yl)-N-hydroxy-2'-oxo-3,4-dihydro-1H-spiro[naphthalene-2,3'-pyrrolidine]-7-carboxamide (I-31);

(R)-1'-(1H-benzo[d]imidazol-2-yl)-N-hydroxy-2'-oxo-3,4-dihydro-1H-spiro[naphthalene-2,3'-pyrrolidine]-7-carboxamide (I-32);

(S)—N-hydroxy-1'-(1-(2-methoxyethyl)-1H-benzo[d]imidazol-2-yl)-2'-oxo-3,4-dihydro-1H-spiro[naphthalene-2,3'-pyrrolidine]-7-carboxamide (I-33);

(R)—N-hydroxy-1'-(1-(2-methoxyethyl)-1H-benzo[d]imidazol-2-yl)-2'-oxo-3,4-dihydro-1H-spiro[naphthalene-2,3'-pyrrolidine]-7-carboxamide (I-34);

(S)-1'-benzyl-N-hydroxy-2'-oxo-3,4-dihydro-1H-spiro[naphthalene-2,3'-pyrrolidine]-7-carboxamide (I-35);

(R)-1'-benzyl-N-hydroxy-2'-oxo-3,4-dihydro-1H-spiro[naphthalene-2,3'-pyrrolidine]-7-carboxamide (I-36);

(S)-1'-(4-chlorobenzyl)-N-hydroxy-2'-oxo-3,4-dihydro-1H-spiro[naphthalene-2,3'-pyrrolidine]-7-carboxamide (I-37);

(R)-1'-(4-chlorobenzyl)-N-hydroxy-2'-oxo-3,4-dihydro-1H-spiro[naphthalene-2,3'-pyrrolidine]-7-carboxamide (I-38);

(S)-1'-((5-chloropyridin-2-yl)methyl)-N-hydroxy-2'-oxo-3,4-dihydro-1H-spiro[naphthalene-2,3'-pyrrolidine]-7-carboxamide (I-39);

(R)-1'-((5-chloropyridin-2-yl)methyl)-N-hydroxy-2'-oxo-3,4-dihydro-1H-spiro[naphthalene-2,3'-pyrrolidine]-7-carboxamide (I-40);

(S)-1'-(4-fluorobenzyl)-N-hydroxy-2'-oxo-3,4-dihydro-1H-spiro[naphthalene-2,3'-pyrrolidine]-7-carboxamide (I-41);

(R)-1'-(4-fluorobenzyl)-N-hydroxy-2'-oxo-3,4-dihydro-1H-spiro[naphthalene-2,3'-pyrrolidine]-7-carboxamide (I-42);

(R)—N-hydroxy-2'-oxo-1'-(pyridin-2-yl)-3,4-dihydro-1H-spiro[naphthalene-2,3'-pyrrolidine]-7-carboxamide (I-43);

(S)—N-hydroxy-2'-oxo-1'-(pyridin-2-yl)-3,4-dihydro-1H-spiro[naphthalene-2,3'-pyrrolidine]-7-carboxamide (I-44);

(S)—N-hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-7-carboxamide (I-45);

(R)—N-hydroxy-1'-((1-(2-methoxyethyl)-1H-benzo[d]imidazol-2-yl)methyl)-2'-oxo-3,4-dihydro-1H-spiro[naphthalene-2,3'-pyrrolidine]-7-carboxamide (I-46);

(S)—N-hydroxy-2'-oxo-3,4-dihydro-1H-spiro[naphthalene-2,3'-pyrrolidine]-7-carboxamide (I-47);

(R)—N-hydroxy-2'-oxo-3,4-dihydro-1H-spiro[naphthalene-2,3'-pyrrolidine]-7-carboxamide (I-48);

(S)-1'-((2-chlorothiazol-5-yl)methyl)-N-hydroxy-2'-oxo-3,4-dihydro-1H-spiro[naphthalene-2,3'-pyrrolidine]-7-carboxamide (I-49);

(S)—N-hydroxy-1'-((2-hydroxythiazol-5-yl)methyl)-2'-oxo-3,4-dihydro-1H-spiro[naphthalene-2,3'-pyrrolidine]-7-carboxamide (I-50);

(R)—N-hydroxy-1'-(4-(methylsulfonyl)benzyl)-2'-oxo-3,4-dihydro-1H-spiro[naphthalene-2,3'-pyrrolidine]-7-carboxamide (I-51);

(S)—N-hydroxy-2'-oxo-1'-propyl-3,4-dihydro-1H-spiro[naphthalene-2,3'-pyrrolidine]-7-carboxamide (I-52);

(S)-1'-(cyclobutylmethyl)-N-hydroxy-2'-oxo-3,4-dihydro-1H-spiro[naphthalene-2,3'-pyrrolidine]-7-carboxamide (I-53);

(S)—N-hydroxy-1'-isopentyl-2'-oxo-3,4-dihydro-1H-spiro[naphthalene-2,3'-pyrrolidine]-7-carboxamide (I-54);

(S)-1'-(but-2-yn-1-yl)-N-hydroxy-2'-oxo-3,4-dihydro-1H-spiro[naphthalene-2,3'-pyrrolidine]-7-carboxamide (I-55);

(S)—N-hydroxy-1'-(2-methoxyethyl)-2'-oxo-3,4-dihydro-1H-spiro[naphthalene-2,3'-pyrrolidine]-7-carboxamide (I-56);

(S)—N-hydroxy-2'-oxo-1'-((tetrahydro-2H-pyran-4-yl)methyl)-3,4-dihydro-1H-spiro[naphthalene-2,3'-pyrrolidine]-7-carboxamide (I-57);

(S)-1'-cinnamyl-N-hydroxy-2'-oxo-3,4-dihydro-1H-spiro[naphthalene-2,3'-pyrrolidine]-7-carboxamide (I-58);

(S)—N-hydroxy-1'-(2-methylbenzyl)-2'-oxo-3,4-dihydro-1H-spiro[naphthalene-2,3'-pyrrolidine]-7-carboxamide (I-59);

(S)—N-hydroxy-2'-oxo-1'-(2-(trifluoromethyl)benzyl)-3,4-dihydro-1H-spiro[naphthalene-2,3'-pyrrolidine]-7-carboxamide (I-60);

(S)-1'-(2-chlorobenzyl)-N-hydroxy-2'-oxo-3,4-dihydro-1H-spiro[naphthalene-2,3'-pyrrolidine]-7-carboxamide (I-61);

(S)—N-hydroxy-2'-oxo-1'-(2-(trifluoromethoxy)benzyl)-3,4-dihydro-1H-spiro[naphthalene-2,3'-pyrrolidine]-7-carboxamide (I-62);

(S)-1'-(benzo[c][1,2,5]oxadiazol-5-ylmethyl)-N-hydroxy-2'-oxo-3,4-dihydro-1H-spiro[naphthalene-2,3'-pyrrolidine]-7-carboxamide (I-63);

(S)—N-hydroxy-1'-(2-morpholino-2-oxoethyl)-2'-oxo-3,4-dihydro-1H-spiro[naphthalene-2,3'-pyrrolidine]-7-carboxamide (I-64);

(S)—N-hydroxy-1'-(2-methoxybenzyl)-2'-oxo-3,4-dihydro-1H-spiro[naphthalene-2,3'-pyrrolidine]-7-carboxamide (I-65);

(S)—N-hydroxy-1'-((1-isopropyl-1H-benzo[d]imidazol-2-yl)methyl)-2'-oxo-3,4-dihydro-1H-spiro[naphthalene-2,3'-pyrrolidine]-7-carboxamide (I-66);

(S)-1'-(2,5-dichlorobenzyl)-N-hydroxy-2'-oxo-3,4-dihydro-1H-spiro[naphthalene-2,3'-pyrrolidine]-7-carboxamide (I-67);

(S)-1'-(2,6-dichlorobenzyl)-N-hydroxy-2'-oxo-3,4-dihydro-1H-spiro[naphthalene-2,3'-pyrrolidine]-7-carboxamide (I-68);

(S)—N-hydroxy-1'-(3-methoxybenzyl)-2'-oxo-3,4-dihydro-1H-spiro[naphthalene-2,3'-pyrrolidine]-7-carboxamide (I-69);

(S)—N-hydroxy-2'-oxo-1'-(pyridin-3-ylmethyl)-3,4-dihydro-1H-spiro[naphthalene-2,3'-pyrrolidine]-7-carboxamide (I-70);

(S)—N-hydroxy-2'-oxo-1'-(pyridin-2-ylmethyl)-3,4-dihydro-1H-spiro[naphthalene-2,3'-pyrrolidine]-7-carboxamide (I-71);

(S)-1'-(3-fluorobenzyl)-N-hydroxy-2'-oxo-3,4-dihydro-1H-spiro[naphthalene-2,3'-pyrrolidine]-7-carboxamide (I-72);

(S)—N-hydroxy-2'-oxo-1'-(4-(trifluoromethoxy)benzyl)-3,4-dihydro-1H-spiro[naphthalene-2,3'-pyrrolidine]-7-carboxamide (I-73);

(S)-1'-(3-chlorobenzyl)-N-hydroxy-2'-oxo-3,4-dihydro-1H-spiro[naphthalene-2,3'-pyrrolidine]-7-carboxamide (I-74);

(S)—N-hydroxy-1'-(4-methoxybenzyl)-2'-oxo-3,4-dihydro-1H-spiro[naphthalene-2,3'-pyrrolidine]-7-carboxamide (I-75);

(S)-1'-(2-fluorobenzyl)-N-hydroxy-2'-oxo-3,4-dihydro-1H-spiro[naphthalene-2,3'-pyrrolidine]-7-carboxamide (I-76);

(S)—N-hydroxy-1'-(naphthalen-2-ylmethyl)-2'-oxo-3,4-dihydro-1H-spiro[naphthalene-2,3'-pyrrolidine]-7-carboxamide (I-77);

(S)-1'-(2-(difluoromethoxy)benzyl)-N-hydroxy-2'-oxo-3,4-dihydro-1H-spiro[naphthalene-2,3'-pyrrolidine]-7-carboxamide (I-78);

(R)—N-hydroxy-2'-oxo-1'-propyl-3,4-dihydro-1H-spiro[naphthalene-2,3'-pyrrolidine]-7-carboxamide (I-79);

(R)—N-hydroxy-1'-(3-hydroxypropyl)-2'-oxo-3,4-dihydro-1H-spiro[naphthalene-2,3'-pyrrolidine]-7-carboxamide (I-80);

(R)-1'-(cyclobutylmethyl)-N-hydroxy-2'-oxo-3,4-dihydro-1H-spiro[naphthalene-2,3'-pyrrolidine]-7-carboxamide (I-81);

(R)—N-hydroxy-1'-isopentyl-2'-oxo-3,4-dihydro-1H-spiro[naphthalene-2,3'-pyrrolidine]-7-carboxamide (I-82);

(R)-1'-(but-2-yn-1-yl)-N-hydroxy-2'-oxo-3,4-dihydro-1H-spiro[naphthalene-2,3'-pyrrolidine]-7-carboxamide (I-83);

(R)—N-hydroxy-1'-(2-methoxyethyl)-2'-oxo-3,4-dihydro-1H-spiro[naphthalene-2,3'-pyrrolidine]-7-carboxamide (I-84);

(R)—N-hydroxy-2'-oxo-1'-((tetrahydro-2H-pyran-4-yl)methyl)-3,4-dihydro-1H-spiro[naphthalene-2,3'-pyrrolidine]-7-carboxamide (I-85);

(R)-1'-cinnamyl-N-hydroxy-2'-oxo-3,4-dihydro-1H-spiro[naphthalene-2,3'-pyrrolidine]-7-carboxamide (I-86);

(R)—N-hydroxy-1'-(2-methylbenzyl)-2'-oxo-3,4-dihydro-1H-spiro[naphthalene-2,3'-pyrrolidine]-7-carboxamide (I-87);

(R)—N-hydroxy-2'-oxo-1'-(2-(trifluoromethyl)benzyl)-3,4-dihydro-1H-spiro[naphthalene-2,3'-pyrrolidine]-7-carboxamide (I-88);

(R)-1'-(2-chlorobenzyl)-N-hydroxy-2'-oxo-3,4-dihydro-1H-spiro[naphthalene-2,3'-pyrrolidine]-7-carboxamide (I-89);

(R)—N-hydroxy-2'-oxo-1'-(2-(trifluoromethoxy)benzyl)-3,4-dihydro-1H-spiro[naphthalene-2,3'-pyrrolidine]-7-carboxamide (I-90);

(R)-1'-(benzo[c][1,2,5]oxadiazol-5-ylmethyl)-N-hydroxy-2'-oxo-3,4-dihydro-1H-spiro[naphthalene-2,3'-pyrrolidine]-7-carboxamide (I-91);

(R)—N-hydroxy-1'-(2-morpholino-2-oxoethyl)-2'-oxo-3,4-dihydro-1H-spiro[naphthalene-2,3'-pyrrolidine]-7-carboxamide (I-92);

(R)—N-hydroxy-1'-(2-methoxybenzyl)-2'-oxo-3,4-dihydro-1H-spiro[naphthalene-2,3'-pyrrolidine]-7-carboxamide (I-93);

(R)-1'-(2,5-dichlorobenzyl)-N-hydroxy-2'-oxo-3,4-dihydro-H-spiro[naphthalene-2,3'-pyrrolidine]-7-carboxamide (I-94);

(R)-1'-(2,6-dichlorobenzyl)-N-hydroxy-2'-oxo-3,4-dihydro-1H-spiro[naphthalene-2,3'-pyrrolidine]-7-carboxamide (I-95);

(R)—N-hydroxy-1'-(3-methoxybenzyl)-2'-oxo-3,4-dihydro-1H-spiro[naphthalene-2,3'-pyrrolidine]-7-carboxamide (I-96);

(R)—N-hydroxy-2'-oxo-1'-(pyridin-3-ylmethyl)-3,4-dihydro-1H-spiro[naphthalene-2,3'-pyrrolidine]-7-carboxamide (I-97);

(R)—N-hydroxy-2'-oxo-1'-(pyridin-2-ylmethyl)-3,4-dihydro-1H-spiro[naphthalene-2,3'-pyrrolidine]-7-carboxamide (I-98);

(R)-1'-(3-fluorobenzyl)-N-hydroxy-2'-oxo-3,4-dihydro-1H-spiro[naphthalene-2,3'-pyrrolidine]-7-carboxamide (I-99);

(R)—N-hydroxy-2'-oxo-1'-(4-(trifluoromethoxy)benzyl)-3,4-dihydro-1H-spiro[naphthalene-2,3'-pyrrolidine]-7-carboxamide (I-100);

(R)-1'-(3-chlorobenzyl)-N-hydroxy-2'-oxo-3,4-dihydro-1H-spiro[naphthalene-2,3'-pyrrolidine]-7-carboxamide (I-101);

(R)—N-hydroxy-1'-(4-methoxybenzyl)-2'-oxo-3,4-dihydro-1H-spiro[naphthalene-2,3'-pyrrolidine]-7-carboxamide (I-102);

(R)-1'-(2-fluorobenzyl)-N-hydroxy-2'-oxo-3,4-dihydro-1H-spiro[naphthalene-2,3'-pyrrolidine]-7-carboxamide (I-103);

(R)—N-hydroxy-1'-(naphthalen-2-ylmethyl)-2'-oxo-3,4-dihydro-H-spiro[naphthalene-2,3'-pyrrolidine]-7-carboxamide (I-104);

(R)-1'-(2-(difluoromethoxy)benzyl)-N-hydroxy-2'-oxo-3,4-dihydro-1H-spiro[naphthalene-2,3'-pyrrolidine]-7-carboxamide (I-105);

(R)—N-hydroxy-2'-oxo-1'-(4-phenoxyphenyl)-3,4-dihydro-1H-spiro[naphthalene-2,3'-pyrrolidine]-7-carboxamide (I-106);

(R)—N-hydroxy-2'-oxo-1'-(quinolin-3-yl)-3,4-dihydro-1H-spiro[naphthalene-2,3'-pyrrolidine]-7-carboxamide (I-107);

(R)-1'-(2,3-dihydrobenzofuran-7-yl)-N-hydroxy-2'-oxo-3,4-dihydro-1H-spiro[naphthalene-2,3'-pyrrolidine]-7-carboxamide (I-108);

(R)-1'-(1,3-dimethyl-1H-pyrazol-4-yl)-N-hydroxy-2'-oxo-3,4-dihydro-1H-spiro[naphthalene-2,3'-pyrrolidine]-7-carboxamide (I-109);

(R)—N-hydroxy-1'-(imidazo[1,2-a]pyridin-6-yl)-2'-oxo-3,4-dihydro-1H-spiro[naphthalene-2,3'-pyrrolidine]-7-carboxamide (I-110);

(R)—N-hydroxy-1'-(imidazo[1,2-a]pyridin-3-yl)-2'-oxo-3,4-dihydro-1H-spiro[naphthalene-2,3'-pyrrolidine]-7-carboxamide (I-111);

(S)-1'-(3,4-dichlorophenyl)-N-hydroxy-2'-oxo-3,4-dihydro-1H-spiro[naphthalene-2,3'-pyrrolidine]-7-carboxamide (I-112);
(S)-1'-(2,4-dimethylphenyl)-N-hydroxy-2'-oxo-3,4-dihydro-1H-spiro[naphthalene-2,3'-pyrrolidine]-7-carboxamide (I-113);
(S)—N-hydroxy-1'-(2-methoxyphenyl)-2'-oxo-3,4-dihydro-1H-spiro[naphthalene-2,3'-pyrrolidine]-7-carboxamide (I-114);
(S)-1'-(benzo[d][1,3]dioxol-5-yl)-N-hydroxy-2'-oxo-3,4-dihydro-1H-spiro[naphthalene-2,3'-pyrrolidine]-7-carboxamide (I-115);
(S)—N-hydroxy-2'-oxo-1'-(4-phenoxyphenyl)-3,4-dihydro-1H-spiro[naphthalene-2,3'-pyrrolidine]-7-carboxamide (I-116);
(R)—N-hydroxy-1'-(3-(2-morpholinoethoxy)phenyl)-2'-oxo-3,4-dihydro-1H-spiro[naphthalene-2,3'-pyrrolidine]-7-carboxamide (I-117);
(S)—N-hydroxy-2'-oxo-1'-(quinolin-3-yl)-3,4-dihydro-1H-spiro[naphthalene-2,3'-pyrrolidine]-7-carboxamide (I-118);
(S)-1'-(4-(2-(dimethylamino)ethyl)phenyl)-N-hydroxy-2'-oxo-3,4-dihydro-1H-spiro[naphthalene-2,3'-pyrrolidine]-7-carboxamide (I-119);
(R)—N-hydroxy-1'-methyl-2'-oxo-3,4-dihydro-1H-spiro[naphthalene-2,3'-pyrrolidine]-7-carboxamide (I-120);
(S)—N-hydroxy-1'-methyl-2'-oxo-3,4-dihydro-1H-spiro[naphthalene-2,3'-pyrrolidine]-7-carboxamide (I-121);
(S)—N-hydroxy-1'-(4-methylbenzyl)-2'-oxo-3,4-dihydro-1H-spiro[naphthalene-2,3'-pyrrolidine]-7-carboxamide (I-122);
(R)—N-hydroxy-1'-(4-methylbenzyl)-2'-oxo-3,4-dihydro-1H-spiro[naphthalene-2,3'-pyrrolidine]-7-carboxamide (I-123);
(S)-1'-(3-fluoro-4-(trifluoromethyl)benzyl)-N-hydroxy-2'-oxo-3,4-dihydro-1H-spiro[naphthalene-2,3'-pyrrolidine]-7-carboxamide (I-124);
(R)-1'-(3-fluoro-4-(trifluoromethyl)benzyl)-N-hydroxy-2'-oxo-3,4-dihydro-1H-spiro[naphthalene-2,3'-pyrrolidine]-7-carboxamide (I-125);
(S)—N-hydroxy-2'-oxo-1'-(4-(trifluoromethyl)benzyl)-3,4-dihydro-1H-spiro[naphthalene-2,3'-pyrrolidine]-7-carboxamide (I-126);
(R)—N-hydroxy-2'-oxo-1'-(4-(trifluoromethyl)benzyl)-3,4-dihydro-1H-spiro[naphthalene-2,3'-pyrrolidine]-7-carboxamide (I-127);
(R)-1'-(4-fluorobenzyl)-N-hydroxy-5'-oxo-3,4-dihydro-1H-spiro[naphthalene-2,3'-pyrrolidine]-7-carboxamide (I-128);
(S)-1'-(4-fluorobenzyl)-N-hydroxy-5'-oxo-3,4-dihydro-1H-spiro[naphthalene-2,3'-pyrrolidine]-7-carboxamide (I-129);
(R)—N-hydroxy-1'-methyl-5'-oxo-3,4-dihydro-1H-spiro[naphthalene-2,3'-pyrrolidine]-7-carboxamide (I-130);
(S)—N-hydroxy-1'-methyl-5'-oxo-3,4-dihydro-1H-spiro[naphthalene-2,3'-pyrrolidine]-7-carboxamide (I-131);
(S)—N-hydroxy-5'-oxo-1'-phenyl-3,4-dihydro-1H-spiro[naphthalene-2,3'-pyrrolidine]-7-carboxamide (I-132);
(R)-1'-(cyclobutylmethyl)-N-hydroxy-5'-oxo-3,4-dihydro-1H-spiro[naphthalene-2,3'-pyrrolidine]-7-carboxamide (I-133);
(S)-1'-(cyclobutylmethyl)-N-hydroxy-5'-oxo-3,4-dihydro-1H-spiro[naphthalene-2,3'-pyrrolidine]-7-carboxamide (I-134);
(R)—N-hydroxy-'-(3-methoxypropyl)-5'-oxo-3,4-dihydro-1H-spiro[naphthalene-2,3'-pyrrolidine]-7-carboxamide (I-135);
(S)—N-hydroxy-1'-(3-methoxypropyl)-5'-oxo-3,4-dihydro-1H-spiro[naphthalene-2,3'-pyrrolidine]-7-carboxamide (I-136);
(R)—N-hydroxy-1'-isobutyl-5'-oxo-3,4-dihydro-1H-spiro[naphthalene-2,3'-pyrrolidine]-7-carboxamide (I-137);
(S)—N-hydroxy-1'-isobutyl-5'-oxo-3,4-dihydro-1H-spiro[naphthalene-2,3'-pyrrolidine]-7-carboxamide (I-138);
(R)—N-hydroxy-1'-isopropyl-5'-oxo-3,4-dihydro-1H-spiro[naphthalene-2,3'-pyrrolidine]-7-carboxamide (I-139);
(S)—N-hydroxy-1'-isopropyl-5'-oxo-3,4-dihydro-1H-spiro[naphthalene-2,3'-pyrrolidine]-7-carboxamide (I-140);
(S)-1'-cyclopropyl-N-hydroxy-5'-oxo-3,4-dihydro-1H-spiro[naphthalene-2,3'-pyrrolidine]-7-carboxamide (I-141);
(R)-1'-ethyl-N-hydroxy-5'-oxo-3,4-dihydro-1H-spiro[naphthalene-2,3'-pyrrolidine]-7-carboxamide (I-142);
(S)-1'-ethyl-N-hydroxy-5'-oxo-3,4-dihydro-1H-spiro[naphthalene-2,3'-pyrrolidine]-7-carboxamide (I-143);
(S)—N-hydroxy-5'-oxo-1'-(2,2,2-trifluoroethyl)-3,4-dihydro-1H-spiro[naphthalene-2,3'-pyrrolidine]-7-carboxamide (I-144);
(R)—N-hydroxy-5'-oxo-1'-phenyl-3,4-dihydro-1H-spiro[naphthalene-2,3'-pyrrolidine]-7-carboxamide (I-145);
(R)—N-hydroxy-1'-(oxetan-3-ylmethyl)-5'-oxo-3,4-dihydro-1H-spiro[naphthalene-2,3'-pyrrolidine]-7-carboxamide (I-146);
(S)—N-hydroxy-1'-(oxetan-3-ylmethyl)-5'-oxo-3,4-dihydro-1H-spiro[naphthalene-2,3'-pyrrolidine]-7-carboxamide (I-147);
(R)-1'-cyclopropyl-N-hydroxy-5'-oxo-3,4-dihydro-H-spiro[naphthalene-2,3'-pyrrolidine]-7-carboxamide (I-148);
(R)—N-hydroxy-5'-oxo-1'-(2,2,2-trifluoroethyl)-3,4-dihydro-1H-spiro[naphthalene-2,3'-pyrrolidine]-7-carboxamide (I-149);
(R)-1'-cyclobutyl-N-hydroxy-5'-oxo-3,4-dihydro-1H-spiro[naphthalene-2,3'-pyrrolidine]-7-carboxamide (I-150);
(S)-1'-cyclobutyl-N-hydroxy-5'-oxo-3,4-dihydro-1H-spiro[naphthalene-2,3'-pyrrolidine]-7-carboxamide (I-151);
(R)-1'-cyclopentyl-N-hydroxy-5'-oxo-3,4-dihydro-1H-spiro[naphthalene-2,3'-pyrrolidine]-7-carboxamide (I-152); or
(S)-1'-cyclopentyl-N-hydroxy-5'-oxo-3,4-dihydro-1H-spiro[naphthalene-2,3'-pyrrolidine]-7-carboxamide (I-153).

20. A compound of claim 13 selected from:
N-hydroxy-1'-(4-methoxybenzoyl)spiro[chromane-2,4'-piperidine]-7-carboxamide (II-1);
N-hydroxy-1'-((4-methoxyphenyl)sulfonyl)spiro[chromane-2,4'-piperidine]-7-carboxamide (II-2);
1'-(cyclohexylsulfonyl)-N-hydroxyspiro[chromane-2,4'-piperidine]-7-carboxamide (II-3);
N7-hydroxy-N1'-phenylspiro[chromane-2,4'-piperidine]-1',7-dicarboxamide (II-4);
1'-(cyclohexanecarbonyl)-N-hydroxyspiro[chromane-2,4'-piperidine]-7-carboxamide (II-5);
1'-cyclohexyl-N-hydroxyspiro[chromane-2,4'-piperidine]-7-carboxamide (II-6); or
N-hydroxy-1'-(4-methoxybenzyl)spiro[chromane-2,4'-piperidine]-7-carboxamide (II-7).

21. A compound of claim 1 selected from:
N-hydroxy-1'-methyl-3,4-dihydro-1H-spiro[naphthalene-2,3'-piperidine]-7-carboxamide (I-154);
N-hydroxy-1-methyl-3',4'-dihydro-1'H-spiro[azepane-3,2'-naphthalene]-7'-carb oxamide (I-155);
N-hydroxy-1-methyl-3',4'-dihydro-1'H-spiro[azocane-3,2'-naphthalene]-7'-carboxamide (I-156);
N-hydroxy-1'-methyl-2'-oxo-3,4-dihydro-1H-spiro[naphthalene-2,3'-piperidine]-7-carboxamide (I-157);
N-hydroxy-1-methyl-2-oxo-3',4'-dihydro-1'H-spiro[azepane-3,2'-naphthalene]-7'-carboxamide (I-158);
N-hydroxy-1-methyl-2-oxo-3',4'-dihydro-1'H-spiro[azocane-3,2'-naphthalene]-7'-carboxamide (I-159);
N-hydroxy-1'-methyl-6'-oxo-3,4-dihydro-1H-spiro[naphthalene-2,3'-piperidine]-7-carboxamide (I-160);
N-hydroxy-1-methyl-7-oxo-3',4'-dihydro-1'H-spiro[azepane-3,2'-naphthalene]-7'-carboxamide (I-161); or
N-hydroxy-1-methyl-8-oxo-3',4'-dihydro-1'H-spiro[azocane-3,2'-naphthalene]-7'-carboxamide (I-162).

22. A pharmaceutical composition comprising a compound of claim 1 or claim 13 and a pharmaceutically acceptable carrier.

23. A method of treating a cancer, selected from lung cancer, ovarian cancer, hepatocellular carcinoma, lymphoma, leukemia, non small cell lung carcinoma, breast cancer, cutaneous T-cell lymphoma, peripheral T-cell lymphoma, Hodgkin lymphoma, melanoma, squamous cell caricinoma, myeloproliferative neoplasms, metastic solid tumor, myelodysplastic syndrome, myelofibrosis, urothelial cancer, or multiple myeloma, comprising administering to a subject in need thereof an effective amount of a compound of claim 1 or claim 13.

24. A method of treating a neurodegenerative disease selected from Alzheimer's disease, Parkinson's Disease, Huntington's Disease, ALS, depression, Rett Syndrome, or Chartot-Marie-Tooth Disease, comprising administering to a subject in need thereof an effective amount of a compound of claim 1 or claim 13.

25. A method of treating an immunological disease selected from systemic lupus erythematosus, rheumatoid arthritis, inflammatory bowel disease; or allograft transplantation, comprising administering to a subject in need thereof an effective amount of a compound of claim 1 or claim 13.

26. A method of inhibiting a histone deacetylase, comprising administering to a subject in need thereof an effective amount of a compound of claim 1 or claim 13.

27. The method of claim 26, wherein the compound inhibits a zinc-dependent histone deacetylase.

28. The method of claim 26, wherein the compound inhibits the HDAC6 isozyme zinc-dependent histone deacetylase.

29. The method of claim 26, wherein the compound inhibits the HDAC11 isozyme zinc-dependent histone deacetylase.

30. The method of claim 23, wherein the lymphoma is selected from B-cell lymphoma or non-Hodgkin's lymphoma.

31. The method of claim 23, wherein the leukemia is selected from acute myeloid leukemia and chronic lymphocytotic leukemia.

* * * * *